US009403905B2

(12) United States Patent
Rosen et al.

(10) Patent No.: US 9,403,905 B2
(45) Date of Patent: *Aug. 2, 2016

(54) VASCULAR ENDOTHELIAL GROWTH FACTOR 2

(71) Applicant: HUMAN GENOME SCIENCES, INC., Rockville, MD (US)

(72) Inventors: Craig Rosen, Pasadena, MD (US); Vivian Albert, Rockville, MD (US); Steven M. Ruben, Brookeville, MD (US); Ruth Wager, Rockville, MD (US)

(73) Assignee: HUMAN GENOME SCIENCES, INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/278,068

(22) Filed: May 15, 2014

(65) Prior Publication Data

US 2014/0342405 A1 Nov. 20, 2014

Related U.S. Application Data

(63) Continuation of application No. 13/749,157, filed on Jan. 27, 2013, now Pat. No. 8,784,809, which is a continuation of application No. 13/460,217, filed on Apr. 30, 2012, now abandoned, which is a continuation of application No. 13/096,144, filed on Apr. 28, 2011, now Pat. No. 8,206,708, which is a continuation of application No. 11/980,495, filed on Oct. 31, 2007, now Pat. No. 8,216,569, which is a continuation of application No. 11/730,696, filed on Apr. 3, 2007, now Pat. No. 7,850,963, which is a continuation of application No. 10/120,414, filed on Apr. 12, 2002, now Pat. No. 7,208,582.

(60) Provisional application No. 60/350,366, filed on Jan. 24, 2002, provisional application No. 60/283,385, filed on Apr. 13, 2001.

(51) Int. Cl.

| | |
|---|---|
| *C12P 21/08* | (2006.01) |
| *C12N 15/11* | (2006.01) |
| *C12N 5/16* | (2006.01) |
| *C07K 16/22* | (2006.01) |
| *C12N 15/09* | (2006.01) |
| *C12N 15/13* | (2006.01) |
| *C12N 15/70* | (2006.01) |
| *C12N 15/64* | (2006.01) |
| *C12N 15/85* | (2006.01) |
| *C07K 14/52* | (2006.01) |
| *C07K 16/24* | (2006.01) |
| *G01N 33/574* | (2006.01) |
| *G01N 33/74* | (2006.01) |
| *A61K 38/00* | (2006.01) |
| *A61K 48/00* | (2006.01) |
| *A61K 39/00* | (2006.01) |

(52) U.S. Cl.
CPC ............... *C07K 16/22* (2013.01); *C07K 14/52* (2013.01); *C07K 16/24* (2013.01); *G01N 33/574* (2013.01); *G01N 33/74* (2013.01); *A01K 2217/05* (2013.01); *A01K 2217/075* (2013.01); *A61K 38/00* (2013.01); *A61K 48/00* (2013.01); *A61K 2039/505* (2013.01); *C07K 2317/21* (2013.01); *C07K 2317/622* (2013.01); *C12N 2799/026* (2013.01); *Y10S 435/81* (2013.01)

(58) Field of Classification Search
CPC .. C07K 16/22; C07K 14/52; C07K 2317/622; C07K 2317/21; A61K 2039/505; C12N 15/13; C12N 15/70; C12N 15/79
See application file for complete search history.

(56) References Cited

U.S. PATENT DOCUMENTS

| | | |
|---|---|---|
| 5,073,492 A | 12/1991 | Chen et al. |
| 5,194,596 A | 3/1993 | Tischer et al. |
| 5,219,739 A | 6/1993 | Tischer et al. |
| 5,234,908 A | 8/1993 | Szabo et al. |
| 5,240,848 A | 8/1993 | Keck et al. |
| 5,283,354 A | 2/1994 | Lemischka |
| 5,326,695 A | 7/1994 | Andersson et al. |
| 5,607,918 A | 3/1997 | Eriksson et al. |
| 5,633,147 A | 5/1997 | Meissner et al. |
| 5,652,225 A | 7/1997 | Isner |
| 5,661,133 A | 8/1997 | Leiden et al. |
| 5,693,622 A | 12/1997 | Wolff et al. |

(Continued)

FOREIGN PATENT DOCUMENTS

| | | |
|---|---|---|
| AU | 710696 B2 | 9/1999 |
| EP | 0186084 A2 | 7/1986 |

(Continued)

OTHER PUBLICATIONS

Achen et al., Vascular endothelial growth factor D (VEGF-D) is a ligand for the tyrosine kinases VEGF receptor 2 (Flk1) and VEGF receptor 3 (Flt4), *Proc. Natl. Acad. Sci. USA*, 95(2):548-53 (1998).
Alderson et al., Vascular endothelial cell growth factor (VEGF)-2 enhances development of rat photoreceptor cells in vitro, Keystone Symposium, *Ocular Cell and Molec. Biol.* 202, Wiley-Liss (1999).
Altschuler et al. Taurine promotes the differentiation of a vertebrate retinal cell type in vitro, *Development*, 119:1317-28, Company of Biologists Limited (1993).
Anderson, Human gene therapy, *Nature*, 392(6679Suppl):25-30 (1998).
Anderson, Human gene therapy, *Science*, 256(5058):808-13 (1992).
Andersson et al., Assignment of interchain disulfide bonds in platelet-derived growth factor (PDGF) and evidence for agonist activity of monomeric PDGF, *J. Biol. Chem.* 267(16):11260-6 (1992).
Aprelikova et al., FLT4, a novel class III receptor tyrosine kinase in chromosome 5q33-qter, *Cancer Res.* 52(3):746-8 (1992).
Bell et al., Human epidermal growth factor precursor: cDNA sequence, expression in vitro and gene organization, *Nucleic Acids Res.* 14(21):8427-46 (1986).

(Continued)

*Primary Examiner* — Phuong Huynh
(74) *Attorney, Agent, or Firm* — Marshall, Gerstein & Borun LLP

(57) ABSTRACT

Disclosed are human VEGF-2 antibodies, antibody fragments, or variants thereof. Also provided are processes for producing such antibodies. The present invention relates to methods and compositions for preventing, treating or ameliorating a disease or disorder comprising administering to an animal, preferably a human, an effective amount of one or more VEGF-2 antibodies or fragments or variants thereof.

12 Claims, 53 Drawing Sheets

(56) References Cited

U.S. PATENT DOCUMENTS

| | | |
|---|---|---|
| 5,716,981 A | 2/1998 | Hunter et al. |
| 5,776,755 A | 7/1998 | Alitalo et al. |
| 5,792,453 A | 8/1998 | Hammond et al. |
| 5,840,693 A | 11/1998 | Eriksson et al. |
| 5,861,301 A | 1/1999 | Terman et al. |
| 5,932,540 A | 8/1999 | Hu et al. |
| 5,935,820 A | 8/1999 | Hu et al. |
| 6,040,157 A | 3/2000 | Hu et al. |
| 6,121,246 A | 9/2000 | Isner |
| 6,130,071 A | 10/2000 | Alitalo et al. |
| 6,221,839 B1 | 4/2001 | Alitalo et al. |
| 6,245,530 B1 | 6/2001 | Alitalo et al. |
| 6,342,219 B1 | 1/2002 | Thorpe et al. |
| 6,361,946 B1 | 3/2002 | Alitalo et al. |
| 6,383,484 B1 | 5/2002 | Achen et al. |
| 6,403,088 B1 | 6/2002 | Alitalo et al. |
| 6,451,764 B1 | 9/2002 | Lee et al. |
| 6,608,182 B1 | 8/2003 | Rosen et al. |
| 6,645,933 B1 | 11/2003 | Alitalo et al. |
| 6,734,285 B2 | 5/2004 | Hu et al. |
| 6,818,220 B1 | 11/2004 | Alitalo et al. |
| 6,884,879 B1 | 4/2005 | Baca et al. |
| 6,958,147 B1 | 10/2005 | Alitalo et al. |
| 7,109,308 B1 | 9/2006 | Rosen et al. |
| 7,115,392 B2 | 10/2006 | Rosen et al. |
| 7,124,714 B2 | 10/2006 | Yamaoka et al. |
| 7,153,827 B1 | 12/2006 | Hu et al. |
| 7,153,942 B2 | 12/2006 | Hu et al. |
| 7,186,688 B1 | 3/2007 | Hu et al. |
| 7,208,582 B2 | 4/2007 | Rosen et al. |
| 7,223,724 B1 | 5/2007 | Alderson et al. |
| 7,227,005 B1 | 6/2007 | Hu et al. |
| 7,273,751 B2 | 9/2007 | Coleman |
| 7,402,312 B2 | 7/2008 | Rosen et al. |
| 7,423,125 B2 | 9/2008 | Alitalo et al. |
| 7,439,333 B2 | 10/2008 | Hu et al. |
| 7,498,417 B2 | 3/2009 | Hu et al. |
| 7,524,501 B2 | 4/2009 | Alderson et al. |
| 7,576,189 B2 | 8/2009 | Rosen et al. |
| 7,709,270 B2 | 5/2010 | Alitalo et al. |
| 7,727,761 B2 | 6/2010 | Alitalo et al. |
| 7,794,756 B1 | 9/2010 | Alitalo et al. |
| 7,807,412 B2 | 10/2010 | Alitalo et al. |
| 7,829,091 B2 | 11/2010 | Alitalo |
| 7,850,963 B2 | 12/2010 | Rosen et al. |
| 7,855,178 B2 | 12/2010 | Alitalo et al. |
| 8,206,708 B2 | 6/2012 | Rosen et al. |
| 8,216,569 B2 | 7/2012 | Rosen et al. |
| 8,282,931 B2 | 10/2012 | Alitalo et al. |
| 8,444,957 B2 | 5/2013 | Alitalo et al. |
| 2006/0014252 A1 | 1/2006 | Lyman |
| 2008/0286288 A1 | 11/2008 | Rosen et al. |
| 2011/0229466 A1 | 9/2011 | Rosen et al. |

FOREIGN PATENT DOCUMENTS

| | | |
|---|---|---|
| EP | 0399816 A1 | 11/1990 |
| EP | 0476983 A1 | 3/1992 |
| EP | 0506477 A1 | 9/1992 |
| JP | 64-38100 | 2/1989 |
| JP | 2117698 | 5/1990 |
| WO | WO-91/02058 A1 | 2/1991 |
| WO | WO-92/14748 A1 | 9/1992 |
| WO | WO-94/11506 A1 | 5/1994 |
| WO | WO-95/19985 A1 | 7/1995 |
| WO | WO-95/24414 A1 | 9/1995 |
| WO | WO-95/24473 A1 | 9/1995 |
| WO | WO-96/05856 A1 | 2/1996 |
| WO | WO-96/39515 A1 | 12/1996 |
| WO | WO-97/00271 A1 | 1/1997 |
| WO | WO-97/05250 A2 | 2/1997 |
| WO | WO-97/08320 A1 | 3/1997 |
| WO | WO-97/09427 A1 | 3/1997 |
| WO | WO-97/17442 A1 | 5/1997 |
| WO | WO-97/19694 A1 | 6/1997 |
| WO | WO-98/06844 A1 | 2/1998 |
| WO | WO-98/07832 A1 | 2/1998 |
| WO | WO-98/24811 A2 | 6/1998 |
| WO | WO-98/33917 A1 | 8/1998 |
| WO | WO-98/39035 A1 | 9/1998 |
| WO | WO-98/49300 A2 | 11/1998 |
| WO | WO-98/55619 A1 | 12/1998 |
| WO | WO-98/56936 A1 | 12/1998 |
| WO | WO-99/02545 A2 | 1/1999 |
| WO | WO-99/08522 A1 | 2/1999 |
| WO | WO-99/20749 A1 | 4/1999 |
| WO | WO-99/21590 A1 | 5/1999 |
| WO | WO-99/46364 A1 | 9/1999 |
| WO | WO-00/45835 A1 | 8/2000 |
| WO | WO-00/73430 A2 | 12/2000 |
| WO | WO-00/75163 A1 | 12/2000 |
| WO | WO-01/57226 A1 | 8/2001 |
| WO | WO-01/58956 A2 | 8/2001 |
| WO | WO-02/11769 A1 | 2/2002 |
| WO | WO-02/083704 A1 | 10/2002 |
| WO | WO-02/083849 A2 | 10/2002 |
| WO | WO-02/083850 A2 | 10/2002 |
| WO | WO-03/097660 A1 | 11/2003 |
| ZA | 9403464 A | 11/1995 |

OTHER PUBLICATIONS

Bellomo et al., Mice lacking the vascular endothelial growth factor-B gene (Vegfb) have smaller hearts, dysfunctional coronary vasculature, and impaired recovery from cardiac ischemia, *Circ. Res.* 86(2):E29-35 (2000).

Benjamin et al., A plasticity window for blood vessel remodelling is defined by pericyte coverage of the preformed endothelial network and is regulated by PDGF-B and VEGF, *Development*, 125(9):1591-8 (1998).

Berse et al., Vascular permeability factor (vascular endothelial growth factor) gene is expressed differentially in normal tissues, macrophages, and tumors, *Mol. Biol. Cell*, 3(2):211-20 (1992).

Betsholtz et al., cDNA sequence and chromosomal localization of human platelet-derived growth factor A-chain and its expression in tumour cell lines, *Nature*, 320(6064):695-9 (1986).

Better et al., *Escherichia coli* secretion of an active chimeric antibody fragment, *Science*, 240(4855):1041-3 (1988).

Bocker-Meffert et al., Erythropoietin and VEGF promote neural outgrowth from retinal explants in postnatal rats, Invest. Opthalmol. *Vis. Sci.* 43(6):2021-6 (2002).

Borg et al., Biochemical characterization of two isoforms of FLT4, a VEGF receptor-related tyrosine kinase, *Oncogene*, 10(5):973-84 (1995).

Breier et al., Expression of vascular endothelial growth factor during embryonic angiogenesis and endothelial cell differentiation, *Development*, 114(2):521-32 (1992).

Brown et al., Tolerance of single, but not multiple, amino acid replacements in antibody VH CDR 2: a means of minimizing B cell wastage from somatic hypermutation?, *J. Immunol.* 156(9):3285-91 (1996).

Capogrossi, Gene therapy of coronary artery disease, Project No. Z01 AG00811-01, Abstract (1994).

Capogrossi, Gene therapy of coronary artery disease, Project No. Z01 AG00811-02, Abstract (1995).

Choi et al., Angiogenesis and mineralization during distraction osteogenesis, *J. Korean Med. Sci.* 17(4):435-47 (2002).

Claffey et al., Vascular endothelial growth factor. Regulation by cell differentiation and activated second messenger pathways, *J. Biol. Chem.* 267(23):16317-22 (1992).

Cockerill et al., Angiogenesis: models and modulators, *Int. Rev. Cytol.* 159:113-60 (1995).

Colwell et al., Method for generating a high frequency of hybridomas producing monoclonal IgA antibodies, *Methods Enzymol.*, 121:42-51 (1986).

Corson et al., Fibrillin binds calcium and is coded by cDNAs that reveal a multidomain structure and alternatively spliced exons at the 5' end, *Genomics*, 17(2):476-84 (1993).

Danis et al., Anti-angiogenic therapy of proliferative diabetic retinopathy, *Expert. Opin. Pharmacother.* 2(3):395-407 (2001).

(56) References Cited

OTHER PUBLICATIONS

Declaration of Dr. Kari Alitalo, in re of: U.S. Appl. No. 08/585,895, Alitalo et al., filed Jan. 12, 1996, submitted Nov. 26, 1997.
Dermer, Another anniversary for the war on cancer, *Bio/Technol.* 12:320 (1994).
Dias et al., Vascular endothelial growth factor (VEGF)-C signaling through FLT-4 (VEGFR-3) mediates leukemic cell proliferation, survival, and resistance to chemotherapy, *Blood*, 99(6):2179-84 (2002).
Dignam et al., Balbiani ring 3 in Chironomus tentans encodes a 185-kDa secretory protein which is synthesized throughout the fourth larval instar, *Gene*, 88(2):133-40 (1990).
Duda et al., VEGF-targeted cancer therapy strategies: current progress, hurdles and future prospects, *Trends Mol. Med.* 13(6):223-30 (2007).
EBI Accession No. AAW27553, Knappik et al., Human Ab heavy chain variable region VH3 consensus, Jan. 23, 1998.
Eichmann et al., Avian VEGF-C: cloning, embryonic expression pattern and stimulation of the differentiation of VEGFR2-expressing endothelial cell precursors, *Development*, 125(4):743-52 (1998).
English language abstract of JP 64-38100 A, Derwent Accession No. 1989-088700/198912, document FP2 on Form PTO/SB/08A.
English language abstract of JP 64-38100 A, Derwent Accession No. 1990-181364/199024 document FP3 on Form PTO/SB/08A.
Enholm et al., Vascular endothelial growth factor-C: a growth factor for lymphatic and blood vascular endothelial cells, *Trends Cardiovasc. Med.* 8(7):292-7 (1998).
European Supplementary Search Report, Application No. EP01963814, mailed Jul. 14, 2004.
Fan et al., Controlling the vasculature: angiogenesis, anti-angiogenesis and vascular targeting of gene therapy, *Trends Pharmacol. Sci.* 16(2):57-66 (1995).
Ferrara et al., Molecular and biological properties of the vascular endothelial growth factor family of proteins, *Endocr. Rev.* 13(1):18-32 (1992).
Ferrara et al., The vascular endothelial growth factor family of polypeptides, *J. Cell Biochem.* 47(3):211-8 (1991).
Ferrara, Vascular endothelial growth factor and the regulation of angiogenesis, *Recent Prog. Horm. Res.* 55:15-35 (2000).
Finnerty et al., Molecular cloning of murine FLT and FLT4, *Oncogene*, 8(8):2293-8 (1993).
Friedmann, A brief history of gene therapy, *Nat. Genet.* 2(2):93-8 (1992).
Gamble et al., Regulation of in vitro capillary tube formation by anti-integrin antibodies, *J. Cell Biol.* 121(4):931-43 (1993).
George et al., Current methods in sequence comparison and analysis, Macromolecular Sequence and Synthesis Selected Method—Application (Alan R. Liss), pp. 127-149 (1988).
Gerhardinger et al., Expression of vascular endothelial growth factor in the human retina and in nonproliferative diabetic retinopathy, *Am. J. Pathol.* 152(6):1453-62 (1998).
Goldspiel et al., Human gene therapy, *Clin. Pharm.* 12(7):488-505 (1993).
Grimmond et al., Cloning and characterization of a novel human gene related to vascular endothelial growth factor, *Genome Res.*, 6(2):124-31 (1996).
Gura, Systems for identifying new drugs are often faulty, *Science*, 278(5340):1041-2 (1997).
Guzman et al., Efficient gene transfer into myocardium by direct injection of adenovirus vectors, *Circ. Res.* 73(6):1202-7 (1993).
Halin et al., Antibody-Based targeting of angiogenesis, *Crit. Rev. Ther. Drug Carrier Syst.* 18(3):299-339 (2001).
Hannink et al., Deletions in the C-terminal coding region of the v-sis gene: Dimerization is required for transformation, *Mol. Cell Biol.*, 6(4):1304-14 (1986).
Heldin et al., Structure of platelet-derived growth factor: implications for functional properties, *Growth Factors*, 8(4):245-52 (1993).
Henry et al., A prostate-specific membrane antigen-targeted monoclonal antibody-chemotherapeutic conjugate designed for the treatment of prostate cancer, *Cancer Res.* 64(21):7995-8001 (2004).
Hirai et al., Expression of vascular endothelial growth factors (VEGF-A/VEGF-1 and VEGF-C/VEGF-2) in postmenopausal uterine endometrial carcinoma, *Gynecol. Oncol.* 80(2):181-8 (2001).
Hockel et al., Therapeutic angiogenesis, *Arch. Surg.* 128(4):423-9 (1993).
Houck et al., The vascular endothelial growth factor family: identification of a fourth molecular species and characterization of alternative splicing of RNA, *Mol. Endocrinol.* 5(12):1806-14 (1991).
Hu et al., A novel regulatory function of proteolytically cleaved VEGF-2 for vascular endothelial and smooth muscle cells, *FASEB J.* 11(6):498-504 (1997).
Hyde et al., Correction of the ion transport defect in cystic fibrosis transgenic mice by gene therapy, *Nature*, 362(6417):250-5 (1993).
International Search Report, Application No. PCT/US01/24658, mailed on Dec. 12, 2001.
International Search Report, Application No. PCT/US02/26246, mailed on May 21, 2003.
International Search Report, Application No. PCT/US94/05291, mailed on Nov. 4, 1994.
International Search Report, Application No. PCT/US99/05021, mailed on Jun. 11, 1999.
Isner et al., Arterial gene therapy for therapeutic angiogenesis in patients with peripheral artery disease, *Circulation*, 91(11):2687-92 (1995).
Isner et al., Gene therapy for arterial disease, *Lancet*, 344:1653-4 (1994).
Isner et al., Physiologic assessment of angiogenesis by arterial gene therapy with vascular endothelial growth factor, *J. Cell. Biochem.* Suppl. 21 a:378, Abstract C6-215 (1995).
Isner, Therapeutic angiogenesis in vascular medicine, Project No. R01 HL53354-01, Abstract (Mar. 1995).
Joosten et al., The production of antibody fragments and antibody fusion proteins by yeasts and filamentous fungi, *Microbial Cell Fact.* 2:1, BioMed Central (Jan. 2003).
Joukov et al., Proteolytic processing regulates receptor specificity and activity of VEGF-C, *EMBO J.* 16(13):3898-911 (1997).
Joukov et al., Proteolytic processing regulates receptor specificity and activity of VEGF-C, *EMBO J.* 16:3898-911 (1997).
Kaipainen et al., The related FLT4, FLT1, and KDR receptor tyrosine kinases show distinct expression patterns in human fetal endothelial cells, *J. Exp. Med.* 178:2077-2088 (1993).
Kay et al., In vivo gene therapy of hemophilia B: sustained partial correction in factor IX-deficient dogs, *Science*, 262(5130):117-9 (1993).
Keck et al., Vascular permeability factor, an endothelial cell mitogen related to PDGF, *Science*, 246(4935):1309-12 (1989).
Kelley et al., Regulation of proliferation and photoreceptor differentiation in fetal human retinal cell cultures, *Invest. Ophthalmol. Vis. Sci.* 36(7):1280-9 (1995).
Kingsley, The TGF-beta superfamily: new members, new receptors, and new genetic tests of function in different organisms, *Genes Dev.* 8(2):133-46 (1994).
Klimka et al., Human anti-CD30 recombinant antibodies by guided phage antibody selection using cell panning, *Br. J. Cancer*, 83(2):252-60 (2000).
Kolodka et al., Hepatic gene therapy: efficient retroviral-mediated gene transfer into rat hepatocytes in vivo, *Somat. Cell Mol. Genet.*, 19(5):491-7 (1993).
Kubo et al., Blockade of vascular endothelial growth factor receptor-3 signaling inhibits fibroblast growth factor-2-induced lymphangiogenesis in mouse cornea, *Proc. Natl. Acad. Sci. USA*, 99(13):8868-73 (2002).
Kukk et al., VEGF-C receptor binding and pattern of expression with VEGFR-3 suggests a role in lymphatic vascular development, *Development*, 122(12):3829-37 (1996).
Kuzuya et al., Induction of endothelial cell differentiation in vitro by fibroblast-derived soluble factors, *Exp. Cell Res.* 215(2):310-8 (1994).
Landolfi et al., The integrity of the ball-and-socket joint between V and C domains is essential for complete activity of a humanized antibody, *J. Immunol.* 166(3):1748-54 (2001).

(56) References Cited

OTHER PUBLICATIONS

Lee et al., Vascular endothelial growth factor-related protein: a ligand and specific activator of the tyrosine kinase receptor Flt4, *Proc. Natl. Acad. Sci. USA*, 93(5):1988-92 (1996).

Letter from John J. Chicca II, Ph.D., Molecular Diagnostic Services, Inc. regarding a fourth progress report for a project entitled "Cloning and expression of VEGF-2 gene and the efficacy of VEGF-2 protein utilizing the 3-D collagen angiogenesis assay and proliferation", dated Feb. 16, 2006.

Letter from John J. Chicca II, Ph.D., Molecular Diagnostic Services, Inc. regarding a third progress report for a project entitled "Cloning and expression of VEGF-2 gene and the efficacy of VEGF-2 protein utilizing the 3-D collagen angiogenesis assay and proliferation", dated Feb. 16, 2006.

Leung et al., Vascular endothelial growth factor is a secreted angiogenic mitogen, *Science*, 246(4935):1306-9 (1989).

Litwin et al., "Role of Cytokines in Endothelial Cell Functions", pp. 101-129, Human Cytokines: Their Role in Disease and Therapy, Blackwell Science (1995).

Liu et al., Fine mapping of the antigen-antibody interaction of scFv215, a recombinant antibody inhibiting RNA polymerase II from *Drosophila melanogaster*, *J. Mol. Recognit.* 12(2):103-11 (1999).

Longo et al., Anti-angiogenic therapy: rationale, challenges and clinical studies, *Angiogenesis*, 5(4):237-56 (2002).

Maglione et al., Isolation of a human placenta cDNA coding for a protein related to the vascular permeability factor, *Proc. Natl. Acad. Sci. USA*, 88(20):9267-71 (1991).

Maglione et al., Two alternative mRNAs coding for the angiogenic factor, placenta growth factor (PlGF), are transcribed from a single gene of chromosome 14, Oncogene, 8(4):925-31 (1993).

Maher, Stimulation of endothelial cell proliferation by vanadate is specific for microvascular endothelial cells, *J. Cell Physiol.* 151(3):549-54 (1992).

Massague et al., The transforming growth factor-beta family, *Annu. Rev. Cell Biol.* 6:597-641 (1990).

Matthews et al., A receptor tyrosine kinase cDNA isolated from a population of enriched primitive hematopoietic cells and exhibiting close genetic linkage to c-kit, *Proc. Natl. Acad. Sci. USA*, 88(20):9026-30 (1991).

Maynard et al., Antibody engineering, *Annu. Rev. Biomed. Eng.* 2:339-76 (2000).

Merz et al., the protein folding problem and tertiary structure prediction, *Trends Biochem. Sci.* 20:129-30 (1995).

Mesri et al., Expression of vascular endothelial growth factor from a defective herpes simplex virus type 1 amplicon vector induces angiogenesis in mice, *Circ. Res.* 76(2):161-7 (1995).

Millauer et al., Glioblastoma growth inhibited in vivo by a dominant-negative Flk-1 mutant, *Nature*, 367(6463):576-9 (1994).

Millauer et al., High affinity VEGF binding and developmental expression suggest Flk-1 as a major regulator of vasculogenesis and angiogenesis, *Cell*, 72(6):835-46 (1993).

Morea et al., Antibody modeling: implications for engineering and design, *Methods*, 20(3):267-79 (2000).

Muhlhauser et al., In vivo gene transfer into porcine cardiac cells with a replication-deficient recombinant adenovirus vector, *Circulation*, 88:1-475 abstract No. 2558 (1992).

Muhlhauser et al., VEGF165 expressed by a replication-deficient recombinant adenovirus vector induces angiogenesis in vivo, *Circ. Res.* 77(6):1077-86 (1995).

NCBI Entrez, GenBank Report, Accession No. AF010302, Mandriota et al., Rattus norvegicus vascular endothelial growth factor-C mRNA, partial cds, Jul. 16, 1997.

NCBI Entrez, GenBank Report, Accession No. AJ000185, Achen et al., *Homo sapiens* mRNA for vascular endothelial growth factor-D, Feb. 11, 1998.

NCBI Entrez, GenBank Report, Accession No. D88689, Finnerty et al., Mus musculus mRNA for flt-1, complete cds, Apr. 14, 2000.

NCBI Entrez, GenBank Report, Accession No. K03212, Anderson et al., Human c-src-1 proto-oncogene, exon 6, Jan. 13, 1995.

NCBI Entrez, GenBank Report, Accession No. K03213, Anderson et al., Human c-src-1 proto-oncogene, exon 7, Jan. 13, 1995.

NCBI Entrez, GenBank Report, Accession No. K03214, Anderson et al., Human c-src-1 proto-oncogene, exon 8, Jan. 13, 1995.

NCBI Entrez, GenBank Report, Accession No. K03215, Anderson et al., Human c-src-1 proto-oncogene, exon 9, Jan. 13, 1995.

NCBI Entrez, GenBank Report, Accession No. K03216, Tanaka et al., Human c-src-1 proto-oncogene, exon 10, Jan. 13, 1995.

NCBI Entrez, GenBank Report, Accession No. K03217, Tanaka et al., Human c-src-1 proto-oncogene, exon 11, Jan. 13, 1995.

NCBI Entrez, GenBank Report, Accession No. K03218, Tanaka et al., Human c-src-1 proto-oncogene, exon 12, Jan. 13, 1995.

NCBI Entrez, GenBank Report, Accession No. L04947, Terman et al., *Homo sapiens* (clones BT3.081.8, BT3.129.5 and BT4.169, Jan. 6, 1995.

NCBI Entrez, GenBank Report, Accession No. L07296, Finnerty et al., Mus musculus receptor tyrosine kinase (FLT4) mRNA, complete cds, Aug. 9, 1993.

NCBI Entrez, GenBank Report, Accession No. L19896, Corson et al., Human fibrillin (FBN1) gene, 5' end including alternative exons A, B, and C, and exon M, Nov. 8, 1994.

NCBI Entrez, GenBank Report, Accession No. L22473, Oltvai et al., Human Bax alpha mRNA, complete cds, Dec. 15, 1993.

NCBI Entrez, GenBank Report, Accession No. L22474, Oltvai et al., Human Bax beta mRNA, complete cds, Dec. 15, 1993.

NCBI Entrez, GenBank Report, Accession No. M13994, Tsujimoto et al., Human B-cell leukemia/lymphoma 2 (bcl-2) proto-oncogene mRNA encoding bcl-2-alpha protein, complete cds, Oct. 31, 1994.

NCBI Entrez, GenBank Report, Accession No. M13995, Tsujimoto et al., Human B-cell leukemia/lymphoma 2 (bcl-2) proto-oncogene mRNA encoding bcl-3-alpha protein, complete cds, Oct. 31, 1994.

NCBI Entrez, GenBank Report, Accession No. M16237, Tanaka et al. Human c-src-1 proto-oncogene, exon 2, Jan. 13, 1995.

NCBI Entrez, GenBank Report, Accession No. M16243, Tanaka et al. Human c-src-1 proto-oncogene, exon 3, Jan. 13, 1995.

NCBI Entrez, GenBank Report, Accession No. M16244, Tanaka et al. Human c-src-1 proto-oncogene, exon 4, Jan. 13, 1995.

NCBI Entrez, GenBank Report, Accession No. M16245, Tanaka et al. Human c-src-1 proto-oncogene, exon 5, Jan. 13, 1995.

NCBI Entrez, GenBank Report, Accession No. M24276, Dignam et al., C. tentans 140-kd secretory protein (sp140) mRNA, partial cds, clone pCt140.1, Apr. 26, 1993.

NCBI Entrez, GenBank Report, Accession No. M24277, Dignam et al. C. tentans 140-kd secretory protein (sp140) mRNA, partial cds, clone pCt140.2, Apr. 26, 1993.

NCBI Entrez, GenBank Report, Accession No. M27281, Keck et al., Human vascular permeability factor mRNA, complete cds, Aug. 3, 1993.

NCBI Entrez, GenBank Report, Accession No. M63971, Tischer et al., Human vascular endothelial cell growth factor gene, exon 1, Aug. 3, 1993.

NCBI Entrez, GenBank Report, Accession No. M63972, Tischer et al., Human vascular endothelial cell growth factor gene, exon 2, Aug. 3, 1993.

NCBI Entrez, GenBank Report, Accession No. M63973, Tischer et al., Human vascular endothelial cell growth factor gene, exon 3, Aug. 3, 1993.

NCBI Entrez, GenBank Report, Accession No. M63974, Tischer et al., Human vascular endothelial cell growth factor gene, exon 4, Aug. 3, 1993.

NCBI Entrez, GenBank Report, Accession No. M63975, Tischer et al., Human vascular endothelial cell growth factor gene, exon 5, Aug. 3, 1993.

NCBI Entrez, GenBank Report, Accession No. M63976, Tischer et al., Human vascular endothelial cell growth factor gene, exon 6, Aug. 3, 1993.

NCBI Entrez, GenBank Report, Accession No. M63977, Tischer et al., Human vascular endothelial cell growth factor gene, exon 7, Aug. 3, 1993.

NCBI Entrez, GenBank Report, Accession No. M63978, Tischer et al., Human vascular endothelial cell growth factor gene, exon 8, Aug. 3, 1993.

(56) References Cited

OTHER PUBLICATIONS

NCBI Entrez, GenBank Report, Accession No. M95200, Claffey et al., Mouse vascular endothelial growth factor mRNA, complete cds, Apr. 27, 1993.
NCBI Entrez, GenBank Report, Accession No. S08167, Paulsson et al., Balbiani ring 3 protein—midge (Chironomus tentans), 1990.
NCBI Entrez, GenBank Report, Accession No. S57152, Maglione et al., *Homo sapiens* placenta growth factor 2 (PIGR-2) gene, partial cds, Mar. 5, 2001.
NCBI Entrez, GenBank Report, Accession No. X04571, Bell et al., Human mRNA for kidney epidermal growth factor (EGF) precursor, Mar. 21, 1995.
NCBI Entrez, GenBank Report, Accession No. X52263, Paulsson et al., C tentans balbiani ring 3 (BR3) gene, Dec. 18, 1992.
NCBI Entrez, GenBank Report, Accession No. X54936, Maglione et al., *H. sapiens* mRNA for placenta growth factor (PIGF), Nov. 12, 1991.
NCBI Entrez, GenBank Report, Accession No. X59397, Matthews et al., Mouse Flk-1 mRNA for tyosine kinase receptor, Nov. 6, 1991.
NCBI Entrez, GenBank Report, Accession No. X63556, Corson et al., *H. sapiens* mRNA for fibrillin, Feb. 17, 1997.
NCBI Entrez, GenBank Report, Accession No. X68203, Aprelikova et al., "*H. sapiens* mRNA for FLT4, class III receptor tyrosine kinase", Nov. 30, 1993.
NCBI Entrez, GenBank Report, Accession No. M24160, Dignma et al., C. tentans 185-kd secretory protein (sp185) mRNA, partial cds, clone pCt185, Apr. 26, 1993.
Ngo et al., The Protein Folding Problem and Tertiary Structure Prediction, pp. 492-495, Merz et al. (eds.), Boston: Birkhauser (1994).
Oikawa et al., Three isoforms of platelet-derived growth factors all have the capability to induce angiogenesis in vivo, *Biol. Pharm. Bull.* 17(12):1686-8 (1994).
Oltvai et al., Bcl-2 heterodimerizes in vivo with a conserved homolog, Bax, that accelerates programmed cell death, *Cell*, 74(4):606-19 (1993).
Pajusola et al., FLT4 receptor tyrosine kinase contains seven immunoglobulin-like loops and is expressed in multiple human tissues and cell lines, *Cancer Res.* 52(20):5738-43 (1992).
Pajusola et al., Signalling properties of FLT4, a proteolytically processed receptor tyrosine kinase related to two VEGF receptors, *Oncogene*, 9(12):3545-55 (1994).
Pajusola et al., Two human FLT4 receptor tyrosine kinase isoforms with distinct carboxy terminal tails are produced by alternative processing of primary transcripts, *Oncogene*, 8(11):2931-7 (1993).
Paulsson et al., The Balbiani ring 3 gene in Chironomus tentans has a diverged repetitive structure split by many introns, *J. Mol. Biol.* 211(2):331-49 (1990).
Pepper et al., In vitro angiogenic and proteolytic properties of bovine lymphatic endothelial cells, *Exp. Cell Res.* 210(2):298-305 (1994).
Plate, From angiogenesis to lymphangiogenesis, *Nat. Med.* 7(2):151-2 (2001).
Presta et al., Humanization of an anti-vascular endothelial growth factor monoclonal antibody for the therapy of solid tumors and other disorders, *Cancer Res.* 57(20):4593-9 (1997).
Riemer et al., Matching of trastuzumab (Herceptin) epitope mimics onto the surface of Her-2/neu—a new method of epitope definition, *Mol. Immunol.* 42(9):1121-4 (2005).
Roitt et al. (eds.), Chapter 5, Immunology, 2nd edition, pp. 5.8-5.9, Gower Medical Publishing (1989).
Rudikoff et al., Single amino acid substitution altering antigen-binding specificity, *Proc. Natl. Acad. Sci. USA*, 79(6):1979-83 (1982).
Schlaeppi et al., Characterization of a new potent, in vivo neutralizing monoclonal antibody to human vascular endothelial growth factor, *J. Cancer Res. Clin. Oncol.* 125(6):336-42 (1999).
Schratzberger et al., Reversal of experimental diabetic neuropathy by VEGF gene transfer, *J. Clin. Invest.* 107(9):1083-92 (2001).
Schulz-Key et al., Ciliary neurotrophic factor as a transient negative regulator of rod development in rat retina, *Invest. Ophthalmol. Vis. Sci.* 43(9):3099-108 (2002).

Seigel, The golden age of retinal cell culture, *Mol. Vis.* 4:4 (1999).
Shibuya et al., Nucleotide sequence and expression of a novel human receptor-type tyrosine kinase gene (flt) closely related to the fms family, *Oncogene*, 5(4):519-24 (1990).
Silins et al., Analysis of the promoter region of the human VEGF-related factor gene, *Biochem. Biophys. Res. Commun.* 230(2):413-8 (1997).
Skerra et al., Assembly of a functional immunoglobulin Fv fragment in *Escherichia coli*, *Science*, 240(4855):1038-41 (1988).
Spranger et al., New concepts in pathogenesis and treatment of diabetic retinopathy, *Exp. Clin. Endocrinol. Diabetes*, 109 Suppl 2: S438-50 (2001).
Stacker et al., The vascular endothelial growth factor family: Signaling for vascular development, *Growth Factors*, 17(1):1-11 (1999).
Stancovski et al., Mechanistic aspects of the opposing effects of monoclonal antibodies to the ERBB2 receptor on tumor growth, *Proc. Natl. Acad. Sci. USA*, 88(19):8691-5 (1991).
Statutory declaration of Frances John Ballard, executed on Dec. 12, 2001, and accompanying Exhibit 1.
Statutory declaration of Frances John Ballard, executed on Feb. 16, 2000, and accompanying Exhibit 1.
Statutory declaration of Francis John Ballard, executed on Jul. 16, 2002.
Statutory declaration of Gary Baxter Cox, executed on Dec. 13, 2000, and accompanying Exhibits GBC 1 to 23.
Statutory declaration of Gary Baxter Cox, executed on Mar. 22, 2002, and accompanying GBC24 (statutory declaration of Peter Adrian Walters, executed on Oct. 26, 2001).
Statutory declaration of Jennifer Ruth Gamble, executed on Dec. 12, 2000, and accompanying Exhibits JRG 1 to 3.
Statutory declaration of John Stanley Mattick, executed on Dec. 12, 2000, and accompanying Exhibits JSM1 to JSM4.
Statutory declaration of Kari Alitalo, executed on Aug. 14, 2002, and accompanying Exhibits KA-1 and K-2.
Statutory declaration of Kari Alitalo, executed on Feb. 15, 2000, and accompanying Exhibits 1 to 3.
Statutory declaration of Kari Alitalo, executed on Jul. 16, 2002, and accompanying Exhibit 1.
Statutory declaration of Kari Alitalo, executed on Sep. 24, 2001, and accompanying Exhibit 1 and 2.
Statutory declaration of Nicholas Kim Hayward, executed on Dec. 8, 2000, and accompanying Exhibits NKH 1 and 2.
Statutory declaration of Nicholas Kim Hayward, executed on Mar. 26, 2002.
Statutory declaration of Peter Adrian Walton Rogers, executed on Aug. 9, 2002.
Statutory declaration of Peter Adrian Walton Rogers, executed on Feb. 16, 2000, and accompanying Exhibit 1.
Statutory declaration of Peter Adrian Walton Rogers, executed on Nov. 12, 2001, and accompanying Exhibits PAWR1 and PAWR 14.
Statutory declaration of Stuart A. Aaronson, executed on Dec. 14, 2000, and accompanying CV.
Statutory declaration of Stuart A. Aaronson, executed on Mar. 22, 2002 and accompanying Appendices I to III.
Statutory declaration of Susan Power, executed on Dec. 13, 2000, and accompanying Appendices 1 to 2 and Figure 1.
Statutory declaration of Susan Power, executed on Mar. 22, 2002, and accompanying Appendices I to IV.
Statutory declaration of Tom Rapoport, executed on Dec. 13, 2000, and accompanying Exhibits TP 1 and 2.
Stewart et al., Insulin delivery by somatic cell gene therapy, *J. Mol. Endocrinol.* 11(3):335-41 (1993).
Supplementary European Search Report, Application No. EP02726730, mailed Oct. 25, 2004.
Supplementary Partial European Search Report, Application No. EP00905992, mailed Nov. 8, 2004.
Supplementary Partial European Search Report, Application No. EP02721715, mailed Jan. 10, 2005.
Supplementary Partial European Search Report, Application No. EP02721715, mailed Oct. 22, 2004.
Supplementary Partial European Search Report, Application No. EP02726730, mailed Aug. 4, 2004.

(56) References Cited

OTHER PUBLICATIONS

Symes et al., Angiogenesis: potential therapy for ischaemic disease, *Curr. Opin. Lipidol.* 5(4):305-12 (1994).
Takeshita et al., In vivo evidence of enhanced angiogenesis following direct arterial gene transfer of the plasmid encoding vascular endothelial growth factor, *Circulation*, 88:1476, Abstract No. 2565 (1993).
Takeshita et al., Therapeutic angiogenesis. A single intraarterial bolus of vascular endothelial growth factor augments revascularization in a rabbit ischemic hind limb model, *J. Clin. Invest.* 93(2):662-70 (1994).
Tanaka et al., DNA sequence encoding the amino-terminal region of the human c-src protein: implications of sequence divergence among src-type kinase oncogenes, *Mol. Cell Biol.* 7(5):1978-83 (1987).
Terman et al., Identification of a new endothelial cell growth factor receptor tyrosine kinase, *Oncogene*, 6(9):1677-83 (1991).
Terman et al., Identification of the KDR tyrosine kinase as a receptor for vascular endothelial cell growth factor, *Biochem. Biophys. Res. Commun.* 187(3):1579-86 (1992).
Tischer et al., The human gene for vascular endothelial growth factor. Multiple protein forms are encoded through alternative exon splicing, *J. Biol. Chem.* 266(18):11947-54 (1991).
Tischer et al., Vascular endothelial growth factor: a new member of the platelet-derived growth factor gene family, *Biochem. Biophys. Res. Commun.* 165(3):1198-206 (1989).
Townson et al., Characterization of the murine VEGF-related factor gene, *Biochem. Biophys. Res. Commun.* 220(3):922-8 (1996).
Tsujimoto et al., Analysis of the structure, transcripts, and protein products of bcl-2, the gene involved in human follicular lymphoma, *Proc. Natl. Acad. Sci. USA*, 83(14):5214-8 (1986).
Vajdos et al., Comprehensive functional maps of the antigen-binding site of an anti-ErbB2 antibody obtained with shotgun scanning mutagenesis, *J. Mol. Biol.* 320(2):415-28 (2002).
Vale et al., Percutaneous electromechanical mapping demonstrates efficacy of pVG1.1 (VEGF2) in an animal model of chronic myocardial ischemia, *Circulation*, 100:1.22 (1999).
Vale et al., Randomized, single-blind, placebo-controlled pilot study of catheter-based myocardial gene transfer for therapeutic angiogenesis using left ventricular electromechanical mapping in patients with chronic myocardial ischemia, *Circulation*, 103(17):2138-43 (2001).
van der Flier et al., Antibody neutralization of vascular endothelial growth factor (VEGF) fails to attenuate vascular permeability and brain edema in experimental pneumococcal meningitis, *J. Neuroimmunol.* 160(1-2):170-7 (2005).
Verma et al., Gene therapy—promises, problems and prospects, *Nature*, 389(6648):239-42 (1997).
Walsh et al., Angiogenesis in the pathogenesis of inflammatory joint and lung diseases, *Arthritis Res.* 3(3):147-53 (2001).
Walsh et al., Gene therapy for human hemoglobinopathies, *Proc. Soc. Exp. Biol. Med.* 204(3):289-300 (1993).
Walsh, Angiogenesis and arthritis, Rheumatology (Oxford), 38(2):103-12 (1999).
Williams, Southwestern Internal Medicine Conference: prospects for gene therapy of ischemic heart disease, *Am. J. Med. Sci.* 306(2):129-36 (1993).
Winkler et al., Changing the antigen binding specificity by single point mutations of an anti-p24 (HIV-1) antibody, *J. Immunol.* 165(8):4505-14 (2000).
Witte et al., Monoclonal antibodies targeting the VEGF receptor-2 (Flk1/KDR) as an anti-angiogenic therapeutic strategy, *Cancer Metastasis Rev.* 17(2):155-61 (1998).
Witzenbichler et al., Vascular endothelial growth factor-C (VEGF-C/VEGF-2) promotes angiogenesis in the setting of tissue ischemia, *Am. J. Pathol.* 153(2):381-94 (1998).
Wu et al., Humanization of a murine monoclonal antibody by simultaneous optimization of framework and CDR residues, *J. Mol. Biol.* 294(1):151-62 (1999).
Yang et al., Flk-1, a receptor for vascular endothelial growth factor (VEGF), is expressed by retinal progenitor cells, *J. Neurosci.* 16(19):6089-99 (1996).
Yeung, VEGF-2 (St Elizabeth's Medical Center), *Curr. Opin. Investig. Drugs*, 2(6):796-800 (2001).
Yourey et al., Vascular endothelial cell growth factors promote the in vitro development of rat photoreceptor cells, *J. Neurosci.* 20(18):6781-8 (2000).
Yourey et al., Vascular endothelial cell growth factors promote the in vitro development of rat photoreceptor cells, Mol. Biol. Cell, 10:39A (1999) and 39th Annual Meeting of the American Society of Cell Biology, Washington, DC (1999) (abstract 227).
Yu et al., Interaction between bevacizumab and murine VEGF-A: a reassessment, *Invest. Ophthalmol. Vis. Sci.* 49(2):522-7 (2008).
Zhu et al., Inhibition of tumor growth and metastasis by targeting tumor-associated angiogenesis with antagonists to the receptors of vascular endothelial growth factor, *Invest. New Drugs*, 17(3):195-212 (1999).

FIG. 1A

```
361  AGATCTTGAAAAGTATTGATAATGAGTGGAGAAAGACTCAATGCATGCCACGGGGAGGTGT
     ----------+---------+---------+---------+---------+---------+  420
     TCTAGAACTTTTCATAACTATTACTCACCTCTTTCTGAGTTACGTACGGTGCCCTCCACA
     I  L  K  S  I  D  N  E  W  R  K  T  Q  C  M  P  R  E  V  C

421  GTATAGATGTGGGGAAGGAGTTTGGAGTCGCCGACAAACACCTTCTTTAAACCTCCATGTG
     ----------+---------+---------+---------+---------+---------+  480
     CATATCTACACCCCTTCCTCAAACCTCAGCGCTGTTTGTGGAAGAAATTTGGAGGTACAC
     I  D  V  G  K  E  F  G  V  A  T  N  T  F  F  K  P  P  C  V

481  TGTCCGTCCTACAGATGTGGGGGTTGCTGCAGTAGTGAGGGCTGCAGTGCATGAACACCA
     ----------+---------+---------+---------+---------+---------+  540
     ACAGGCAGATGTCTACACCCCCAACGACGTTATCACTCCCGACGTCATCACGTACTTGTGGT
     S  V  R  C  G  G  C  N  S  E  G  L  Q  C  M  N  T  S

541  GCACGAGCTACCTCAGCAAGAACGTTATTTGAAATTACAGTGCCTCTCTCTCAAGGCCCCA
     ----------+---------+---------+---------+---------+---------+  600
     CGTGCTCGATGGAGTCGTTCTGCAATAAACTTTAATGTCACGGAGAGAGTTCCGGGGT
     T  S  Y  L  S  K  T  L  F  E  I  T  V  P  L  S  Q  G  P  K

601  AACCAGTAACAATCAGTTTGTTGCCAATCACACTTCCTGCCGATGCATGTCTAAACTGGATG
     ----------+---------+---------+---------+---------+---------+  660
     TTGGTCATTGTTAGTCAAAACGGTTAGTCAAGGACGGCTACGTCAGATTTGACCTAC
     P  V  T  I  S  F  A  N  H  T  S  C  R  C  M  S  K  L  D  V
```

FIG. 1B

```
661  TTTACAGACAAGTCATTCATTCCATTATTAGACGTTCCCTGCCAGCAACACTACCACAGTGTC
     ---------+---------+---------+---------+---------+---------+  720
     AAATGTCTGTTCAAGTAAGGTAATAATCTGCAAGGGACGGTCGTTGTGATGGTGTCACAG
      Y  R  Q  V  H  S  I  I  R  R  S  L  P  A  T  L  P  Q  C  Q

721  AGGCAGGCGAACAAGACCTGCCCCACCAATTACATGGAATAATCACATCNGCAGATGCC
     ---------+---------+---------+---------+---------+---------+  780
     TCCGTCGCTTGTTCTGGACGGGGTGGTTAATGTACACCTTATTAGTGTAGACGTCTACGG
      A  A  N  K  T  C  P  T  N  Y  M  W  N  N  H  I  C  R  C  L

781  TGGCTCTCAGGAAGATTTTATGTTCTTCCTCGGAGATGCTGGAGATGACTCAACAGATCC
     ---------+---------+---------+---------+---------+---------+  840
     ACCGAGTCCTTCTAAAATACAAGAAGGAGCCTACGACCTACTGAGTTGTCTACTAAGG
      A  Q  E  D  P  M  F  F  S  S  D  A  G  D  D  S  T  D  G  F  H

841  ATGACATCTGTGGACCCAAACAAGGAGCTGGATGAAGAACCTGTCAGTGTGTCTGCAGAG
     ---------+---------+---------+---------+---------+---------+  900
     TACTGTAGACACCTGGTTTGTTCCTCGACCTACTTCTTGGACAGTCACAGACAGACGTCTC
      D  I  C  G  P  N  K  E  L  D  E  E  T  C  Q  C  V  C  R  A

901  CGGGGGCTTCGGCCTGCCAGCTGTGGACCCTGGGGTGTTCTAACAAAGACTAGACATGCCAGT
     ---------+---------+---------+---------+---------+---------+  960
     GCCCGAAGCCGGACGGTCGACGGTCGACACCTGGGGTGTTCTNATCTGTCTTGAGTACGGTCA
      G  L  R  P  A  S  C  G  P  H  K  E  L  D  R  N  S  C  Q  C
```

FIG. 1C

```
961   GTGTCTGTAAAAACAAACTCTTCCCCAGCCAATGTGGGCCAACCGAGAATTTGATGAAA  1020
      CACAGACATTTTGTTTGTTGAGAAGGGGTCGGTTACACCCGGTTGGCTCTTAAACTACTTT
       V  C  K  N  K  L  F  P  S  Q  C  G  A  N  R  E  F  D  E  N

1021  ACACATGCCAGTGTGTATGTAAAAGAACCTGCCCCAGAAATCAACCCCTAAATCCTGGAA  1080
      TGTGTACGGTCACACATACATTTCTTGGACGGGGTCTTTAGTTGGGATTTAGGACCTT
       T  C  Q  C  V  C  K  R  T  C  P  R  N  Q  P  L  N  P  G  K

1081  AATGTGCCTGTGAATGTACAGAAAGTCCACAGAAATGCTGTTAAAGGAAAGAAGTTCC  1140
      TTACACGGACACTTACATGTCTTTCAGGTGTCTTTACGACAATTTCCTTTCTTCAAGG
       C  A  E  C  T  E  S  P  Q  K  C  L  L  K  G  K  K  F  H

1141  ACCACCAAACATGCAGCTGTTACAGACGGCCATGTACGAACCGCCAGAAGGCTTGTGAGC  1200
      TGGTGGTTTGTACGTCGACAATGTCTGCCGGTACATGCTTGGCGGTCTTCCGAACACTCG
       H  Q  T  C  S  C  Y  R  R  P  C  T  N  R  Q  K  A  C  E  P

1201  CAGGATTTTCATATAGTGAAGAAGTGTGTCGTTCGTTGTCCCTTCATATGGCAAAGACCAC  1260
      GTCCTAAAAGTATATCACTTCTTCACACAGCAACACAGGAAGTATAACCGTTTCTGGTG
       G  P  S  Y  S  E  E  V  C  R  C  V  P  S  Y  W  Q  R  P  Q
```

FIG. 10

```
1261  AAATGAGCTAAGATTGTACTGTTTCCAGTTCATCGATTTTCTATTATGGAAAACTGTGT
      ----------+---------+---------+---------+---------+---------+  1320
      TTTACTCGATTCTAACATGACAGAAAGGTCAAGTAGCTAAAAGATAATACCTTTGACACA
                                                              M  S  *

1321  TGCCACAGTAGAACTGTCTCTGAACAGAGAGACCCTTGTGGGTCCATGCTAACAAAGACA
      ----------+---------+---------+---------+---------+---------+  1380
      ACGGTGTCATCTTGACAGAGACACTTGTCTCTCTGGGAACACCCAGGTACGATTGTTTCTGT

1381  AAAGTCTGTCTTTCCTGAACCATGTGGATAACTTTACAGAATGGACTGGAGCTCATCTG
      ----------+---------+---------+---------+---------+---------+  1440
      TTTCAGACAGAAAGGACTTGGTACACCTATTGAAATGTCTTTACCTGACCTCGAGTAGAC

1441  CAAAAGGCCCTCTTGTAAAGACTGGTTTTCTGCCAATGACCAAACAGCCAAGATTTCCTC
      ----------+---------+---------+---------+---------+---------+  1500
      GTTTTCCGGGAGAACATTTCTGACCAAAAGACGGTTACTGGTTTGTCGGTTCTAAAAGGAG

1501  TTTGTGATTTCTTTAAAGAATGACTATATAATTTATTCCACTAAAAGAATTGTTTCTGC
      ----------+---------+---------+---------+---------+---------+  1560
      AACACTAAAGAAATTTCTTACTGATATATTAAATAAGGTGATTTTTATAACAAAGACG

1561  ATTCATTTTTATAGCAACAACAATTGGTAAAACTCACTGTGATCAATATTTTATATCAT
      ----------+---------+---------+---------+---------+---------+  1620
      TAAGTAAAAATATCGTTGTTGTTAACCATTTTGAGTGACACTAGTTATAAAATATAGTA

1621  GCAAAATATGTTTAAAATAAATGAAAATTGTATTTATAAAAAAAAAAAAAA
      ----------+---------+---------+---------+---------+  1674
      CGTTTTATACAAATTTTATTTTACTTTTAACATAAATATTTTTTTTTTTTT
```

FIG. 1E

```
  1  CGAGGCCACGGCTTATGCAAGCAAAGATCTGGAGGAGCCAGTTACGGTCTGTGTCCAGTGT
     ------+---------+---------+---------+---------+---------+
                                                              R

61  AGATGAACTCATGACTGTACTCTACCCAGAATATTGGAAAATGTACAAGTGTCAGCTAAG
     ------+---------+---------+---------+---------+---------+
           M  T  V  L  Y  P  E  Y  W  K  M  Y  K  C  Q  L  R

121  GAAAGGAGGCTGGCAACATAACAGAGAACAGGCCAACTCAAGGACAGAGAGAC
     ------+---------+---------+---------+---------+---------+
      K  G  G  W  Q  H  N  R  E  Q  A  N  L  N  S  R  T  E  E  T

181  TATAAAATTTGCTGCAGCACATTATAATACAGAGATCTTGAAAACTATTGATAATGAGTG
     ------+---------+---------+---------+---------+---------+
       I  K  F  A  A  A  H  Y  N  T  E  I  L  K  S  I  D  N  E  W

241  GAGAAAGACTCAATGCATGCCAGGGAGGTGTGTATAGATGTGGGGAAGGAGTTTGGAGT
     ------+---------+---------+---------+---------+---------+
        R  K  T  Q  C  M  P  R  E  V  C  I  D  V  G  K  E  F  G  V

301  CGGCGACAAACACCTTCTTTAAACCTCCATGTGTCCGTCTACAGATGTGGGGGTTGCTG
     ------+---------+---------+---------+---------+---------+
        A  T  N  T  F  F  K  P  P  C  V  S  V  Y  R  C  G  G  C
```

FIG. 2A

```
361  CAATAGTGAGGGCCTCCAGTGCATGAACACCAGCACGAGCTACCTCAGCGAAGACGTTATT
     ------------+------------+------------+------------+------------+------------+
      N  S  E  G  L  Q  C  M  N  T  S  T  S  Y  L  S  K  T  L  F

421  TGAAATTACACTGCCCTCTCTCAAGGCCCCAAACCAGTAACAATCAGTTTTGCCAATCA
     ------------+------------+------------+------------+------------+------------+
      E  I  T  V  P  L  S  Q  G  P  K  P  V  T  I  S  F  A  N  H

481  CACTTCCTGCCGATGCATGTCTAAACTGGATGTTTACAGACAAGTTCATTCCATTATTAG
     ------------+------------+------------+------------+------------+------------+
      T  S  C  R  C  M  S  K  L  D  V  Y  R  Q  V  H  S  I  I  R

541  ACGTTCCCTGCCAGCAACACTACCACAGTGTCAGGCAGGCGAACAAGACCTGCCCACCAA
     ------------+------------+------------+------------+------------+------------+
      R  S  L  P  A  T  L  P  Q  C  Q  A  A  N  K  T  C  P  T  N

601  TTACATGTGGAATAATCACATCTGCAGATGCCTGGCTCAGGAAGATTTTATGTTTTCCTC
     ------------+------------+------------+------------+------------+------------+
      Y  M  W  N  N  H  I  C  R  C  L  A  Q  E  D  F  M  F  S  S

661  GGATGCTGGAGATGACTCAACAGATGGATTCCATGACATCTGTGGACCAAACAAGGAGCT
     ------------+------------+------------+------------+------------+------------+
      D  A  G  D  D  S  T  D  G  F  H  D  I  C  G  P  N  K  E  L
```

FIG. 2B

```
 721  GGATGAAGAGACCTGTCAGTGTCTCTGCAGAGCGGGCCTTCGGCCTGCCAGTGTGGACC
       ----+----|----+----|----+----|----+----|----+----|----+----|
        D  E  E  T  C  Q  C  V  C  R  A  G  L  R  P  A  S  C  G  P

781  CCACAAAGAACTAGACAGAAACTCATGCCAGTGTGTCTGTAAAACAAACTCTTCCCAG
       ----+----|----+----|----+----|----+----|----+----|----+----|
        H  K  E  L  D  R  N  S  C  Q  C  V  C  K  N  K  L  F  P  S

841  CCAATCTGGGCCCAACCGAGAATTTGATGAAACACATGCCAGTGTGTATGTAAAAGAAC
       ----+----|----+----|----+----|----+----|----+----|----+----|
        Q  C  G  A  N  R  E  F  D  E  N  T  C  Q  C  V  C  K  R  T

901  CTGCCCCAGAAATCAACCCCTAAATCCTGGAAAATGTGCCTGTGAATGTACAGAAAGTCC
       ----+----|----+----|----+----|----+----|----+----|----+----|
        C  P  R  N  Q  P  L  N  P  K  C  A  C  E  C  T  E  S  P

961  ACAGAAATGCTTGTTAAAAGGAAAGAAGTTCCACCACCAAACATGCAGCTGTTACAGACG
       ----+----|----+----|----+----|----+----|----+----|----+----|
        Q  K  C  L  L  K  G  K  K  F  H  H  Q  T  C  S  C  Y  R  R

1021  GCCATGTACGAACCGCCAGAAGGCTTGTGAGCCAGGATTTTCATATAGTGAAGAAGTGTG
       ----+----|----+----|----+----|----+----|----+----|----+----|
        P  C  T  N  R  Q  K  A  C  E  P  G  F  S  Y  S  E  E  V  C
```

FIG. 2C

```
1081  TCGTTGTGTCCCTTCATATTGGCAAAGACCACAAATGAGCTAAGATTGTACTGTTTTCCA
       R  C  V  P  S  Y  W  Q  R  P  Q  M  S

1141  GTTCATCGATTTTCTATTATGGAAAACTGTGTTGCCACAGTAGAACTGTCTGTGAACAGA

1201  GAGACCCTTGTGGTCCATGCTAACAAAGACAAAAGTCTGTCTTTCCTGAACCATGTGGA

1261  TAACTTTACAGAAATGGACTGGAGCTCATCTGCAAAAGGCCCTCTTGTAAAGACTGGTTTT

1321  CTGCCAATGACCAAACAGCCAAGATTTTCCCTCTTGTGATTTCTTTAAAAGAATGACTATA

1381  TAATTTTATTTCCACTAAAAATATGTTTTCTGCATTCATTTTTATAGCAACAACAATTGGT

1441  AAAACTCACTGTGATCAATATTTTTATATCATGCAAAATATGTTTAAAATAAAATGAAAA

1501  TTGTATTATAAAAAAAAAAAAA

FIG. 2D
```

```
                                                                                    50
Pdgfa   MRTLACLLL  LGCGYLAHVL  AEEAEIPREV  IERLARSQIH  SIRDLQRLLE
Pdgfb   MNRCWA.LFL  SLCCYLRLVS  AEGDPIPEEL  YEMLSDHSIR  SFDDLQRLLH
Vegf    ......MNFLL  SWVHWSLALL  LY........  ..........  .LHHAKWSQA
Vegf2   .......MTV  LYPEYWKMYK  CQ........  ..........  .LRKGGWQHN 100
Pdgfa   IDSVGSEDSL  DTSLRAHGVH  ATKHVPEKRP  LPTRRKRSI.  .....EEAVP
Pdgfb   GDP.GEEDGA  ELDLNMTRSH  SGGELES...  .LARGRRSLG  SLTIAEPAMI
Vegf    APMAE.....  .....GGCQ  NHHEVVKFMD  .VYQR....  ..........
Vegf2   REQANLNSRT  EETIKFAAAH  YNTEILKSID  NEWRK....  ..........

150
Pdgfa   ANFKIRTVIY  EIPRSQVDPT  SANFLIWPPC  VEVKRCTGCC  NTSSVKCQPS
Pdgfb   AEQKTRTEVF  EISRRLIDRT  NANFLVWPPC  VEVQRCSGCC  NRRNVQCRPT
Vegf    SYCHPIETLV  DIFQEYPDEI  .EYIFKPSC  VPLMRCGGCC  NDEGLECVPT
Vegf2   TQGMPREVCI  DVGKEFGVAT  ..NTFFKPPC  VSVYRCGGCC  NSEGLQCMNT 200
Pdgfa   RVHHRSVKVA  KVEYVRKKPK  LKEVQVRLEE  HLECAC...  ...AT.....
Pdgfb   QVQLRPVQVR  KIEIVRKKPI  FKKATVTLED  HLACKC...  ...ETVAAARPVT
Vegf    EESNITMQIM  RIK.PH..QG  QHIGEMSFLQ  HNKCECRPKK  DRARQEKKSV
Vegf2   STSYLSKTLF  EIT.VPLSQG  PKPVTISFAN  HTSCRCMSKL  DVYRQVHSII

FIG. 3A
```

```
            201                                      250
Pdgfa  .....TSLNPD YREEDTDVR. .......... .......... ..........
Pdgfb  RSPGGSOEQR AKTPQIRVTI RTVRVRRPPK GKHRKFKHTH DKTALKETLG
Vegf   RGK.......  .GKGQKRKRK KSRYKSWSVY VGARCCLMPW SLPGPHP...
Vegf2  RRSLPATLPQ CQAANKTCPT NYMWNNHICR CLAQEDFMFS SDAGDDSTDG 300
Pdgfa  .......... .......... .......... .......... ..........
Pdgfb  A......... .......... .......... .......... ..........
Vegf   ...CGP.... .......... ...CSE RRKHLFVQDP QTCKCSCKNT
Vegf2  FHDICGPNKE LDEETCQCVC RAGLRPASCG PHKEL...DR NSCQCVCKNK 350
Pdgfa  .......... .......... .......... .......... ..........
Pdgfb  .......... .......... .......... .......... ..........
Vegf   ..DSRCKARQ LELNERTCRC DKPRR..... .......... ..........
Vegf2  LFPSQCGANR EFDEMTCQC VCKRTCPRNQ PLNPGKCACE CTESPQKCLL 398
Pdgfa  .......... ....
Pdgfb  .......... ....
Vegf   .......... ....
Vegf2  KGKKFHHQTC SCYRRPCTNR QKACEPGFSY SEEVCRCVPS YWQRPQMS

FIG. 3B
```

PERCENTAGE (%) OF AMINO ACID IDENTITIES BETWEEN
EACH PAIR OF GENES IS SHOWN IN THE
FOLLOWING TABLE

|        | PDGFα | PDGFβ | VEGF | VEGF-2 |
|--------|-------|-------|------|--------|
| PDGFα  |       |       |      |        |
| PDGFβ  | 48.0  |       |      |        |
| VEGF   | 20.7  | 22.7  |      |        |
| VEGF-2 | 28.5  | 22.4  | 30.0 |        |

FIG. 4

Lane 1: 14-C and rainbow M.W. marker
Lane 2: FGF control
Lane 3: VEGF2 (M13-reverse & forward primer)
Lane 4: VEGF2 (M13-reverse & VEGF-F4 primer)
Lane 5: VEGF2 (M13-reverse & VEGF-F5 primer)

Lane M: Marker
Lane 1: Vector medium
Lane 2: VEGF2 medium

Lane M: Marker
Lane 1: vector cytoplasm
Lane 2: vector medium
Lane 3: VEGF2 cytoplasm
Lane 4: VEGF2 medium Lane 1: Molelular weight marker
Lane 2: Precipitates containing VEGF2.

1. Molecular weight marker
2. Umbelical vein endothelial cells
3. Aortic smooth muscle cells
4. Dermal fibroblast 1. Molecular weight marker
2. Blank
3. Control protein-HA
4. Vector control
5. VEGF2-HA 1. Molecular weight marker
2. Blank
3. Control protein-HA
4. VEGF2-HA
5. Vector control

```
                                              -35             OPERATOR 1
1  AAGCTTAAAAAACTGCAAAAAATAGT TTGACT TGTGAGCGGATAAGAAT

-10                    OPERATOR 2
50  TAAGAT GTACCCA ATTGTGAGCGGATAACAAT TCACACATTAA

S/D
94  A GAGGAG AAATTA CATATG
```

FIG. 29

VASCULAR ENDOTHELIAL GROWTH FACTOR 2

CROSS REFERENCE TO RELATED APPLICATIONS

This application is a continuation of U.S. application Ser. No. 13/096,144, filed Apr. 28, 2011, which is a continuation of U.S. application Ser. No. 11/980,495, filed Oct. 31, 2007, which is a continuation of U.S. application Ser. No. 11/730, 696, filed Apr. 3, 2007, now U.S. Pat. No. 7,850,963, which is a continuation of U.S. application Ser. No. 10/120,414, filed Apr. 12, 2002, now U.S. Pat. No. 7,208,582, which claims the benefit of priority under 35 U.S.C. §119(e) of U.S. Provisional Application No. 60/283,385, filed Apr. 13, 2001, and of U.S. Provisional Application No. 60/350,366, filed Jan. 24, 2002, all of which are herein incorporated by reference in their entireties.

REFERENCE TO A SEQUENCE LISTING SUBMITTED ELECTRONICALLY VIA EFS-WEB

The content of the electronically submitted sequence listing in ASCII text file (Name: sequence_listing_ascii.txt; Size: 76,766 bytes; and Date of Creation: Apr. 26, 2012) filed with the application is incorporated herein by reference in its entirety.

BACKGROUND OF THE INVENTION

The present invention relates to newly identified polynucleotides, polypeptides encoded by such polynucleotides, antibodies specific for such polypeptides, the use of such antibodies, as well as the production of such antibodies. The polypeptides of the present invention have been identified as members of the vascular endothelial growth factor family. More particularly, the polypeptides of the present invention are human vascular endothelial growth factor 2 (VEGF-2). Antibodies of the invention are specific for such VEGF-2 polypeptides. The invention also relates to inhibiting the action of such polypeptides.

The formation of new blood vessels, or angiogenesis, is essential for embryonic development, subsequent growth, and tissue repair. Angiogenesis is also an essential part of certain pathological conditions, such as neoplasia (i.e., tumors and gliomas). Abnormal angiogenesis is associated with other diseases such as inflammation, rheumatoid arthritis, psoriasis, and diabetic retinopathy (Folkman, J. and Klagsbrun, M., *Science* 235:442-447 (1987)).

Both acidic and basic fibroblast growth factor molecules are mitogens for endothelial cells and other cell types. Angiotropin and angiogenin can induce angiogenesis, although their functions are unclear (Folkman, J., *Cancer Medicine*, Lea and Febiger Press, pp. 153-170 (1993)). A highly selective mitogen for vascular endothelial cells is vascular endothelial growth factor or VEGF (Ferrara, N. et al., *Endocr. Rev.* 13:19-32 (1992)), which is also known as vascular permeability factor (VPF).

Vascular endothelial growth factor is a secreted angiogenic mitogen whose target cell specificity appears to be restricted to vascular endothelial cells. The murine VEGF gene has been characterized and its expression pattern in embryogenesis has been analyzed. A persistent expression of VEGF was observed in epithelial cells adjacent to fenestrated endothelium, e.g., in choroid plexus and kidney glomeruli. The data was consistent with a role of VEGF as a multifunctional regulator of endothelial cell growth and differentiation (Breier, G. et al., *Development* 1.14:521-532 (1992)).

VEGF shares sequence homology with human platelet-derived growth factors, PDGFa and PDGFb (Leung, D. W., et al., *Science* 246:1306-1309, (1989)). The extent of homology is about 21% and 23%, respectively. Eight cysteine residues contributing to disulfide-bond formation are strictly conserved in these proteins. Although they are similar, there are specific differences between VEGF and PDGF. While PDGF is a major growth factor for connective tissue, VEGF is highly specific for endothelial cells. Alternatively spliced mRNAs have been identified for both VEGF, PLGF, and PDGF and these different splicing products differ in biological activity and in receptor-binding specificity. VEGF and PDGF function as homo-dimers or hetero-dimers and bind to receptors which elicit intrinsic tyrosine kinase activity following receptor dimerization.

VEGF has four different forms of 121, 165, 189 and 206 amino acids due to alternative splicing. VEGF121 and VEGF165 are soluble and are capable of promoting angiogenesis, whereas VEGF189 and VEGF-206 are bound to heparin containing proteoglycans in the cell surface. The temporal and spatial expression of VEGF has been correlated with physiological proliferation of the blood vessels (Gajdusek, C. M., and Carbon, S. J., *Cell Physiol.* 139:570-579 (1989); McNeil, P. L., et al., *J. Cell. Biol.* 109:811-822 (1989)). Its high affinity binding sites are localized only on endothelial cells in tissue sections (Jakeman, L. B., et al., *Clin. Invest.* 89:244-253 (1989)). The factor can be isolated from pituitary cells and several tumor cell lines, and has been implicated in some human gliomas (Plate, K. H., *Nature* 359:845-848 (1992)). Interestingly, expression of VEGF121 or VEGF165 confers on Chinese hamster ovary cells the ability to form tumors in nude mice (Ferrara, N. et al., *J. Clin. Invest.* 91:160-170 (1993)). The inhibition of VEGF function by anti-VEGF monoclonal antibodies was shown to inhibit tumor growth in immune-deficient mice (Kim, K. J., *Nature* 362:841-844 (1993)). Further, a dominant-negative mutant of the VEGF receptor has been shown to inhibit growth of glioblastomas in mice.

Vascular permeability factor (VPF) has also been found to be responsible for persistent microvascular hyperpermeability to plasma proteins even after the cessation of injury, which is a characteristic feature of normal wound healing. This suggests that VPF is an important factor in wound healing. Brown, L. F. et al., *J. Exp. Med.* 176:1375-1379 (1992).

The expression of VEGF is high in vascularized tissues, (e.g., lung, heart, placenta and solid tumors) and correlates with angiogenesis both temporally and spatially. VEGF has also been shown to induce angiogenesis in vivo. Since angiogenesis is essential for the repair of normal tissues, especially vascular tissues, VEGF has been proposed for use in promoting vascular tissue repair (e.g., in atherosclerosis), U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a heterodimer or homodimer. The protein is a mammalian vascular endothelial cell mitogen and, as such, is useful for the promotion of vascular development and repair, as disclosed in European Patent Application No. 92302750.2, published Sep. 30, 1992.

SUMMARY OF THE INVENTION

The polypeptides of the present invention have been putatively identified as a novel vascular endothelial growth factor based on amino acid sequence homology to human VEGF.

In accordance with one aspect of the present invention, there are provided novel mature polypeptides, as well as biologically active and diagnostically or therapeutically useful fragments, analogs, and derivatives thereof. The polypeptides of the present invention are of human origin.

In accordance with another aspect of the present invention, there are provided isolated nucleic acid molecules comprising polynucleotides encoding full length or truncated VEGF-2 polypeptides having the amino acid sequences shown in SEQ ID NOS:2 or 4, respectively, or the amino acid sequences encoded by the cDNA clones deposited in bacterial hosts as ATCC Deposit Number 97149 on May 12, 1995 or ATCC Deposit Number 75698 on Mar. 4, 1994.

The present invention also relates to biologically active and diagnostically or therapeutically useful fragments, analogs, and derivatives of VEGF-2.

In accordance with still another aspect of the present invention, there are provided processes for producing such polypeptides by recombinant techniques comprising culturing recombinant prokaryotic and/or eukaryotic host cells, containing a nucleic acid sequence encoding a polypeptide of the present invention, under conditions promoting expression of said proteins and subsequent recovery of said proteins.

In accordance with yet a further aspect of the present invention, there are provided processes for utilizing such polypeptides, or polynucleotides encoding such polypeptides for therapeutic purposes, for example, to stimulate angiogenesis, wound-healing, growth of damaged bone and tissue, and to promote vascular tissue repair. In particular, there are provided processes for utilizing such polypeptides, or polynucleotides encoding such polypeptides, for treatment of peripheral artery disease, such as critical limb ischemia and coronary disease.

In accordance with yet another aspect of the present invention, there are provided antibodies against such polypeptides, processes for producing such polypeptides, and there are provided processes for utilizing such antibodies.

Using phage display technology, the present inventors have identified single chain antibody molecules ("scFvs") that immunospecifically bind to VEGF-2, (e.g., scFvs that immunospecifically bind to full-length VEGF-2, scFvs that immunospecifically bind the mature form of VEGF-2 polypeptide, scFvs that immunospecifically bind the pro-protein form of VEGF-2, scFvs that immunospecifically bind the secreted form of VEGF-2 and/or scFvs that immunospecifically bind to both the full-length form and the secreted form of VEGF-2. Molecules comprising, or alternatively consisting of, fragments or variants of these scFvs (e.g., including VH domains, VH CDRs, VL domains, or VL CDRs having an amino acid sequence of any one of those referred to in Table 2), that immunospecifically bind to full-length VEGF-2, the mature form of VEGF-2 polypeptide, the pro-protein form of VEGF-2, the secreted form of VEGF-2 and/or both the full-length form and the secreted form of VEGF-2 are also encompassed by the invention, as are nucleic acid molecules that encode these scFvs, and/or molecules.

In particular, the invention relates to scFvs comprising, or alternatively consisting of, an amino acid sequence selected from the group consisting of SEQ ID NOs: 72-83 referred to in Table 2 below. Molecules comprising, or alternatively consisting of, fragments or variants of these scFvs (e.g., including VH domains, VH CDRs, VL domains, or VL CDRs having an amino acid sequence of any one of those referred to in Table 2), that immunospecifically bind to full-length VEGF-2, the pro-protein form of VEGF-2, the secreted form of VEGF-2 and/or both the full-length form and the secreted form of VEGF-2 are also encompassed by the invention, as are nucleic acid molecules that encode these scFvs, and/or molecules.

The present invention encompasses antibodies (including molecules comprising, or alternatively consisting of, antibody fragments or variants thereof) that immunospecifically bind to a VEGF-2 polypeptide or polypeptide fragment or variant of a VEGF-2. In particular, the invention encompasses antibodies (including molecules comprising, or alternatively consisting of, antibody fragments or variants thereof) that immunospecifically bind to a polypeptide or polypeptide fragment or variant of human VEGF-2 such as those of SEQ ID NO:2, SEQ ID NO:4, SEQ ID NO:18, the full length VEGF-2 polypeptide, the pro-protein form of VEGF-2 polypeptide, the mature VEGF-2 polypeptide, or the secreted form of the VEGF-2 polypeptide.

In preferred embodiments, the invention encompasses antibodies (including molecules comprising, or alternatively consisting of, antibody fragments or variants thereof) that immunospecifically bind to full length VEGF-2. In other preferred embodiments, the invention encompasses antibodies (including molecules comprising, or alternatively consisting of, antibody fragments or variants thereof) that immunospecifically bind to the secreted form of VEGF-2.

The present invention relates to methods and compositions for preventing, treating or ameliorating a disease or disorder comprising administering to an animal, preferably a human, an effective amount of one or more antibodies or fragments or variants thereof, or related molecules, that immunospecifically bind to a VEGF-2 polypeptide or a fragment or variant thereof. In specific embodiments, the present invention relates to methods and compositions for preventing, treating or ameliorating a disease or disorder associated with VEGF-2 function or VEGF-2 receptor (e.g., flt-4, or flk-1) function or aberrant VEGF-2 or VEGF-2 receptor (e.g., flt-4, or flk-1) expression, comprising administering to an animal, preferably a human, an effective amount of one or more antibodies or fragments or variants thereof, or related molecules, that immunospecifically bind to a VEGF-2 or a fragment or variant thereof. In highly preferred embodiments, the present invention relates to antibody-based methods and compositions for preventing, treating or ameliorating tumors and tumor metastasis, particularly those associated with breast, brain, colon or prostate cancers or lymphangiomas. Other diseases and disorders which can be treated, prevented and/or ameliorated with the antibodies of the invention include, but are not limited to, inflammatory disorders, rheumatoid arthritis, psoriasis, diabetic retinopathy, and proliferative disorders.

The present invention also encompasses methods and compositions for detecting, diagnosing, or prognosing diseases or disorders comprising administering to an animal, preferably a human, an effective amount of one or more antibodies or fragments or variants thereof, or related molecules, that immunospecifically bind to VEGF-2 or a fragment or variant thereof. In specific embodiments, the present invention also encompasses methods and compositions for detecting, diagnosing, or prognosing diseases or disorders associated with VEGF-2 function or VEGF-2 receptor function or aberrant VEGF-2 or VEGF-2 receptor expression, comprising administering to an animal, preferably a human, an effective amount of one or more antibodies or fragments or variants thereof, or related molecules, that immunospecifically bind to VEGF-2 or a fragment or variant thereof.

In highly preferred embodiments, the present invention relates to antibody-based methods and compositions for detecting, diagnosing, or prognosing tumors and tumor metastasis, particularly those associated with breast, brain, colon or prostate cancers or lymphangiomas. Other diseases and disorders which can be detected, diagnosed, or prognosed with the antibodies of the invention include, but are not limited to, inflammatory disorders, rheumatoid arthritis, psoriasis, diabetic retinopathy, and proliferative disorders.

Another embodiment of the present invention includes the use of the antibodies of the invention as a diagnostic tool to monitor the expression of VEGF-2 expression in biologic samples.

The present invention also provides antibodies that bind one or more VEGF-2 polypeptides which are coupled to a detectable label, such as an enzyme, a fluorescent label, a luminescent label, or a bioluminescent label. The present invention also provides antibodies that bind one or more VEGF-2 polypeptides which are coupled to a therapeutic or cytotoxic agent. The present invention also provides antibodies that bind one or more VEGF-2 polypeptides which are coupled to a radioactive material.

The present invention also provides antibodies that bind VEGF-2 polypeptides and act as either VEGF-2 agonists or VEGF-2 antagonists.

The present invention farther provides antibodies that inhibit or abolish VEGF-2 binding to its receptor (e.g., flk-1 and/or flt-4) (see, for example, Example 33). In other embodiments, the antibodies of the invention inhibit VEGF-2 induced phosphorylation of Elk-1 (e.g., see Example 35): In still other embodiments, the antibodies of the invention inhibit VEGF-2 induced proliferation of vascular and or endothelial cell proliferation (e.g., see Example 34). In still other preferred embodiments, antibodies of the present invention inhibit angiogenesis (e.g., see Examples 16 or 23).

In highly preferred embodiments of the present invention, VEGF-2 antibodies are used to treat, prevent or ameliorate tumors and tumor metastasis. In other highly preferred embodiments, VEGF-2 antibodies of the present invention are administered to an individual alone or in combination with other therapeutic compounds, especially anti-cancer agents, to treat, prevent or ameliorate tumors and tumor metastasis. In still other highly preferred embodiments, VEGF-2 antibodies of the present invention are administered to an individual, alone or in conjunction with other anti-cancer treatments (e.g., radiation therapy or surgery), to treat, prevent or ameliorate tumors and tumor metastasis.

The present invention also provides for a nucleic acid molecule(s), generally isolated, encoding an antibody (including molecules, such as scFvs, VH domains; or VL domains, that comprise, or alternatively consist of, an antibody fragment or variant thereof) of the invention. The present invention also provides a host cell transformed with a nucleic acid molecule encoding an antibody (including molecules, such as scFvs, VH domains, or VL domains, that comprise, or alternatively consist of, an antibody fragment or variant thereof) of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail, below.

In accordance with yet another aspect of the present invention, there are provided antagonists to such polypeptides, which may be used to inhibit the action of such polypeptides, for example, to prevent tumor angiogenesis and thus inhibit the growth of tumors, to treat diabetic retinopathy, inflammation, rheumatoid arthritis and psoriasis.

In accordance with another aspect of the present invention, there are provided nucleic acid probes comprising nucleic acid molecules of sufficient length to specifically hybridize to nucleic acid sequences of the present invention.

In accordance with another aspect of the present invention, there are provided methods of diagnosing diseases or a susceptibility to diseases related to mutations in nucleic acid sequences of the present invention and proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A-1E show the full length nucleotide (SEQ ID NO:1) and the deduced amino acid (SEQ ID NO:2) sequence of VEGF-2. The polypeptide comprises approximately 419 amino acid residues of which approximately 23 represent the leader sequence. The standard one letter abbreviations for amino acids are used. Sequencing was performed using the Model 373 Automated DNA Sequencer (Applied Biosystems, Inc.). Sequencing accuracy is predicted to be greater than 97%.

FIGS. 2A-2D show the nucleotide (SEQ ID NO:3) and the deduced amino acid (SEQ ID NO:4) sequence of a truncated, biologically active form of VEGF-2. The polypeptide-comprises approximately 350 amino acid residues of which approximately the first 24 amino acids represent the leader sequence.

FIGS. 3A-3B are an illustration of the amino acid sequence homology between PDGFa (SEQ ID NO:5), PDGFb (SEQ ID NO:6), VEGF (SEQ ID NO:7), and VEGF-2 (SEQ ID NO:4). The boxed areas indicate the conserved sequences and the location of the eight conserved cysteine residues.

FIG. 4 shows, in table-form, the percent homology between PDGFa; PDGFb, VEGF, and VEGF-2.

FIGS. 26A-26G depict ability of VEGF-2 to affect the diastolic blood pressure in spontaneously hypertensive rats (SHR). FIGS. 26A-26B depict the dose-dependent decrease in diastolic blood pressure achieved with VEGF-2. FIGS. 26C-26D depict the decreased mean arterial pressure (MAP) observed with VEGF-2. FIG. 26E shows the effect of increasing doses of VEGF-2 on the mean arterial pressure (MAP) of SHR rats. FIG. 26F shows the effect of VEGF-2 on the diastolic pressure of SHR rats. FIG. 26G shows the effect of VEGF-2 on the diastolic blood pressure of SHR rats.

FIG. 29 shows the nucleotide sequence of the regulatory elements of the pHE4a promoter (SEQ ID NO:17). The two lac operator sequences, the Shine-Delgarno sequence (S/D), and the terminal HindIII and NdeI restriction sites (italicized) are indicated.

FIG. 30A shows the effect of αVEGF-2 antibodies on MDA-MB-231 human breast carcinoma growth in nude mice. FIG. 30B shows the effect of VEGF-2 antibodies on PC-3 tumor volume after 42 days of exposure to VEGF-2 antibody. FIG. 30C shows the effect of VEGF-2 antibodies on lymph node metastatic frequency. FIG. 30D shows the effect of VEGF-2 antibodies on PC-3 tumor weights after 43 days of exposure to VEGF-2 antibody. FIG. 30E shows the effect of VEGF-2 antibodies on PC-3 tumor growth rate over a period just over 40 days. FIG. 30F shows the effect of VEGF-2 antibodies on PC-3 tumor volume after 42 days of exposure to VEGF-2 antibody.

DETAILED DESCRIPTION OF THE PREFERRED EMBODIMENTS

Figure 1A:
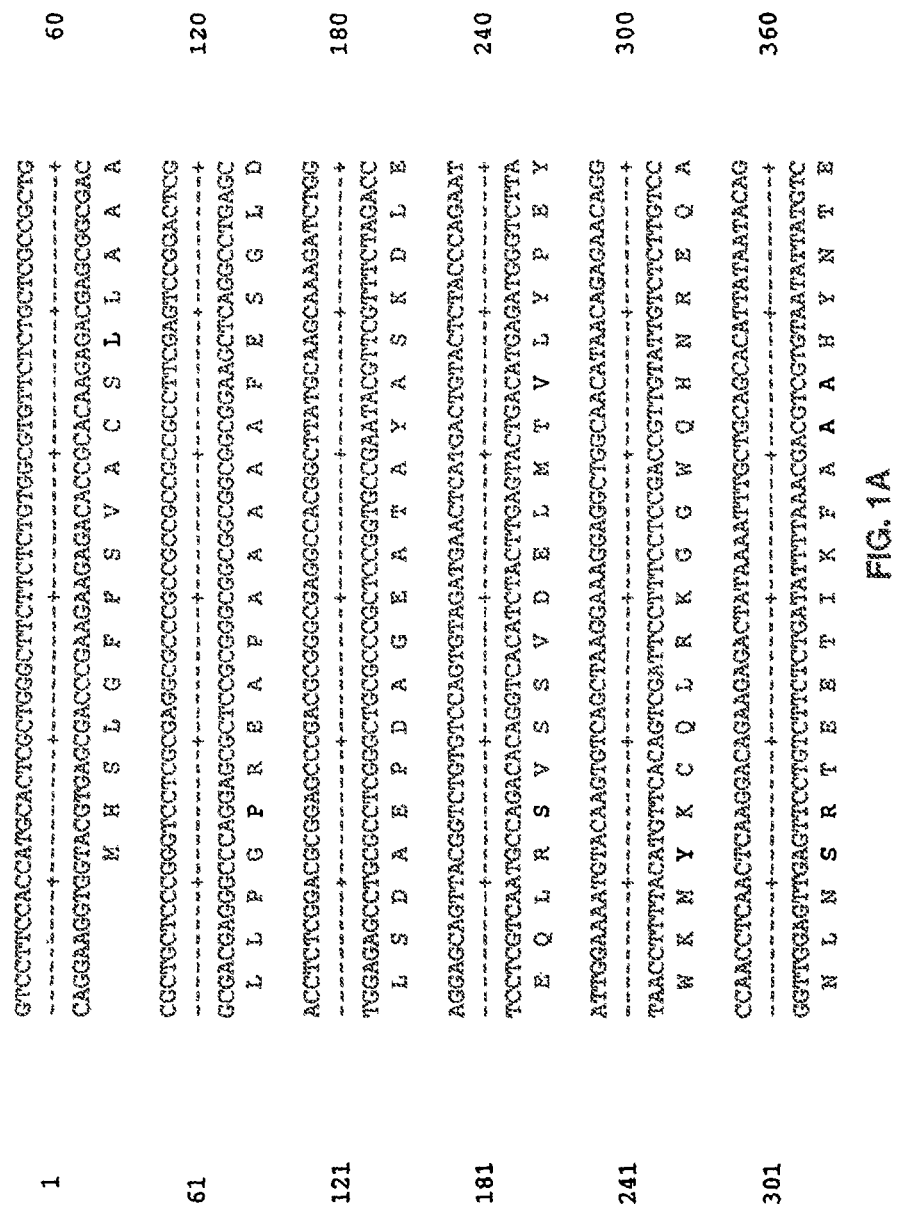
Figure 5:
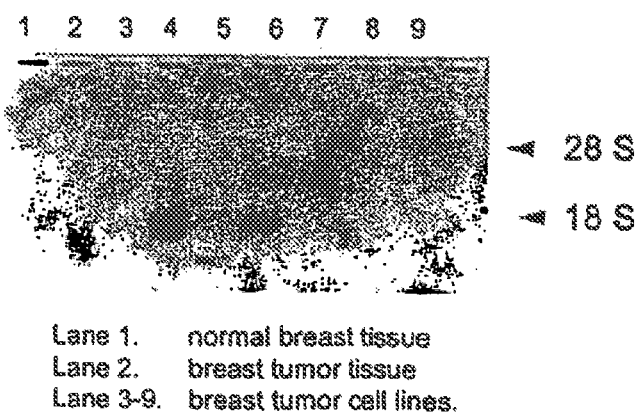
FIG. 5 shows the presence of VEGF-2 mRNA in human breast tumor cell lines.

In accordance with one aspect of the present invention, there are provided isolated nucleic acid molecules comprising a polynucleotide encoding a VEGF-2 polypeptide having the deduced amino acid sequence of FIG. 1 (SEQ ID NO:2), which was determined by sequencing a cloned cDNA. The nucleotide sequence shown in SEQ ID NO:1 was obtained by sequencing a cDNA clone, which was deposited on May 12, 1995 at the American Type Tissue Collection (ATCC), 10801 University Boulevard, Manassas, Va. 20110-2209, and given ATCC Deposit No. 97149.

In accordance with another aspect of the present invention, there are provided isolated nucleic acid molecules comprising a polynucleotide encoding a truncated VEGF-2 polypeptide having the deduced amino acid sequence of FIG. 2 (SEQ ID NO:4), which was determined by sequencing a cloned cDNA. The nucleotide sequence shown in SEQ ID NO:3 was obtained by sequencing a cDNA clone, which was deposited on Mar. 4, 1994 at the American Type Tissue Collection (ATCC), 10801 University Boulevard, Manassas, Va. 20110-2209, and given ATCC Deposit Number 75698.

Unless otherwise indicated, all nucleotide sequences determined by sequencing a DNA, molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors: Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. It contains an open reading frame encoding a protein of about 419 amino acid residues of which approximately the first 23 amino acid residues are the putative leader sequence such that the mature protein comprises 396 amino acids, and which protein exhibits the highest amino acid sequence homology to human vascular, endothelial growth factor (30% identity), followed by PDGFa (24%) and PDGFb (22%) (See FIG. 4). It is particularly important that all eight cysteines are conserved within all four members of the family (see boxed areas of FIG. 3). In addition, the signature for the PDGF/VEGF family, PXCVXXXRCXGCCN, (SEQ ID NO:8) is conserved in VEGF-2 (see FIG. 3). The homology between VEGF-2, VEGF and the two PDGFs is at the protein sequence level. No nucleotide sequence homology can be detected, and therefore, it would be difficult to isolate the VEGF-2 through simple approaches such as low stringency hybridization.

The VEGF-2 polypeptide of the present invention is meant to include the full length polypeptide and polynucleotide sequence which encodes for any leader sequences and for active fragments of the fall length polypeptide. Active fragments are meant to include any portions of the full length amino acid sequence which have less than the full 419 amino acids of the full length amino acid sequence as shown in SEQ ID NO:2, but still contain the eight cysteine residues shown conserved in FIG. 3 and that still have VEGF-2 activity.

There are at least two alternatively spliced VEGF-2 mRNA sequences present in normal, tissues. The two bands in FIG. 7, lane 5 indicate the presence of the alternatively spliced mRNA encoding the VEGF-2 polypeptide of the present invention.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or FIG. 2, or that of the deposited clones, or may be a different coding sequence which, as a result of the redundancy or degeneracy of the genetic code, encodes the same, mature polypeptide as the DNA of FIG. 1, FIG. 2, or the deposited cDNAs.

The polynucleotide which encodes for the mature polypeptide of FIG. 1 or FIG. 2 or for the mature polypeptides encoded by the deposited cDNAs may include: only the coding sequence for the mature polypeptide; the coding sequence for the mature polypeptide and additional coding sequences such as a leader or secretory sequence or a proprotein sequence; the coding sequence for the mature polypeptide (and optionally additional coding sequences) and non-coding sequences, such as introns or non-coding sequence 5' and/or 3' of the coding sequence for the mature polypeptide.

Thus, the term "polynucleotide encoding a polypeptide" encompasses a polynucleotide which includes only coding sequences for the polypeptide as well as a polynucleotide which includes additional coding and/or non-coding sequences.

The present invention further relates to variants of the hereinabove described polynucleotides which encode for fragments, analogs, and derivatives of the polypeptide having the deduced amino acid sequence of FIG. 1 or 2, or the polypeptide encoded by the cDNA of the deposited clones. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or 2 or the same mature polypeptide encoded by the cDNA of the deposited clones as well as variants of such polynucleotides which variants encode for a fragment, derivative, or analog of the polypeptides of FIG. 1 or 2, or the polypeptide encoded by the cDNA of the deposited clones. Such nucleotide variants include deletion variants, substitution variants, and addition or insertion variants.

As hereinabove indicated, the polynucleotide may have a coding sequence which is a naturally occurring allelic variant of the coding sequence shown in FIG. 1 or 2, or of the coding sequence of the deposited clones. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell* 37:767 (1984)).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino kid sequence in SEQ ID NO:2, but lacking the N-terminal methionine; (c) a nucleotide sequence encoding the polypeptide having the amino acid sequence at positions from about 1 to about 396 in SEQ ID NO:2; (d) a nucleotide sequence encoding the polypeptide having the amino acid sequence encoded by the cDNA clone contained in ATCC Deposit No. 97149; (e) a nucleotide sequence encoding the mature VEGF-2 polypeptide having the amino acid sequence encoded by the cDNA clone contained in ATCC Deposit No. 97149; or (f) a nucleotide sequence complementary to any of the nucleotide sequences in (a), (b), (c), (d), or (e).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:4; (b) a nucleotide sequence encoding the polypeptide having the amino acid sequence in SEQ ID NO:4, but lacking the N-terminal methionine; (c) a nucleotide sequence encoding the polypeptide having the amino acid sequence at positions from about 1 to about 326 in SEQ ID NO:4; (d) a nucleotide sequence encoding the polypeptide having the amino acid sequence encoded by the cDNA clone contained in ATCC, Deposit No. 75698; (e) a nucleotide sequence encoding the mature VEGF-2 polypeptide having the amino acid sequence encoded by the cDNA clone contained in ATCC Deposit No. 75698; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a VEGF-2 polypeptide is intended that the nucleotide sequence of the polynucleotide is identical to the reference sequence except that the polynucleotide sequence may include up to five point mutations per each 100 nucleotides of the reference nucleotide sequence encoding the VEGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted Into the reference sequence. These mutations of the reference sequence may occur at the 5N or 3N terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NOS:1 or 3, or to the nucleotides sequence of the deposited cDNA clone(s) can be determined conventionally: using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As described in detail below, the polypeptides of the present invention can be used to raise polyclonal and monoclonal antibodies, which are useful in diagnostic assays for detecting VEGF-2 protein expression as described below or as agonists and antagonists capable of enhancing or inhibiting VEGF-2 protein function. Further, such polypeptides can be used in the yeast two-hybrid system to "capture" VEGF-2 protein binding proteins which are also candidate agonist and antagonist according to the present invention. The yeast two hybrid system is described in Fields and Song, Nature 340: 245-246 (1989).

In another aspect, the invention provides a peptide or polypeptide comprising an epitope-bearing portion of a polypeptide of the invention. As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptide and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767-778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30, 40, 50, 60, 70, 80, 90, 100, or 150 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred:

Non-limiting examples of antigenic polypeptides or peptides that can be used to generate VEGF-2-specific antibodies include the following: a polypeptide comprising amino acid residues from about leu-37 to about glu-45 in SEQ ID NO:2, from about Tyr-58 to about Gly-66 in SEQ ID NO:2, from about Gln-73 to about Glu-81 in SEQ ID NO:2, from about Asp 100 to about Cys-108 in SEQ ID NO:2, from about Gly-140 to about Leu-148 in SEQ ID NO.2: from about Pro-168 to about Val-176 in SEQ ID NO:2, from about His-183 to about Lys-191 in SEQ ID NO:2, from about Ile-201 to about Thr-209 in SEQ ID NO:2, from about Ala-216 to about Tyr-224 in SEQ ID NO:2, from about Asp-244 to about His-254 in SEQ ID NO:2, from about Gly-258 to about Glu-266 in SEQ ID NO:2, from about Cys-272 to about Ser-280 in SEQ ID NO:2, from about Pro-283 to about Ser-291 in SEQ ID NO:2, from about Cys-296 to about Gln-304 in SEQ ID NO:2, from about Ala-307 to about Cys-316 in SEQ ID NO:2, from about Val-319 to about Cys-335 in SEQ ID NO:2, from about Cys-339 to about Leu-347 in SEQ ID NO:2, from about Cys-360 to about Glu-373 in SEQ ID NO:2, from about Tyr-378 to about Val-386 in SEQ ID NO:2, and from about Ser-388 to about Ser-396 in SEQ ID NO:2. These polypeptide fragments have been determined to bear antigenic epitopes of the VEGF-2 protein by the analysis of the Jameson-Wolf antigenic index.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide that acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci*. USA 82:5131-5135. This "Simultaneous Multiple Peptide Synthesis (SNIPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows. 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe of al., supra; Wilson et al., supra; Chow, M. et al., *Proc. Natl. Acad. Sci. USA* 82:910-914; and Bittle, F. J. et al., *J. Gen. Viral.* 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For, instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 mg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide, antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a Amimotope) which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of The epitope-bearing peptides of the invention also can be made routinely by these methods.

As one of skill in the art will appreciate, VEGF-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)).

In accordance with the present invention, novel variants of VEGF-2 are also described. These can be produced by deleting or substituting one or more amino acids of VEGF-2. Natural mutations are called allelic variations. Allelic variations can be silent (no change in the encoded polypeptide) or may have altered amino acid sequence.

In order to attempt to improve or alter the characteristics of native VEGF-2, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions. Set forth below are examples of mutations that can be constructed.

Amino Terminal and Carboxy Terminal Deletions

Figure 6:
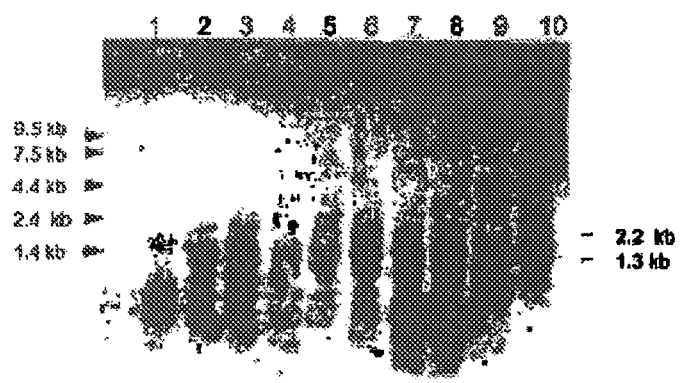
FIG. 6 depicts the results of a Northern blot analysis of VEGF-2 in human adult tissues.

Furthermore, VECF-2 appears to be proteolytically cleaved upon expression resulting in polypeptide fragments of the following sizes when run on a SDS-PAGE gel (sizes area approximate) (See, FIGS. 6-8, for example): 80, 59, 45, 43, 41, 40, 39, 38, 37, 36, 31, 29, 21, and 15 kDa. These polypeptide fragments are the result of proteolytic cleavage at both the N-terminal and C-terminal portions of the protein. These proteolytically generated fragments appears to have activity, particularly the 21 kDa fragment.

In addition, protein engineering may be employed in order to improve or alter one or more characteristics of native VEGF-2. The deletion of carboxyterminal amino acids can enhance the activity of proteins. One example is interferon gamma that shows up to ten times higher activity by deleting ten amino acid residues from the carboxy terminus of the protein (Dobeli et al., *J. of Biotechnology* 7:199-216 (1988)). Thus, one aspect of the invention is to provide polypeptide analogs of VEGF-2 and nucleotide sequences encoding such analogs that exhibit enhanced stability (e.g., when exposed to typical pH, thermal conditions or other storage conditions) relative to the native VEGF-2 polypeptide.

Particularly preferred VEGF-2 polypeptides are shown below (numbering starts with the first amino acid in the protein (Met) (FIG. 1 (SEQ ID NO:18)): Ala (residue 25) to Ser (residue 419); Pro (26) to Ser (419); Ala (27) to Ser (419); Ala (28) to Ser (419); Ala (29) to Ser (419); Ala (30) to Ser (419); Ala (31) to Ser (419); Phe (32) to Ser (419); Glu (33) to Ser (419); Ser (34) to Ser (419); Gly (35) to Ser (419); Leu (36) to Ser (419); Asp (37) to Ser (419); Leu (38) to (Ser (419); Ser (39) to Ser (419); Asp (40) to Ser (419); Ala (41) to Ser (419); Glu (42) to Ser (419); Pro (43) to Ser (419); Asp (44) to Ser (419); Ala (45) to Ser (419); Gly (46) to Ser (419); Glu (47) to Ser (419); Ala (48) to Ser (419); Thr (49) to Ser (419); Ala (50) to Ser (419); Tyr (51) to Ser (419); Ser (53) to Ser (419); Asp (55) Ser (419); Val (63) to Ser (419); Val (66) to Ser (419); Met(1), Glu (24), or Ala (25) to Met (418); Met (1), Glu (24), or Ala (25) to Gln (417); Met (1), Glu (24), or Ala (25) to Pro (416); Met(1), Glu (24), or Ala (25) to Arg (415); Met(1), Glu (24), or Ala (25) to Gln (414); Met(1), Glu (24), or Ala (25) to Trp (413); Met (1), Glu (24), or Ala (25) to Tyr (412); Met(1), Gln (24), or Ala (25) to Ser (411); Met(1), Glu (24), or Ala (25) to Pro (410); Met(1), Glu (24), or Ala (25) to Val (409); Met(1), Glu (24), or Ala (25) to Cys (408); Met(1), Glu (24), or Ala (25) to Arg (407); Met(1), Glu (24), or Ala (25) to Cys (406); Met(1), Glu (24), or Ala (25) to Val (405); Met(1), Glu (24), or Ala (25) to Glu (404); Met(1), Glu (24), or Ala (25) to Glu (403); Met(1), Glu (24), or Ala (25) to Ser (402); Met(1), Glu (24), or Ala (25) to Gly (398); Met(1), Glu (24), or Ala (25) to Pro (397); Met(1), Glu (24), or Ala (25) to Lys (393); Met(1), Glu (24), or Ala (25) to Met(263); Met(1), Glu (24), or Ala (25) to Asp(311); Met(1), Glu (24), or Ala (25) to Pro 366); Met(1) to Ser (419); Met(1) to Ser(228); Glu(47) to Ser(419); Ala(111) to Lys(214); Ala(112) to Lys (214); His(113) to Lys(214); Tyr(114) to Lys(214); Asn(115) to Lys(214); Thr(116) to Lys(214); Thr(103) to Leu(215); Glu(104) to Leu(215); Glu(105) to Leu(215); Thr(06) to Leu (215); Ile(107) to Leu(215); Lys(108) to Leu(215); Phe(109) to Leu(215); Ala(110) to Leu(215); Ala(111) to Leu(215); Ala(112) to Leu(215); His(113) to Leu(215); Tyr(114) to Leu(215); Asn(115) to Leu(215); Thr(116) to Leu(215); Thr (103) to Ser(228); Glu(104) to Ser(228); Glu(105) to Ser (228); Thr(106) to Ser(228); Ile(107) to Ser(228); Lys(108) to Ser(228); Phe(109) to Ser(228); Ala(110) to Ser(228); Ala (111) to Ser(228); Ala(112) to Ser(228); His(113) to Ser (228); Tyr(114) to Ser(228); Asn(115) to Ser(228); Thr(116) to Ser(228); Thr(103) to Leu(229); Glu(104) to Leu(229); Thr(103) to Arg(227); Glu(104) to Arg(227); Glu(105) to Arg (227); Thr(106) to Arg (227); Ile(107) to Arg (227); Lys(108) to Arg (227); Phe(109) to Arg (227); Ala(110) to Arg (227); Ala(111) to Arg (227); Ala(112) to Arg (227); His(113) to Arg (227); Tyr(114) to Arg (227); Asn(115) to Arg (227); Thr (116) to Mg (227); Thr(103) to Ser(213); Glu(104) to Ser (213); Glu(105) to Ser(213); Thr(106) to Ser(213); Ile(107) to Ser(213); Lys(108) to Ser(213); Phe(109) to Ser(213); Ala(110) to Ser(213); Ala(111) to Ser(213); Ala(112) to Ser (213); His(113) to Ser(213); Tyr(114) to Ser(213); Asn(115) to Ser(213); Thr(116) to Ser(213); Thr(103) to Lys(214); Glu(104) to Lys(214); Glu(105) to Lys(214); Thr(106) to Lys(214); Ile(107) to Lys(214); Lys(108) to Lys(214); Phe (109) to Lys(214); Ala(110) to Lys(214); Glu(105) to Leu (229); Thr(106) to Leu(229); Ile(107) to Leu(229); Lys(108) to Leu(229); Phe(109) to Leu(229); Ala(110) to Leu(229); Ala(111) to Leu(229); Ala(112) to Leu(229); His(113) to Leu(229); Tyr(114) to Leu(229); Asn(115) to Leu(229); Thr (116) to Leu(229).

Preferred embodiments include the following deletion mutants: Thr(103)—Arg(227); Glu(104)—Arg(227); Ala (112)—Arg (227); Thr(103)—Ser(213); Glu(104)—Ser (213); Thr(103)—Leu(215); Glu(47)—Ser(4.19); Met(1), Glu (24), or Ala (25)—Met(263); Met(1), Glu (24), or Ala (25)—Asp(311); Met(1), Glu (24), or Ala (25)—Pro (366); Met(1)—Ser(419); and Met(1)—Ser(228) of (FIG. 1 (SEQ ID NO:18)).

Also included by the present invention are deletion mutants having amino acids deleted from both the N-terminus and the C-terminus Such mutants include all combinations of the N-terminal deletion mutants and C-terminal deletion mutants described above. Those combinations can be made using recombinant techniques known to those skilled in the art.

Particularly, N-terminal deletions of the VEGF-2 polypeptide can be described by the general formula m-396, where m is an integer from −23 to 388, where m corresponds to the position of the amino acid residue identified in SEQ ID NO:2. Preferably, N-terminal deletions retain the conserved boxed area of FIG. 3 (PXCVXXXRCXGCCN) (SEQ ID NO:8). N-terminal deletions of the polypeptide of the invention shown as SEQ ID NO:2 include polypeptides comprising the amino acid sequence of residues: E-1 to S-396; A-2 to S-396; P-3 to S-396; A-4 to S-396; A-5 to S-396; A-6 to S-396; A-7 to S-396; A-8 to S-396; F-9 to S-396; E-10 to S-396; S-11 to S-396; G-12 to S-396; L-13 to S-396; D-14 to S-396; L-15 to S-396; S-16 to S-396; D-17 to S-396; A-18 to S-396; E-19 to S-396; P-20 to S-396; D-21 to S-396; A-22 to S-396; G-23 to S-396; E-24 to S-396; A-25 to S-396; T-26 to S-396; A-27 to S-396; Y-28 to S-396; A-29 to S-396; S-30 to S-396; K-31 to S-396; D-32 to S-396; L-33 to S-396; E-34 to S-396; E-35 to S-396; Q-36 to S-396; L-37 to S-396; R-38 to S-396; S-39 to S-396; V-40 to S-396; S-41 to S-396; S-42 to S-396; V-43 to S-396; D-44 to S-396; E-45 to S-396; L-46 to S-396; M-47 to S-396; T-48 to S-396; V-49 to S-396; L-50 to S-396; Y-51 to S-396; P-52 to S-396; E-53 to S-396; Y-54 to S-396; W-55 to S-396; K-56 to S-396; M-57 to S-396; Y-58 to S-396; K-59 to S-396; C-60 to S-396; Q-61 to S-396; L-62 to S-396; R-63 to S-396; K-64 to S-396; G-65 to S-396; G-66 to S-396; W-67 to S-396; Q-68 to S-396; H-69 to S-396; N-70 to S-396; R-71 to S-396; E-72 to S-396; Q-73 to S-396; A-74 to S-396; N-75 to S-396; L-76 to S-396; N-77 to S-396; S-78 to S-396; R-79 to S-396; T-80 to S-396; E-81 to S-396; E-82 to S-396; T-83 to S-396; 1-84 to S-396; K-85 to S-396; F-86 to S-396; A-87 to S-396; A-88 to S-396; A-89 to S-396; H-90 to S-396; Y-91 to S-396; N-92 to S-396; T-93 to S-396; E-94 to S-396; 1-95 to S-396; L-96 to S-396; K-97 to S-396; S-98 to S-396; 1-99 to S-396; D-100 to S-396; N-101 to S-396; E-102 to S-396; W-103 to S-396; R-104 to S-396; K-105 to S-396; T-106 to S-396; Q-107 to S-396; C-108 to S-396; M-109 to S-396; P-110 to S-396; R-111 to S-396; E-112 to S-396; V-113 to S-396; C-114 to S-396; I-115 to S-396; D-116 to S-396; V-117 to S-396; G-118 to S-396; K-119 to S-396; E-120 to S-396; F-121 to S-396; G-122 to S-396; V-123 to S-396; A-124 to S-396; T-125 to S-396; N-126 to S-396; T-127 to S-396; F-128 to S-396; F-129 to S-396; K-130 to S-396; P-131 to S-396; P-132 to S-396; C-133 to S-396; V-134 to S-396; S-135 to S-396; V-136 to S-396; Y-137 to S-396; R-138 to S-396; C-139 to S-396; G-140 to S-396; G-141 to S-396; C-142 to S-396; C-143 to S-396; N-144 to S-396; S-145 to S-396; E-146 to S-396; G-147 to S-396; L-148 to S-396; Q-149 to S-396; C-150 to S-396; M-151 to S-396; N-152 to S-396; T-153 to S-396; S-154 to S-396; T-155 to S-396; S-156 to S-396; Y-157 to S-396; L-158 to S-396; S-159 to S-396; K-160 to S-396; T-161 to S-396; L-162 to S-396; F-163 to S-396; E-164 to S-396; 1-165 to S-396; T-166 to S-396; V-167 to S-396; P-168 to S-396; L-169 to S-396; S-170 to S-396; Q-171 to S-396; G-172 to S-396; P-173 to S-396; K-174 to S-396; P-175 to S-396; V-176 to S-396; T-177 to S-396; 178 to S-396; S-179 to S-396; F-180 to S-396; A-181 to S-396; N-182 to S-396; H-183 to S-396; T-184 to S-396; S-185 to S-396; C-186 to S-396; R-187 to S-396; C-188 to S-396; M-189 to S-396; S-190 to S-396; K-191 to S-396; L-192 to S-396; D-193 to S-396; V-194 to S-396; Y-195 to S-396; R-196 to S-396; Q-197 to S-396; V-198 to S-396; H-199 to S-396; S-200 to S-396; 1-201 to S-396; 1-202 to S-396; R-203 to S-396; R-204 to S-396; S-205 to S-396; L-206 to S-396; 207 to S-396; A-208 to S-396; T-209 to S-396; L-210 to S-396; P-211 to S-396; Q-212 to S-396; C-213 to S-396; Q-214 to S-396; A-215 to S-396; A-216 to S-396; N-217 to S-396; K-218 to S-396; T-219 to S-396; C-220 to S-396; P-221 to S-396; T-222 to S-396; N-223 to S-396; Y-224 to S-396; M-225 to S-396: W-226 to S-396; N-227 to S-396; N-228 to S-396; H-229 to S-396; I-230 to S-396; C-231 to S-396; R-232 to S-396; C-233 to S-396; L-234 to S-396; A-235 to S-396; Q-236 to S-396; E-237 to S-396; D-238 to S-396; F-239 to S-396; M-240 to S-396; F-241 to S-396; S-242 to S-396; S-243 to S-396: D-244 to S-396; A-245 to S-396; G-246 to S-396; D-247 to S-396; D-248 to S-396; S-249 to S-396; T-250 to S-396; D-251 to S-396; G-252 to S-396; F-253 to S-396; H-254 to S-396; D-255 to S-396; 1-256 to S-396; C-257 to S-396; G-258 to S-396; P-259 to S-396; N-260 to S-396; K-261 to S-396; E-262 to S-396; L-263 to S-396; D-264 to S-396; E-265 to S-396; E-266 to S-396; T-267 to S-396; C-268 to S-396; Q-269 to S-396; C-270 to S-396; V-271 to S-396; C-272 to S-396; R-273 to S-396; A-274 to S-396; G-275 to S-396; L-276 to S-396; R-277 to S-396; P-278 to S-396; A-279 to S-396; S-280 to S-396; C-281 to S-396; G-282 to S-396; P-283 to S-396; H-284 to S-396; K-285 to S-396; E-286 to S-396; L-287 to S-396; D-288 to S-396; R-289 to S-396; N-290 to S-396; S-291 to S-396; C-292 to S-396; Q-293 to S-396; C-294 to S-396; V-295 to S-396; C-296 to S-396; K-297 to S-396; N-298 to S-396; K-299 to S-396; L-300 to S-396; F-301 to S-396; P-302 to S-396; S-303 to S-396; Q-304 to S-396; C-305 to S-396; G-306 to S-396; A-307 to S-396; N-308 to S-396; R-309 to S-396; E-310 to S-396; F-311 to S-396; D-312 to S-396; E-313 to S-396; N-3.14 to S-396; T-315 to S-396; C-316 to S-396; Q-317 to S-396; C-318 to S-396; V-319 to S-396; C-320 to S-396; K-321 to S-396; R-322 to S-396; T-323 to S-396; C-324 to S-396; P-325 to S-396; R-326 to S-396; N-327 to S-396; Q-328 to S-396; P-329 to S-396; L-330 to S-396; N-331 to S-396; P-332 to S-396; G-333 to S-396; K-334 to S-396; C-335 to S-396; A-336 to S-396; C-337 to S-396; E-338 to S-396; C-339 to S-396; T-340 to S-396; E-341 to S-396; S-342 to S-396; P-343 to S-396; Q-344 to S-396; K-345 to S-396; C-346 to S-396; L-347 to S-396; L-348 to S-396; K-349 to S-396; G-350 to S-396; K-351 to S-396; K-352 to S-396; F-353 to S-396; H-354 to S-396; H-355 to S-396; Q-356 to S-396; T-357 to S-396; C-358 to S-396; S-359 to S-396; C-360 to S-396; Y-361 to S-396; R-362 to S-396; R-363 to S-396; P-364 to S-396; C-365 to S-396; T-366 to S-396; N-367 to S-396; R-368 to 5-396; Q-369 to S-396; K-370 to S-396; A-371 to S-396; C-372 to S-396; E-373 to S-396; P-374 to S-396; G-375 to S-396; F-376 to S-396; S-377 to S-396; Y-378 to S-396; S-379 to S-396; E-380 to S-396; E-381 to S-396; V-382 to S-396; C-383 to S-396; R-384 to S-396; C-385 to S-396; V-386 to S-396; P-387 to S-396; S-388 to S-396; Y-389 to S-396; W-390 to S-396; Q-391 to S-396 of SEQ ID NO:2. One preferred embodiment comprises amino acids S-205 to S-396 of SEQ ID NO:2. Also preferred are polynucleotides encoding these polypeptides.

Moreover, C-terminal deletions of the VEGF-2 polypeptide can also be described by the general formula-23-n, where n is an integer from −15 to 395 where n corresponds to the position of amino acid residue identified in SEQ ID NO:2. Preferably, C-terminal deletions retain the conserved boxed area of FIG. 3 (PXCVXXXRCXGCCN) (SEQ ID NO:8). C-terminal deletions of the polypeptide of the invention shown as SEQ ID NO:2 include polypeptides comprising the amino acid sequence of residues: E-1 to M-395; E-1 to Q-394; E-1 to P-393; E-1 to R-392; E-1 to Q-391; E-1 to W-390; E-1 to Y-389; E-1 to S-388; E-1 to P-387; E-1 to V-386; E-1 to C-385; E-1 to R-384; E-1 to C-383; E-1 to V-382; E-1 to E-381; E-1 to E-380; E-1 to S-379; E-1 to Y-378; E-1 to S-377; E-1 to F-376; E-1 to G-375; E-1 to P-374; E-1 to E-373; E-1 to C-372; E-1 to A-371; E-1 to K-370; E-1 to Q-369; E-1 to R-368; E-1 to N-367; E-1 to T-366; E-1 to C-365; E-1 to P-364; E-1 to R-363; E-1 to R-362; E-1 to Y-361; E-1 to C-360; E-1 to S-359; E-1 to C-358; E-1 to T-357; E-1 to Q-356; E-1 to H-355; E-1 to H-354; E-1 to F-353; E-1 to K-352; E-1 to K-351; E-1 to G-350; E-1 to K-349; E-1 to L-348; E-1 to L-347; E-1 to C-346; E-1 to K-345; E-1 to Q-344; E-1 to P-343; E-1 to S-342; E-1 to E-341; E-1 to T-340; E-1 to C-339; E-1 to E-338; E-1 to C-337; E-1 to A-336; E-1 to C-335; E-1 to K-334; E-1 to G-333; E-1 to P-332; E-1 to N-331; E-1 to L-330; E-1 to P-329; E-1 to Q-328; E-1 to N-327; E-1 to R-326; E-1 to P-325; E-1 to C-324; E-1 to T-323; E-1 to R-322; E-1 to K-321; E-1 to C-320; E-1 to V-319; E-1 to C-318; E-1 to Q-317; E-1 to C-316; E-1 to T-315; E-1 to N-314; E-1 to E-313; E-1 to D-312; E-1 to F-311; E-1 to E-310; E-1 to R-309; E-1 to N-308; E-1 to A-307; E-1 to G-306; E-1 to C-305; E-1 to Q-304; E-1 to S-303; E-1 to P-302; E-1 to F-301; E-1 to L-300; E-1 to K-299; E-1 to N-298; E-1 to K-297; E-1 to C-296; E-1 to V-295; E-1 to C-294; E-1 to Q-293; E-1 to C-292; E-1 to S-291; E-1 to N-290; E-1 to R-289; E-1 to D-288; E-1 to L-287; E-1 to E-286; E-1 to K-285; E-1 to H-284; E-1 to P-283; E-1 to G-282; E-1 to C-281; E-1 to S-280; E-1 to A-279; E-1 to P-278; E-1 to R-277; E-1 to L-276; E-1 to G-275; E-1 to A-274; E-1 to R-273; E-1 to C-272; E-1 to V-271; E-1 to C-270; E-1 to Q-269; E-1 to C-268; E-1 to T-267; E-1 to E-266; E-1 to E-265; E-1 to D-264; E-1 to L-263; E-1 to E-262; E-1 to K-261; E-1 to N-260; E-1 to P-259; E-1 to G-258; E-1 to C-257; E-1 to 1-256; E-1 to D-255; E-1 to H-254; E-1 to F-253; E-1 to G-252; E-1 to D-251; E-1 to T-250; E-1 to S-249; E-1 to D-248; E-1 to D-247; E-1 to G-246; E-1 to A-245; E-1 to D-244; E-1 to S-243; E-1 to S-242; E-1 to F-241; E-1 to M-240; E-1 to F-239; E-1 to D-238; E-1 to E-237; E-1 to Q-236; E-1 to A-235; E-1 to L-234; E-1 to C-233; E-1 to R-232; E-1 to C-231; E-1 to 1-230; E-1 to H-229; E-1 to N-228; E-1 to N-227; E-1 to W-226; E-1 to M-225; E-1 to Y-224; E-1 to N-223; E-1 to T-222; E-1 to P-221; E-1 to C-220; E-1 to T-219; E-1 to K-218; E-1 to N-217; E-1 to A-216; E-1 to A-215; E-1 to Q-214; E-1 to C-213; E-1 to Q-212; E-1 to P-211; E-1 to L-210; E-1 to T-209; E-1 to A-208; E-1 to P-207; E-1 to L-206; E-1 to S-205; E-1 to R-204; E-1 to R-203; E-1 to 1-202; E-1 to I-201; E-1 to S-200; E-1 to H-199; E-1 to V-198; E-1 to Q-197; E-1 to R-196; E-1 to Y-195; E-1 to V-194; E-1 to D-193; E-1 to L-192; E-1 to K-191; E-1 to S-190; E-1 to M-189; E-1 to C-188; E-1 to R-187; E-1 to C-186; E-1 to S-185; E-1 to T-184; E-1 to H-183: E-1 to N-182; E-1 to A-181; E-1 to F-180; E-1 to S-179; E-1 to I-178; E-1 to T-177; E-1 to V-176; E-1 to P-175; E-1 to K-174; E-1 to P-173; E-1 to G-172; E-1 to Q-171; E-1 to S-170; E-1 to L-169; E-1 to P-168; E-1 to V-167; E-1 to T-166; E-1 to 1-165; E-1 to E-164; E-1 to F-163; E-1 to L-162; E-1 to T-161; E-1 to K-160; E-1 to S-159; E-1 to L-158; E-1 to Y-157; E-1 to S-156; E-1 to T-155; E-1 to S-154; E-1 to T-153; E-1 to N-152; E-1 to M-151; E-1 to C-150; E-1 to Q-149; E-1 to L-148; E-1 to G-147; E-1 to E-146; E-1 to S-145; E-1 to N-144; E-1 to C-143; E-1 to C-142; E-1 to G-141; E-1 to G-140; E-1 to C-139; E-1 to R-138; E-1 to Y-137; E-1 to V-136; E-1 to S-135; E-1 to V-134; E-1 to C-133; E-1 to P-132; E-1 to P-131; E-1 to K-130; E-1 to F-129; E-1 to F-128; E-1 to T-127; E-1 to N-126; E-1 to T-125; E-1 to A-124; E-1 to V-123; E-1 to G-122; E-1 to F-121; E-1 to E-120; E-1 to K-119; E-1 to G-118; E-1 to V-117; EA to D-116; E-1 to 1-115; E-1 to C-114; E-1 to V-113; E-1 to E-112; E-1 to R-111; E-1 to P-110; E-1 to M-109; E-1 to C-108; E-1 to Q-107; E-1 to T-106; E-1 to K-105; E-1 to R-104; E-1 to W-103; E-1 to E-102; E-1 to N-101; E-1 to D-100; E-1 to 1-99; E-1 to S-98; E-1 to K-97; E-1 to L-96; E-1 to 1-95; E-1 to E-94; E-1 to T-93; E-1 to N-92; E-1 to Y-91; E-1 to H-90; E-1 to A-89; E-1 to A-88; E-1 to A-87; E-1 to F-86; E-1 to K-85; E-1 to 1-84; E-1 to T-83; E-1 to E-82; E-1 to E-81; E-1 to T-80; E-1 to R-79; E-1 to S-78; E-1 to N-77; E-1 to L-76; E-1 to N-75; E-1 to A-74; E-1 to Q-73; E-1 to E-72; E-1 to R-71; E-1 to N-70; E-1 to H-69; E-1 to Q-68; E-1 to W-67; E 1 to G-66; E-1 to G-65; E-1 to K-64; E-1 to R-63; E-1 to L-62; E-1 to Q-61; E-1 to C-60; E-1 to K-59; E-1 to Y-58; E-1 to M-57; E-1 to K-56; E-1 to W-55; E-1 to Y-54; E-1 to E-53; E-1 to P-52; E-1 to Y-51; E-1 to L-50; E-1 to V-49; E-1 to T-48; E-1 to M-47; E-1 to L-46; E-1 to E-45; E-1 to D-44; E-1 to V-43; E-1 to S-42; E-1 to S-41; E-1 to V-40; E-1 to S-39; E-1 to R-38; E-1 to L-37; E-1 to Q-36; E-1 to E-35; EA to E-34; E-1 to L-33; E-1 to D-32; E-1 to K-31; E-1 to S-30; E-1 to A-29; E-1 to Y-28; E-1 to A-27; EA to T-26; E-1 to A-25; E-1 to E-24; E-1 to G-23; E-1 to A-22; E-1 to D-21; E-1 to P-20; E-1 to E-19; E-1 to A-18; E-1 to D-17; E-1 to S-16; E-1 to L-15; E-1 to D-14; E-1 to L-13; E-1 to G-12; E-1 to S-11; E-1 to E-10; E-1 to F-9; E-1 to A-8; E-1 to A-7 of SEQ ID NO:2. Also preferred are polynucleotides encoding these polypeptides.

Moreover, the invention also provides polypeptides having one or more amino acids deleted from both the amino and the carboxyl termini, which may be described generally as having residues m-n of SEQ ID NO:2, where n and m are integers as described above.

Likewise, also preferred are C-terminal deletions of the VEGF-2 polypeptide of the invention shown as SEQ ID NO:2 which include polypeptides comprising the amino acid sequence of residues: F-9 to M-395; F-9 to Q-394; F-9 to P-393; F-9 to R-392; F-9 to Q-391; F-9 to W-390; F-9 to Y-389; F-9 to S-388; F-9 to P-387; F-9 to V-386; F-9 to C-385; F-9 to R-384; F-9 to C-383; F-9 to V-382; F-9 to E-381; F-9 to E-380; F-9 to S-379; F-9 to Y-378; F-9 to S-377; F-9 to F-376; F-9 to G-375; F-9 to P-374; F-9 to E-373; F-9 to C-372; F-9 to A-371; F-9 to K-370; F-9 to Q-369; F-9 to R-368; F-9 to N-367; F-9 to T-366; F-9 to C-365; F-9 to P-364; F-9 to R-363; F-9 to R-362; F-9 to Y-361; F-9 to C-360; F-9 to S-359; F-9 to C-358; F-9 to T-357; F-9 to Q-356; F-9 to H-355; F-9 to H-354; F-9 to F-353; F-9 to K-352; F-9 to K-351; F-9 to G-350; F-9 to K-349; F-9 to L-348; F-9 to L-347; F-9 to C-346; F-9 to K-345; F-9 to Q-344; F-9 to P-343; F-9 to S-342; F-9 to E-341; F-9 to T-340; F-9 to C-339; F-9 to E-338; F-9 to C-337; F-9 to A-336; F-9 to C-335; F-9 to K-334; F-9 to G-333; F-9 to P-332; F-9 to N-331; F-9 to L-330; F-9 to P-329; F-9 to Q-328; F-9 to N-327; F-9 to R-326; F-9 to P-325; F-9 to C-324; F-9 to T-323; F-9 to R-322; F-9 to K-321; F-9 to C-320; F-9 to V-319; F-9 to C-318; F-9 to Q-317; F-9 to C-316; F-9 to T-315; F-9 to N-314; F-9 to E-313; F-9 to D-312; F-9 to F-311; F-9 to E-310; F-9 to R-309; F-9 to N-308; F-9 to A-307; F-9 to G-306; F-9 to C-305; F-9 to Q-304; F-9 to S-303; F-9 to P-302; F-9 to F-301; F-9 to L-300; F-9 to K-299; F-9 to N-298; F-9 to K-297; F-9 to C-296; F-9 to V-295; F-9 to C-294; F-9 to Q-293; F-9 to C-292; F-9 to S-291; F-9 to N-290; F-9 to R-289; F-9 to D-288; F-9 to L-287; F-9 to E-286; F-9 to K-285; F-9 to H-284; F-9 to P-283; F-9 to G-282; F-9 to C-281; F-9 to S-280; F-9 to A-279; F-9 to P-278; F-9 to R-277; F-9 to L-276; F-9 to G-275; F-9 to A-274; F-9 to R-273; F-9 to C-272; F-9 to V-271; F-9 to C-270; F-9 to Q-269; F-9 to C-268; F-9 to T-267; F-9 to E-266; F-9 to E-265; F-9 to D-264; F-9 to L-263; F-9 to E-262; F-9 to K-261; F-9 to N-260; F-9 to P-259; F-9 to G-258; F-9 to C-257; F-9 to 1-256; F-9 to D-255; F-9 to H-254; F-9 to F-253; F-9 to G-252; F-9 to D-251; F-9 to T-250; F-9 to S-249; F-9 to D-248; F-9 to D-247; F-9 to G-246; F-9 to A-245; F-9 to D-244; F-9 to S-243; F-9 to S-242; F-9 to F-241; F-9 to M-240; F-9 to F-239; F-9 to D-238; F-9 to E-237; F-9 to Q-236; F-9 to A-235; F-9 to L-234; F-9 to C-232; F-9 to R-232; F-9 to C-231; F-9 to 1-230; F-9 to H-229; F-9 to N-228; F-9 to N-227; F-9 to W-226; F-9 to M-225; F-9 to Y-224; F-9 to N-223; F-9 to T-222; F-9 to P-221; F-9 to C-220; F-9 to T-219; F-9 to K-218; F-9 to N-217; F=9 to A-216; F-9 to A-215; F-9 to Q-214; F-9 to C-213; F-9 to Q-212; F-9 to P-211; F-9 to L-210; F-9 to T-209; F-9 to A-208; F-9 to P-207; F-9 to L-206;

F-9 to S-205; F-9 to R-204; F-9 to R-203; F-9 to 1-202; F-9 to 1-201; F-9 to S-200; F-9 to H-199; F-9 to V-198; F-9 to Q-197; F-9 to R-196; F-9 to Y-195; F-9 to V-194; F-9 to D-193; F-9 to L-192; F-9 to K-191; F-9 to S-190; F-9 to M-189; F-9 to C-188; F-9 to R-187; F-9 to C-186; F-9 to S-185; F-9 to T-184; F-9 to 1-1-183; F-9 to N-182; F-9 to A-181; F-9 to F-180; F-9 to S-179; F-9 to 1-178; F-9 to T-177; F-9 to V-176; F-9 to P-175; F-9 to K-174; F-9 to P-173; F-9 to G-172; F-9 to Q-171; F-9 to S-170; F-9 to L-169; F-9 to P-168; F-9 to V-167; F-9 to T-166; F-9 to 1-165; F-9 to E-164; F-9 to F-163; F-9 to L-162; F-9 to T-161; F-9 to K-160; F-9 to S-159; F-9 to L-158; F-9 to Y-157; to S-156; F-9 to 1-155; F-9 to S-154; F-9 to T-153; F-9 to N-152; F-9 to M-151; F-9 to C-150; F-9 to Q-149; F-9 to L-148; F-9 to G-147; F-9 to E-146; F-9 to S-145; F-9 to N-144; F-9 to C-143; F-9 to C-142; F-9 to G-141; F-9 to G-140; F-9 to C-139; F-9 to R-138; F-9 to Y-137; F-9 to V-136; F-9 to S-135; F-9 to V-134; F-9 to C-133; F-9 to P-132; F-9 to P-131; F-9 to K-130; F-9 to F-129; F-9 to F-128; F-9 to T-127; F-9 to N-126; F-9 to T-125; F-9 to A-124; F-9 to V-123; F-9 to G-122; F-9 to F-121; F-9 to E-120; F-9 to K-119; F-9 to G-118; F-9 to V-117; F-9 to D-116; F-9 to 1-115; F-9 to C-114; F-9 to V-113; F-9 to E-112; F-9 to R-111; F-9 to P-110; F-9 to M-109; F-9 to C-108; F-9 to Q-107; F-9 to T-106; F-9 to K-105; F-9 to R-104; F-9 to W-103; F-9 to E-102; F-9 to N-101; F-9 to D-100; F-9 to 1-99; F-9 to S-98; F-9 to K-97; F-9 to L-96; F-9 to 1-95; F-9 to E-94; F-9 to T-93; F-9 to N-92; F-9 to Y-91; F-9 to H-90; F-9 to A-89; F-9 to A-88; F-9 to A-87; F-9 to F-86; F-9 to K-85; F-9 to 1-84; F-9 to T-83; F-9 to E-82; F-9 to E-81; F-9 to T-80; F-9 to R-79; F-9 to S-78; F-9 to N-77; F-9 to L-76; F-9 to N-75; F-9 to A-74; F-9 to Q-73; F-9 to E-72; F-9 to R-71; F-9 to N-70; F-9 to H-69; F-9 to Q-68; F-9 to W-67; F-9 to G-66; F-9 to G-65; F-9 to K-64; F-9 to R-63; F-9 to L-62; F-9 to Q-61; F-9 to C-60; F-9 to K-59; F-9 to Y-58; F-9 to M-57; F-9 to K-56; F-9 to W-55; F-9 to Y-54; F-9 to E-53; F-9 to P-52; F-9 to Y-51; F-9 to L-50; F-9 to V-49; F-9 to T-48; F-9 to M-47; F-9 to L-46; F-9 to E-45; F-9 to D-44; F-9 to V-43; F-9 to S-42; F-9 to S-41; F-9 to V-40; F-9 to S-39; F-9 to R-38; F-9 to L-37; F-9 to Q-36; F-9 to E-35; F-9 to E-34; F-9 to L-33; F-9 to D-32; F-9 to K-31; F-9 to S-30; F-9 to A-29; F-9 to Y-28; F-9 to A-27; F-9 to 1-26; F-9 to A-25; F-9 to E-24; F-9 to G-23; F-9 to A-22; F-9 to D-21; F-9 to P-20; F-9 to E-19; F-9 to A-18; F-9 to D-17; F-9 to S-16; F-9 to L-15; of SEQ ID NO:2. Specifically preferred is the polypeptide fragment comprising amino acid residues F-9 to R-203 of SEQ ID NO:2, as well as polynucleotides encoding this polypeptide. This F-9 to R-203 of SEQ ID NO:2 polypeptide preferably is associated with a S-205 to S-396 of SEQ ID NO:2 polypeptide. Association may be through disulfide, covalent or noncovalent interactions, by linkage via a: linker (e.g. serine, glycine; proline linkages), or by an antibody.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1660 of SEQ ID NO:1, b is an integer of 15 to 1674, where both a and b correspond to the positions of nucleotide residues shown in SEQ ID NO:1, and where the b is greater than or equal to a+14.

Thus, in one aspect, N-terminal deletion mutants are provided by the present invention. Such mutants include those comprising the amino acid sequence shown in FIG. 1 (SEQ ID NO:18) except for a deletion of at least the first 24 N-terminal amino acid residues (i.e. a deletion of at least Met (1)—Glu (24)) but not more than the first 115 N-terminal amino acid residues of FIG. 1 (SEQ ID NO:18). Alternatively, first 24 N-terminal amino acid residues (i.e., a deletion of at least Met (1)—Glu (24)) but not more than the first 103 N-terminal amino acid residues of FIG. 1 (SEQ ID NO:18) etc.

In another aspect, C-terminal deletion mutants are provided by the present invention. Such mutants include those comprising the amino acid sequence shown in FIG. 1 (SEQ ID NO:18) except for a deletion of at least the last C-terminal amino acid residue (Ser (419)) but not more than the last 220 C-terminal amino acid residues (i.e., a deletion of amino acid residues Val-(199)—Ser (419)) of FIG. 1 (SEQ ID NO:18). Alternatively, the deletion will include at least the last C-terminal amino acid residue but not more than the last 216 C-terminal amino acid residues of FIG. 1 (SEQ ID NO:18). Alternatively, the deletion will include at least the last C-terminal amino acid residue but not more than the last 204 C-terminal amino acid residues of FIG. 1 (SEQ ID NO:18). Alternatively, the deletion will include at least the last C-terminal amino acid residues but not more than the last 192 C-terminal amino acid residues of FIG. 1 (SEQ ID NO:18). Alternatively; the deletion will include at least the last C-terminal amino acid residues but not more than the last 156 C-terminal amino acid residues of FIG. 1 (SEQ ID NO:18). Alternatively, the deletion will include at least the last C-terminal amino acid residues but not more than the last 108 C-terminal amino acid residues of FIG. 1 (SEQ ID NO:18). Alternatively, the deletion will include at least the last C-terminal amino acid residues but not more than the last 52 C-terminal amino acid residues of FIG. 1 (SEQ ID NO:18).

In yet another aspect, also included by the present invention are deletion mutants having amino acids deleted from both the N-terminal and C-terminal residues. Such mutants include all combinations of the N-terminal deletion mutants and C-terminal deletion mutants described above.

The term "gene" means the segment of DNA involved in producing a polypeptide chain; it includes regions preceding and following the coding region (leader and trailer) as well as intervening sequences (introns) between individual coding segments (exons).

The present invention is further directed to fragments of the isolated nucleic acid molecules described herein. By a fragment of an isolated nucleic acid molecule having the nucleotide sequence of the deposited cDNA(s) or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments of 50, 75, 100, 125, 150, 175, 200, 225, 250, 275, 300, 325, 350, 375, 400, 425, 450, 475, 500, 525, 550, 575, 600, 625, 650, 675; 700, 725, 750, 775, 800, 825, 850, 875, 900, 925, 950, 975, 1000, 1025, 1050, 1075, 1100, 1125, 1150, 1175; 1200, 1225, 1250, 1275, 1300, 1325, 1350, 1375, 1400, 1425, 1450, 1475, 1500, 1525, 1550, 1575, 1600, 1625, 1650 or 1674 nt in length are also useful according to the present invention as are fragments corresponding to most, if not all, of the nucleotide sequence of the deposited cDNA(s) or as shown in SEQ ID NO:1 or SEQ ID NO:3. By a fragment at least 20 nt in length, for example, is intended fragments which include 20 or more contiguous bases from the nucleotide sequence of the deposited cDNA(s) or the nucleotide sequence as shown in SEQ ID NOS:1 or 3.

Moreover, representative examples of VEGF-2 polynucleotide fragments include, for example, fragments having a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, or 951 to the end of SEQ ID NO:1 or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

A VEGF-2 "polynucleotide" also includes those polynucleotides capable of hybridizing, under stringent hybridization conditions, to sequences contained in SEQ ID NO:1 or for instance, the cDNA clone(s) contained in ATCC Deposit Nos. 97149 or 75698, the complement thereof "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the VEGF-2 polynucleotides at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SUS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

By a polynucleotide which hybridizes to a "portion" of a polynucleolide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO: 1). Of course, a polynucleotide which hybridizes only to a poly A sequence (such as the 3N terminal poly(A) tract of the VEGF-2 cDNA shown in SEQ ID NOS:1 or 3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The present application is directed to nucleic acid molecules at least 95%, 96%, 97%, 98% or 99% identical to the nucleic acid sequence shown in SEQ JD NOS:1 or 3 or to the nucleic acid sequence of the deposited cDNA(s), irrespective of whether they encode a polypeptide having VEGF-2 activity. This is because even where a particular nucleic acid molecule does not encode a polypeptide having VEGF-2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having VEGF-2 activity include inter alia, (1) isolating the VEGF-2 gene or allelic variants thereof in a cDNA library; (2) in situ hybridization (e.g., "FISH") to metaphase chromosomal spreads to provide precise chromosomal location of the VEGF-2 gene, as described in Verma et al., *Human Chromosomes: A Manual of Basic Techniques*, Pergamon Press, New York (1988); and Northern Blot analysis for detecting VEGF-2 mRNA expression in specific tissues.

Preferred, however, are nucleic acid molecules having sequences at least 95%, 96%, 97%, 98% or 99% identical to a nucleic acid sequence shown in SEQ ID NOS:1 or 3 or to a nucleic, acid sequence of the deposited cDNA(s) which do, in fact, encode a polypeptide having VEGF-2 protein activity. By "a polypeptide having VEGF-2 activity" is intended polypeptides exhibiting VEGF-2 activity in a particular biological assay. For example, VEGF-2 protein activity can be measured using, for example, mitogenic assays and endothelial cell migration assays. See, e.g., Olofsson et al., *Proc. Natl. Acad. Sci. USA* 93:2576-2581 (1996) and Joukov et al., *EMBO J.* 5:290-298 (1996).

Of course, due to the degeneracy of the genetic code, one of ordinary skill in the art will immediately: recognize that a large number of the nucleic acid molecules having a sequence at least 90%, 95%, 96%, 97%, 98%, or 99% identical to a nucleic acid sequence of the deposited cDNA(s) or the nucleic acid sequence shown in SEQ ID NO:1 or SEQ ID NO:3 will encode a polypeptide "having VEGF-2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having VEGF-2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Thus, the present invention is directed to polynucleotides having at least a 70% identity, preferably at least 90% and more preferably at least a 95%, 96%, 97%, or 98% identity to a polynucleotide which encodes the polypeptides of SEQ ID NOS:2 or 4, as well as fragments thereof, which fragments have at least 30 bases and preferably at least 50 bases and to polypeptides encoded by such polynucleotides.

"Identity" per se has an art-recognized meaning and can be calculated using published techniques. (See, e.g.: (COMPUTATIONAL MOLECULAR BIOLOGY, Lesk, A.M., ed., Oxford University Press, New. York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A.M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER., Gribskov, M. and Devereux, J., eds. M Stockton Press, New York, (1991).) While there exists a number of methods to measure identity between two polynucleotide or polypeptide sequences, the term "identity" is well known to skilled artisans. (Carillo, H., and Lipton, D., *SIAM J. Applied Math* 48:1073 (1988).) Methods commonly employed to determine identity or similarity between two sequences include, but are not limited to, those disclosed in "Guide to Huge Computers," Martin J. Bishop, ed., Academic Press, San Diego, (1994), and Carillo; and Lipton, D., *SIAM J. Applied Math.* 48:1073 (1988). Methods for aligning polynucleotides Or polypeptides are codified in computer programs, including the GCG program package (Devereux, J., et al., *Nucleic Acids Research* 12(1):387 (1984)), BLASTP, BLASTN, FASTA (Atschul, S. F. et al., *J. Molec. Biol.* 215: 403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, *Advances in Applied Mathematics* 2:482-489 (1981)). By a polynucleotide having a nucleotide, sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the VEGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence SEQ ID NO:1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1; Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence; as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually, among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in SEQ ID NO:2, SEQ ID NO:4, SEQ ID NO:18 or to the amino acid sequence encoded by deposited DNA clones can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci*. (1990) 6:237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty—0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

VEGF-2 Polypeptides

The present invention further relates to polypeptides which have the deduced amino acid sequence of FIG. 1 or 2, or which has the amino acid sequence encoded by the deposited cDNAs, as well as fragments, analogs, and derivatives of such polypeptides.

The terms "fragment," "derivative" and "analog" when referring to the polypeptide of FIG. 1 or 2 or that encoded by the deposited cDNA, means a polypeptide which retains the conserved motif of VEGF proteins as shown in FIG. 3 and essentially the same biological function or activity.

In the present invention, a "polypeptide fragment" refers to a short amino acid sequence contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1-20, 21-40, 41-60, 61-80, 81-100, 102-120, 121-140, 141-160, 161-180, 181-200, 201-220, 221-240, 241-260, 261-280, or 281 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted VEGF-2 protein (which is preferably a dimer of amino acids beginning at residue 101, 102, 103, 104, 105, 106, 107, 108, 109, 110, 111, 112, 113, or 114 of SEQ ID NO:18 and ending at amino acid residue 221, 222, 223, 224, 225, 226, 227, 228, or 229 of SEQ ID NO:18, the pro-protein form (which is preferably about amino acid 32-419 of SEQ ID NO:18), and mature form. Other preferred polypeptide fragments include the mature form having a continuous series of deleted residues from the amino or the carboxy terminus, or both. For example, any number of amino acids, ranging from 1-60, can be deleted from the amino terminus of either the secreted VEGF-2 polypeptide or the mature form. Similarly, any number of amino acids, ranging from 1-30, can be deleted from the carboxy terminus of the secreted VEGF-2 protein or mature form. Furthermore, any combination of the above amino and carboxy terminus deletions are preferred. Similarly, polynucleotide fragments encoding these VEGF-2 polypeptide fragments are also preferred.

Also preferred are VEGF-2 polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. (See FIG. 2.) Moreover, polynucleotide fragments encoding these domains are also contemplated.

Other preferred fragments are biologically active VEGF-2 fragments. Biologically active fragments are those exhibiting activity similar, but not necessarily identical, to an activity of the VEGF-2 polypeptide. The biological activity of the fragments may include an improved desired activity, or a decreased undesirable activity.

The polypeptides of the present invention may be recombinant polypeptides, natural polypeptides, or synthetic polypeptides, preferably recombinant polypeptides.

It will be recognized in the art that some amino acid sequences of the VEGF-2 polypeptide can be varied without significant effect of the structure or function of the protein. If such differences in sequence are contemplated, it should be remembered that there will be critical areas on the protein which determine activity.

Thus, the invention further includes variations of the VEGF-2 polypeptide which show substantial VEGF-2 polypeptide activity or which include regions of VEGF-2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragments, derivatives, or analogs of the polypeptides of FIG. 1 or 2, or that encoded by the deposited cDNAs may be: (I) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence; or (v) one in which comprises fewer amino acid residues shown in SEQ ID NOS: 2 or 4, and retains the conserved motif and yet still retains activity characteristics of the VEGF family of polypeptides. Such fragments, derivatives, and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the VEGF-2 protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-a to only one of the two known types of TNF receptors. Thus, the VEGF-2 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given VEGF-2 polypeptide will not be more than 50, 40, 30, 25, 20, 15, 10, 5 or 3.

Amino acids in the VEGF-2 protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of VEGF-2 coding sequence, but do not comprise all or a portion of any VEGF-2 intron. In another embodiment, the nucleic acid comprising VEGF-2 coding sequence does not contain coding sequences of a genomic flanking gene (i.e., 5' or 3' to the VEGF-2 gene in the genome).

The polypeptides of the present invention include the polypeptides of SEQ ID NOS:2 and 4 (in particular the mature polypeptide) as well as polypeptides which have at least 70% similarity (preferably at least 70% identity) to the polypeptides of SEQ ID NOS:2 and 4, and more preferably at least 90% similarity (more preferably at least 95% identity) to the polypeptides of SEQ ID NOS:2 and 4, and still more preferably at least 95% similarity (still more preferably at least 90% identity) to the polypeptides of SEQ ID NOS:2 and 4 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The polypeptides of the present invention include the polypeptide encoded by the deposited cDNA including the leader; the mature polypeptide encoded by the deposited the cDNA minus the leader (i.e., the mature protein); a polypeptide comprising amino acids about −23 to about 396 in SEQ ID NO:2; a polypeptide comprising amino acids about −22 to about 396 in SEQ ID NO:2; a polypeptide comprising amino acids about 1 to about 396 in SEQ ID NO:2; as well as polypeptides which are at least 95% identical, and more preferably at least 96%, 97%, 98% or 99% identical to the polypeptides described above and also include portions of such polypeptides with at least 30 amino acids and more preferably at least 50 amino acids.

Fusion Proteins

Any VEGF-2 polypeptide can be used to generate fusion proteins. For example, the VEGF-2 polypeptide, when fused to a second protein, can be used as an antigenic tag. Antibodies raised against the VEGF-2 polypeptide can be used to indirectly detect the second protein by binding to the VEGF-2. Moreover, because secreted proteins target cellular locations based on trafficking signals, the VEGF-2 polypeptides can be used as a targeting molecule once fused to other proteins.

Examples of domains that can be fused to VEGF-2 polypeptides include not only heterologous signal sequences, but also other heterologous functional regions. The fusion does not necessarily need to be direct, but may occur through linker sequences.

Moreover, fusion proteins may also be engineered to improve characteristics of the VEGF-2 polypeptide. For instance, a region of additional amino acids, particularly charged amino acids, may be added to the N-terminus of the VEGF-2 polypeptide to improve stability and persistence during purification from the host cell or subsequent handling and storage. Also, peptide moieties may be added to the VEGF-2 polypeptide to facilitate purification. Such regions may be removed prior to final preparation of the VEGF-2 polypeptide. The addition of peptide moieties to facilitate handling of polypeptides are familiar and routine techniques in the art.

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also, been found to be more efficient in binding and neutralizing other molecules than, monomeric secreted polypeptides or fragments thereof alone. See, e.g., Fountoulakis et al., J. Biochem., 270:3958-3964 (1995). Nucleic acids encoding the above polypeptides can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., *J. Molecular Recognition* 8:52-58 (1995); K. Johanson et al., *J. Biol. Chem.* 270:9459-9471 (1995).)

Moreover, the VEGF-2 polypeptides can be fused to marker sequences, such as a peptide which facilitates purification of VEGF-2. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., *Cell* 37:767 (1984).)

Thus, any of these above fusions can be engineered using the VEGF-2 polynucleotides or the polypeptides.

Biological Activities of VEGF-2

VEGF-2 polynucleotides and polypeptides can be used in assays to test for one or more biological activities. If VEGF-2 polynucleotides and polypeptides do exhibit activity in a particular assay, it is likely that VEGF-2 may be involved in the diseases associated with the biological activity. Therefore, VEGF-2 or VEGF-2 antibodies could be used to treat the associated disease.

Anti-Angiogenesis Activity

The naturally occurring balance between endogenous stimulators and inhibitors of angiogenesis is one in which inhibitory influences predominate. Rastinejad et al.,. *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630-634 (1991); Folkman et al., *N. Engl. J. Med.*, 333:1757-1763 (1995); Auerbach et al., *J. Microvasc. Res.* 29:401-411 (1985); Folkman, Advances in Cancer Research, eds. Klein and Weinhouse, Academic Press, New York, pp. 175-203 (1985); Patz, *Am. J. Opthalmol.* 94:715-743 (1982); and Folkman et al., *Science* 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment of diseases or disorders associated with neovascularization by administration of the antibodies of the invention. Malignant and metastatic conditions which can be treated with the antibodies of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating an angiogenesis-related disease and/or disorder, comprising administering to an individual in need thereof a therapeutically effective amount of an antibody of the invention. For example, antibodies may be utilized in a variety of additional methods in order to therapeutically treat a cancer or tumor. Cancers which may be treated with antibodies include, but are not limited to solid tumors, including prostate, lung, breast, brain, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non small cell lung cancer; colorectal cancer; advanced malignancies; and blood born tumors such as leukemias. For example, antibodies may be delivered topically, in order to treat cancers such as skin cancer, head and neck tumors, breast tumors, and Kaposi's sarcoma.

Within yet other aspects, antibodies may be utilized to treat superficial forms of bladder cancer by, for example, intravesical administration. Antibodies may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Antibodies may be useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating hypertrophic scars and keloids, comprising the step of administering a antibodies of the invention to a hypertrophic scar or keloid.

Within one embodiment of the present invention antibodies of the invention are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, ocular disorders associated with neovascularization which can be treated with the antibodies of the present invention include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above, including antibodies) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological, processes (e.g., graft rejection and Stevens-Johnson's syndrome), alkali burns, trauma, inflammation (of any cause); toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the antibodies described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of an antibody to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a an antibody to the eyes, such that the formation of blood vessels is inhibited.

Within particularly preferred embodiments of the invention, proliferative diabetic retinopathy may be treated by injection into the aqueous humor or the vitreous, in order to increase the local concentration of the antibodies in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of an antibody to the eye, such that the formation of blood vessels is inhibited. The compound may be administered topically, via intravitreous injection and/or via intraocular implants.

Additionally, disorders which can be treated with antibodies include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated, prevented, diagnosed, and/or prognosed with the antibodies of the invention include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vasculogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa); ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method.

Antibodies may also be used in controlling menstruation or administered as either a peritoneal lavage fluid or for peritoneal implantation in the treatment of endometriosis.

Antibodies of the present invention may be incorporated into surgical sutures in order to prevent stitch granulomas.

Antibodies may be utilized in a wide variety of surgical procedures. For example, within one aspect of the present invention a compositions (in the form of, for example, a spray or film) may be utilized to coat or spray an area prior to removal of a tumor, in order: to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering an antibody to the resection margins of a tumor subsequent to excision, such that the local recurrence of cancer and the formation of new blood vessels at the site is inhibited. Within one embodiment of the invention, the anti-angiogenic compound, for example VEGF-2 antibody, is administered directly to the tumor excision site (e.g., applied by swabbing, brushing or otherwise coating the resection margins of the tumor with the VEGF-2 antibody). Alternatively, the VEGF-2 antibodies may be incorporated into known surgical pastes prior to administration. Within particularly preferred embodiments of the invention, VEGF-2 antibodies are applied after hepatic resections for malignancy, and after neurosurgical operations.

Within one aspect of the present invention, VEGF-2 antibodies may be administered to the resection margin of a wide variety of tumors, including for example, breast, colon, brain and hepatic tumors. For example, within one embodiment of the invention, VEGF-2 antibodies may be administered to the site of a neurological tumor subsequent to excision, such that the formation of new blood vessels at the site are inhibited.

Antibodies of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenmun oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-1.7326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynaminolmidazole; and metalloproteinase inhibitors such as BB94.

Immune Activity

VEGF-2 antibodies may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, VEGF-2 antibodies can be used as a marker or detector of a particular immune: system disease or disorder.

VEGF-2 antibodies may be useful in treating or detecting deficiencies or disorders of hematopoietic cells. VEGF-2 antibodies could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection; HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, VEGF-2 antibodies can also be used to modulate hemostatic (the stopping of bleeding) or thrombolytic activity (clot formation). For example, by increasing hemostatic or thrombolytic activity, VEGF-2 antibodies could be used to treat blood coagulation disorders (e.g., afibrinogenemia, factor deficiencieS), blood platelet disorders (e.g. thrombocytopenia), or wounds resulting from trauma, surgery, or other causes. Alternatively, VEGF-2 antibodies that can decrease hemostatic or thromboltic activity could be used to inhibit or dissolve clotting, important in the treatment of heart attacks (infarction), strokes, or scarring.

VEGF-2 antibodies may also be useful, in treating or detecting autoimmune disorders. Many autoimmune disorders result from inappropriate recognition of self as foreign material by immune cells. This inappropriate recognition results in an immune response leading to the destruction of the host tissue. Therefore, the administration of VEGF-2 antibodies that can inhibit an immune response, particularly the proliferation, differentiation, or chemotaxis of T-cells, may be an effective therapy in preventing autoimmune disorders.

Examples of autoimmune disorders that can be treated or detected by VEGF-2 antibodies include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by VEGF-2 antibodies. Moreover, VEGF-2 antibodies can be used to treat anaphylaxis, hypersensitivity to an antigenic molecule, or blood group incompatibility.

VEGF-2 antibodies may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of VEGF-2 antibodies that inhibits an immune response, particularly the proliferation, differentiation, or chemotaxis of T-cells, may be an effective therapy in preventing organ rejection or GVHD.

Similarly, VEGF-2 antibodies may also be used to modulate inflammation. For example, VEGF-2 antibodies may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

VEGF-2 antibodies of the invention, can be used to treat or detect hyperproliferative disorders, including neoplasms. VEGF-2 antibodies may inhibit the proliferation of the disorder through direct or indirect initeractions. Alternatively, VEGF-2 antibodies may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by VEGF-2 antibodies include, but are not limited to neoplasms located in the abdomen, bone, breast, digestive system, liver, pancreas, peritoneum, endocrine glands (adrenal, parathyroid, pituitary, testicles, ovary, thymus, thyroid), eye, head and neck, brain, nervous (central and peripheral), lymphatic system, pelvic, skin, soft tissue, spleen, prostate, thoracic, and urogenital. In preferred embodiments, VEGF-2 antibodies may be used to treat, prevent or ameliorate breast-cancer. In other preferred embodiments, VEGF-2 antibodies may be used to treat, prevent or ameliorate brain cancer. In other preferred embodiments, VEGF-2 antibodies may be used to treat, prevent or ameliorate prostate cancer. In other preferred embodiments, VEGF-2 antibodies may be used to treat, prevent or ameliorate colon cancer. In other preferred embodiments, VEGF-2 antibodies may be used to treat, prevent or ameliorate Kaposi's sarcoma.

Similarly, other hyperproliferative disorders can also be treated or detected by VEGF-2 antibodies. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Binding Activity

VEGF-2 polypeptides may be used to screen for molecules that bind to VEGF-2 or for molecules to which VEGF-2 binds. The binding of VEGF-2 and the molecule may activate (agonist), increase, inhibit (antagonist), or decrease activity of the VEGF-2 or the molecule bound. Examples of such molecules include antibodies, oligonucleotides, proteins (e.g., receptors), or small molecules.

Preferably, the molecule is closely related to the natural ligand of VEGF-2, e.g., a fragment of the ligand, or a natural substrate, a ligand, a structural or functional mimetic. (See, Coligan et al., *Current Protocols in Immunology* 1(2): Chapter 5 (1991).) Similarly, the molecule can be closely related to the natural receptor to which VEGF-2 binds (i.e., flk-1 or flt-4), or at least, a fragment of the receptor capable of being bound by VEGF-2 (e.g., active site). In either case, the molecule can be rationally designed using known techniques. Preferably, the screening for these molecules involves producing appropriate cells which express VEGF-2, either as a secreted protein or on the cell membrane. Preferred cells include cells from mammals, yeast, *Drosophila*, or *E. coli*. Cells expressing VEGF-2(or cell membrane containing the expressed polypeptide) are then preferably contacted with a test compound potentially containing the molecule to observe binding, stimulation, or inhibition of activity of either VEGF-2 or the molecule.

The assay may simply test binding of a candidate compound to VEGF-2, wherein binding is detected by a label, or in an assay involving competition with a labeled competitor. Further, the assay may test whether the candidate compound results in a signal generated by binding to VEGF-2.

Alternatively, the assay can be carried out using cell-free preparations, polypeptide/molecule affixed to a solid support, chemical libraries, or natural product mixtures. The assay may also simply comprise the steps of mixing a candidate compound with a solution containing VEGF-2, measuring VEGF-2/molecule activity or binding, and comparing the VEGF-2/molecule activity or binding to a standard.

Preferably, an ELISA assay can measure VEGF-2 level or activity in a sample (e.g., biological sample) using a monoclonal or polyclonal antibody. The antibody can measure VEGF-2 level or activity by either binding, directly or indirectly, to VEGF-2 or by competing with VEGF-2 for a substrate.

All of these above assays can be used as diagnostic or prognostic markers. The molecules discovered using these assays can be used to treat disease or to bring about a particular result in a patient (e.g., blood vessel growth) by activating or inhibiting the VEGF-2/molecule. Moreover, the assays can discover agents which may inhibitor enhance the production of VEGF-2 from suitably manipulated cells or tissues.

Therefore, the invention includes a method of identifying compounds which bind to VEGF-2 comprising the steps of: (a) incubating a candidate binding compound with VEGF-2; and (b) determining if binding has occurred. Moreover, the invention includes a method of identifying agonists/antagonists comprising the steps of: (a) incubating a candidate compound with VEGF-2, (b) assaying a biological activity, and (b) determining if a biological activity of VEGF-2 has been altered.

Targeted Delivery

In another embodiment, the invention provides a method of delivering compositions to targeted cells expressing a receptor for VEGF-2 polypeptides, or cells expressing a cell bound form of VEGF-2 polypeptide.

As discussed herein, antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering antibodies of the invention that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering VEGF-2 antibodies of the invention in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of VEGF-2 polypeptides. Such a method would include contacting the polypeptide of the present invention with a selected compound(s) suspected of having antagonist or agonist activity, and assaying the activity of these polypeptides following binding.

This invention is particularly useful for screening therapeutic compounds by using the VEGF-2 polypeptides, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by VEGF-2 polypeptides. These methods comprise contacting such an agent with a VEGF-2 polypeptide or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form; and the amount of free or uncomplexed label is a measure of the ability of a particular agent to bind to VEGF-2 polypeptides.

Another technique for drug screening provides high throughput screening for compounds having suitable binding affinity to VEGF-2 polypeptides, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding VEGF-2 polypeptides specifically compete with a test compound for binding to the VEGF-2 polypeptides or fragments thereof. In this manner, the antibodies are used to detect the presence of any peptide which shares one or more antigenic epitopes with a polypeptide of the invention.

Binding Peptides and other Molecules

The invention also encompasses screening methods for identifying polypeptides and nonpolypeptides that bind VEGF-2 polypeptides, and the binding molecules identified thereby. These binding molecules are useful, for example, as agonists and antagonists, such as VEGF-2 antibodies, of the VEGF-2 polypeptides. Such antibodies can be used, in accordance with the invention, in the therapeutic embodiments described in detail, below.

This method comprises the steps of: contacting VEGF-2 polypeptides with a plurality of molecules; and identifying a molecule that binds VEGF-2 polypeptides.

The step of contacting VEGF-2 polypeptides with the plurality of molecules may be effected in a number of ways. For example, one may contemplate immobilizing the VEGF-2 polypeptides on a solid support and bringing a solution of the plurality of molecules in contact with the immobilized VEGF-2 polypeptides. Such a procedure would be akin to an affinity chromatographic process, with the affinity matrix being comprised of the immobilized polypeptides of the invention. The molecules having a selective affinity for the VEGF-2 polypeptides can then be purified by affinity selection. The nature of the solid support; process for attachment of the polypeptides to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the polypeptides of the invention, optionally in the presence of an inducer should one be required for expression, to determine if any selective affinity interaction takes place between the polypeptides and the individual clone. Prior to contacting the VEGF-2 polypeptides with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for polypeptides of the invention. Furthermore, the amino acid sequence of the polypeptide having a selective affinity for the polypeptides of the invention can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound polypeptides from a mixture of the VEGF-2 polypeptides and the plurality of polypeptides prior to attempting to determine or to detect the presence of a selective affinity interaction. Such a wash step may be particularly desirable when the VEGF-2 polypeptides or the plurality of polypeptides are bound to a solid support.

The plurality of molecules provided according to this method may be provided by way of diversity libraries, such as random or combinatorial peptide or nonpeptide libraries which can be screened for molecules that specifically VEGF-2 polypeptides. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710; Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghien et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lerner, 1992, Proc. Natl. Acad. Sci. USA 89:5381-5383.

Examples of phage display libraries are described in Scott and Smith, 1990, Science 249:386-390; Devlin et al., 1990, Science, 249:404-406; Christian, R. B., et al., 1992, J. Mol. Biol. 227:711-718); Lenstra, 1992, J. Immunol. Meth. 152: 149-157; Kay et al., 1993, Gene 128:59-65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

The variety of non-peptide libraries that are useful in the present invention is great. For example, Ecker and Crooke, 1995, Bio/Technology 13:351-360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be amolecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med, Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. Nos. 5,096,815, 5,223,409, and 5,198,346, all to Ladner et al.; Rebar and Pabo, 1993, Science 263:671-673; and CT Publication No. WO 94/18318.

In a specific embodiment, screening to identify a molecule that binds VEGF-2 polypeptides can be carried out by contacting the library members with polypeptides of the invention immobilized on a solid phase and harvesting those library members that bind to VEGF-2 polypeptides. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited herein.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to VEGF-2 polypeptides.

Where the binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a binding molecule that is a polypeptide, the polypeptide may have about 6 to less than about 60 amino acid residues, preferably about 6 to about 10 amino acid residues, and most preferably, about 6 to about 22 amino acids. In another embodiment, a binding polypeptide has in the range of 15-0.100 amino acids, or 20-50 amino acids.

The selected binding polypeptide can be obtained by chemical synthesis or recombinant expression.

Vectors, Host Cells, and Protein Production

The present invention also relates to recombinant vectors, which include the isolated nucleic acid molecules of the present invention, and to host cells containing the recombinant vectors, as well as to methods of making such vectors and host cells and for using them for production of VEGF-2 polypeptides or peptides by recombinant techniques.

Host cells are genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the VEGF-2 genes of the invention. The culture conditions, such as temperature, pH and the like, are those previously used with the host cell selected for expression, and will be apparent to the skilled artisan.

The polynucleotides of the present invention may be employed for producing polypeptides by recombinant techniques. Thus, for example, the polynucleotide sequence may be included in any one of a variety of expression vectors for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain at least one selectable marker gene to provide a phenotypic trait for selection of transformed host cells. Such markers include dihydrofolate reductase (DHFR) or neomycin resistance for eukaryotic cell culture, and tetracycline or ampicillin resistance for culturing in *E. coli* and other bacteria.

The vector containing the appropriate DNA sequence as herein above described, as well as an appropriate promoter or control sequence, may be employed to transform an appropriate host to permit the host to express the protein. Representative examples of appropriate hosts, include but are not limited to: bacterial cells, such as *E. coli, Salmonella typhimurium*, and *Streptomyces*; fungal cells, such as yeast; insect cells, such as *Drosophila* S2 and *Spodoptera* Sf9; animal cells such as CHO, COS, and Bowes melanoma; and plant cells. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example—bacterial: pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figure 28:
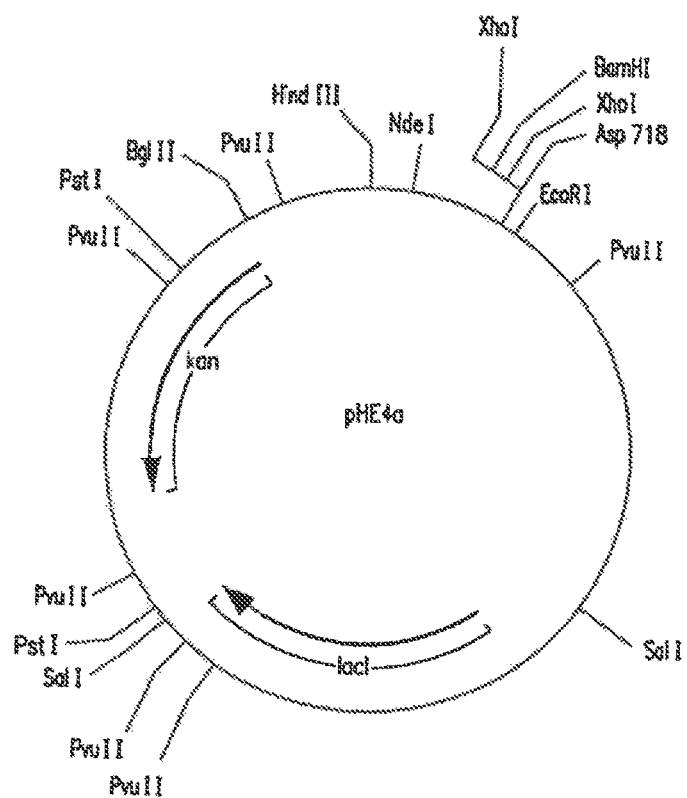
FIG. 28 shows a schematic representation of the pHE4a expression vector (SEQ ID NO:16). The locations of the kanamycin resistance marker gene, the multiple cloning site linker region, the oriC sequence, and the lacIq coding sequence are indicated.
Figure 30A:
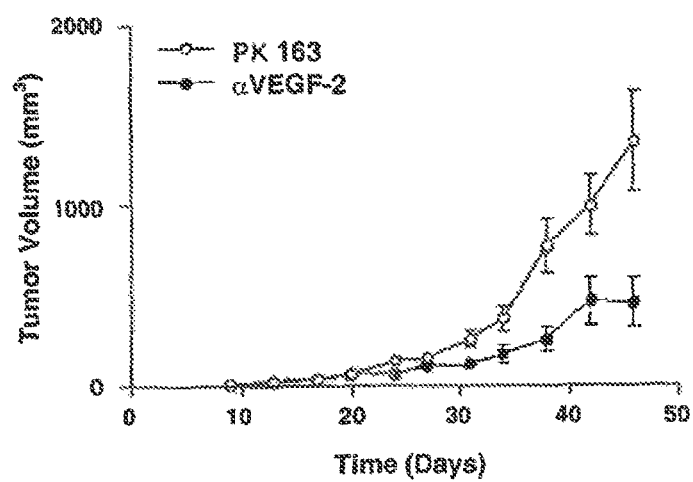
FIGS. 30A-30F show the effect of VEGF-2 antibodies on tumor size, weight, and metastasis.
Figure 30B:
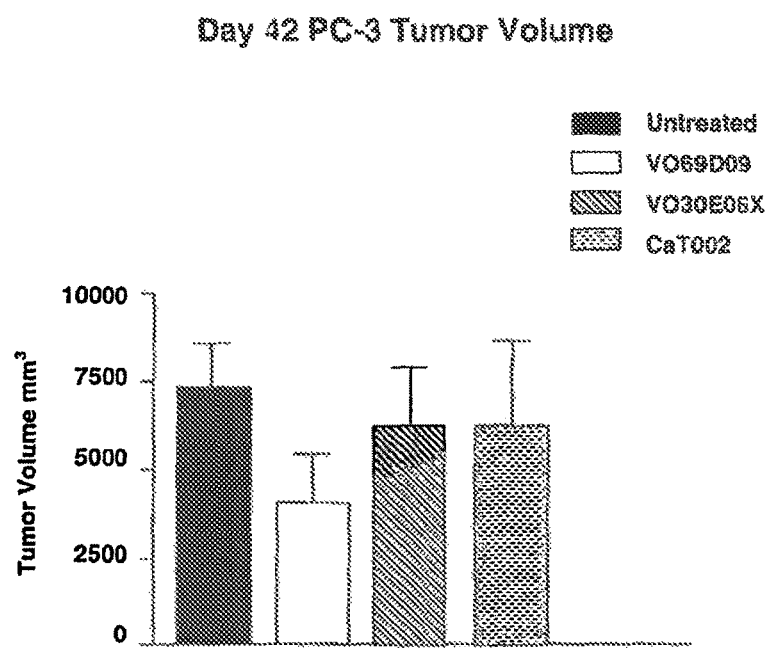
Figure 30C:
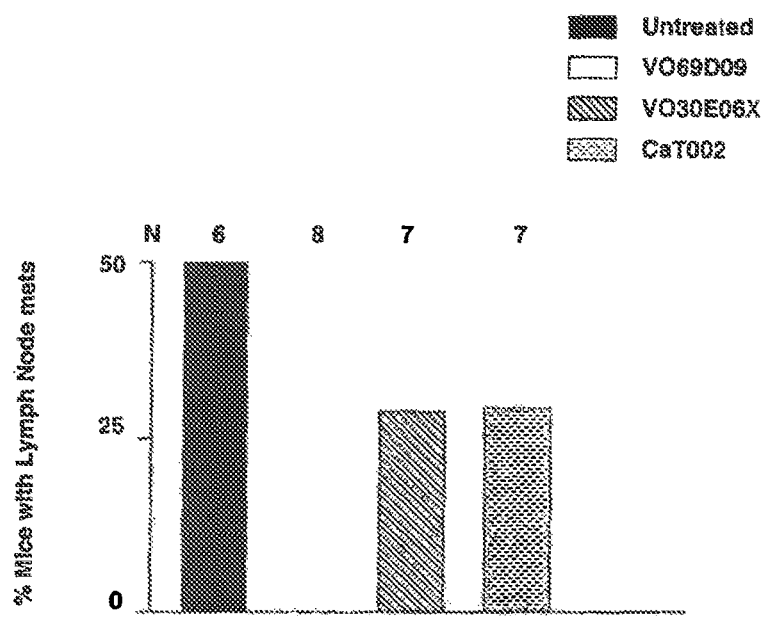
Figure 30D:
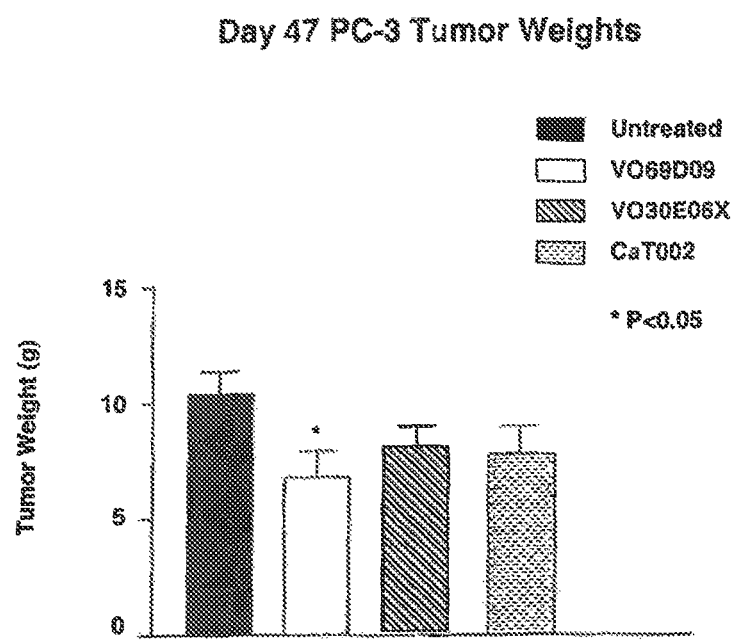
Figure 30E:
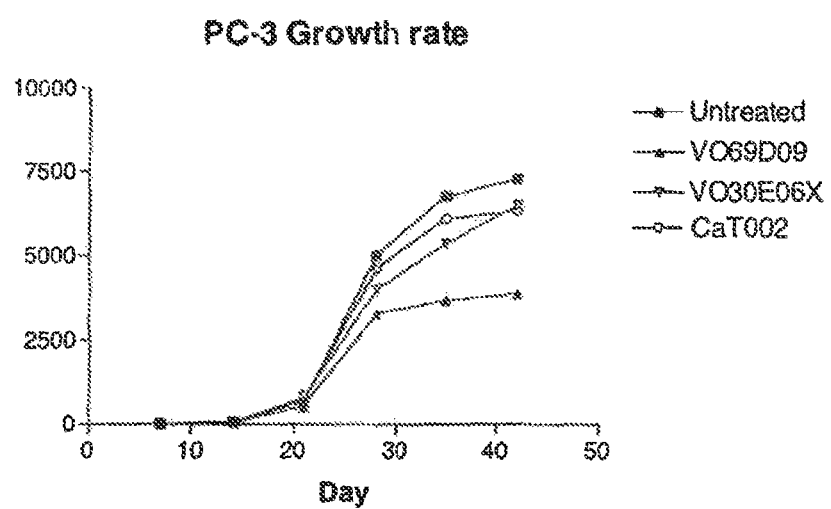
Figure 30F:
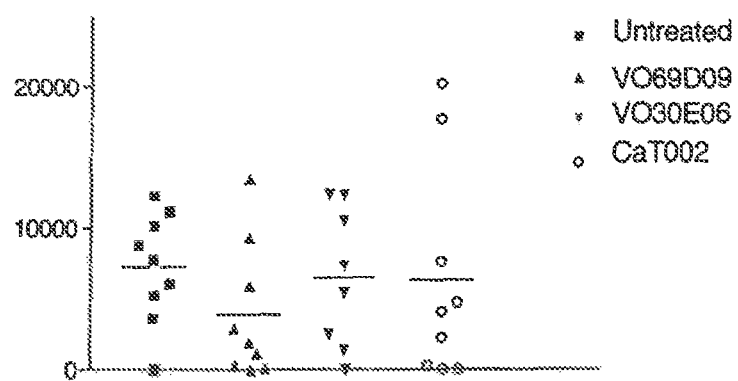

As summarized in FIGS. 28 and 29, components of the pHE4a vector (SEQ ID NO:16) include: 1) a neomycinphosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215-216, CLONTECH, 1020 East Meadow Circle, Palo Alto, Calif. 94303. The pHE4a vector was deposited with the ATCC on Feb. 25, 1998, and given accession number 209645.

A nucleotide sequence encoding VEGF-2 (SEQ ID NO: 1), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding VEGF-2 (SEQ ID NO:1) having the appropriate restriction sites is generated, for example, according to the PCR protocol described in Example1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac operator. Amann, E. et al., *Gene* 69:301-315' (1988); Stark, M., *Gene* 51:255-267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG) VEGF-2 thus is not produced in appreciable quantities in uninduced host cells containing the pHE4a vector. Induction of these host cells by the addition of an agent such as IPTG, however, results in the expression of the VEGF-2 coding sequence.

The promoter/operator sequences of the pHE4a vector (SEQ ID NO:17) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802-807.

The pHE4 series of vectors contain all of the components of the pHE4a vector except for the VEGF-2 coding sequence. Features of the pHE4a vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4a vector (SEQ ID NO: 16).

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early. HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, electroporation, transduction, infection, or other methods (Davis, L., et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*. Second Edition, Cold Spring Harbor Laboratory, Cold Spring Harbor, N.Y. (1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRPI gene, and a promoter derived from a highly-expressed gene tob direct transcription of a downstream structural sequence. Such promoters can be derived from operons encoding glycolytic enzymes such as 3-phosphoglycerate kinase (PGK), a-factor; acid phosphatase, or heat shock proteins, among others. The heterologous structural sequence is: assembled in appropriate phase with translation initiation and termination sequences; and preferably, a leader sequence capable of directing secretion of translated protein into, the periplasmic space or, extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, well known to those skilled in the art, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome for example, SV40 origin, early promoter, enhancer, splice, and polyadenylation sites may be used to provide the required nontranscribed genetic elements.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., VEGF-2 sequence), and/or to include genetic material (e.g., heterologous promoters) that is operably associated with VEGF-2 sequence of the invention, and which activates, alters, and/or amplifies endogenous VEGF-2 polynucleotides. For example, techniques known in the art may be used to operably associate heterologous control regions and endogenous polynucleotide sequences (e.g. encoding VEGF-2) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932-8935 (1989); and Zijlstra et al., *Nature* 342:435-438 (1989), the disclosures of each of which are incorporated by reference in their entireties).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the protein expressed.

The polypeptides can be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. It is preferred to have low concentrations (approximately 0.1-5 mM) of calcium ion present during purification (Price et-al., *J. Biol. Chem.* 244: 917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

In addition, polypeptides of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). For example, a peptide corresponding to a fragment of the VEGF-2 polypeptides of the invention can be synthesized by use of a peptide synthesizer. Furthermore, if desired, nonclassical amino acids or chemical amino acid analogs can be introduced as a substitution or addition into the VEGF-2 polynucleotide sequence. Nonclassical amino acids include, but are not limited to, to the D-isomers of the common amino acids, 2,4-diaminobutyric acid, α-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses VEGF-2 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of VEGF-2 which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulthydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The VEGF-2 polypeptides of the invention may be in monomers or multimers (i.e., dimers, trimers, tetramers and higher multimers). Accordingly, the present invention relates to monomers and multimers of the VEGF-2 polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only VEGF-2 polypeptides of the invention (including VEGF-2 fragments, variants, splice variants, and fusion proteins, as described herein). These homomers may contain VEGF-2 polypeptides having identical or different amino acid sequences. In a specific embodiment, a homomer of the invention is a multimer containing only VEGF-2 polypeptides having an identical amino acid sequence. In another specific embodiment, a homomer of the invention is a multimer containing VEGF-2 polypeptides having different amino acid sequences. In specific embodiments, the multimer of the invention is a homodimer (e.g., containing VEGF-2 polypeptides having identical or different amino acid sequences) or a homotrimer (e.g., containing VEGF-2 polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the VEGF-2 polypeptides of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the VEGF-2 polypeptides of the invention. Such covalent associations may involve one or more amino acid residues contained in the polypeptide sequence (e.g., that recited in SEQ ID NO:2, or contained in the polypeptide encoded by the deposited clone.) In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterlogous polypeptide sequence in a VEGF-2 fusion protein. In one example, covalent associations are between the heterologous sequence contained in a fusion protein of the invention (see, e.g., U.S. Pat. No. 5,478,925). In a specific example, the covalent associations are between the heterologous sequence contained in a VEGF-2-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, osteoprotegerin (see, e.g., International Publication No. WO 98/49305, the contents of which are herein incorporated by reference in its entirety).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Therapeutic Uses

Figure 12:
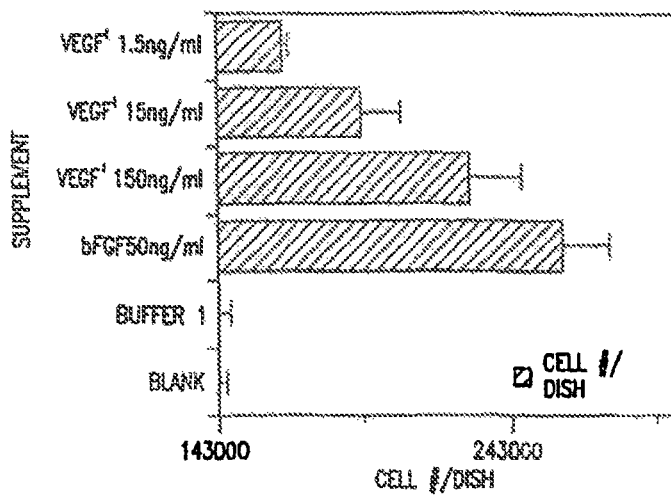
FIG. 12 is a bar graph illustrating the effect of partially-purified VEGF-2 protein on the growth of vascular endothelial cells in comparison to basic fibroblast growth factor.
Figure 13:
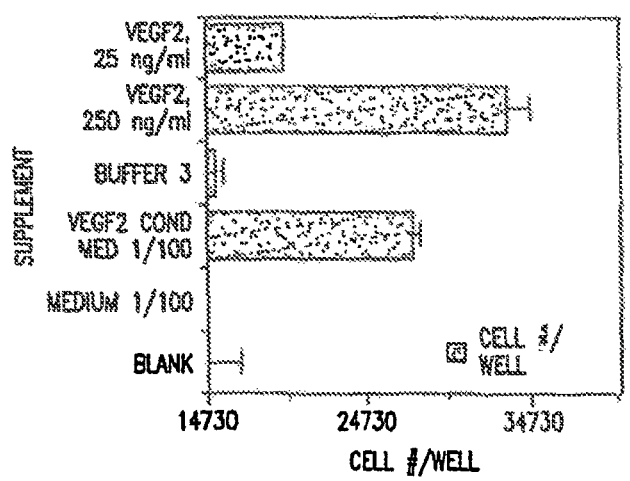
FIG. 13 is a bar graph illustrating the effect of purified VEGF-2 protein on the growth of Vascular endothelial cells.

The VEGF-2 polypeptide of the present invention is a potent mitogen for vascular and lymphatic endothelial cells. As shown in FIGS. 12 and 13, the VEGF-2 polypeptide of SEQ ID NO:2, minus the initial 46 amino acids, is a potent mitogen for vascular endothelial cells and stimulates their growth and proliferation. The results of a Northern blot analysis performed for the VEGF-2 nucleic acid sequence encoding this polypeptide wherein 20 mg of RNA from several human tissues were probed with $^{32}$P-VEGF-2, illustrates that this protein is actively expressed in the heart and lung which is further evidence of mitogenic activity.

VEGF-2 agonistic antibodies, which enhance the activity of VEGF-2, may be employed to treat vascular trauma by promoting angiogenesis. For example, to stimulate the growth of transplanted tissue where coronary bypass surgery is performed. The VEGF-2 agonistic antibodies may also be employed to promote wound healing, particularly to re-vascularize damaged tissues or stimulate collateral blood flow during ischemia and where new capillary angiogenesis is desired. Such antibodies can be employed to treat full-thickness wounds such as dermal ulcers, including pressure sores, venous ulcers, and diabetic ulcers. In addition, VEGF-2 agonistic antibodies, may be employed to treat full-thickness burns and injuries where a skin graft or flap is used to repair such burns and injuries. Furthermore, the VEGF-2 agonistic antibodies of the invention may be employed for use in plastic surgery, for example, for the repair of lacerations, burns, or other trauma. The VEGF-2 agonistic antibodies of the invention can also be used to promote healing of wounds and injuries to the eye as well as to treat eye diseases.

Along these same lines, agonistic antibodies can also be used to induce the growth of damaged bone, periodontium or ligament tissue. Such VEGF-2 agonistic antibodies may also be employed for regenerating supporting tissues of the teeth, including cementum and periodontal ligament, that have been damaged by, e.g., periodontal disease or trauma.

Since angiogenesis is important in keeping wounds clean and non-infected, agonistic antibodies that enhance the activity of VEGF-2, may be employed in association with surgery and following the repair of incisions and cuts. These VEGF-2 antibodies may also be employed for the treatment of abdominal wounds where there is a high risk of infection.

VEGF-2 agonistic antibodies may be employed for the promotion of endothelialization in vascular graft surgery. In the case of vascular grafts using either transplanted or synthetic material, these antibodies can be applied to the surface of the graft or at the junction to promote the growth of vascular endothelial cells. Antibodies acting as agonists of VEGF-2 can be employed to repair damage of myocardial tissue as a result of myocardial infarction and may also be employed to repair the cardiac vascular system after ischemia. VEGF-2 agonistic antibodies may also be employed to treat damaged vascular tissue as a result of coronary artery disease and peripheral and CNS vascular disease.

VEGF-2 agonistic antibodies may also be employed to coat artificial prostheses or natural organs which are to be transplanted in the body to minimize rejection of the transplanted material and to stimulate vascularization of the transplanted materials.

Agonistic antibodies of VEGF-2 may also be employed for vascular tissue repair of injuries resulting from trauma, for example, that occurring during arteriosclerosis and required following balloon angioplasty where vascular tissues are damaged.

VEGF-2 agonistic antibodies may also be used to treat peripheral arterial disease. Accordingly, in a further aspect, there is provided a process for utilizing VEGF-2 agonistic antibodies to treat peripheral arterial disease. Preferably, a VEGF-2 agonistic antibody is administered to an individual for the purpose of alleviating or treating peripheral arterial disease. Suitable doses, formulations, and administration routes are described below.

Agonistic antibodies of VEGF-2 can promote the endothelial function of lymphatic tissues and vessels, such as to treat the loss of lymphatic vessels, and occlusions of lymphatic vessels. Agonistic antibodies of VEGF-2 may also be used to stimulate lymphocyte production. Antagonistic VEGF-2 antibodies may be used to treat lymphangiomas.

Agonistic antibodies may also be used to treat hemangioma in newborns. Accordingly, in a further aspect, there is provided a process for utilizing VEGF-2 antibodies to treat hemangioma in newborns. Preferably, an antibody is administered to an individual for the purpose of alleviating or treating hemangioma in newborns. Suitable doses, formulations, and administration routes are described below.

VEGF-2 agonistic antibodies may also be used to prevent or treat abnormal retinal development in premature newborns. Accordingly, in a further aspect, there is provided a process for utilizing VEGF-2 antibodies to treat abnormal retinal development in premature newborns. Preferably, a VEGF-2 antibody is administered to an individual for the purpose of alleviating or treating abnormal retinal development in premature newborns. Suitable doses, formulations, and administration routes are described below.

VEGF-2 agonistic antibodies may be used to treat primary (idiopathic) lymphademas, including Milroy's disease and Lymphedema praecox. Preferably, a VEGF-2 antibody is administered to an individual for the purpose of alleviating or treating primary (idiopathic) lymphademas, including Milroy's disease and Lymphedema praecox: VEGF-2 antibodies may also be used to treat edema as well as to effect blood pressure in an animal. Suitable doses, formulations, and administration routes are described below.

VEGF-2 agonistic antibodies may also be used to treat secondary (obstructive) lymphedema including those that result from (I) the removal of lymph nodes and vessels, (ii) radiotherapy and surgery in the treatment of cancer, and (iii) trauma and infection. Preferably, a VEGF-2 antibody is administered to an individual for the purpose of secondary (obstructive) lymphedema including those that result from (I) the removal of lymph nodes and vessels, (ii) radiotherapy and surgery in the treatment of cancer, and (iii) trauma and infection. Suitable doses, formulations, and administration routes are described below.

VEGF-2 agonistic antibodies may also be used to treat Kaposi's Sarcoma. Preferably, a VEGF-2 antibody is administered to an individual for the purpose of alleviating or treating Kaposi's Sarcoma. Suitable doses, formulations, and administration routes are described below.

VEGF-2 antibodies can be used to treat cancer by inhibiting the angiogenesis necessary to support cancer and tumor growth.

Cardiovascular Disorders

The present inventors have shown that VEGF-2 stimulates the growth of vascular endothelial cells, stimulates endothelial cell migration, stimulates angiogenesis in the CAM assay, decreases blood pressure in spontaneously hypertensive rats, and increases blood flow to ischemic limbs in rabbits. Accordingly, agonistic antibodies that enhance the activity of VEGF-2 may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right veitricle, tricuspid atresia, persistent truncus arteriosus and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiornmyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary, atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis; coronary, thrombosis; coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease. CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisnis. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

VEGF-2 antibodies, which enhance the activity of VEGF-2, are especially effective for the treatment of critical limb ischemia and coronary disease. As shown in Example 18, administration of VEGF-2 polynucleotides and polypeptides to an experimentally induced ischemia rabbit hind limb restored blood pressure ratio, blood flow, angiographic score, and capillary density.

Antibodies may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. VEGF-2 antibodies may be administered as part of a pharmaceutical composition, described in more detail below. Methods of delivering VEGF-2 antibodies are described in more detail below.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the VEGF-2 polypeptide of the present invention. This method requires a polynucleotide which codes for a VEGF-2 polypeptide operatively linked to a promoter and any other genetic elements necessary for the expression of the polypeptide by the target tissue. Such gene therapy and delivery techniques are known in the art, see, for example, WO 90/11092, which is herein incorporated by reference.

Thus, for example, cells from a patient may be engineered with a polynucleotide (DNA or RNA) comprising a promoter operably linked to a VEGF-2 polynucleotide ex vivo, with the engineered cells then being provided to a patient to be treated with the polypeptide. Such methods are well-known in the art. For example, see Belldegrun, A., et al., *J. Natl. Cancer Inst.* 85: 207-216 (1993); Ferrantini, M. et al., *Cancer Research* 53: 1107-1112 (1993); Ferrantini, M. et al., *J. Immunology* 153: 4604-4615 (1994): Kaido, f., et al., *Int. J. Cancer* 60: 221-229 (1995); Ogura, H., et al., *Cancer Research* 50: 5102-5106 (1990); Santodonato, L., et al.; *Human Gene Therapy* 7:1-10 (1996); Santodonato, L., et al., *Gene Therapy* 4:1246-

1255 (1997); and Zhang, J.-F. et al., *Cancer Gene Therapy* 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the VEGF-2 polynucleotide constructs can be delivered by any method that delivers injectable materials to the cells of an animal, such as injection into the interstitial space of tissues (heart, muscle, skin, lung, liver, and the like). The VEGF-2 polynucleotide constructs may be delivered in a pharmaceutically acceptable liquid or aqueous carrier.

In one embodiment, the VEGF-2 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the VEGF-2 polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The VEGF-2 polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of VEGF-2 DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for VEGF-2.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The VEGF-2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue esheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells, which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked VEGF-2 DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

As is evidenced by Example 18, naked VEGF-2 nucleic acid sequences can be administered in vivo results in the successful expression of VEGF-2 polypeptide in the femoral arteries of rabbits.

The constructs may also be delivered with delivery vehicles such as viral sequences, viral particles, liposome formulations, lipofectin, precipitating agents, etc. Such methods of delivery are known in the art.

In certain embodiments, the VEGF-2 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* (1987) 84:7413-7416, which is herein incorporated by reference); mRNA (Malone et al., *Proc. Natl. Acad. Sci. USA* (1989) 86:6077-6081, which is herein incorporated by reference); and purified transcription factors (Debs et al., *J. Biol. Chem.* (1990) 265:10189-10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl. Acad. Sci. USA* (1987) 84:7413-7416, which is herein incorporated by reference). Other commercially available liposomes include transfectace (DDAB/DOPE) and DOTAP/DOPE (Boehringer).

Other cationic liposomes can be prepared from readily available materials using techniques well known in the art.

See, e.g. PCT Publication No. WO 90/11092 (Which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., *Proc. Natl. Acad. Sci. USA* 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE) among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., *Methods of Immunology* (1983); 101:512-527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include. $Ca^{2+}$-EDTA chelation (Papahadjopoulos et al., *Biochim. Biophys. Acta* (1975) 394:483; Wilson et al., *Cell* (1979) 17:77); ether injection (Deamer, D. and Bangham, A., *Biochim. Biophys. Acta* (1976) 443:629; Ostro et al., *Biochem. Biophys. Res. Commun* (1977) 76:836; Fraley et al., *Proc. Natl. Acad. Sci. USA* (1979) 76:3348); detergent dialysis (Enoch, H. and Strittmatter, P., *Proc. Natl. Acad. Sci. USA* (1979) 76:145); and reverse-phase evaporation (REV) (Fraley et al., *J. Biol. Chem.* (1980) 255:10431; Szoka, F. and Papahadjopoulos, D., *Proc. Natl. Acad. Sci. USA* (1978) 75:145; Schaefer-Ridder et al., *Science* (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding VEGF-2. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14×, VT-19-17-H2, RCRE, RCRIP, GP+E–86, GP+envAm12, and DAN cell lines as described in Miller, *Human Gene Therapy* 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding VEGF-2. Such retroviral vector particles then may be employed, to transduce eukaryotic cells, either in vitro or in vivo. The transduced eukaryotic cells will express VEGF-2.

In certain other embodiments, cells are engineered, ex vivo or in vivo, with VEGF-2 polynucleotide contained in an adenovirus vector. Adenovirus can be manipulated such that it, encodes and expresses VEGF-2, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109:233-238). Finally, adenovirus mediated gene transfer has been demonstrated in a number of instances including transfer of alpha-1-antitrypsin and CFTR to the lungs of cotton rats (Rosenfeld, M. A. et al. (1991) *Science* 252:431-434; Rosenfeld et al., (1992) *Cell* 68:143-155), Furthermore, extensive studies to attempt to establish adenovirus as a causative agent in human cancer were uniformly negative (Green, M. et al. (1979) *Proc. Natl. Acad. Sci. USA* 76:6606).

Suitable adenoviral vectors useful in the present invention are described, for example, in Kozarsky and Wilson, *Curr. Opin. Genet. Devel.* 3:499-503 (1993); Rosenfeld et al., *Cell* 68:143-155 (1992); Engelhardt et al., *Human Genet. Ther.* 4:759-769 (1993); Yang et al., *Nature Genet.* 7:362-369 (1994); Wilson et al., *Nature* 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the HARP promoter of the present invention, but cannot replicate in most cells. Replication deficient adenoviruses may be deleted in one or more of all or a portion of the following genes: E1a, E1b. E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., *Curr. Topics in Microbio Immunol.* 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The VEGF-2 polynucleotide construct is inserted into the AAV vector using standard cloning methods, such as those found in Sambrook et al., *Molecular Cloning: A Laboratory Manual*, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the VEGF-2 polynucleotide construct. These viral particles are then used to transduce eukaryotic cells, either ex vivo or in vivo. The transduced cells will contain the VEGF-2 polynucleotide construct integrated into its genome, and will express VEGF-2.

Another method of gene therapy involves operably associating heterologous control regions and endogenous polynucleotide sequences (e.g. encoding VEGF-2) via homologous recombination (see, e.g., U.S. Pat. No. 5,641,670, issued Jun. 24, 1997; International. Publication No. WO 96/29411, published Sep. 26, 1996; International Publication No. WO 94/12650, published Aug. 4, 1994; Koller et al., *Proc. Natl. Acad. Sci. USA* 86:8932-8935 (1989); and Zijlstra et al., *Nature* 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the VEGF-2 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction, with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous VEGF-2 sequence is placed under the control of the promoter. The promoter then drives the expression of the endogenous VEGF-2 sequence.

The polynucleotides encoding VEGF-2 may be administered along with other polynucleotides encoding other angiongenic proteins. Angiogenic proteins include, but are not limited to, acidic and basic fibroblast growth factors, VEGF-1, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding VEGF-2 contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., *Science* 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189: 11277-11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Nucleic Acid Utilities

VEGF-2 nucleic acid sequences and VEGF-2 polypeptides may also be employed for in vitro purposes related to scientific research, synthesis of DNA and manufacture of DNA vectors, and for the production of diagnostics and therapeutics to treat human disease. For example, VEGF-2 may be employed for in vitro culturing of vascular endothelial cells, where it is added to the conditional medium in a concentration from 10 pg/ml to 10 ng/ml.

Fragments of the full length VEGF-2 gene may be used as a hybridization probe for a cDNA library to isolate other genes which have a high sequence similarity to the gene or similar biological activity. Probes of this type generally have at least 50 base pairs, although they may have a greater number of bases. The probe may also be used to identify a cDNA clone corresponding to a full length transcript and a genomic clone or clones that contain the complete VEGF-2 gene including regulatory and promoter regions, exons, and introns. An example of a screen comprises isolating the coding region of the VEGF-2 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides methods for identification of VEGF-2 receptors. The gene encoding the receptor can be identified by numerous methods known to those of skill in the art, for example, ligand panning and FACS sorting (Coligan et al., *Current Protocols in Immun.,* 1(2), Chapter 5, (1991)). Preferably, expression cloning, is employed wherein polyadenylated RNA is prepared from a cell responsive to VEGF-2, and a cDNA library created from this RNA is divided into pools and used to transfect COS cells or other cells that are not responsive to VEGF-2. Transfected cells which are grown on glass slides are exposed to labeled VEGF-2. VEGF-2 can be labeled by a variety of means including, iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled VEGF-2 can be photoaffinity linked with cell membrane or extract preparations that express the receptor molecule. Cross-linked material is resolved by PAGE and exposed to X-ray film. The labeled complex containing VEGF-2 is then excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

VEGF-2 Agonist and Antagonists

This invention is also related to a method of screening compounds to identify those which are VEGF-2 agonists or antagonists. An example of such a method takes advantage of the ability of VEGF-2 to significantly stimulate the proliferation of human endothelial cells in the presence of the comitogen Con A. Endothelial cells are obtained and cultured in 96-well flat-bottomed culture plates (Costar, Cambridge, Mass.) in a reaction mixture supplemented with Con-A (Calbiochem, La Jolla, Calif.). Con-A, polypeptides of the present invention and the compound to be screened are added. After incubation at 37 degrees C., cultures are pulsed with 1 FCi of $^3$[H]thymidine (5 Ci/mmol; 1 Ci=37 BGq; NEN) for a sufficient time to incorporate the $^3$[H] and harvested onto glass fiber filters (Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]thymidine incorporation, as compared to a control assay where the compound is excluded, indicates stimulation of endothelial cell proliferation.

To assay for antagonists, the assay described above is performed and the ability of the compound to inhibit $^3$[H]thymidine incorporation in the presence of VEGF-2 indicates that the compound is an antagonist to VEGF-2. Alternatively, VEGF-2 antagonists may be detected by combining VEGF-2 and a potential antagonist with membrane-bound VEGF-2 receptors or recombinant receptors under appropriate conditions for a competitive inhibition assay. VEGF-2 can be labeled, such as by radioactivity, such that the number of VEGF-2 molecules bound to the receptor can determine the effectiveness of the potential antagonist.

Alternatively, the response of a known second messenger system following interaction of VEGF-2 and receptor would be measured and compared in the presence or absence of the compound. Such second messenger systems include but are not limited to, cAMP guanylate cyclase, ion channels or phosphoinositide hydrolysis. In another method, a mammalian cell or membrane preparation expressing the VEGF-2 receptor is incubated with labeled VEGF-2 in the presence of the compound. The ability of the compound to enhance or block this interaction could then be measured.

Potential VEGF-2 antagonists include an antibody, or in some cases, an oligonucleotide, which binds to the polypeptide and effectively eliminates VEGF-2 function. Alternatively, a potential antagonist may be a closely related protein which binds to VEGF-2 receptors, however, they are inactive forms of the polypeptide and thereby prevent the action of VEGF-2. Examples of these antagonists include a dominant negative mutant of the VEGF-2 polypeptide, for example, one chain of the hetero-dimeric form of VEGF-2 may be dominant and may be mutated such that biological activity is not retained. An example of a dominant negative mutant includes truncated versions of a dimeric VEGF-2 which is capable of interacting with another dimer to form wild type VEGF-2, however, the resulting homo-dimer is inactive and fails to exhibit characteristic VEGF activity.

Another potential VEGF-2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix: —see Lee et al., *Nucl. Acids Res.*6:3073 (1979); Cooney et al., *Science* 241:456 (1988); and Dervan et al., *Science* 251: 1360 (1991)), thereby preventing transcription and the production of VEGF-2. The antisense RNA oligonucleotide hybridizes to the mRNA in vivo and blocks translation of the mRNA molecule into the VEGF-2 polypeptide (Antisense—Okano, *J. Neurochem.* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of VEGF-2.

Potential VEGF-2 antagonists also include small molecules which bind to and occupy the active site of the polypeptide thereby making the catalytic site inaccessible to substrate such that normal biological activity is prevented. Examples of small molecules include but are not limited to small peptides or peptide-like molecules.

The antagonists, such as VEGF-2 antibodies, may be employed to limit angiogenesis necessary for solid tumor metastasis. The identification of VEGF-2 can be used for the generation of certain inhibitors of vascular endothelial growth factor. Since angiogenesis and neovascularization are essential steps in solid tumor growth, inhibition of angiogenic activity of the vascular endothelial growth factor is very useful to prevent the further growth, retard, or even regress solid tumors. Although the level of expression of VEGF-2 is extremely low in normal tissues including breast, it can be found expressed at moderate levels in at least two breast tumor cell lines that are derived from malignant tumors. It is, therefore, possible that VEGF-2 is involved in tumor angiogenesis and growth.

Gliomas are also a type of neoplasia which may be treated with the antagonists of the present invention.

The antagonists, such as VEGF-2 antibodies, may also be used to treat chronic inflammation caused by increased vascular permeability. In addition to these disorders, the antagonists may also be employed to treat retinopathy associated with diabetes, rheumatoid arthritis and psoriasis.

The antagonists, such as VEGF-2 antibodies, may be employed in a composition with a pharmaceutically acceptable carrier, e.g., as hereinafter described.

Pharmaceutical Compositions

The VEGF-2 antibodies may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the pharmaceutical compositions are administered in an amount of at least about 10 mg/kg body weight and in most cases they will be administered in an amount not in excess of about 8 mg/Kg body weight per day. In most cases, the dosage is from about 10 mg/kg to about 1 mg/kg body weight daily, taking into account the routes of administration, symptoms, etc.

The VEGF-2 antibodies which are polypeptides may also be employed in accordance with the present invention by expression of such polypeptide in vivo, which is often referred to as "gene therapy," described above.

Thus, for example, cells such as bone marrow cells may be engineered with a polynucleotide (DNA or RNA) encoding for the polypeptide, or an VEGF-2 antibody, ex vivo, the engineered cells are then provided to a patient to be treated with the polypeptide. Such methods are well-known in the art. For example, cells may be engineered by procedures known in the art by use of a retroviral particle containing RNA encoding the polypeptide of the present invention.

Similarly, cells may be engineered in vivo for expression of a polypeptide, or an VEGF-2 antibody, in vivo, for example, by procedures known in the art. As known in the art, a producer cell for producing a retroviral particle containing RNA encoding VEGF-2 antibodies of the present invention may be administered to a patient for engineering cells in vivo and expression of VEGF-2 antibodies in vivo. These and other methods for administering VEGF-2 antibodies of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus; and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques* 7:980-990 (1989), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thyrnidine kinase promoter; retroviral LTRs (including the modified retroviral LTRs hereinabove described); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, y-2, y-AM, PA12, T19-14×, VT-19-17-H2, yCRE, yCRIP, GP+E-86, GP+envAm12, and DAN cell lines as described in Miller, *Human Gene Therapy* 1:5-14 (1990), which is incorporated herein by reference in its entirety. The vector nay transduce the packaging cells through any means known in the art. Such means include, but are not limited, to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector partiles which include the nucleic acid sequence(s) encoding the polypeptides. Such retroviral vector particles then may be employed, to transduce eukaryotic cells, either in vitro or in vivo The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic: stem cells, hepatocytes, fibroblasts, myoblasts, keratinocytes, endothelial cells, and bronchial epithelial cells.

Diagnostic Assays

This invention is also related to the use of the VEGF-2 gene as part of a diagnostic assay for detecting diseases or susceptibility to diseases related to the presence of mutations in VEGF-2 nucleic acid sequences.

Individuals carrying mutations in the VEGF-2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., *Nature* 324:163-166 (1986)) prior to analysis. RNA or cDNA may also be used for the same purpose. As an example, PCR primers complementary to the nucleic acid encoding VEGF-2 can be used to identify and analyze VEGF-2 mutations. For example, deletions and insertions can be detected by a change in size of the amplified product in comparison to the normal genotype. Point mutations can be identified by hybridizing amplified DNA to radiolabeled VEGF-2 RNA or alternatively, radiolabeled VEGF-2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations may also be revealed by nuclease protection assays, such as RNase and S1 protection or the chemical cleavage method (e.g., Cotton et al., *PNAS, USA* 85:4397-4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of VEGF-2 protein in various tissues since an over-expression of the proteins compared to normal control tissue samples may detect the presence of a disease or susceptibility to a disease, for example, abnormal cellular differentiation. Assays used to detect levels of VEGF-2 protein in a sample derived from a host are well-known to those of skill in the art and include radioimmunoassays, competitive-binding assays, Western Blot analysis, ELISA assays and "sandwich" assay. An ELISA assay (Coligan et al., *Current Protocols in Immunology* 1(2), Chapter 6, (1991)) initially comprises preparing an antibody specific to the VEGF-2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a-non-specific protein, such as, bovine serum albumen. Next, the monoclonal antibody is incubated in the dish during which time the monoclonal antibodies attach to any VEGF-2 proteins attached to the polystyrene dish. All unbound monoclonal antibody is washed out with buffer. The reporter antibody linked to horseradish peroxidase is placed in the dish resulting in binding of the reporter antibody to any monoclonal antibody bound to VEGF-2. Unattached reporter antibody is then washed out. Peroxidase substrates are then added to the dish and the amount of color developed in a given time period is a measurement of the amount of VEGF-2 protein present in a given volume of patient sample when compared against a standard curve.

A competition assay may be employed wherein antibodies specific to VEGF-2 are attached to a solid support. Polypeptides of the present invention are then labeled, for example, by radioactivity, and a sample derived from the host are passed over the solid support and the amount of label detected, for example by liquid scintillation chromatography, can be correlated to a quantity of VEGF-2 in the sample.

A "sandwich" assay is similar to an ELISA assay. In a "sandwich" assay VEGF-2 is passed over a solid support and binds to antibody attached to a solid support. A second antibody is then bound to the VEGF-2. A third antibody which is labeled and specific to the second antibody is then passed over the solid support and binds to the second antibody and an amount can then be quantified.

Chromosome Identification

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with probes from the cDNA as short as 50 or 60 base pairs. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

Antisense

The present invention is further directed to inhibiting VEGF-2 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al., *Nucl. Acids Res.* 6:3073 (1979); Cooney et al., *Science* 241:456 (1988); and Dervan et al. *Science,* 251:1360 (199.1), thereby preventing transcription and the production of VEGF-2. The antisense RNA oligonucleotide hybridizes to the mRNA in vivo and blocks translation of an mRNA molecule into the VEGF-2' (antisense—Okano, *J. Neurochem.* 56:560 (1991); *Oligodeoxynucleotides as Antisense Inhibitors of Gene Expression*, CRC Press, Boca Raton, Fla. (1988)).

Alternatively, the oligonucleotides described above can be delivered to cells by procedures in the art such that the antisense RNA or DNA may be expressed in vivo to inhibit production of VEGF-2 in the manner described above.

Antisense constructs to VEGF-2, therefore, may inhibit the angiogenic activity of the VEGF-2 and prevent the further growth or even regress solid tumors, since angiogenesis and neovascularization are essential steps in solid tumor growth. These antisense constructs may also be used to treat rheumatoid arthritis, psoriasis, diabetic retinopathy and Kaposi's sarcoma which are all characterized by abnormal angiogenesis.

Epitope-Bearing Portions

The present invention encompasses polypeptides comprising, or alternatively consisting of, an epitope of the polypeptide having an amino acid sequence of SEQ ID NO:2, SEQ ID NO:4 or SEQ ID NO:18 (or fragments or variants thereof), or the full length polypeptide (or fragments or variant thereof), encoded by a polynucleotide sequence contained in ATCC deposit Nos. 97149 or 75698 or encoded by a polynucleotide that hybridizes to the complement of the sequence of SEQ ID NOs:1 or 3 or contained in ATCC deposit Nos. 97149 or 75698 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NOs:2, 4, and 18), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

In another aspect, the invention provides peptides and polypeptides comprising epitope-bearing portions of the polypeptides of the present invention as well as polynucleotides encoding these epitopes-bearing portions. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al. (1983) Proc. Natl. Acad. Sci. USA 81:3998-4002. However, antibodies can be made to any antigenic epitope, regardless of whether it is an immunogenic epitope, by using methods such as phage display. See e.g., Petersen G. et al. (1995) Mol. Gen. Genet. 249:425-431. Therefore, included in the present invention are both immunogenic epitopes and antigenic epitopes.

It is particularly pointed out that the immunogenic epitopes comprises predicted critical amino acid residues determined by the Jameson-Wolf analysis. Thus, additional flanking residues on either the N-terminal, C-terminal, or both N- and C-terminal ends may be added to these sequences to generate an epitope-bearing polypeptide of the present invention. Therefore, the immunogenic epitopes may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

Antibodies are preferably prepared from these regions or from discrete fragments in these regions. However, antibodies can be prepared from any region of the peptide as described herein. A preferred fragment produces an antibody that diminishes or completely prevents binding of VEGF-2 to its receptor (e.g., flk-1, or flt-4). Antibodies can be developed against the full length VEGF-2 or portions of the receptor, for example, the secreted form of VEGF-2 polypeptide or any portions of these regions. Antibodies may also be developed against specific functional sites, such as the site of receptor binding or sites that are glycosylated, phosphorylated, myristoylated, or amidated.

Fragments which function as epitopes may be produced by any conventional means. (See, e.g., Houghten, Proc. Natl. Acad. Sci. USA 82:5131-5135 (1985), further described in U.S. Pat. No. 4,631,211).

Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10; 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immunogenic and antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at least 15 contiguous amino acid residues in length could occupy on the amino acid sequence of SEQ ID NO:2, SEQ ID NO:4, or SEQ ID NO:18 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., Antibodies: A Laboratory Manual, (Cold Spring Harbor Laboratory Press; 2nd Ed. 1988).

Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37; 767-778 (1984); Sutcliffe et al., Science 219:660-666 (1983)).

Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10-20 mgs of 248 individual and distinct 13 residue peptides representing single amino acid variants of a segment of the HA1 polypeptide, all of which were prepared and characterized (by ELISA-type binding studies) in less than four weeks (Houghten, R. A. Proc. Natl. Acad. Sci. USA 82:5131-5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously (Houghten et al. (1985) Proc. Natl. Acad. Sci. 82:5131-5135 at 5134.

Epitope bearing peptides of the invention may also be synthesized as multiple antigen peptides (MAPs), first described by J. P. Tam in *Proc. Natl. Acad. Sci. U.S.A.* 85:5409 which is incorporated by reference herein in its entirety. MAPs consist of multiple copies of a specific peptide attached to a non-immunogenic lysine core. Map peptides usually contain four or eight copies of the peptide often refferred to as MAP-4 or MAP-8 peptides. By way of non-limiting example, MAPs may be synthesized onto a lysine core matrix attached to a polyethylene glycol-polystyrene (PEG-PS) support. The peptide of interest is synthesized onto the lysine residues using 9-fluorenylmethoxycarbonyl (Fmoc) chemistry. For example, Applied Biosystems (Foster City, Calif.) offers MAP resins, such as, for example, the Fmoc Resin 4 Branch and the Fmoc Resin 8 Branch which can be used to synthesize MAPs. Cleavage of MAPs from the resin is performed with standard trifloroacetic acid (TFA)-based cocktails known in the art. Purification of MAPs, except for desalting, is not necessary. MAP peptides may be used as an immunizing vaccine which elicits antibodies that recognize both the MAP and the native protein from which the peptide was derived.

Epitope bearing polypeptides of the invention may be modified, for example, by the addition of amino acids at the amino- and/or carboxy termini of the peptide. Such modifications may be performed, for example, to alter the conformation of the epitope bearing polypeptide such that the epitope will have a conformation more closely related to the structure of the epitope in the native protein. An example of a modified epitope-bearing polypeptide of the invention is a polypeptide in which one or more cysteine residues have been added to the polypeptide to allow for the formation of a disulfide bond between two cysteines, resulting in a stable loop structure of the epitope bearing polypeptide under non-reducing conditions. Disulfide bonds may form between a cysteine residue added to the polypeptide and a cysteine residue of the naturally occurring epitope, or may form between two cysteines which have both been added to the naturally occurring epitope bearing polypeptide. Additionally, it is possible to modify one or more amino acid residues of the naturally occurring epitope bearing polypeptide by substituting them with cysteines to promote the formation of disulfide bonded loop structures. Cyclic thioether molecules of synthetic peptides may be routinely generated using techniques known in the art and are described in PCT publication WO 97/46251, incorporated in its entirety by reference herein. Other modifications of epitope-bearing polypeptides contemplated by this invention include biotinylation.

Epitope-bearing polypeptides of the present invention are used to induce antibodies according to methods well known in the art including, but not limited to, in vivo immunization, in vitro immunization, and phage display methods. See, e.g., Sutcliffe et al., supra; Wilson, et al., supra, and Bittle, et al. (1985) J. Gen. Virol. 66:2347-2354. If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides or MAP peptides, for instance, by intraperitoneal and/or intradermal injection of emulsions containing about 100 µgs of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof), may be fused with the constant domain of immunoglobulins (IgA, IgE, IgG; IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1.998, herein incorporated by reference in their entirety)). In a preferred embodiment, polypeptides and/or antibodies of the present invention (including fragments or variants-thereof) are fused with the mature form of human serum albumin (i.e., amino acids 1-585.0f human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO S99/04813). IgG. Fusion proteins that have a disulfide-linked dimeric structure due to the IgG portion desulfide bonds have also been found to be more efficient in binding and neutralizing other molecules, than monomeric polypeptides or fragments thereof alone. See, e.g., Fountoulakis et. al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1 or SEQ ID NO:3 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

The present invention further relates to antibodies and T-cell antigen receptors (TCR) which specifically bind the polypeptides of the present invention polypeptide, polypeptide fragment, or variant of SEQ ID NO:2, SEQ ID NO:4OR SEQ ID NO:18, or the full length polypeptide (or fragments or variant thereof), the pro-protein polypeptide sequence, or the secreted polypeptide encoded by a polynucleotide sequence contained in ATCC deposit Nos. 97149 or 75698, and/or an epitope of the present invention (as determined by immunoassays well known in the art for assaying specific antibody-antigen binding).

The VEGF-2 polypeptides bound by the antibodies of the invention may be in monomers or multimers (i.e., dimers, trimers, tetramers and higher multimers). Accordingly, the present invention relates to antibodies that bind monomers and multimers of the VEGF-2 polypeptides of the invention, their preparation, and compositions (preferably, pharmaceutical compositions) containing them. In specific embodiments, the VEGF-2 polypeptides bound by the antibodies of the invention are monomers, dimers, trimers or tetramers. In additional embodiments, the polypeptides bound by the antibodies of the invention of the invention are at least dimers, at least trimers, or at least tetramers.

Multimeric VEGF-2 bound by the antibodies of the invention may be homomers or heteromers. A VEGF-2 homomer, refers to a multimer containing only VEGF-2 polypeptides (including VEGF-2 fragments, variants, and fusion proteins, as described herein). These homomers may contain VEGF-2 polypeptides having identical or different amino acid sequences. In specific embodiments, the VEGF-2 multimer bound by antibodies of the invention is a homodimer (e.g., containing two VEGF-2 polypeptides having identical or different amino acid sequences) or a homotrimer (e.g., containing three VEGF-2 polypeptides having identical or different amino acid sequences). In a preferred embodiment, the antibodies of the invention bind homotrimers of VEGF-2. In additional embodiments, the homomeric VEGF-2 multimer bound by the antibodies of the invention is at least a homodimer, at least a homotrimer, or at least a homotetramer.

Heteromeric VEGF-2 refers to a multimer containing heterologous polypeptides (i.e., polypeptides of a different protein) in addition to the VEGF-2 polypeptides of the invention. In a specific embodiment, the VEGF-2 multimer bound by the antibodies of the invention is a heterodimer, a heterotrimer, or a heterotetramer. In additional embodiments, the heteromeric VEGF-2 multimer bound by the antibodies of the invention is at least a heterodimer, at least a heterotrimer, or at least a heterotetramer.

VEGF-2 multimers bound by the antibodies of the invention may be the result of hydrophobic, hydrophilic, ionic and/or covalent associations and/or may be indirectly linked, by for example, liposome formation. Thus, in one embodiment, VEGF-2 multimers, such as, for example, homodimers or homotrimers, are formed when polypeptides of the invention contact one another in solution. In another embodiment, VEGF-2 heteromultimers, such as, for example, VEGF-2 heterotrimers or VEGF-2 heterotetrainers, are formed when polypeptides of the invention contact antibodies to the polypeptides of the invention (including antibodies to the heterologous polypeptide sequence in a fusion protein of the invention) in solution. In other embodiments, VEGF-2 multimers are formed by covalent associations with and/or between the VEGF-2 polypeptides of the invention. Such covalent associations may involve one or more amino acid residues contained in the polypeptide sequence (e.g., that recited in SEQ ID NO:2, SEQ ID NO:14 or SEQ ID NO:18). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a VEGF-2 fusion protein. In one example, covalent associations are between the heterologous sequence contained in a fusion protein (see, e.g., U.S. Pat. No. 5,478,925). In a specific example, the covalent associations are between the heterologous sequence contained in a VEGF-2-Fc fusion protein. In another specific example, covalent associations of fusion proteins of the invention are between heterologous polypeptide sequence from another PDGF/VEGF family ligand/receptor member that is capable of forming covalently associated multimers. Examples include those peptide linkers described in U.S. Pat. No. 5,073,627 (hereby incorporated by reference). Proteins comprising multiple VEGF-2 polypeptides separated by peptide linkers may be produced using conventional recombinant DNA technology.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, Fundamental Immunology Ch. 7 (Paul, W., ed., 2nd d. Raven Press, N.Y. (1989)) (incorporated by reference in its entirety for all purposes). The variable regions of each light/ heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the heavy and the ligt chains of each pair are aligned by the framework regions, enabling binding to a specific epitope. From N-terminal to C-terminal, both light and heavy chains comprise the domains FR1, CDR1, FR2; CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196: 901-917 (1987); Chothia et al. Nature 342:878-883 (1989).

A bispecific or bifunctional antibody is an artificial hybrid antibody having two different heavy/light chain pairs and two different binding, sites. Bispecific antibodies can be produced by a variety of methods including fusion of hybridomas or linking of Fab' fragments. See, e.g., Songsivilai & Lachmann Clin. Exp. Immunol. 79: 315-321 (1990), Kostelny et al. J. Immunol. 148:1547 1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" EMBO J. 10:3655-3659 (1991) and Traunecker et al. "Janusin: new molecular design for bispecific reagents" Int J Cancer Suppl 7:51-52 (1992)).

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly-made antibodies (i.e., intrabodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The antibodies of the present invention include IgG (including IgG1, IgG2, IgG3, and IgG4), IgA (including IgA1 and IgA2), IgD, IgE, or IgM, and IgY. In a preferred embodiment, the immunoglobulin is an IgG1 isotype. In another preferred embodiment, the immunoglobulin is an IgG2 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802, WO 91/00360; WO 92/05793; Tutt, A. et al. (1991) J. Immunol: 147:60-69; U.S. Pat. Nos. 5,573,920, 4,474,893, 5,601,819, 4,714,681, 4,925,648; Kostelny, S. A. et al. (1992) J. Immunol. 148:1547-1553.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. In preferred embodiments, the antibodies of the invention bind the full length VEGF-2 protein encoded by a polynucleotide sequence contained in ATCC deposit Nos. 97149 or 75698. In preferred embodiments, the antibodies of the invention bind the pro-protein form of the VEGF-2 protein encoded by a polynucleotide sequence contained in ATCC deposit Nos. 97149 or 75698. In preferred embodiments, the antibodies of the invention bind the secreted VEGF-2 protein encoded by a polynucleotide sequence contained in ATCC deposit Nos. 97149 or 75698. In other preferred embodiments, the antibodies of the invention bind the secreted VEGF-2 protein but not the full length. VEGF-2 protein encoded by a polynucleotide sequence contained in ATCC deposit Nos. 97149 or 75698.

In other preferred embodiments, the antibodies of the invention bind both the secreted form of VEGF-2 protein and the full length VEGF-2 protein encoded by a polynucleotide sequence contained in ATCC deposit Nos. 97149 or 75698.

In other preferred embodiments, the antibodies of the invention bind amino acids 103 to 227 of SEQ ID NO:18. In other embodiments the antibodies of the invention bind dimeric VEGF-2 polypeptides consisting of two polypeptides each consisting of amino acids 103 to 227 of SEQ ID NO:18. In still other preferred embodiments, the antibodies of the invention bind amino acids 112 to 227 of SEQ ID NO:18. In still other embodiments the antibodies of the invention bind dimeric VEGF-2 polypeptides consisting of two polypeptides each consisting of amino acids 112 to 227 of SEQ ID NO:18.

Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 0.80%, less than 75%, less than 70%, less than 65%, less than 60%, less than 55%, and less than 50% identity (as calculated using methods known in the art and described herein) to a polypeptide of the present invention are also included in the present invention. In specific embodiments, antibodies of the present invention cross-react with murine, monkey, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which only bind polypeptides encoded by polynucleotides which hybridize to a polynucleotide of the present invention under stringent hybridization conditions (as described herein).

The antibodies of the invention (including molecules comprising, or alternatively consisting of, antibody fragments or variants thereof) immunospecifically bind to a polypeptide or polypeptide fragment or variant of human VEGF-2 (SEQ ID NO:2, SEQ ID NO:4 OR. SEQ ID NO:18) and/or monkey VEGF-2. Preferably, the antibodies of the invention bind immunospecifically to human VEGF-2. Preferably, the antibodies of the invention bind immunospecifically to human and monkey VEGF-2. Also preferably, the antibodies of the invention bind immunospecifically to human VEGF-2 and murine VEGF-2. More preferably, antibodies of the invention, bind immunospecifically and with higher affinity to human VEGF-2 than to murine VEGF-2.

In preferred embodiments, the antibodies of the present invention (including molecules comprising, or alternatively consisting of, antibody fragments or variants thereof), immunospecifically bind to VEGF-2 and do not cross-react with any other antigens. In preferred embodiments, the antibodies of the invention immunspecifically bind to VEGF-2 and do not cross-react with other members of the VEGF/PDGF family such as, for example, VEGF, VEGF-1, VEGF-3 (VEGF-B), VEGF-4 (VEGF-D), PDGFa or PDGFb.

In other preferred embodiments, the antibodies of the invention immunspecifically bind to VEGF-2 and cross-react with other members of the VEGF/PDGF family such as, for example, VEGF, VEGF-1, VEGF-3 (VEGF-B), VEGF-4 (VEGF-D), PDGFa or PDGFb.

In a preferred embodiment, antibodies of the invention preferentially bind VEGF-2 (SEQ ID NO:2, SEQ ID NO:4OR SEQ ID NO:18), or fragments and variants thereof relative to their ability to bind other antigens, (such as, for example, other chemokine receptors).

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity that is at least one order of magnitude less than the antibody's $K_D$ for the second antigen. In another non-limiting embodiment, an antibody may be considered to bind a first antigen preferentially if it binds said first antigen with an affinity that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with an affinity that is at least one order of magnitude less than the antibody's $k_{off}$ for the second antigen. In another non-limiting embodiment, an antibody may be considered to bind a first antigen preferentially if it binds said first antigen with an affinity that is at least two orders of magnitude less than the antibody's $k_{off}$ for the second antigen.

Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^3$ M, $5\times10^{-4}$ M, $10^{-4}$ M. More preferred binding affinities include those with a dissociation constant or Kd less than $5\times10^{-5}$ M, $10^{-5}$ M, $5\times10^{-6}$ M, $10^{-6}$M, $5\times10^{-7}$ M, $10^{-7}$ M, $5\times10^{-8}$ M or $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-12}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%; at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998) Blood 92(6):1981-1988; Chen, Z. et al. (1998) Cancer Res. 58(16):3668-3678; Harrop, J. A. et al. (1998) J. Immunol. 161(4):1786-1794; Zhu, Z. et al. (1998) Cancer Res. 58(15): 3209-3214; Yoon, D. Y. et al. (1998) J. Immunol. 160(7): 3170-3179; Prat, M. et al. (1998) J. Cell. Sci. 111(Pt2):237-247; Pitard, V. et al. (1997) J. Immunol. Methods 205(2):177-190; Liautard, J. et al. (1997) Cytokinde 9(4):233-241; Carlson, N. G. et al. (1997) J. Biol. Chem. 272(17):11295-11301; Taryman, R. E et al. (1995) Neuron 14(4):755-762; Muller, Y. A. et al. (1998) Structure 6(9):1153-1167; Bartunek, P. et al. (1996) Cytokine 8(1):14-20 (said references incorporated by reference in their entireties).

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to inhibit VEGF-2 binding to its receptor (e.g., flk-1 and/or flt-4) (e.g., see Example 33), the ability to inhibit VEGF-2 induced phosphorylation of Elk-1 (e.g., see Example 35), the ability to inhibit VEGF-2 induced proliferation of vascular and/or lymphatic endothelial cells (e.g., see Example 34), the ability to inhibit angiogenesis (e.g., see Examples 0.16 and 23), and/or the ability to inhibit tumor growth and/or tumor metastasis (e.g., see Examples 37 and 38). Optionally, the antibodies of the invention will bind to the same epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that neutralize VEGF-2, said antibodies comprising, or alternatively consisting of, a portion (e.g., VH CDR1, VH CDR2, VH CDR3, VL CDR1, VL CDR2, and/or VL CDR3) of a VH or VL domain of an scFv referred to in Table 2. An antibody that "neutralizes VEGF-2 or a fragment or variant thereof" is, for example, an antibody that inhibits VEGF-2 binding to its receptor (e.g., flk-1 and/or flt-4) (e.g., see Example 33), inhibits VEGF-2 induced phosphorylation of Elk-1 (e.g., see Example 35), inhibits VEGF-2 induced proliferation of vascular and/or lymphatic endothelial cells (e.g., see Example 34), inhibits angiogenesis (e.g., see Examples 16 and 23), and/or inhibits tumor growth and/or tumor metastasis (e.g., see Examples 37 and 38). In one embodiment, an antibody that neutralizes VEGF-2, comprises, or alternatively consists of, a polypeptide having the amino acid sequence of a VH domain of an scFv referred to in Table 2, or a fragment or variant thereof and a VL domain of an scFv referred to in Table 2, or a fragment or variant thereof. In another embodiment, an antibody that neutralizes VEGF-2, comprises, or alternatively consists of, a polypeptide having the amino acid sequence of a VH domain and a VL domain from a single antibody (or scFv or Fab fragment) of the invention, or fragments or variants thereof. In one embodiment, an antibody that neutralizes VEGF-2, comprises, or alternatively consists of, a polypeptide having the amino acid sequence of a VH domain of an scFv referred to in Table 2, or a fragment or variant thereof. In another embodiment, an antibody that neutralizes VEGF-2, comprises, or alternatively consists of, a polypeptide having the amino acid sequence of a VL domain of an scFv referred to in Table 2, or a fragment or variant thereof. In another embodiment, an antibody that neutralizes VEGF-2 or a fragment or variant thereof, comprises, or alternatively consists of, a polypeptide having the amino acid sequence of a VH CDR domain of an scFv referred to in Table 2, or a fragment or variant thereof. In a preferred embodiment, an antibody that neutralizes VEGF-2 or a fragment or variant thereof, comprises, or alternatively consists of, a polypeptide having the amino acid sequence of a VH CDR3 of an scFv referred to in Table 2, or a fragment or variant thereof. In another embodiment, an antibody that neutralizes VEGF-2 or a fragment or variant thereof, comprises, or alternatively consists of, a polypeptide having the amino acid sequence of a VL CDR of an scFv referred to in Table 2, or a fragment or variant thereof. In another preferred embodiment, an antibody that neutralizes VEGF-2 or a fragment or variant thereof, comprises, or alternatively consists of, a polypeptide having the amino acid sequence of a VL CDR3 of an scFv referred to in Table 2, of a fragment or variant thereof. Nucleic acid molecules encoding these antibodies are also encompassed by the invention.

The present invention also provides for antibodies (including molecules comprising, or alternatively consisting of, antibody fragments or variants thereof), that inhibits VEGF-2 binding to its receptor (e.g., flk-1 and/or flt-4) (e.g. see Example 33). Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an scFv referred to in Table 2 or a fragment or variant thereof. In one embodiment, an antibody that inhibits VEGF-2 binding to its receptor (e.g., flk-1 and/or flt-4) comprises, or alternatively consists of, a polypeptide having the amino acid sequence of a VH domain of an scFv referred to in Table 2, or a fragment or variant thereof and a VL domain of an scFv referred to in Table 2, or a fragment or variant thereof. In another embodiment, an antibody that inhibits VEGF-2 binding to its receptor (e.g., flk-1 and/or flt-4) comprises, or alternatively consists of, a polypeptide having the amino acid sequence of a VH domain and a VL domain from a single antibody (or scFv or Fab fragment) of the invention, or fragments or variants thereof. In one embodiment, an antibody that inhibits VEGF-2 binding to its receptor (e.g., flk-1 and/or flt-4) comprises, or alternatively consists of, a polypeptide having the amino acid sequence of a VH domain of an scFv referred to in Table 2, or a fragment or variant thereof. In another embodiment, an antibody that inhibits VEGF-2 binding to its receptor (e.g., flk-1 and/or flt-4) comprises, or alternatively consists of, a polypeptide having the amino acid sequence of a VL domain of an scFv referred to in Table 2, or a fragment or variant thereof. In a preferred embodiment, an antibody that inhibits VEGF-2 binding to its receptor (e.g., flk-1 and/or flt-4) comprises, or alternatively consists of, a polypeptide having the amino acid sequence of a VH CDR3 of an scFv referred to in Table 2, or a fragment or, variant thereof. In another preferred embodiment, an antibody that inhibits VEGF-2 binding to its receptor (e.g., flk-1 and/or flt-4) comprises, or alternatively consists of, a polypeptide having the amino acid sequence of a VL CDR3 of an scFv referred to in Table 2, or a fragment or variant thereof. Nucleic acid molecules encoding these antibodies ate also encompassed by the invention.

The present invention also provides for antibodies (including molecules comprising, or alternatively consisting of, antibody fragments or variants thereof), that inhibit VEGF-2 induced phosphorylation of Elk-1 as determined by any method known in the art such as, for example, the assays described in Example 35. Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an scFv referred to in Table 2 or a fragment or variant thereof. In one embodiment, an antibody that inhibits VEGF-2 induced phosphorylation of Elk-1, comprises, or alternatively consists of, a polypeptide having the amino acid sequence of a VH domain of an scFv referred to in Table 2, or a fragment or variant thereof and a VL domain of an scFv referred to in Table 2, or a fragment or variant thereof. In another embodiment, an antibody that inhibits VEGF-2 induced phosphorylation of Elk-1, comprises, or alternatively consists of, a polypeptide having the amino acid sequence of a VH domain and a VL domain from a single antibody (or scFv or Fab fragment) of the invention, or fragments or variants thereof. In one embodiment, an antibody that inhibits VEGF-2 induced phosphorylation of Elk-1, comprises, or alternatively consists of, a polypeptide having the amino acid sequence of a VH domain of an scFv referred to in Table 2, or a fragment or variant: thereof. In another embodiment, an antibody that inhibits VEGF-2 induced phosphorylation of Elk-1, comprises, or alternatively consists of, a polypeptide having the amino acid sequence of a VL domain of an scFv referred to in Table 2, or a fragment or variant thereof. In a preferred embodiment, an antibody that inhibits VEGF-2 induced phosphorylation of Elk-1, comprises, or alternatively consists of, a polypeptide having the amino acid sequence of a VH CDR3 of an scFv referred to in Table 2, or a fragment or variant thereof. In another preferred embodiment, an antibody inhibits VEGF-2 induced phosphorylation of Elk-1, comprises, or alternatively consists of, a polypeptide having the amino acid sequence of a VL CDR3 of an scFv referred to in Table 2, or a fragment or variant thereof. Nucleic acid molecules encoding these antibodies are also encompassed by the invention.

The present invention also provides for antibodies (including molecules comprising, or alternatively consisting of, antibody fragments or variants thereof), that inhibit VEGF-2 induced proliferation of vascular and/or lymphatic endothelial cells (e.g., see Example 34). Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an scFv referred to in Table 2 or a fragment or variant thereof. In one embodiment, an antibody that inhibits VEGF-2 induced proliferation of vascular and/or lymphatic endothelial cells, comprises, or alternatively consists of, a polypeptide having the amino acid sequence of a VH domain of an scFv referred to in Table 2, or a fragment or variant thereof and a VL domain of an scFv referred to in Table 2, or a fragment or variant thereof. In another embodiment, an antibody that inhibits VEGF-2 induced proliferation of vascular and/or lymphatic endothelial cells, comprises, or alternatively consists of, a polypeptide having the amino acid sequence of a VH domain and a VL domain from a single antibody (or scFv or Fab fragment) of the invention, or fragments or variants thereof. In one embodiment, an antibody that inhibits VEGF-2 induced proliferation of vascular and/or lymphatic endothelial cells, comprises, or alternatively consists of, a polypeptide having the amino acid sequence of a VH domain of an scFv referred to in Table 2, or a fragment or variant thereof. In another embodiment, an antibody that inhibits VEGF-2 induced proliferation of vascular and/or lymphatic endothelial cells, comprises, or alternatively consists of, a polypeptide having the amino acid sequence of a VL domain of an scFv referred to in Table 2, or a fragment or variant thereof. In a preferred embodiment, an antibody that inhibits VEGF-2 induced proliferation of vascular and/or lymphatic endothelial cells, comprises; or alternatively consists of, a polypeptide having the amino acid sequence of a VH CDR3 of an scFv referred to in Table 2, or a fragment or variant thereof. In another preferred embodiment, an antibody that inhibits VEGF-2 induced proliferation of vascular and/or lymphatic endothelial cells, comprises, or alternatively consists of, a polypeptide having the amino acid sequence of a VL CDR3 of an scFv referred to in Table 2, or a fragment or variant thereof. Nucleic acid molecules encoding these antibodies are also encompassed by the invention.

In highly preferred embodiments, the present invention also provides for antibodies (including molecules comprising, or alternatively consisting of, antibody fragments or variants thereof), that inhibit angiogenesis (e.g., see Examples 16 and 24). Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an scFv referred to in Table 2 or a fragment or variant thereof. In one embodiment, an antibody that inhibits angiogenesis comprises, or alternatively consists of, a polypeptide having the amino acid sequence of a VH domain of an scFv referred to in Table 2, or a fragment or variant thereof and a VL domain of an scFv referred to in Table 2, or a fragment or variant thereof. In another embodiment, an antibody that inhibits angiogenesis comprises, or alternatively consists of, a polypeptide having the amino acid sequence of a VH domain and a VL domain from a single antibody (or scFv or Fab fragment) of the invention, or fragments or variants thereof. In one embodiment, an antibody that inhibits angiogenesis comprises, or alternatively consists of, a polypeptide having the amino acid sequence of a VH domain of an scFv referred to in Table 2, or a fragment or variant thereof. In another embodiment, an antibody that inhibits angiogenesis comprises, or alternatively consists of, a polypeptide having the amino acid sequence of a VL domain of an scFv referred to in Table 2, or a fragment or variant thereof. In a preferred embodiment, an antibody that inhibits angiogenesis comprises, or alternatively consists of, a polypeptide having the amino acid sequence of a VH CDR3 of an scFv referred to in Table 2, or a fragment or variant thereof. In another preferred embodiment, an antibody that inhibits angiogenesis comprises, or alternatively consists of, a polypeptide having the amino acid sequence of a VL CDR3 of an scFv referred to in Table 2, or a fragment or variant thereof. Nucleic acid molecules encoding these antibodies are also encompassed by the invention.

In other highly preferred embodiments, the present invention also provides for antibodies (including molecules comprising, or alternatively consisting of, antibody fragments or variants thereof), that inhibit tumor growth and/or tumor metastasis (e.g., see Examples 37 and 38). Said antibodies may comprise, or alternatively consist of, a portion (e.g., VH CDR1, VH CDR2, VH CDR3, VL CDR1, VL CDR2, or VL CDR3) of a VH or VL domain having an amino acid sequence of an scFv referred to in Table 2 or a fragment or variant thereof. In one embodiment, an antibody that inhibits tumor growth and/or tumor metastasis comprises, or alternatively consists of, a polypeptide having the amino acid sequence of a VH domain of an scFv referred to in Table 2, or a fragment or variant thereof and a VL domain of an scFv referred to in Table 2, or a fragment or variant thereof. In another embodiment, an antibody that inhibits tumor growth and/or tumor metastasis comprises, or alternatively consists of, a polypeptide having the amino acid sequence of a VH domain and a VL domain from a single antibody (or scFv or Fab fragment) of the invention, or fragments or variants thereof. In one embodiment, an antibody that inhibits tumor growth and/or tumor metastasis comprises, or alternatively consists of, a polypeptide having the amino acid sequence of a VH domain of an scFv referred to in Table 2, or a fragment or variant thereof. In another embodiment, an antibody that inhibits tumor growth and/or tumor metastasis comprises, or alternatively consists of, a polypeptide having the amino acid sequence of a VL domain of an scFv referred to in Table 2, or a fragment or variant thereof. In a preferred embodiment, an antibody that inhibits tumor growth and/or tumor metastasis comprises, or alternatively consists of, a polypeptide having the amino acid sequence of a VH CDR3 of an scFv referred to in Table 2, or a fragment or variant thereof. In another preferred embodiment, an antibody that inhibits tumor growth and/or tumor metastasis comprises, or alternatively consists of, a polypeptide having the amino acid sequence of a VL CDR3 of an scFv referred to in Table 2, or a fragment or variant thereof. Nucleic acid molecules encoding these antibodies are also encompassed by the invention.

The present invention also provides for antibodies (including molecules comprising, or alternatively consisting of, antibody fragments or variants thereof), that enhance the activity of VEGF-2, said antibodies comprising, or alternatively consisting of, a portion (e.g., VH CDR1, VH CDR2, VH CDR3, VL CDR1, VL CDR2, or VL CDR3) of a VH or VL domain of an scFv referred to in Table 2, or a fragment or variant thereof. By way of non-limiting example, an antibody that "enhances the activity of VEGF-2 or a fragment or variant thereof" is an antibody increases the ability of VEGF-2 to bind to its receptor (e.g., flk-1.0t flt-4), to stimulate the VEGF-2 signalling cascade (e.g., increase VEGF-2 induced phosphorylation of Elk-1, See Example 35), to induce proliferation of vascular and/or lymphatic endothelial cells (e.g. see Example 34), and or to promote angiogenesis. In one embodiment, an antibody that enhances the activity of VEGF-2, comprises, or alternatively consists of, a polypeptide having the amino acid sequence of a VH domain of an scFv referred to in Table 2, or a fragment or variant thereof and a VL domain of an scFv referred to in Table 2, or a fragment or variant thereof. In another embodiment, an antibody that enhances the activity of VEGF-2, comprises, or alternatively consists of, a polypeptide having the amino acid sequence of a VH domain and a VL domain from a single antibody (or scFv or Fab fragment) of the invention, or fragments or variants thereof. In one embodiment, an antibody that enhances the activity of VEGF-2 or a fragment or variant thereof, comprises, or alternatively consists of, a polypeptide having the amino acid sequence of a VH domain of an scFv referred to in Table 2, or a fragment or variant thereof. In another embodiment, an antibody that enhances the activity of VEGF-2 or a fragment or variant thereof, comprises, or alternatively consists of, a polypeptide having the amino acid sequence of a VL domain of an scFv referred to in Table 2, or a fragment or variant thereof. In another embodiment, an antibody that enhances the activity of VEGF-2 or a fragment or variant thereof, comprises, or alternatively consists of, a polypeptide having the amino acid sequence of a VH CDR domain referred to in of an scFv referred to in Table 2 or a fragment or variant thereof. In a preferred embodiment, an antibody that enhances the activity of VEGF-2 or a fragment or variant thereof, comprises, or alternatively consists of, a polypeptide having the amino acid sequence of a VH CDR3 of an scFv referred to in Table 2, or a fragment or variant thereof. In another embodiment, an antibody that enhances VEGF-2 or a fragment or variant thereof, comprises, or alternatively consists of, a polypeptide having the amino acid sequence of a VL CDR domain of an scFv referred to in Table 2, or a fragment or variant thereof. In another preferred embodiment, an antibody that enhances the activity of VEGF-2 or a fragment or variant thereof, comprises, or alternatively consists of, a polypeptide having the amino acid sequence of a VL CDR3 of an scFv referred to in Table 2, or a fragment or variant thereof. Nucleic acid molecules encoding these antibodies are also encompassed by the invention.

The present invention also provides for fusion proteins comprising, or alternatively consisting of, an antibody (including molecules comprising, or alternatively consisting of, antibody fragments or variants thereof), that immunospecifically binds to VEGF-2, and a heterologous polypeptide. Preferably, the heterologous polypeptide to which the antibody is fused to is useful for function or is useful to target the VEGF-2 antibodies to specific cells (tumor cells, especially prostate, breast, brain or colon cancer cells). In one embodiment, a fusion protein of the invention comprises, or alternatively consists of, a polypeptide having the amino acid sequence of any one or more of the VH domains of an scFv referred to in Table 2 or the amino acid sequence of any one or more of the VL domains of an scFv referred to in Table 2 or fragments or variants thereof, and a heterologous polypeptide sequence. In another embodiment, a fusion protein of the present invention comprises, or alternatively consists of, a polypeptide having the amino acid sequence of any one, two, three, or more of the VH CDRs of an scFv referred to in Table 2, or the amino acid sequence of any one, two, three, or more of the VL CDRs of an scFv referred to in Table 2, or fragments or variants thereof, and a heterologous polypeptide sequence. In a preferred embodiment, the fusion protein comprises, or alternatively consists of, a polypeptide having the amino acid sequence of, a VH CDR3 of an scFv referred to in Table 2, or fragments or variant thereof, and a heterologous polypeptide sequence, which fusion protein immunospecifically binds to VEGF-2. In another embodiment, a fusion protein comprises, or alternatively consists of a polypeptide having the amino acid sequence of at least one VH domain of an scFv referred to in Table 2 and the amino acid sequence of at least one VL domain of an scFv referred to in Table 2 or fragments or variants thereof, and a heterologous polypeptide sequence. Preferably, the VH and VL domains of the fusion protein correspond to a single antibody (or scFv or Fab fragment) of the invention. In yet another embodiment, a fusion protein of the invention comprises, or alternatively consists of a polypeptide having the amino acid sequence of any one, two, three or more of the VH CDRs of an scFv referred to in Table 2 and the amino acid sequence of any one, two, three or more of the VL CDRs of an scFv referred to in Table 2, or fragments or variants thereof, and a heterologous polypeptide sequence. Preferably, two, three, four, five, six, or more of the VHCDR(s) or VLCDR(s) correspond to single antibody (or scFv or Fab fragment) of the invention. Nucleic acid molecules encoding these fusion proteins are also encompassed by the invention.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

By way of another non-limiting example, antibodies of the invention may be administered to individuals as a form of passive immunization. Alternatively, antibodies of the present invention may be used for epitope mapping to identify the epitope(s) bound by the antibody. Epitopes identified in this way may, in turn, for example, be used as vaccine candidates, i.e., to immunize an individual to elicit antibodies against the naturally occurring forms of VEGF-2.

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the invention include derivatives that are modified; i.e, by the covalent attachment of any type of molecule to the antibody. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be prepared by any suitable method known in the art. For example, a polypeptide of the present invention or an antigenic fragment thereof can be administered to an animal in order to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide of techniques known in the art including the use of hybridoma and recombinant technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP2/0 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Another well known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference herein. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV. In general, the sample containing human B cells is innoculated with EBV, and cultured for 3-4 weeks. A typical source of EBV is the culture supernatant of the B95-8 cell line (ATCC #VR-1492). Physical signs of EBV transformation can generally be seen towards the end of the 3-4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human x mouse; e.g, SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41-50; Ames, R. S. et al. (1995) J. Imnunol. Methods 184:177-186; Kettleborough, C. A. et al. (1994) Eur. J. Immunol. 24:952-958; Persic, L. et al. (1997) Gene 187 9-18; Burton, D. R. et al. (1994) Advances in Immunology 57:191-280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. (1992) BioTechniques 12(6):864-869; and Sawai, H. et al. (1995) AJRI 34:26-34; and Better, M. et al. (1988) Science 240:1041-1043 (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46-88; Shu, L. et al. (1993) PNAS 90:7995-7999; and Skerra, A. et al. (1988) Science 240:1038-1040. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) J. Immunol. Methods 125:191-202; and U.S. Pat. Nos. 5,807, 715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.)

Antibodies can be humanized using a variety of techniques including CDR-grafting (EP 0 239-0.400; WO 91/09967; U.S. Pat. Nos. 5,530,101; and 5,585,089), veneering or resurfacing (EP 0 592 106; EP 0 519 596; Padlan. E.A., (1991) Molecular Immunology 28(4/5):489-498; Studnicka G. M. et al. (1994) Protein Engineering 7(6):805-814; Roguska M. A. et al. (1994) PNAS 91:969-973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645 (said references incorporated by reference in their entireties).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO. 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby activate or block its biological activity.

Intrabodies are antibodies, often scFvs, that expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595-601 (1994); Marasco, W.A., *Gene Ther.* 4:11-15 (1997); Rondon and Marasco, *Annu. Rev. Microbiol.* 51:257-283 (1997); Proba et al., *J. Mol. Biol.* 275:245-253 (1998); Cohen et al., Oncogene 17:2445-2456 (1.998); Ohage and Steipe, *J. Mol. Biol.* 291:1119-1128 (1999); Ohage et al., *J. Mol. Biol.* 291:1129-1134 (1999); Wirtz and Steipe, *Protein Sci.* 8:2245-2250 (1999); Zhu et al., *J. Immunol. Methods* 231:207-222 (1999); and references cited therein. In particular, a CCR5 intrabody has been produced by Steinberger et al., *Proc. Natl. Acad. Sci. USA* 97:805-810 (2000).

XenoMouse Technology

Antibodies in accordance with the invention may be prepared the utilizing transgenic mouse that has a substantial portion of the human antibody producing genome inserted but that is rendered deficient in the production of endogenous, murine, antibodies (e.g., XenoMouse strains available from Abgenix Inc., Fremont, Calif.). Such mice, then, are capable of producing human immunoglobulin molecules and antibodies and are deficient in the production of murine immunoglobulin molecules and antibodies. Technologies utilized for achieving the same are disclosed in the patents, applications, and references disclosed herein.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies' can, be expected to provide a substantial advantage in the treatment of chronic and recurring human diseases, such as cancer, which require repeated antibody administrations.

One approach towards this goal was to engineer mouse strains deficierit in mouse antibody production with large fragments of the human Ig loci.in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression, of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 8.0% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J. Exp. Med.* 188:483-495 (1998), Green, *Journal of Immunological Methods* 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/710,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/471,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146-156 (1997) and Green and Jakobovits *J. Exp. Med.* 188:483 495 (1998). See also European Patent No., EP 0 471 151 B1, grant published Jun. 12, 1996; International Patent. Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against VEGF-2 polypeptides in order to vitiate concerns and/or effects of HAMA or HACA responses.

Using phage display technology, the present inventors have identified single chain antibody molecules ("scFvs") that immunospecifically bind to VEGF-2. These scFvs are listed in Table 2. For the scFvs that have been deposited with the American Type Tissue Collection (ATCC), 10801 University Blvd., Manassas, Va. 20110-2209, the ATCC Deposit number and date of deposit are also provided in Table 2. Molecules comprising, or alternatively consisting of, fragments or variants of these scFvs (e.g., including VH domains, VH CDRs, VL domains, or VL CDRs having an amino acid sequence of any one of those referenced to in Table 2), that immunospecifically bind to VEGF-2 (or fragments or variants thereof, including the pro-protein from of VEGF-2 and secreted form of VEGF-2) are also encompassed by the invention, as are nucleic acid molecules that encode these scFvs, and/or molecules.

In particular, the invention relates to scFvs comprising, or alternatively consisting of, an amino acid sequence selected from the group consisting of SEQ ID NOs: 72-78 preferably SEQ ID NOs:72 and 73 as referred to in Table 2 below. Molecules comprising, or alternatively consisting of, fragments or variants of these scFvs (e.g., including VH domains, VH CDRs, VL domains, or VL CDRs having an amino acid sequence of any one of those referred to in Table 2), that immunospecifically bind to VEGF-2 are also encompassed by the invention, as are nucleic acid molecules that encode these scFvs, and/or molecules.

The present invention provides antibodies (including molecules comprising, or alternatively consisting of, antibody fragments or variants thereof) that immunospecifically bind to a polypeptide or a polypeptide fragment of VEGF-2. In particular, the invention provides antibodies corresponding to the scFvs referred to in Table 2, such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule, as described in more detail in Example 32, below.

TABLE 2 scFvs that Immunospecifically bind to VEGF-2

| scFv | scFv SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 | Cell Line Expressing antibody | ATCC ™ Deposit Number | ATCC Deposit Date |
|---|---|---|---|---|---|---|---|---|---|---|---|---|
| 69D09 | 79 | 1-118 | 26-35 | 50-66 | 99-107 | 136-247 | 158-170 | 186-192 | 225-236 | NSO-Mouse Myeloma | PTA-4095 | Feb. 21, 2002 |
| 72D09 | 80 | 1-118 | 26-35 | 50-66 | 99-107 | 135-246 | 157-169 | 185-191 | 224-235 | NSO-Mouse Myeloma | PTA-4442 | Jun. 6, 2002 |
| 25A07 | 81 | 1-118 | 26-35 | 50-66 | 99-107 | 136-247 | 141-153 | 169-175 | 208-219 | NSO-Mouse Myeloma | PTA-4179 | Mar. 25, 2002 |
| 32G10X | 82 | 1-128 | 26-35 | 50-66 | 99-117 | 129-235 | 151-161 | 177-183 | 216-224 | NSO-Mouse Myeloma | PTA-4096 | Feb. 21, 2002 |
| 30E06X | 83 | 1-128 | 26-35 | 50-66 | 99-117 | 129-235 | 151-161 | 177-183 | 216-224 | NSO-Mouse Myeloma | PTA-4180 | Mar. 25, 2002 |
| 17D06 | 72 | 1-122 | 26-35 | 50-66 | 99-110 | 139-250 | 161-173 | 189-195 | 228-239 | | | |
| 16C10 | 73 | 1-129 | 26-35 | 50-66 | 99-117 | 146-252 | 168-178 | 194-200 | 233-241 | | | |
| 16B06 | 74 | 1-122 | 26-35 | 50-66 | 99-110 | 138-247 | 160-173 | 189-196 | 228-238 | | | |
| 19B09 | 75 | 1-124 | 26-37 | 52-67 | 100-112 | 140-251 | 162-175 | 191-197 | 230-240 | | | |

TABLE 2-continued scFvs that Immunospecifically bind to VEGF-2

| scFv | scFv SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 | Cell Line Expressing antibody | ATCC™ Deposit Number | ATCC Deposit Date |
|---|---|---|---|---|---|---|---|---|---|---|---|---|
| 20D05 | 76 | 1-127 | 26-35 | 50-66 | 99-115 | 143-253 | 165-177 | 193-199 | 232-242 | | | |
| 20G02 | 77 | 1-118 | 26-35 | 50-66 | 99-106 | 134-244 | 156-169 | 185-191 | 224-233 | | | |
| 20G11 | 78 | 1-121 | 26-35 | 50-66 | 99-109 | 138-248 | 160-172 | 188-194 | 229-237 | | | |

In one embodiment, the present invention provides the scFv of SEQ ID NO:72 (or fragments or variants thereof). In another embodiment, the present invention provides nucleic acid molecules encoding the scFv of SEQ ID NO:72 (or fragments or variants thereof).

In one embodiment, the present invention provides the scFv of SEQ ID NO:73 (or fragments or variants thereof). In another embodiment, the present invention provides nucleic acid molecules encoding the scFv of SEQ ID NO:73 (or fragments or variants thereof).

In one embodiment, the present invention provides the scFv of SEQ ID NO:74 (or fragments or variants thereof). In another embodiment, the present invention provides nucleic acid molecules encoding the scFv of SEQ ID NO:74 (or fragments or variants thereof).

In one embodiment, the present invention provides the scFv of SEQ ID NO:75 (or fragments or variants thereof). In another embodiment, the present invention provides nucleic acid molecules encoding the scFv of SEQ ID NO:75 (or fragments or variants thereof).

In one embodiment, the present invention provides the scFv of SEQ ID NO:76 (or fragments or variants thereof). In another embodiment, the present invention provides nucleic acid molecules encoding the scFv of SEQ ID NO:76 (or fragments or variants thereof).

In one embodiment, the present invention provides the scFv of SEQ ID NO:77 (or fragments or variants thereof). In another embodiment, the present invention provides nucleic acid molecules encoding the scFv of SEQ ID NO:77 (or fragments or variants thereof).

In one embodiment, the present invention provides the scFv of SEQ ID NO:78 (or fragments or variants thereof). In another embodiment, the present invention provides nucleic acid molecules encoding the scFv of SEQ ID NO:78 (or fragments or variants thereof).

In one embodiment, the present invention provides the scFv of SEQ ID NO:79 (or fragments or variants thereof). In another embodiment, the present invention provides nucleic acid molecules encoding the scFv of SEQ ID NO:79 (or fragments or variants thereof), for example, as found in SEQ ID NO: 84.

In one embodiment, the present invention provides the scFv of SEQ ID NO:80 (or fragments or variants thereof). In another embodiment, the present invention provides nucleic acid molecules encoding the scFv of SEQ ID NO:80 (or fragments or variants thereof), for example, as found in SEQ ID NO: 85.

In one embodiment, the present invention provides the scFv of SEQ ID NO:81 (or fragments or variants thereof). In another embodiment, the present invention provides nucleic acid molecules encoding the scFv of SEQ ID NO:81 (or fragments or variants thereof).

In one embodiment, the present invention provides the scFv of SEQ ID NO:82 (or fragments or variants thereof). In another embodiment, the present invention provides nucleic acid molecules encoding the scFv of SEQ ID NO:82 (or fragments or variants thereof).

In one embodiment, the present invention provides the scFv of SEQ ID NO:83 (or fragments or variants thereof). In another embodiment, the present invention provides nucleic acid molecules encoding the scFv of SEQ ID NO:83 (or fragments or variants thereof).

The present invention encompasses antibodies (including molecules comprising, or alternatively consisting of, antibody fragments or variants thereof) that immunospecifically bind to a VEGF-2 polypeptide or a fragment, variant, or fusion protein thereof. A VEGF-2 polypeptide includes, but is not limited to, the VEGF-2 polypeptide of SEQ ID NO:2, SEQ ID NO:4 OR SEQ ID NO:18 or the polypeptide encoded by the cDNA contained in ATCC Deposit Numbers 97149 or 75698 deposited May 12, 1995 and May 4, 1995, respectively. The VEGF-2 polypeptide bound by the antibodies of the invention may be the full-length protein, the pro-protein, or the secreted form of VEGF-2. VEGF-2 may be produced through recombinant expression of nucleic acids encoding the polypeptides of SEQ ID NO:2, SEQ ID NO:4 OR SEQ ID NO:18, (e.g., the cDNA in ATCC Deposit Numbers 97149 or 75698).

In one embodiment of the present invention, antibodies that immunospecifically bind to a VEGF-2 or a fragment or variant thereof, comprise a polypeptide having the amino acid sequence of any one of the VH domains of the scFvs referred to in Table 2 and/or any one of the VL domains of the scFvs referred to in Table 2. In preferred embodiments, antibodies of the present invention comprise the amino acid sequence of a VH domain and VL domain from the same scFv selected from the group consisting of the scFvs referred to in Table 2 In alternative embodiments, antibodies of the present invention comprise the amino acid sequence of a VH domain and a VL domain from different scFvs referred to in Table 2. Molecules comprising, or alternatively consisting of, antibody fragments or variants of the VH and/or VL domains of the scFvs referred to in Table 2 that immunospecifically bind to a VEGF-2 are also encompassed by the invention, as are nucleic acid molecules encoding these VH and VL domains, molecules, fragments and/or variants.

The present invention also provides antibodies that immunospecifically bind to a polypeptide, or polypeptide fragment or variant of a VEGF-2, wherein said antibodies comprise, or alternatively consist of, a polypeptide having an amino acid sequence of any one, two, three, or more of the VH CDRs contained in a VH domain of one or more scFvs referred to in Table 2. In particular, the invention provides antibodies that immunospecifically bind a VEGF-2, comprising, or alternatively consisting of, a polypeptide having the amino acid sequence of a VH CDR1 contained in a VH domain of one or more scFvs referred to in Table 2. In another embodiment, antibodies that immunospecifically bind a VEGF-2, comprise, or alternatively consist of, a polypeptide having the amino acid sequence of a VH CDR2 contained in a VH domain of one or more scFvs referred to in Table 2. In a preferred embodiment, antibodies that immunospecifically bind a VEGF-2, comprise, or alternatively consist of a polypeptide having the amino acid sequence of a VH CDR3 contained in a VH domain of one or more scFvs referred to in Table 2. Molecules comprising, or alternatively consisting of, these antibodies, or antibody fragments or variants thereof, that immunospecifically bind to VEGF-2 or a VEGF-2 fragment or variant thereof are also encompassed by the invention, as are nucleic acid molecules encoding these antibodies, molecules, fragments and/or variants.

The present invention also provides antibodies that immunospecifically bind to a polypeptide, or polypeptide fragment or variant of a VEGF-2, wherein said antibodies comprise, or alternatively consist of, a polypeptide having an amino acid sequence of any one, two, three, or more of the VL CDRs contained in a VL domain of one or more scFvs referred to in Table 2. In particular, the invention provides antibodies that immunospecifically bind a VEGF-2, comprising, or alternatively consisting of, a polypeptide having the amino acid sequence of a VL CDR1 contained in a VL domain of one or more scFvs referred to in Table 2. In another embodiment, antibodies that immunospecifically bind a VEGF-2, comprise, or alternatively consist of, a polypeptide having the amino acid sequence of a VL CDR2 contained in a VL domain of one or more scFvs referred to in Table 2. In a preferred embodiment, antibodies that immunospecifically bind a VEGF-2, comprise, or alternatively consist of a polypeptide having the amino acid sequence of a VL CDR3 contained in a VL domain of one or more scFvs referred to in Table 2. Molecules comprising, or alternatively consisting of, these antibodies, or antibody fragments or variants thereof, that immunospecifically bind to VEGF-2 or a VEGF-2 fragment or variant thereof are also encompassed by the invention, as are nucleic acid molecules encoding these antibodies, molecules, fragments and/or variants.

The present invention also provides, antibodies (including molecules comprising, or alternatively consisting of, antibody fragments or variants) that immunospecifically bind to a VEGF-2 polypeptide or polypeptide fragment or variant of a VEGF-2, wherein said antibodies comprise, or alternatively consist of, one, two, three, or more VH. CDRs and one, two, three or more VL CDRs, as contained in a VH domain or VL domain of one or more scFvs referred to in Table 2. In particular, the invention provides for antibodies that immunospecifically bind to a polypeptide or polypeptide fragment or variant of a VEGF-2, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a VH domain or VL domain of one or more scFvs referred to in Table 2. In a preferred embodiment, one or more of these combinations are from the same scFv as disclosed in Table 2. Molecules comprising, or alternatively consisting of, fragments or variants of these antibodies, that immunospecifically bind to VEGF-2 are also encompassed by the invention, as are nucleic acid molecules encoding these antibodies, molecules, fragments or variants.

Nucleic Acid Molecules Encoding VEGF-2 Antibodies Corresponding to scFvs.

The present invention also provides for nucleic acid molecules, generally isolated, encoding an antibody of the invention (including molecules comprising, or alternatively consisting of, antibody fragments or variants thereof). In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of the scFvs referred to in Table 2 and a VL domain having an amino acid sequence of any one of the VL domains of the scFvs referred to in Table 2. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of the scFvs referred to in Table 2 or a VL domain having an amino acid sequence of any one of the VL domains of the scFvs referred to in Table 2.

The present invention also provides antibodies that comprise, or alternatively consist of, variants (including derivatives) of the antibody molecules (e.g., the VH domains and/or VL domains) described herein, which antibodies immunospecifically bind to a VEGF-2 or fragments or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino Acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a VEGF-2).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybriodma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind a VEGF-2) can be determined using techniques described herein or by routinely modifying techniques known in the art.

In a specific embodiment, an antibody of the invention (including a molecule comprising, or alternatively consisting of, an antibody fragment or variant thereof), that immunospecifically binds VEGF-2 polypeptides or fragments or variants thereof, comprises, or alternatively consists of, an amino acid sequence encoded by a nucleotide sequence that hybridizes to a nucleotide sequence that is complementary to that encoding one of the VH or VL domains of one or more scFvs referred to in Table 2, under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989*, Current Protocols in Molecular Biology*, Vol. (Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that immunospecifically binds to a VEGF-2 polypeptide or fragments or variants of a VEGF-2 polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of an scFv referred to in Table 2.

In another embodiment, an antibody (including a molecule comprising, or alternatively consisting of, an antibody fragment or variant thereof), that immunospecifically binds to a VEGF-2 polypeptide or fragments or variants of a VEGF-2 polypeptide, comprises, or alternatively consists of, a VL domain having an amino acid sequence that is at least 35%, at least 40%, at least 45% at least 50%, at least 55%, at least 60%, at least 65%, at least 70%, at least 75%, at least 80%, at least 85%, at least 90%, at least 95%, or at least 99% identical, to the amino acid sequence of a VL domain of an scFv referred to in Table 2.

Polynucleotides Encoding Antibodies

Antibodies of the invention (including antibody fragments or variants) can be produced by any method known in the art. For example, it will be appreciated that antibodies in accordance with the present invention, can be expressed in cell lines other than hybridoma cell lines. Sequences encoding the cDNAs or genomic clones for the particular antibodies can be used for transformation of a suitable mammalian or nonmammalian host cells of to generate phage display libraries, for example. Additionally, polypeptide antibodies of the invention may be chemically synthesized or produced through the use of recombinant expression systems.

One way to produce the antibodies of the invention would be to clone the VH and/or VL domains of the scFvs referred to in Table 2. In order to isolate the VH and VL domains from the hybridoma cell lines, PCR primers including VH or VL nucleotide sequences (See Example 32), may be used to amplify the expressed VH and VL sequences expressed by phage. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art.

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH domains may be cloned into vectors expressing the appropriate immunoglobulin constant region, e.g., the human IgG1 or IgG4 constant region for VH domains, and the human kappa or lambda constant regions for kappa and lambda VL domains, respectively.

Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., Immunol. Methods 184:177-86 (1995) which are herein incorporated in their entireties by reference).

The invention further provides polynucleotides comprising a nucleotide sequence encoding an antibody of the invention and fragments thereof. The invention also encompasses polynucleotides that hybridize-under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2, SEQ ID NO:4OR SEQ ID NO:18.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence (See Example 32) or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques; site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties, to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

For some uses, such as for in vitro affinity maturation of an antibody of the invention, it may be useful to express the VH and VL domains of one or more antibodies of the invention as single chain antibodies or Fab fragments in a phage display library. For example, the cDNAs encoding the VH and VL domains of one or more antibodies of the invention may be expressed in all possible combinations using a phage display library, allowing for the selection of VH/VL combinations that bind a VEGF-2 polypeptides with preferred binding characteristics such as improved affinity or improved off rates. Additionally, VH and VL segments—the CDR regions of the VH and VL domains of one or more antibodies of the invention, in particular, may be mutated in vitro. Expression of VH and VL domains with "mutant" CDRs in a phage display library allows for the selection of VH/VL combinations that bind a VEGF-2 receptor polypeptides with preferred binding characteristics such as improved affinity or improved off-rates.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a VEGF-2 polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/O1 134; PCT publications WO 90/02809; WO 91/10737; WO 92/01047; WO 92/18719; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis, by intracellular immunization (i.e., intrabody technology), or preferably, by recombinant expression techniques. Methods of producing antibodies include; but are not limited to, hybridoma technology, EBV transformation, and other methods discussed herein as well as through the use recombinant DNA technology, as discussed below.

Recombinant expression of an antibody of the invention, or fragment, derivative, variant or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule; vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van ieeke & Schuster, J. Biol. Chem. 24:5503-5509 (1989)); and the like pGEX vectors may also be used to express foreign polypeptides as fusion proteins with glutathione S-Transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used, as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be, used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can, be employed in tk-, hgprt- or aprt-cells, respectively. Also, antimetabolite resistance can be used as the basis of selection for the following genes: dhfr, which confers resistance tomethotrexate (Wigler et al., Natl. Acad. Sci. USA 77:357 (1980); O'Hare-et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Sience 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.). Current Protocols in Molecular Biology, John Wiley & Sons. NY (1993); Kriegler; Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host-cell will increase the number of copies of the marker gene. Since the amplified region is associated with the antibody gene, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. Vectors that use glutamine synthase as the selectable marker include, but pre not limited to, the pEE6 expression vector described in Stephens and Cockett, Nucl. Acids. Res 17:7110 (1989). A glutamine synthase expression system and components thereof are detailed in PCT publications: WO87/04462; WO86/05807; WO89/01036; WO89/10404; and WO91/06657 which are incorporated in their entireties by reference herein. Additionally glutamine synthsse expression vectors that may be used according to the present invention are commercially available from suplliers, including, for example Lonza Biologics, Inc. (Portsmouth, N.H.). Expression and production of monoclonal antibodies using a GS expression system in murine myeloma cells is described in Bebbington et al., Bio/technology 10:169 (1992) and in Biblia and Robinson Biotechnol. Prog. 11:1 (1995) which are incorporated in their entirities by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibody Conjugates

Further included in the present invention are antibodies recombinantly fused or chemically conjugated (including both covalently and non-covalently conjugations) to a polypeptide of the present invention. The antibodies may be specific for antigens other than polypeptides of the present invention for example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91-99; U.S. Pat. No. 5,474,981; Gillies, S. O. et al. (1992) PNAS 89:1428-1432; Fell, H. P. et al. (1991) J. Immunol. 146:2446-2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535-10539; Zheng, X. X. et al. (1995) J. Immunol. 154:5590-5600; and Vil, H. et al. (1992) PNAS 89:11337-11341 (said references incorporated by reference in their entireties).

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Polypeptides and/or antibodies of the present invention (including fragments or variants thereof) may be fused to either the N- or C-terminal end of the heterologous protein (e.g., immunoglobulin Fc polypeptide or human serum albumin polypeptide). Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polynucleotides encoding fusion proteins of the invention are also encompassed by the invention. Such fusion proteins may, for example, facilitate purification and may increase half-life in vivo. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146: 2446-2452 (1991), which are incorporated by reference in their entireties.

The present invention further includes compositions comprising the polypeptides of the present invention fused or bonjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present, invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NO:2, SEQ ID NO:4, or SEQ ID NO:18 may be fused or conjugated to the above antibody portions to increase the in vivo half life of the polypeptides or for use in immunoassays using methods known in the art. Further, the polypeptides corresponding to SEQ ID NO:2, SEQ ID NO:4, or SEQ ID NO:18 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{33}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

In specific embodiments, VEGF-2 polypeptides of the invention are attached to macrocyclic chelators useful for conjugating radiometal ions, including but not limited to, $^{111}$In, $^{177}$Lu, $^{90}$Y, $^{166}$Ho, and $^{153}$Sm, to polypeptides. In a preferred embodiment, the radiometal ion associated with the macrocyclic chelators attached to VEGF-2 polypeptides of the invention is $^{111}$In. In another preferred embodiment, the radiometal ion associated with the macrocyclic chelator attached to VEGF-2 polypeptides of the invention is $^{90}$Y. In specific embodiments, the macrocyclic chelator is 1,4,7,10-tetraazacyclododecane-N,N',N'',N'''-tetraacetic acid (DOTA). In other specific embodiments, the DOTA is attached to VEGF-2 polypeptide of the invention via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 Which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties: Though U.S. Pat. Nos. 5,652,361 and 5,756,065 focus on conjugating chelating agents to antibodies, one skilled in the art could readily adapt the methods disclosed therein in order to conjugate. chelating agents to other polypeptides.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, . . . and anthramycin (AMC)), and anti-mitotic agents (e.g., vincristine and vinblastine).

The antibody conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.,* 6:1567-1574 (1994)), VEGI (See, International Publication No. WO 99/23105), a thrombotic agent or an anti-angiogenic agent, e.g, angiostatin or endostatin; or, biological response modifiers such as, for example, lymphokines, interleukin-1 ("L-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as BIAcore analysis (see, e.g., Example 33), FACS (Fluorescence activated cell sorter) analysis, immunofluorescence, immunocytochemistry, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate; incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis: One of skill in the art would be knowledgeable as to the parameters that can be modified to inicrease the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or 1251) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art, would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I), or fragment or variant thereof, with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., compound labeled with $^3$H or $^{125}$I) in the presence of increasing amounts of an unlabeled second antibody. This kind of competitive assay between two antibodies, may also be used to determine if two antibodies bind the same or different epitopes.

In a preferred embodiment, BIAcore kinetic analysis is used to determine the binding on and off rates of antibodies (including antibody fragments or variants thereof) to a VEGF-2, or fragments of VEGF-2 BIAcore kinetic analysis comprises analyzing the binding and dissociation of antibodies from chips with immobilized VEGF-2 on their surface as described in detail in Example 33.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, and anti-retroviral agents. In a highly preferred embodiment, antibodies of the invention may be administered alone or in combination with and anti-angiogenic agents. Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M; $10^{-4}$ M. More preferred binding affinities include those with a dissociation constant or Kd less than $5\times10^{-5}$M, $10^{-5}$M, $5\times10^{-6}$ M, $10^{-6}$M, $5\times10^{-7}$ M, $10^7$ M, $5\times10^{-8}$ M or $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press; NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate knediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation; microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this inary be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity bf: the therapeutic target, i.e., the brain, thus requiring only a fraction of the systemic dose (see, e.g., Goodson, in Medical Applications of Controlled Release, supra, vol. 2, pp. 115-138: (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering, it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a bomeobox like peptide which is known to enter the nucleus (see e.g., Joliot et al., Proc. Natl. Acad. Sci. USA 88:1864-1868, (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived, from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imagine

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide: gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell Biol. 105:3087-3096 (1987)). Other antibody-based methods useful for detecting protein gene expression include immunoassays, such as the enzyme linked imniunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease- or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one-embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined.

Typically, the reporter is an enzyme which is detected by incubating the solid phase in the presence of a suitable fluorometric, luminescent or colorimetric substrate (Sigma; St. Louis, Mo.).

The solid surface reagent in the above assay is prepared by known techniques for attaching protein material to solid support material, such as polymeric beads dip sticks; 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface bound recombinant antigens, and a reporter-labeled anti-human antibody for detecting surface-bound anti-antigen antibody.

Antibodies may further be used in an immunoassay to detect the presence of tumors in certain individuals. Enzyme immunoassay can be performed from the blood sample of an individual. Elevated levels of VEGF-2 can be considered diagnostic of cancer.

Truncated versions of VEGF-2 can also be produced that are capable of interacting with wild type VEGF-2 to form dimers that fail to activate endothelial cell growth, therefore inactivating the endogenous VEGF-2. Or, mutant forms of VEGF-2 form dimers themselves and occupy the ligand binding domain of the proper tyrosine kinase receptors on the target cell surface, but fail to activate cell growth.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of VEGF-2 since Receptor sites are occupied. In these ways; the action of the VEGF-2 is prevented and the antagonist/inhibitors may be used therapeutically as an anti-tumor drug by occupying the receptor sites of tumors which are recognized by VEGF-2 or by inactivating VEGF-2 itself. The antagonist/inhibitors may also be used to prevent inflammation due to the increased vascular permeability action of VEGF-2. The antagonist/inhibitors may also be used to treat solid tumor growth, diabetic retinopathy, psoriasis and rheumatoid arthritis.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently-occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 Fl of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37EC are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.* 8:4057 (1980).

"Oligonucleotides" refer to either a single stranded polydeoxynucleotideor two complementary polydeoxynucleotide strands, which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Sambrook et al., *Molecular Cloning: A Laboratory Manual*, Second Edition, Cold Spring Harbor Laboratory, Cold Spring Harbor, N.Y. (1989), p. 146). Unless otherwise provided, ligation may be accomplished using known buffers and conditions with 10 units of T4 DNA ligase ("ligase") per 0.5 mg of approximately equimolar amounts of the DNA fragments to be ligated.

Unless otherwise stated, transformation was performed as described, by the method of Graham, F. and Van der Eb, A., *Virology* 52:456-457 (1973).

EXAMPLES

Example 1

Expression Pattern of VEGF-2 in Human Tissues and Breast Cancer Cell Lines

Northern blot analysis was carried out to examine the levels of expression of VEGF-2 in human tissues and breast cancer cell lines in human tissues. Total cellular RNA samples were isolated with RNAzol™ B system (Biotecx Laboratories, Inc.). About 10 mg of total RNA isolated from each breast tissue and cell line specified was separated on 1% agarose gel and blotted onto a nylon filter, (Sambrook et al., *Molecular Cloning: A Laboratory Manual*, Second Edition, Cold Spring Harbor Laboratory, Cold Spring Harbor, N.Y. (1989)). The labeling reaction was done according to the Stratagene Prime It kit with 50 ng DNA fragment. The labeled DNA was purified with a Select-G-50 column from 5 Prime÷3 Prime, Inc (Boulder, Colo.). The filter was then hybridized with a radioactive labeled full length VEGF-2 gene at 1,000,000 cpm/ml in 0.5 M $NaPO_4$ and 7% SDS overnight at 65° C. After washing twice at room temperature and twice at 60° C. with 0.5×SSC, 0.1% SDS, the filters were then exposed at −70° C. overnight with an intensifying screen. A message of 1.6 Kd was observed in 2 breast cancer cell lines. FIG. 5, lane #4 represents a very tumorigenic cell line that is estrogen independent for growth.

Also, 10 mg of total RNA from 10 human adult tissues were separated on an agarose gel and blotted onto a nylon filter. The filter was then hybridized with radioactively labeled VEGF-2 probe in 7% SDS, 0.5 M NaPO$_4$, pH 7.2; 1% BSA overnight at 65bC. Following washing in 0.2×SSC at 65° C., the filter was exposed to film for 24 days at −70° C. with intensifying screen. See FIG. 6.

Example 2

Expression of the Truncated Form of VEGF-2 (SEQ ID NO:4) by in vitro Transcription and Translation The VEGF-2 cDNA was transcribed and translated in vitro to determine the size of the translatable polypeptide encoded by the truncated form of VEGF-2 and a partial VEG-2 cDNA. The two inserts of VEGF-2 in the pBluescript SK vector were amplified by PCR with three pairs of primers, 1) M13-reverse and forward primers; 2) M13-reverse primer and VEGF primer F4; and 3) M13-reverse primer and VEGF primer F5. The sequence of these primers are as follows.

M13-2 reverse primer: 5'-ATGCTTCCGGCTCGTATG-3' (SEQ ID NO:9) This sequence is located upstream of the 5' end of the VEGF-2 cDNA insert in the pBlueScript vector and is in an anti-sense orientation as the cDNA. A T3 promoter sequence is located between this primer and the VEGF-2 cDNA.

M13-2 forward primer: 5 GGGTTTTCCCAGTCACGAC-3' (SEQ ID NO:10). This sequence is located downstream of the 3' end of the VEGF-2 cDNA insert in the pBluescript vector and is in an anti-sense orientation as the cDNA insert.

VEGF primer F4: 5'-CCACATGGTTCAGGAAAGACA-3' (SEQ ID NO:11). This sequence is located within the VEGF-2 cDNA in an anti-sense orientation from bp 1259-1239, which is about 169 bp away from the 3' end of the stop codon and about 266 bp before the last nucleotide of the cDNA.

PCR reaction with all three pairs of primers produce amplified products with T3 promoter sequence in front of the cDNA insert. The first and third pairs of primers produce PCR products that encode the polypeptide of VEGF-2 shown in SEQ ID NO:4. The second pair of primers produce PCR product that misses 36 amino acids coding sequence at the C-terminus of the VEGF-2 polypeptide.

Approximately 0.5 mg of PCR product from first pair of primers, 1 mg from second pair of primers, 1 mg from third pair of primers were used for in vitro transcription/translation. The in vitro transcription/translation reaction was performed in a 25 Fl of volume, using the T$_N$TJ Coupled Reticulocyte Lysate Systems (Promega, CAT#L4950). Specifically, the reaction contains 12.5 Fl of T$_N$T rabbit reticulocyte lysate 2 Fl of T$_N$T reaction buffer, 1 Fl of T3 polymerase, 1 Fl of 1 mM amino acid mixture (minus methionine), 4 Fl of $^{35}$S-methionine (>1000 Ci/mmol, 10 mCi/ml), 1 Fl of 40 U/μl; RNasin ribonuclease inhibitor, 0.5 or 1 mg of PCR products. Nuclease-free H$_2$O was added to bring the volume to 25 Fl. The reaction was incubated at 30° C. for 2 hours. Five microliters of the reaction product was analyzed on a 4-20% gradient SDS-PAGE gel. After fixing in 25% isopropanol and 10% acetic acid, the gel was dried and exposed to an X-ray film overnight at 70° C.

Figure 7:
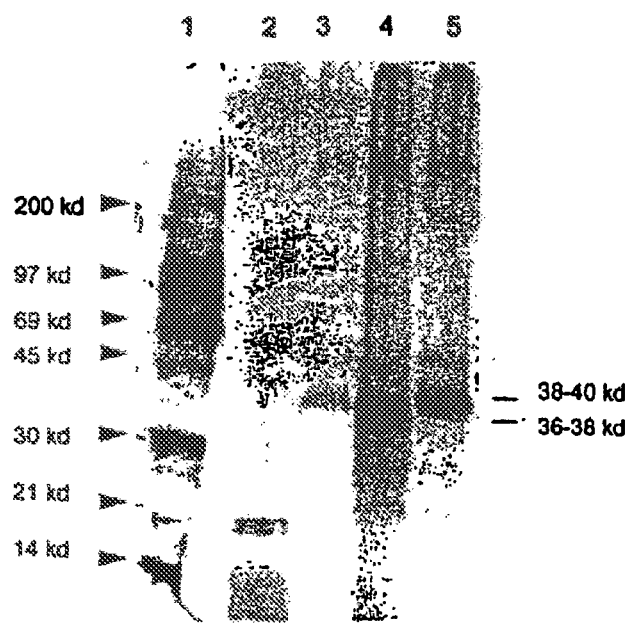
FIG. 7 shows a photograph of an SDS-PAGE gel after in vitro transcription, translation and electrophoresis of the polypeptide of the present invention. Lane 1: $^{14}C$ and rainbow M. W. marker; Lane 2: FGF control; Lane 3: VEGF-2 produced by M13-reverse and forward primers; Lane 4: VEGF-2 produced by M13 reverse and VEGF-F4 primers; Lane 5: VEGF-2 produced by M13 reverse and VEGF-F5 primers.
Figure 8A:
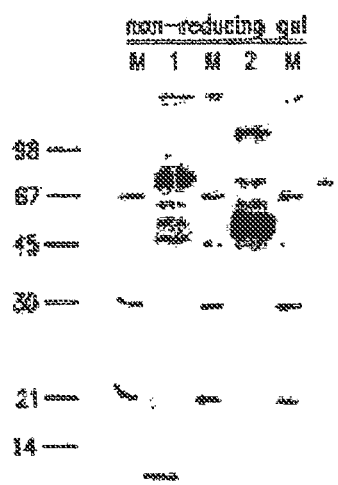
FIGS. 8A-B depict photographs of SDS-PAGE gels. VEGF-2 polypeptide was expressed in a baculovirus system consisting of Sf9 cells. Protein from the medium and cytoplasm of cells were analyzed by SDS-PAGE under non-reducing (FIG. 8A) and reducing (FIG. 8B) conditions.
Figure 8B:
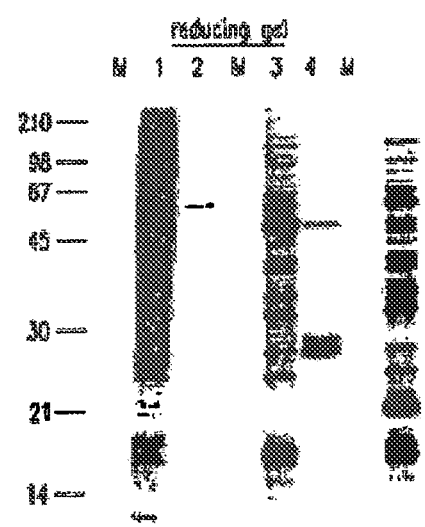

As shown in FIG. 7, PCR products containing the truncated VEGF-2 cDNA (i.e., as depicted in SEQ ID NO:3) and the cDNA missing 266 bp in the 3' un-translated region (3'-UTR) produced the same length of translated products, whose molecular weights are estimated to be 38-40 dk (lanes 1 and 3). The cDNA missing all the 3 UTR and missing sequence encoding the C-terminal 36 amino acids was translated into a polypeptide with an estimated molecular weight of 36-38 kd (lane 2).

Example 3

Cloning and Expression of VEGF-2 Using the Baculovirus Expression System

The DNA sequence encoding the VEGF-2 protein without 46 amino acids at the N-terminus, see ATCC No. 97149, was amplified using PCR oligonucleotide primers corresponding to the 5' and 3' sequences of the gene:

The 5' primer has the sequence TGT AAT ACG ACT CAC TAT AGG GAT CCC GCC ATG GAG GCC ACG GCT TAT GC (SEQ ID NO:12) and contains a BamHI restriction enzyme site (in bold) and 17 nucleotide sequence complementary to the 5' sequence of VEGF-2 (nt. 150-166).

The 3' primer has the sequence GATC TCT AGA TTA GCT CAT TTG TGG TCT (SEQ ID NO:13) and contains the cleavage site for the restriction enzyme XbaI and 18 nucleotides complementary to the 3' sequence of VEGF-2, including the stop codon and 15 nt sequence before stop codon.

The amplified sequences were isolated from a 1% agarose gel using a commercially available kit ("Geneclean,"BIO 101, Inc., La Jolla, Calif.). The fragment was then digested with the endonuclease BamHI and XbaI and then purified again on a 1% agarose gel. This fragment was ligated to pAcGP67A baculovirus transfer vector (Pharmingen) at the BamHI and XbaI sites. Through this ligation, VEGF-2 cDNA was cloned in frame with the signal sequence, of baculovirus gp67 gene and was located at the 3' end of the signal sequence in the vector. This is designated pAcGP67A-VEGF-2.

To clone VEGF-2 with the signal sequence of gp67 gene to the pRGI vector for expression, VEGF-2 with the signal sequence and some upstream sequence were excised from the pAcGP67A-VEGF-2 plasmid at the Xho restriction endonuclease site located upstream of the VEGF-2 cDNA and at the XbaI restriction endonuclease site by XhoI and XbaI restriction enzyme. This fragment was separated from the rest of vector on a 1% agarose gel and was purified using "Geneclean" kit. It was designated F2.

The PRGI vector (modification of pVL941 vector) is used for the expression of the VEGF-2 protein using the baculovirus expression system (for review see: Summers, M. D. and Smith, G. E., "*A Manual of Methods for Baculovirus Vectors and Insect Cell Culture Procedures*," Texas Agricultural Experimental Station Bulletin No. 1555, (1987)). This expression vector contains the strong polyhedrin promoter of the *Autographa californica* nuclear polyhedrosis virus (AcMNPV) followed by the recognition sites for the restriction endonucleases BamHI, SmaI, XbaI, BglII and Asp718. A site for restriction endonuclease XhoI is located upstream of BamHI site. The sequence between XhoI and BamHI is the same as that in PAcGp67A (static on tape) vector. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRGI such as pAc373, pVL941 and pAcIM1 (Luckow, V. A and Summers, M. D., *Virology* 170: 31-39 (1989).

The plasmid was digested with the restriction enzymes XboI and XbaI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E. coli HB101 cells were then transformed and bacteria identified that contained the plasmid (pBac gp67-VEGF-2) with the VEGF-2 gene using the enzymes BamHI and XbaI. The sequence of the cloned fragment was confirmed by DNA sequencing.

5 mg of the plasmid pBac gp67-VEGF-2 was cotransfected with 1.0 mg of a commercially available linearized baculovirus ("BaculoGoldJ baculovirus DNA", Pharmingen, San Diego, Calif.) using the lipofectin method (Felgner et al., Proc. Natl. Acad. Sci. USA 84:7413-7417 (1987)).

1 mg of BaculoGoldJ virus DNA and 5 mg of the plasmid pBac gp67-VEGF-2-were mixed in a sterile well of a microtiter plate containing 50 ml of serum free Grace's mediun (Life Technologies Inc., Gaithersburg, Md.). Afterwards 10 ml Lipofectin plus 90 ml Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith, supra. As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9-10).

Four days after the serial dilution, the virus was added to the cells, blue stained plaques were picked with the tip of an Eppendorf pipette. The agar containing the recombinant viruses was then resuspended in an Eppendorf tube containing 200 ml of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-gp67-VEGF-2 at a multiplicity of infection (MOI) of 1. Six hours later the medium was removed and replaced with SF900 II medium minus methionine and cysteine (Life Technologies Inc., Gaithersburg). 42 hours later 5 mCi of $^{35}$S-methionine and 5 mCi $^{35}$S cysteine (Amersham) were added. The cells were further incubated for 16 hours before they were harvested by centrifugation and the labelled proteins visualized by SDS-PAGE and autoradiography.

Figure 9:
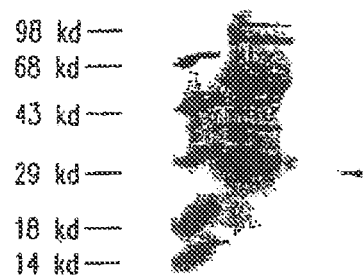
FIG. 9 depicts a photograph of an SDS-PAGE gel. The medium from Sf9 cells infected with a nucleic acid sequence of the present invention was precipitated. The resuspended precipitate was analyzed by SDS-PAGE and stained with Coomassie brilliant blue.

Protein from the medium and cytoplasm of the Sf9 cells was analyzed by SDS-PAGE under non-reducing and reducing conditions. See FIGS. 8A and 8B, respectively. The medium was dialyzed against 50 mM MES, pH 5.8. Precpitates were obtained after dialysis and resuspended in 100 mM NaCltrate, pH 5.0. The resuspended precipitate was analyzed again by SDS-PAGE and was stained with Coomassie Brilliant Blue. See FIG. 9.

Figure 10:
FIG. 10 depicts a photograph of an SDS-PAGE gel. VEGF-2 was purified from the medium supernatant and analyzed by SDS-PAGE in the presence or absence of the reducing agent b-mercaptoethanol and stained by Coomassie brilliant blue.
Figure 11:
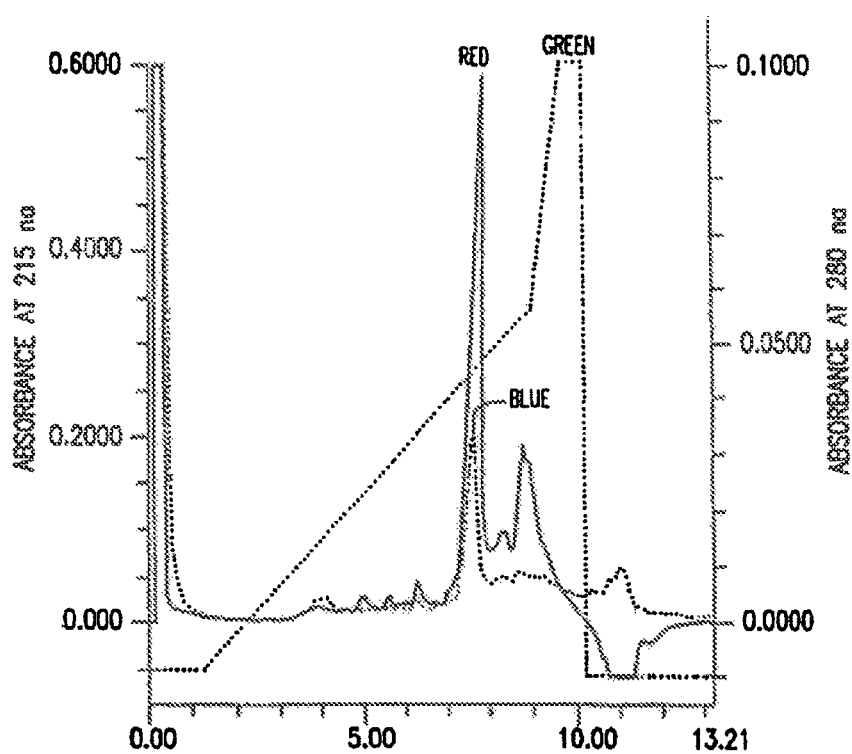
FIG. 11 depicts reverse phase HPLC analysis of purified VEGF-2 using a RP-300 column (0.21×3 cm, Applied Biosystems, Inc.). The column was equilibrated with 0.1% trifluoroacetic acid (Solvent A) and the proteins eluted with a 7.5 min gradient from 0 to 60% Solvent B, composed of acetonitrile containing 0.07% TFA. The protein elution was monitored by absorbance at 215 nm ("red" line) and 280 nm ("blue" line). The percentage of Solvent B is shown by the "green" line.

The medium supernatant was also diluted 1:10 in 50 mM MES, pH 5.8 and applied to an SP-650M column (1.0×6.6 cm, Toyopearl) at a flow rate of 1 ml/min. Protein was eluted with step gradients at 200, 300 and 500 mM NaCl. The VEGF-2 was obtained using the elution at 500 mM. The eluate was analyzed by SDS-PAGE in the presence or absence of reducing agent, b-mercaptoethanol and stained by Coomassie Brilliant Blue. See FIG. 10.

Example 4

Expression of Recombinant VEGF-2 in COS Cells

The expression of plasmid, VEGF-2-HA is derived from a vector pcDNAI/Amp (Invitrogen) containing: 1) SV40 origin of replication, 2) ampicillin resistance gene, 3) E. coli replication origin, 4) CMV promoter followed by a polylinker region, an SV40 intron and polyadenylation site. A DNA fragment encoding the entire VEGF-2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (Wilson et al., Cell 37:767 (1984)). The infusion of HA tag to the target protein allows easy detection of the recombinant protein with an antibody that recognizes the HA epitope. The plasmid construction strategy is described as follows:

The DNA sequence encoding VEGF-2, ATCC No. 97149, was constructed by PCR using two primers: the 5' primer (CGC GGA TCC ATG ACT GTA CTC TAC CCA) (SEQ ID NO:14) contains a BamHI site followed by 18 nucleotides of VEGF-2 coding sequence starting from the initiation codon;

the 3' sequence (CGC TCT AGA TCA AGC GTA GTC TGG GAC GTC GTA TGG GTA CTC GAG GCT CAT TTG TGG TCT 3') (SEQ ID NO:15) contains complementary sequences to an XbaI site, HA tag, XhoI site, and the last 15 nucleotides of the VEGF-2 coding sequence (not including the stop codon).

Therefore, the PCR product contains a BamHI site, coding sequence followed by an XhoI restriction endonuclease site and HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into E. coli strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant VEGF-2, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the VEGF-2-HA protein was detected by radiolabelling and immunoprecipitation method (E. Harlow and D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson et al., Cell 37:767 (1984)). Both cell lysate and culture media were precipitated with an HA specific monoclonal antibody. Proteins precipitated were analyzed on 15% SDS-PAGE gels.

Example 5

The Effect of Partially Purified VEGF-2 Protein on the Growth of Vascular Endothelial Cells On day 1, human umbilical vein endothelial cells (HUVEC) were seeded at $2-5\times10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium was replaced with M199 containing 10% FBS, 8 units/ml heparin. VEGF-2 protein of SEQ ID NO. 2 minus the initial 45 amino acid residues, (VEGF) and basic FGF (bFGF) were added, at the concentration shown. On days 4 and 6, the medium was replaced. On day 8, cell number was determined with a Coulter Counter (See FIG. 12).

Additionally, one of skill in the art could readily modify the above protocol to test the effect of agonists and/or antagonists of VEGF-2 (e.g., VEGF-2 antibodies) on VEGF-2 induced proliferation of HUVEC cells.

Example 6

The Effect of Purified VEGF-2 Protein on the Growth of Vascular Endothelial Cells On day 1, human umbilical vein endothelial cells (HUVEC) were seeded at $2-5\times10^4$ cells/35 mm dish density in M199 medium containing 4% fetal bovine serum (FBS), 16 units/ml heparin, 50 units/ml endothelial cell growth supplements (ECGS, Biotechnique, Inc.). On day 2, the medium was replaced with M199 containing 10% FBS, 8 units/ml heparin. Purified VEGF-2 protein of SEQ ID NO:2 minus initial 45 amino acid residues was added to the medium at this point. On days 4 and 6, the medium was replaced with fresh medium and supplements On day 8, cell number was determined with a Coulter Counter (See FIG. 13).

Additionally, one of skill in the art could readily modify the above protocol to test the effect of agonists and/or antagonists of VEGF-2 (e.g., VEGF-2 antibodies) on VEGF-2 induced proliferation of HUVEC cells.

Example 7

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA* 7:219-225 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained undet conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 8

Expression of VEGF-2 mRNA in Human Fetal and Adult Tissues

Experimental Design

Northern blot analysis was carried out to examine the levels of expression of VEGF-2 mRNA in human fetal and adult tissues. A cDNA probe containing the entire nucleotide sequence of the VEGF-2 protein was labeled with $^{32}P$ using the rediprime° DNA labeling system (Amersham Life Science), according to the manufacturer's instructions. After labeling, the probe was purified using a CHROMA SPIN-100* column (Clontech Laboratories, Inc.), according to manufacturer's protocol number PT1200-1. The purified labeled probe was then used to examine various human tissues for VEGF-2 mRNA.

A Multiple Tissue Northern (MTN) blot containing various human tissues (Fetal Kidney, Fetal Lung, Fetal Liver, Brain, Kidney, Lung, Liver, Spleen, Thymus, Bone Marrow, Testes, Placenta, and Skeletal Muscle) was obtained from Clontech. The MTN blot was examined with the labeled probe using ExpressHyb* hybridization solution (Clontech) according t6 manufacturer's protocol number PT1190-1. Following hybridization and washing, the blot was exposed to film at −70° C. overnight with an intensifying screen and developed according to standard procedures.

Results

Figure 14A:
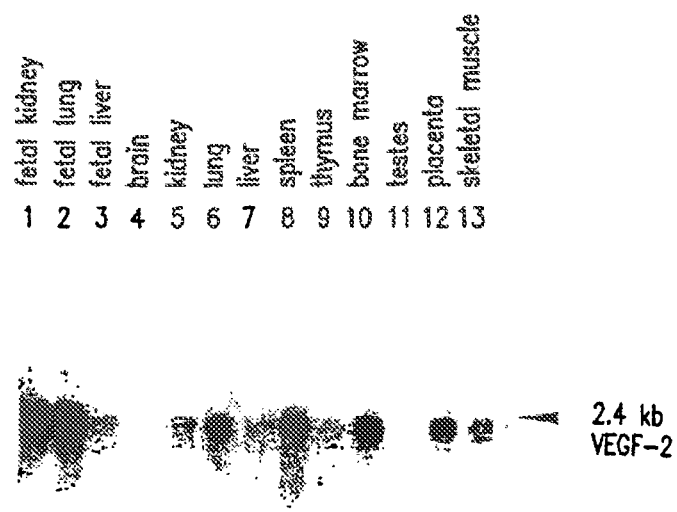
FIGS. 14A-14B depict expression of VEGF-2 mRNA in human fetal and adult tissues.
Figure 14B:
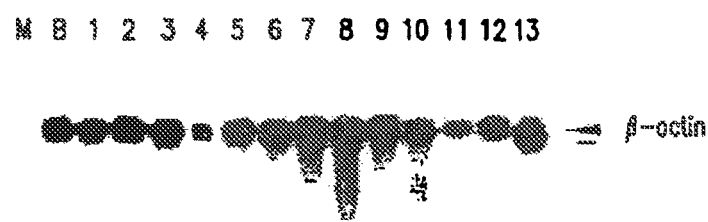

Expression of VEGF-2 mRNA is abundant in vascular smooth muscle and several highly vascularized tissues. VEGF-2 is expressed at significantly higher levels in tissues associated with hematopoetic or angiogenic activities, i.e. fetal kidney, fetal lung, bone marrow, placental, spleen and lung tissue. The expression level of VEGF-2 is low in adult kidney, fetal liver, adult liver, testes; and is almost undetectable in fetal brain, and adult brain (See FIGS. 14A-B).

Figure 15:
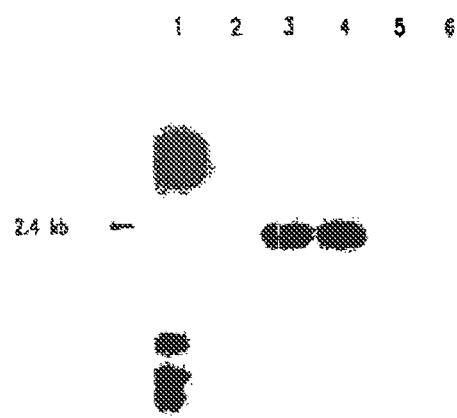
FIG. 15 depicts expression of VEGF-2 mRNA in human primary culture cells.

In primary cultured cells, the expression of VEGF-2 mRNA is abundant in vascular smooth muscle cells and dermal fibroblast cells, but much lower in human umbilical vein endothelial cells (see FIG. 15). This mRNA distribution pattern is very similar to that of VEGF.

Example 9

Construction of Amino Terminal and Carboxy Terminal Deletion Mutants

In order to identify and analyze biologically active VEGF-2 polypeptides, a panel of deletion mutants of VEGF-2 was constructed using the expression vector pHE4a.
1. Construction of VEGF-2 T103-L215 in pHE4

To permit Polymerase Chain Reaction directed amplification and sub-cloning of VEGF-2 T103-L215 (amino acids 103 to 215 in FIG. 1 or SEQ ID NO:18) into the *E. coli* protein expression vector, pHE4, two oligonucleotide primers complementary to the desired region of VEGF-2 were synthesized with the following base sequence:

```
5'Primer (Nde I/START and 18 nt of
coding sequence):
                                (SEQ ID NO: 19)
5'-GCA GCA CAT ATG ACA GAA GAG ACT

ATA AAA-3';

3'Primer (Asp718, STOP, and 15 nt of
coding sequence):
                                (SEQ ID NO: 20)
5'-GCA GCA GGT ACC TCA CAG TTT AGA

CAT GCA-3'.
```

The above described 5' primer (SEQ ID NO: 19), incorporates an NdeI restriction site and the above described 3' Primer (SEQ ID NO:20), incorporates an Asp718 restriction site. The 5' primer (SEQ ID NO:19) also contains an ATG sequence adjacent and in frame with the VEGF-2 coding region to allow translation of the cloned fragment in *E. coli*, while the 3' primer (SEQ ID NO:20) contains one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the ar and the nucleotide sequence for the mature VEGF-2 (aa 24-419 in SEQ ID NO:18) as, for example, constructed in Example 3 as template. The resulting amplicon was restriction digested with NdeI and Asp718 and subcloned into NdeI/Asp718 digested pHE4a expression vector.
2. Construction of VEGF-2 T103-R227 in pHE4

To permit Polymerase Chain Reaction directed amplification and sub-cloning of VEGF-2 T103-R227 (amino acids 103 to 227 in FIG. 1 or SEQ ID NO:18) into the *E. coli* protein expression vector, pHE4, two oligonucleotide primers complementary to the desired region of VEGF-2 were synthesized with the following base sequence:

```
5'Primer (Nde I/START and 18 nt
of coding sequence):
                                (SEQ ID NO: 19)
5'-GCA GCA CAT ATG ACA GAA

GAG ACT ATA AAA-3';

3'Primer (Asp 718, STOP, and 15 nt
of coding sequence):
                                (SEQ ID NO: 21)
5'-GCA GCA GGT ACC TCA

ACG TCT AAT AAT GGA-3',
```

In the case of the above described primers, an NdeI or Asp718 restriction site was incorporated be 5' primer and 3' primer, respectively. The 5' primer (SEQ ID NO:19) also contains an ATG sequence adjacent and in frame with the VEGF-2 coding region to allow translation of the cloned fragment in *E. coli*, while the 3' Primer (SEQ ID NO:21) contains one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the art and the nucleotide sequence for the mature VEGF-2 (aa 24-419 in SEQ ID NO:18) as, for example, constructed in Example 3, as template. The resulting amplicon was restriction digested with NdeI and Asp718 and subcloned into NdeI/Asp718 digested pHE4a protein expression vector.
3. Construction of VEGF-2 T103-L215 in pA2GP In this illustrative example, the plasmid shuttle vector pA2 GP is used to insert the cloned DNA encoding the N-terminal and C-terminal deleted VEGF-2 protein (amino acids 103-215 in FIG. 1 or SEQ ID NO:18), into a baculovirus to express the N-terminal and C-terminal deleted VEGF-2 protein, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39 (1989).

The cDNA sequence encoding the VEGF-2 protein without 102 amino acids at the N-terminus and without 204 amino acids at the C-terminus in FIG. 1, was amplified using PCR oligonucleotide primers corresponding to the 5' and 3' sequences of the gene.

The 5' primer has the sequence 5'-GCA: GCA GGA TCC CAC AGA AGA GAC TAT AAA-3' (SEQ ID NO:22) containing the BamHI restriction enzyme site (in bold) followed by 1 spacer nt to stay in-frame with the vector-supplied signal peptide, and 17 nt of coding sequence bases of VEGF-2 protein. The 3' primer has the sequence, 5'-GCA GCA TCT AGA TCA CAG TTT AGA CAT GCA-3' (SEQ ID NO:23) containing the XbaI restriction site (in bold) followed by a stop codon and 17 nucleotides complementary to the 3' coding sequence of VEGF-2.

The amplified sequences were isolated from a 1% agarose gel using a commercially available kit ("Geneclean," BIO 101, Inc., La Jolla, Calif.). The fragment was then digested with the endonuclease. BamHI and XbaI and then purified again on a 1% agarose gel. This fragment was ligated to pA2 GP baculovirus transfer vector (Supplier) at the BamHI and XbaI sites. Through this ligation, VEGF-2 cDNA representing the N-terminal and C-terminal deleted VEGF-2 protein (amino-acids 103-215 in FIG. 1 or SEQ ID NO:18) was cloned in frame with the signal sequence of baculovirus GP gene and was located at the 3' end of the signal sequence in the vector. This is designated pA2GPVEGF-2.T103-L215.

4. Construction of VEGF-2 T103-R227 in pA2GP

The cDNA sequence encoding the VEGF-2 protein without 102 amino acids at the N-terminus and without 192 amino acids at the C-terminus in FIG. 1 (i.e., amino acids 103-227 of SEQ ID NO:18) was amplified using PCR oligonucleotide primers corresponding to the 5' and 3' sequences of the gene.

The 5'-GCA GCA GGA TCC CAC AGA AGA GAC TAT AAA ATT TGC TGC-3' primer has the sequence (SEQ ID NO:24) containing the BamHI restriction enzyme site (in bold) followed by 1 spacer nt to stay in-frame with the vector-supplied signal peptide, and 26 nt of coding sequence bases of VEGF-2 protein. The 3' primer has the sequence 5'-GCA GCA TCT AGA TCA ACG TCT AA AAT GGA ATG AAC-3' (SEQ ID NO:25) containing the XbaI restriction site (in bold) followed by a stop codon and 21 nucleotides complementary to the 3' coding sequence of VEGF-2.

The amplified sequences were isolated from a 1% agarose gel using a commercially available kit ("Geneclean," BIO 101, Inc., La Jolla, Calif.). The fragment was then digested with the endonuclease BamHI and XbaI and then purified again on a 1% agarose gel. This fragment was ligated to pA2 GP baculovirus transfer vector (Supplier) at the BamHI and XbaI sites. Through this ligation, VEGF-2 cDNA representing the N-terminal and C-terminal deleted VEGF-2 protein (amino acids 103-227 in FIG. 1 or SEQ ID NO:18) was cloned in frame with the signal sequence of baculovirus GP gene and was located at the 3' end of the signal sequence in the vector. This construct is designated pA2GPVEGF-2.T103-R227.

5. Construction of VEGF-2 in pC1

The expression vectors pC 1 and pC4 contain the strong promoter (LTR) of the Rous Sarcoma Virus (Cullen et al., *Molecular and Cellular Biology*, 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3N intron, the polyadenylation and termination signal of the rat preproinsulin gene.

The vector pC1 is used for the expression of VEGF-2 protein. Plasmid pC1 is a derivative of the plasmid pSV2-dhfr [ATCC Accession No. 37146]. Both plasmids contain the mouse DHFR gene under control of the SV40 early promoter.

Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L and Ma, C. 1990, *Biochem et Biophys. Acta,* 1097:107-143, Page, M. J and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., *Molecular and Cellular Biology*, March 1985:438-4470) plus a fragment isolated from the enhancer of the immediate early gene of human cytomegalovirus (CMV) (Boshart et al., *Cell* 41:521-530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3N intron and the polyadenylation site of the rat preproinsulin gene. Other high efficient promoters can also be used for the expression, e.g., the human b-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel;

The DNA sequence encoding VEGF-2, ATCC Accession No. 97149, was constructed by PCR using two primers corresponding to the 5' and 3' ends of the VEGF-2 gene:

```
the 5'Primer (5'-GAT CGA TCC ATC ATG CAC

TCG CTG GGC TTC TTC TCT GTG GCG TGT TCT

CTG CTC G-3'(SEQ ID NO: 26))
contains a Klenow-filled BamHI site and 40 nt
of VEGF-2 coding sequence starting from the
initiation codon;

the 3'primer (5'-GCA GGG TAC GGA TCC TAG

ATT AGC TCA TTT GTG GTC TTT-3'(SEQ ID NO: 27))
contains a BamHI site and 16 nt of VEGF-2 coding
sequence not including the stop codon.
```

The PCR amplified DNA fragment is isolated from a 1% agarose gel as described above and then digested with the endonuclease BamHI and then purified again on a 1% agarose gel. The isolated fragment and the dephosphorylated vector are then ligated with T4 DNA ligase. *E. coli* HB101 cells are then transformed and bacteria identified that contained the plasmid pC1. The sequence and orientation of the inserted gene is confirmed by DNA sequencing. This construct is designated pC1VEGF-2.

6. Construction of pC4SigVEGF-2 T103-L215

Plasmid pC4Sig is plasmid pC4 (Accession No. 209646) containing a human IgG Fc portion as well as a protein signal sequence.

To permit Polymerase Chain Reaction directed amplification and subcloning of VEGF-2 T103-L215 (amino acids 103 to 215 in FIG. 1 or SEQ ID NO:18) into pC4Sig, two oligonucleotide primers complementary to the desired region of VEGF-2 were synthesized with the following base sequence:

```
5'Primer (Bam HI and 26 nt of
coding sequence):
                             (SEQ ID NO: 34)
5'-GCA GCA GGA TCC ACA GAA GAG

ACT ATA AAA TTT OCT GC-3';

3'Primer (Xba I, STOP, and 15 nt of
coding sequence):
                             (SEQ ID NO: 35)
5'-CGT COT TCT AGA TCA CAG

TTT AGA CAT GCA TCG GCA G-3'.
```

The Polymerase Chain Reaction was performed using standard conditions well known to those skilled in the art and the nucleotide sequence for the mature VEGF-2 (aa 24-419) as, for example, constructed in Example 3, as template. The resulting ampliicon was restriction digested with BamHI and XbaI and subcloned into BamHI XbaI digested pC4Sig vector.

7. Construction of pC4SigVEGF-2 T103-R227

To permit Polymerase Chain Reaction directed amplification and sub-cloning of VEGF-2 T103-L215 (amino acids 103 to 227 in FIG. 1 or SEQ ID NO:18) into pC4Sig, two oligonucleotide primers complementary to the desired region of VEGF-2 were synthesized with the following base sequence:

```
5'Primer (Bam HI and 26 nt of
coding sequence):
                             (SEQ ID NO: 34)
5'-GCA GCA GGA TCC ACA GAA GAG

ACT ATA AAA TTT GCT GC-3';

3'Primer (Xba I, STOP, and 21
nt of coding sequence):
                             (SEQ ID NO: 25)
5'-GCA GCA TCT AGA TCA ACG

TCT AAT AAT GGA ATG AAC-3'.
```

The Polymerase Chain Reaction was performed using standard conditions well known to those skilled in the art and the nucleotide sequence for the mature VEGF-2 (aa 24-419) as, for example, constructed in Example 3, as template. The resulting amplicon was restriction digested with BamHI and XbaI and subcloned into BamHI XbaI digested pC4Sig vector.

8. Construction of pC4VEGF-2 M1-M263

The expression vector pC4 contains the strong promoter (LTR) of the Rous Sarcoma Virus (Cullen et al., *Molecular and Cellular Biology*, 438-447 (March, 1985)) plus a fragment of the CMV-enhancer (Boshart et. al., Cell 41:521-530 (1985)). Multiple cloning sites, e.g., with the restriction enzyme cleavage sites BamHI, XbaI and Asp718, facilitate the cloning of the gene of interest. The vector contains in addition the 3N intron, the polyadenylation and termination signal of the rat preproinsulin gene.

In this illustrative example, the cloned DNA encoding the C-terminal deleted VEGF-2 M1-M263 protein (amino acids 1-263 in FIG. 1 or SEQ ID NO:18) is inserted into the plasmid vector pC4 to express the C-terminal deleted VEGF-2 protein.

To permit Polymerase Chain Reaction directed amplification and sub-cloning of VEGF-2 M1-M263 into the expression vector, pC4, two oligonucleotide primers complementary to the desired region of VEGF-2 were synthesized with the following base sequence:

```
5'Primer
                             (SEQ ID NO: 28)
5'-GAC TGG ATC CGC CAC CAT GCA

CTC GCT GGG CTT CTT CTC-3';

3'Primer
                             (SEQ ID NO: 29)
5'-GAC TGG TAC CTT ATC ACA TAA

AAT CTT CCT GAG CC-3'.
```

In the case of the above described 5' primer, an BamHI restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in *E. coli*, while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction digested with BamHI and Asp718 and subcloned into BamHI/Asp718 digested pC4 protein expression vector. This construct is designated pC4VEGF-2 M1-M263.

9. Construction of pC4VEGF-2 M1-D311

In this illustrative example, the cloned DNA encoding the C-terminal deleted VEGF-2 M1-D311 protein (amino acids 1-311 in FIG. 1 or SEQ ID NO:18) is inserted into the plasmid vector pC4 to express the C-terminal deleted VEGF-2 protein.

To permit Polymerase Chain Reaction directed amplification and sub-cloning of VEGF-2 M1-D311 into the expression vector, pC4, two oligonucleotide primers complementary to the desired region of VEGF-2 were synthesized with the following base sequence:

```
5'Primer
                             (SEQ ID NO: 30)
5'-GAC TGG ATC CGC CAC CAT GCA

CTC GCT GGG CTT CTT-3';

3'Primer
                             (SEQ. ID NO: 31)
5'-GAC TGG TAC CTT ATC AGT CTA

GTT CTT TGT GGG G-3'.
```

In the case of the above described 5' primer, an BamHI restriction site was incorporated while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in E: coli, while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction digested with BamHI and Asp718 and subcloned into BamHI/Asp718 digested pC4 protein expression vector.

10. Construction of pC4VEGF-2 M1-Q367

In this illustrative example, the cloned DNA encoding the C-terminal deleted VEGF-2 M1-Q367 protein (amino acids 1-367 in SEQ ID NO:18) is inserted into the plasmid vector pC4 to express the C-terminal deleted VEGF-2 protein.

To permit Polymerase Chain Reaction directed amplification and sub-cloning of VEGF-2 M1-Q367 into the expression vector, pC4, two oligonucleotide primers complementary to the desired region of VEGF-2 were synthesized with the following base sequence:

```
5'Primer
                                  (SEQ ID NO: 32)
5'-GAC TGG ATC CGC CAC CAT GCA

CTC GCT GGG CTT CTT CTC-3';

3'Primer
                                  (SEQ ID NO: 33)
5'-GAC TGG TAC CTC ATT ACT GTG

GAC TTT CTG TAC ATT C-3'.
```

In the case of the above described 5' primer, an BamHI restriction site was incorporated, while in the case of the 3' primer, an Asp718 restriction site was incorporated. The 5'primer also contains 6 nt, 20 nt of VEGF-2 coding sequence, and an ATG sequence adjacent and in frame with the VEGF-2 coding region to allow translation of the cloned fragment in *E. coli*, while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli*.

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction digested with BamHI and Asp718 and subcloned into BamH Asp718 digested pC4 protein expression vector. This construct is designated pC4VEGF-2 M1-Q367.

Example 10

Transient Expression of VEGF-2 Protein in COS-7 Cells

Experimental Design

Expression of the VEGF-2-HA fusion protein from the construct made in Example 4, for example, was detected by radiolabeling and immunoprecipitation, using methods described in, for example Harlow and colleagues (Antibodies: A Laboratory Manual, 2nd Ed.; Cold Spring Harbor Laboratory Press, Cold Spring Harbor, N.Y. (1988)). To this end, two days after transfection, the cells were labeled by incubation in media containing 35S-cysteine for 8 hours. The cells and the media were collected, and the cells were washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson and colleagues (supra). Proteins were precipitated from the cell lysate and from the culture media using an HA-specific monoclonal antibody. The precipitated proteins then were analyzed by SDS-PAGE and autoradiography.

Results

Figure 16A:
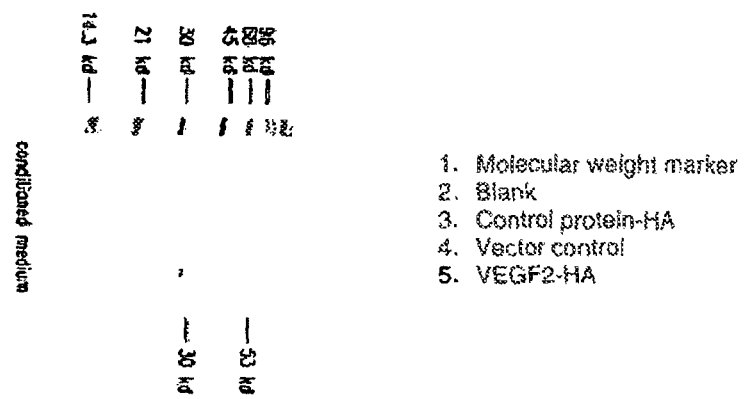
FIGS. 16A-B depict transient expression of VEGF-2 protein in COS-7 cells.
Figure 16B:
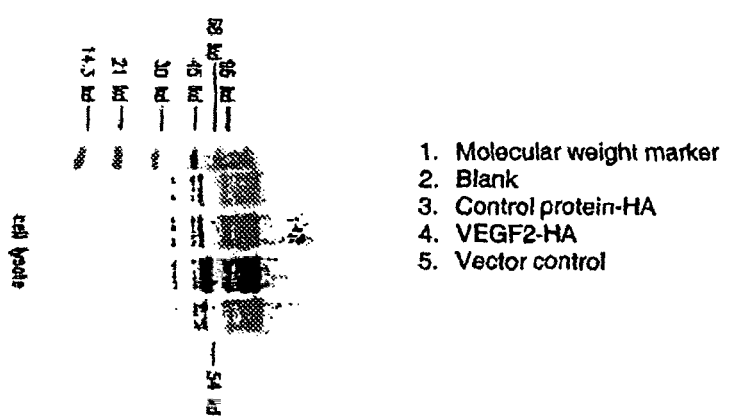

As shown in FIGS. 16A-B, cells transfected with pcDNA VEGF-2HA secreted a 56 kd and a 30 kd protein. The 56 kd protein, but not the 30 kd protein, could also be detected in the cell lysate but is not detected in controls. This suggests the 30 kd protein is likely to result from cleavage of the 56 kd protein. Since the HA-tag is on the C-terminus of VEGF-2, the 30 kd protein must represent the C-terminal portion of the cleaved protein, whereas the N-terminal portion of the cleaved protein would not be detected by immunoprecipitation. These data indicate that VEGF-2 protein expressed in mammalian cells is secreted and processed.

Example 11

Stimulatory Effect of VEGF-2 on Proliferation of Vascular Endothelial Cells

Experimental Design

Expression of VEGF-2 is abundant in highly vascularized tissues. Therefore the role of VEGF-2 in regulating proliferation of several types of endothelial cells was examined.

Endothelial Cell Proliferation Assay

For evaluation of mitogenic activity of growth factors, the colorimetric MTS (3-(4,5-dimethylthiazol-2-yl)-5-(3-carboxymethoxyphenyl)-2-(4-sulfophenyl)$_2$H-tetrazolium) assay with the electron coupling reagent PMS (phenazine methosulfate) was performed (CellTiter 96 AQ, Promega). Cells were seeded in a 96-well plate (5,000 cells/well) in 0.1 mL serum-supplemented medium and allowed to attach overnight. After serum-starvation for 12 hours in 0.5% FBS, conditions (bFGF, VEGF$_{165}$ or VEGF-2 in 0.5% FBS) with or without Heparin (8 U/ml) were added to wells for 48 hours. 20 mg of MTS/PMS mixture (1:0.05) were added per well and allowed to incubate for 1 hour at 37° C. before measuring the absorbance at 490 nm in an ELISA plate reader. Background absorbance from control wells (some media, no cells) was subtracted, and seven wells were performed in parallel for each condition. See, Leak et al. *In Vitro Cell. Dev. Biol.* 30A:512-518 (1994)

Results

Figure 17:
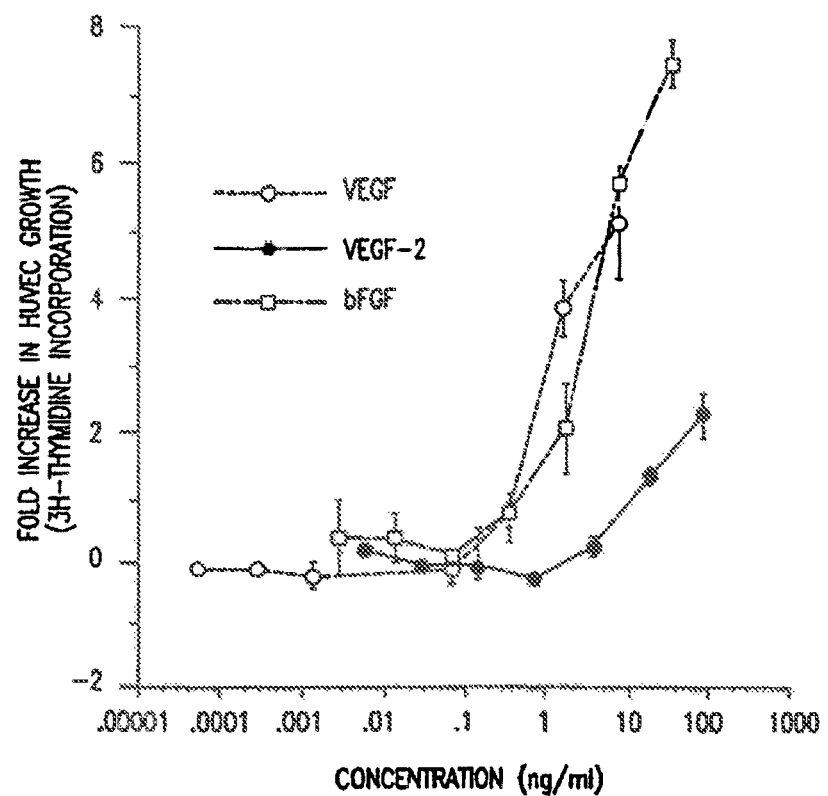
FIG. 17 depicts VEGF-2 stimulated proliferation of human umbilical vein endothelial cells (HUVEC).
Figure 18:
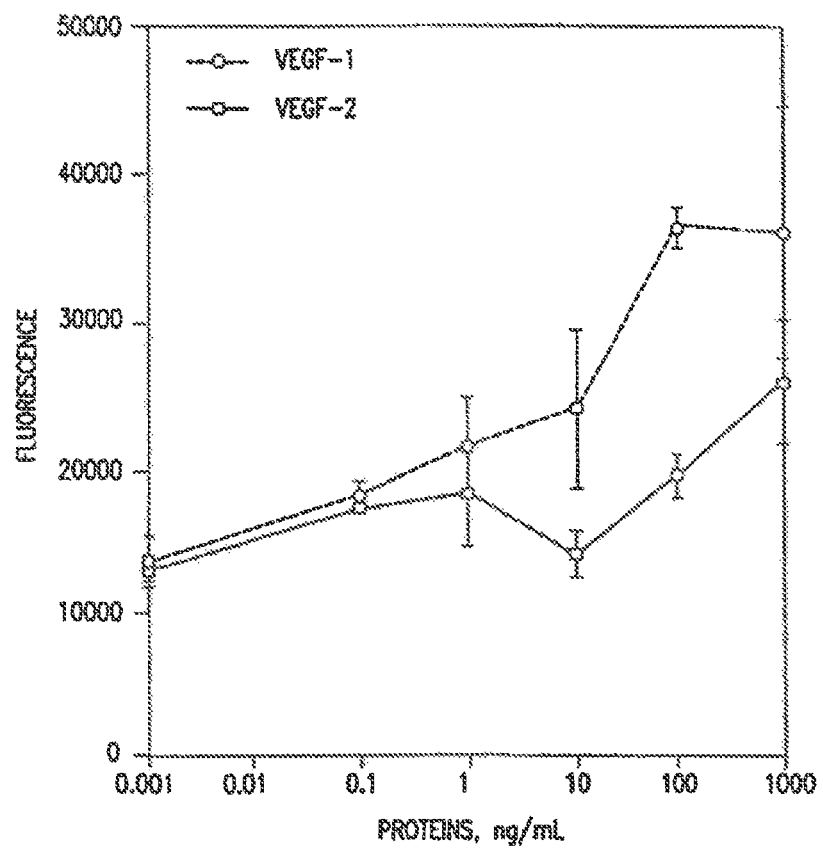
FIG. 18 depicts VEGF-2 stimulated proliferation of dermal microvascular endothelial cells.
Figure 19:
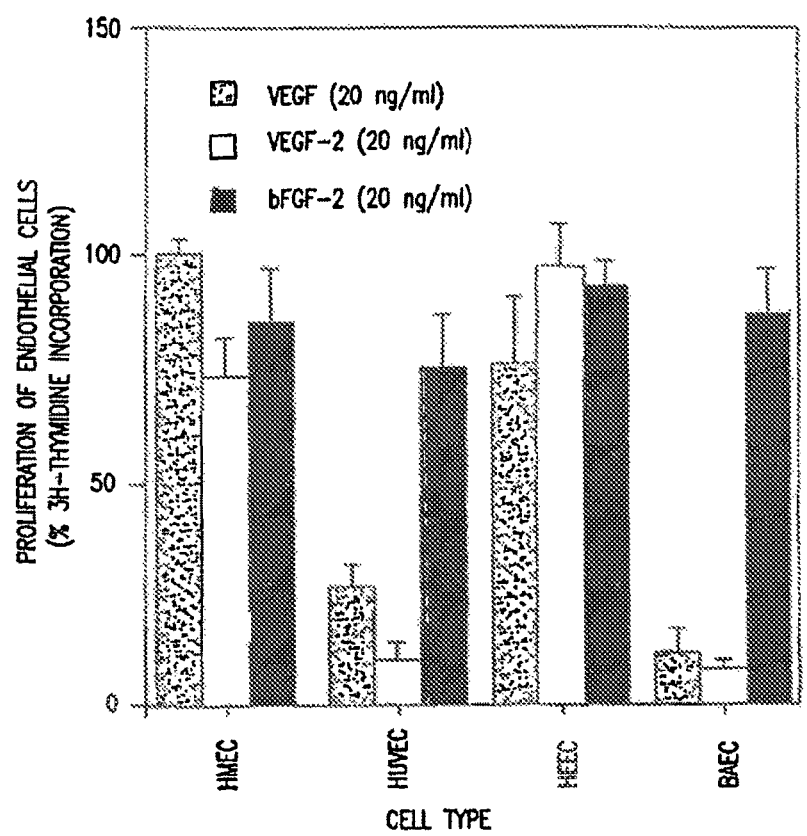
FIG. 19 depicts the stimulatory effect of VEGF-2 on proliferation of microvascular, umbilical cord, endometrial, and bovine aortic endothelial cells.

VEGF-2 stimulated proliferation of human umbilical vein endothelial cells (HUVEC) and dermal microvascular endothelial cells slightly (FIGS. 17 and 18). The stimulatory effect of VEGF-2 is more pronounced on proliferation of endometrial and microvascular endothelial cells (FIG. 19). Endometrial endothelial cells (HEEC) demonstrated the greatest response to VEGF-2 (96% of the effect of VEGF on microvascular endothelial cells). The response of microvasculai endothelial cells (HMEC) to VEGF-2 was 73% compared to VEGF. The response of HUVEC and BAEC (bovine aortic endothelial cells) to VEGF-2 was substantially lower at 10% and 7%, respectively. The activity of VEGF-2 protein has varied between different purification runs with the stimulatory effect of certain batches on HUVEC proliferation being significantly higher than that of other batches.

Additionally, one of skill in the art could readily modify the above protocol to test the effect of agonists and/or antagonists of VEGF-2 (e.g., VEGF-2 antibodies) on VEGF-2 induced proliferation of endothelial cells.

Example 12

Inhibition of PDGF-induced Vascular Smooth Muscle Cell Proliferation

Figure 20A:
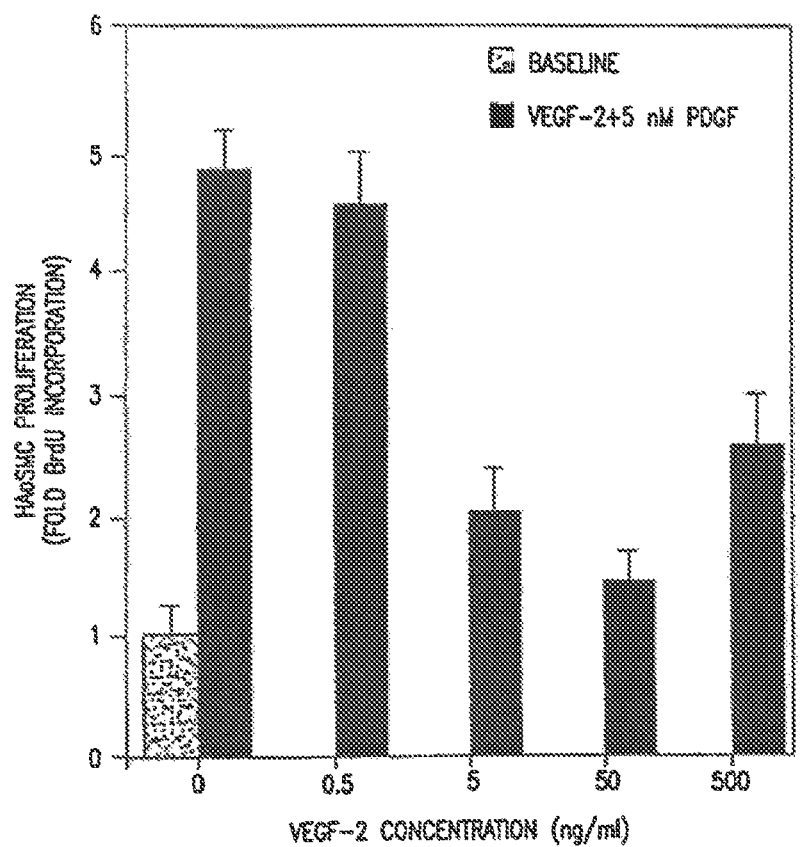
FIGS. 20A-20B depict inhibition of PDGF-induced vascular (human aortic) smooth muscle cell proliferation.
Figure 20B:
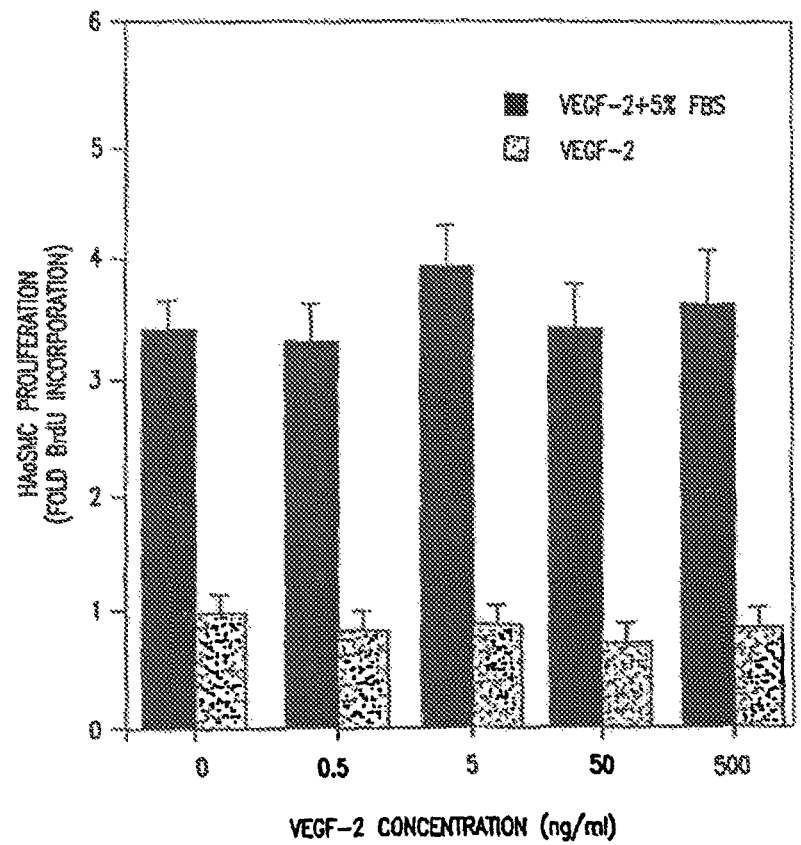

VEGF-2 expression is high in vascular smooth muscle cells. Smooth muscle is an important therapeutic target for vascular diseases, such as restenosis. To evaluate the potential effects of VEGF-2 on smooth muscle cells, the effect of VEGF-2 on human aortic smooth muscle cell (HAoSMC) proliferation was examined.
Experimental Design
HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after exposing to denaturing solution and then with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6;271(36):21985-21992 (1996).
Results
VEGF-2 has an inhibitory effect on proliferation of vascular smooth muscle cells induced by PDGF, but not by Fetal Bovine Serum (FBS) (FIG. 20).

Additionally, one of skill in the art could readily modify the above protocol to test the effect of agonists and/or antagonists of VEGF-2 (e.g., VEGF-2 antibodies) on VEGF-2 inhibition of vascular smooth muscle cell proliferation.

Example 13

Stimulation of Endothelial Cell Migration

Figure 21A:
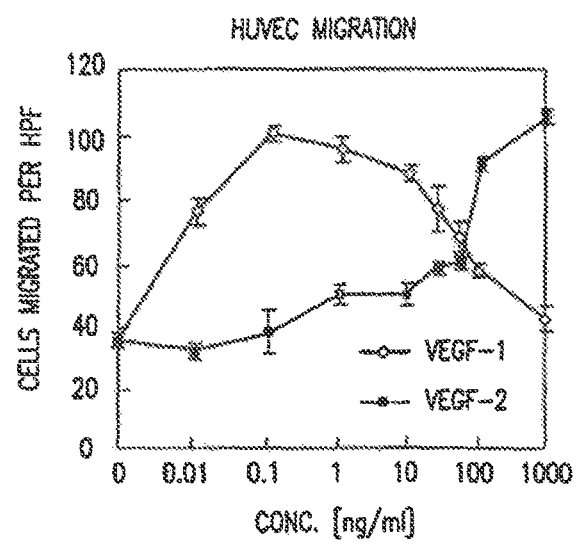
FIGS. 21A-21B depict stimulation of migration of HUVEC and bovine microvascular endothelial cells (BMEC) by VEGF-2.
Figure 21B:
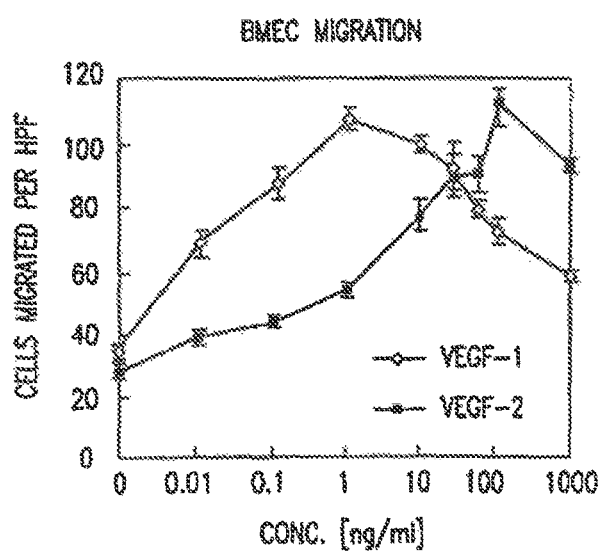

Endothelial cell migration is an important step involved in angiogenesis.
Experimental Design
This example will be used to explore the possibility that VEGF-2 may stimulate lymphatic endothelial cell migration. Currently, there are no published reports of such a model. However, we will be adapting a model of vascular endothelial cell migration for use with lymphatic endothelial cells essentially as follows:
Endothelial cell migration assays are performed using a 48 well microchemotaxis chamber (Neuroprobe Inc., Cabin John, Md.; Falk, W., Goodwin, R. H. J., and Leonard, E. J. "A 48 well micro chemotaxis assembly for rapid and accurate measurement of leukocyte migration." *J. Immunological Methods* 1980; 33:239-247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2-6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40x) in each well, and all groups are performed in quadruplicate.
Results
In an assay examining HUVEC migration using a 43-well microchemotaxis chamber, VEGF-2 was able to stimulate migration of HUVEC (FIGS. 21A-B).

Additionally, one of skill in the art could readily modify the above protocol to test the effect of agonists and/or antagonists of VEGF-2 (e.g., VEGF-2 antibodies) on VEGF-2 induced migration of endothelial cells.

Example 14

Stimulation of Nitric Oxide Production by Endothelial Cells

Nitric oxide released by the vascular endothelium is believed to be a mediator of vascular endothelium relaxation. VEGF-1 has been demonstrated to induce nitric oxide production by endothelial cells in response to VEGF-1. As a result, VEGF-2 activity can be assayed by determining nitric oxide production by endothelial cells in response to VEGF-2.
Experimental Design
Nitric oxide is measured in 96-well plates of confluent microvascular endothelial cells after 24 hours staivation and a subsequent 4 hr exposure to various levels of VEGF-1 and VEGF-2. Nitric oxide in the medium is determined by use of the Griess reagent to measure total nitrite after reduction of nitric oxide-derived nitrate by nitrate reductase. The effect of VEGF-2 on nitric oxide release was examined on HUVEC.

Briefly, NO release from cultured HUVEC monolayer was measured with a NO-specific polarographic electrode connected to a NO meter (Iso-NO, World Precision Instruments Inc.) (1049). Calibration of the NO elements was performed according to the following equation: $2 \ KNO_2 + 2 \ KI + 2H_2SO_4 \ 2 \ NO + I_2 + 2 \ H_2O + 2 \ K_2SO_4$ The standard calibration curve was obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO was previously determined by measurement of NO from authentic NO gas (1050). The culture medium was removed and HUVECs were washed twice with Dulbecco's phosphate buffered saline. The cells were then bathed in 5 ml of filtered Krebs-Henseleit solution in 6-well plates, and the cell plates were kept on a slide warmer (Lab Line Instruments Inc.) To maintain the temperature at 37° C. The NO sensor probe was inserted vertically into the wells, keeping the tip of the electrode 2 mm, under the surface of the solution, before addition of the different conditions. S-nitroso acetyl penicillanin (SNAP) was used as a positive control. The amount of released NO was expressed as picomoles per $1\times10^6$ endothelial cells. All values reported were means of four to six measurements in each group (number of cell culture wells). See, Leak et al. *Biochem and Biophys. Res. Comm.* 217:96-105 (1995).

Results

Figure 22:
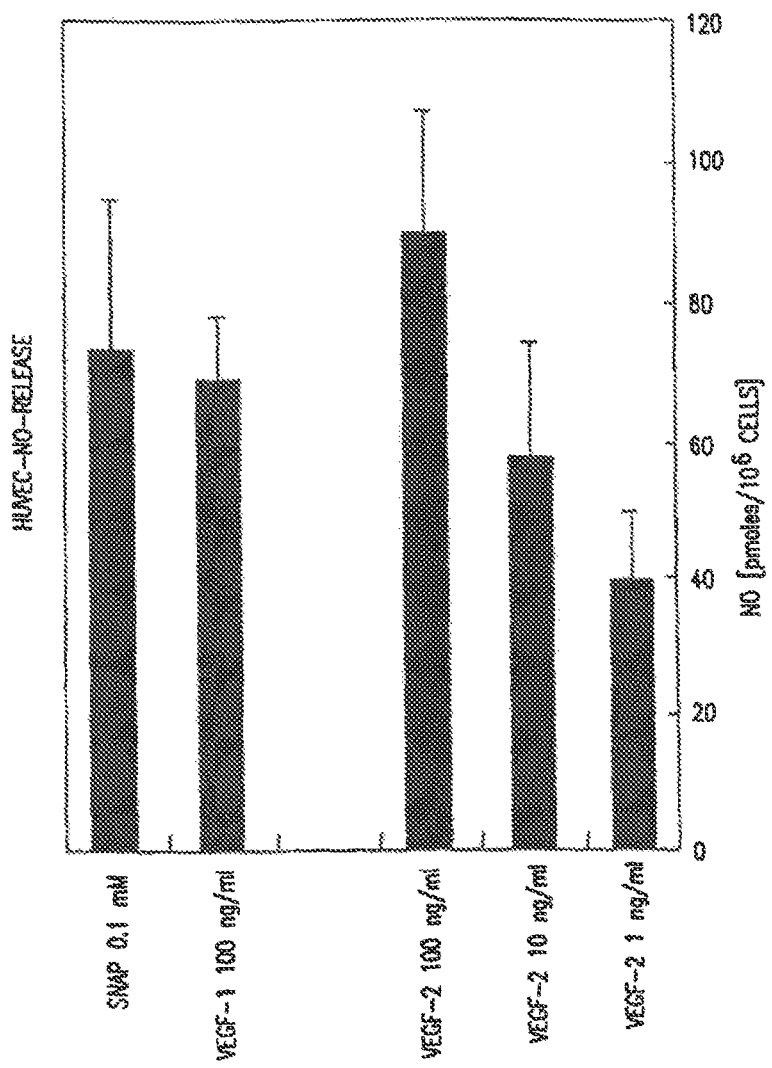
FIG. 22 depicts stimulation of nitric oxide release of HUVEC by VEGF-2 and VEGF-1.

VEGF-2 was capable of stimulating nitric oxide release on HUVEC (FIG. 22) to a higher level than VEGF. This suggested that VEGF-2 may modify vascular permeability and vessel dilation.

Additionally, one of skill in the art could readily modify the above protocol to test the effect of agonists and/or antagonists of VEGF-2 (e.g., VEGF-2 antibodies) on VEGF-2 induced nitric oxide release from endothelial cells.

Example 15

Effect of VEGF-2 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

Experimental Design

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Cord Formation Medium containing control buffer or the protein of the invention (0.1 to 100 ng/ml) and the cells are cultured for an additional 48 hr. The numbers and lengths of the capillary-like cords are quantitated through use of the Boeckeler VIA-170 video image analyzer. All assays are done in triplicate.

Commercial (R&D) VEGF (50 ng/ml) is used as a positive control b-estradiol (1 ng/ml) is used as a negative control. The appropriate buffer (without protein) is also utilized as a control.

Results

Figure 23:
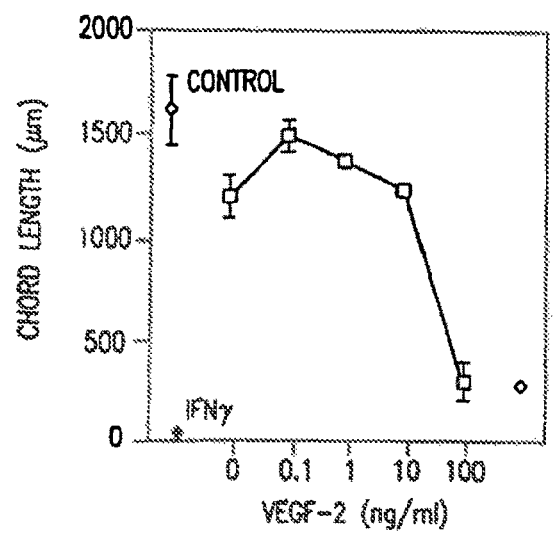
FIG. 23 depicts inhibition of cord formation of microvascular endothelial cells (CADMEC) by VEGF-2.

It has been observed that VEGF-2 inhibits cord formation similar to IFNa which also stimulates endothelial cell proliferation (FIG. 23). This inhibitory effect may be a secondary effect of endothelial proliferation which is mutually exclusive with the cord formation process.

Additionally, one of skill in the art could readily modify the above protocol to test the effect of agonists and/or antagonists of VEGF-2 (e.g., VEGF-2 antibodies) on VEGF-2 inhibition of cord formation.

Example 16

Angiogenic Effect on Chick Chorioallantoic Membrane

Chick chorioallantoic membrane (CAM) is a well-established system to examine angiogenesis. Blood vessel formation on CAM is easily visible and quantifiable. The ability of VEGF-2 to stimulate angiogenesis in CAM was examined.

Experimental Design

Embryos

Fertilized eggs of the White Leghorn chick (*Gallus gallus*) and the Japanese qual (*Coturnix coturnix*) were incubated at 37.8° C. and 80% humidity. Differentiated CAM of 16-day-old chick and 13-day-old qual embryos was studied with the following methods.

CAM Assay

On Day 4 of development, a window was made into the egg shell of chick eggs. The embryos were checked for normal development and the eggs sealed with cellotape. They were further incubated until Day 13. Thermanox coverslips (Nunc, Naperville, Ill.) were cut into disks of about 5 mm in diameter. Sterile and salt-free growth factors were dissolved in distilled water and about 3.3 mg/5 ml was pipetted on the disks. After air-drying, the inverted disks were applied on CAM. After 3 days, the specimens were fixed in 3% glutaraldehyde and 2% formaldehyde and rinsed in 0.12 M sodium cacodylate buffer. They were photographed with a stereo microscope [Wild M8] and embedded for semi- and ultrathin sectioning as described above. Controls were performed with carrier disks alone.

Results

Figure 24:
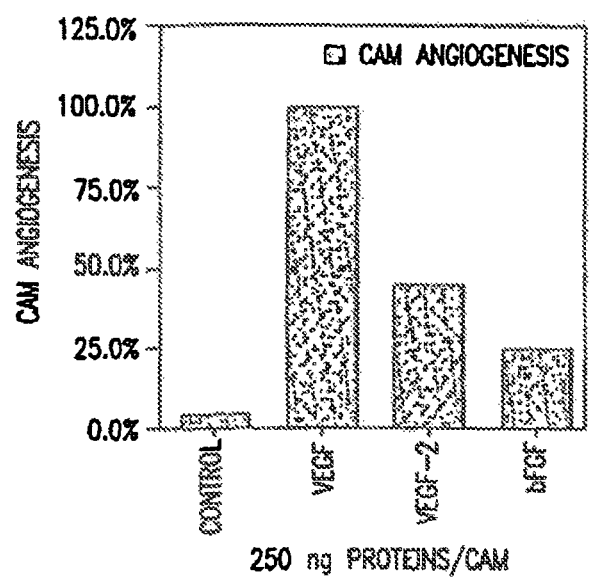
FIG. 24 depicts stimulation of angiogenesis by VEGF, VEGF-2, and bFGF in the CAM assay.

This data demonstrates that VEGF-2 can stimulate angiogenesis in the CAM assay nine-fold compared to the untreated control. However, this stimulation is only 45% of the level of VEGF stimulation (FIG. 24).

Additionally, one of skill in the art could readily modify the above protocol to test the effect of agonists and/or antagonists of VEGF-2 (e.g., VEGF-2 antibodies) on VEGF-2 stimulation of angiogenesis in the CAM assay.

Example 17

Angiogenesis Assay Using a Matrigel Implant in Mouse

Experimental Design

In order to establish an in vivo' model for angiogenesis to test protein activities, mice and rats have been implanted subcutaneously with methylcellulose disks containing either 20 mg of BSA (negative control) and 1 mg of bFGF and 0.5 mg of VEGF-1 (positive control).

It appeared as though the BSA disks contained little vascularization, while the positive control disks showed signs of vessel formation. At day 9, one mouse showed a clear response to the bFGF.

Results

Both VEGF proteins appeared to enhance Matrigel cellularity by a factor of approximately 2 by visual estimation.

An additional 30 mice were implanted with disks containing BSA, bFGF, and varying amounts of VEGF-1, VEGF-2-B8, and VEGF-2-C4. Each mouse received two identical disks, rather than one control and one experimental disk.

Samples of all the disks recovered were immunostained with Von Willebrand's factor to detect for the presence of endothelial cells in the disks, and flk-1 and flt-4 to distinguish between vascular and lymphatic endothelial cells. However, definitive histochemical analysis of neovascularization and lymphangiogenesis could not be determined.

Additionally, one of skill in the art could readily modify the above protocol to test the effect of agonists and/or antagonists of VEGF-2 (e.g., VEGF-2 antibodies) on VEGF-2 modulated angiogenesis.

Example 18

Rescue of Ischemia in Rabbit Lower Limb Model

Experimental Design

To study the in vivo effects of VEGF-2 on ischemia, a rabbit hindlimb ischemia model was created by surgical removal of one femoral artery as described previously (Takeshita, S. et al., *Am J. Pathol* 147:1649-1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J. Pathol* 147:1649-1660 (1995)). An interval of 10 days was allowed for post-operative recovery of rabbits and development of endogenous collateral vessels. At 10 day post-operatively (day 0), after performing a baseline angiogram, the internal iliac artery of the ischemic limb was transfected with 500 mg naked VEGF-2 expression plasmid by arterial gene transfer technology using a hydrogel-coated balloon catheter as described (Riessen, R. et al. *Hum Gene Ther.* 4:749-758 (1993); Leclerc, G. et al. *J. Clin. Invest.* 90: 936-944 (1992)). When VEGF-2 was used in the treatment, a single bolus of 500 mg VEGF-2 protein or control was delivered into the internal iliac artery of the ischemic limb over a period of 1 min. through an infusion catheter. On day 30, various parameters were measured in these rabbits.

Results

Both VEGF-2 protein (FIG. 25A) and naked expression plasmid (FIG. 25B) were able to restore the following parameters in the ischemic limb. Restoration of blood flow, angiographic score seem to be slightly more by administration of 500 mg plasmid compared with by 500 mg protein (FIG. 25C) The extent of the restoration is comparable with that by VEGF in separate experiments (data not shown). A vessel dilator was not able to achieve the same effect, suggesting that the blood flow restoration is not simply due to a vascular dilation effect.

Figure 25A:
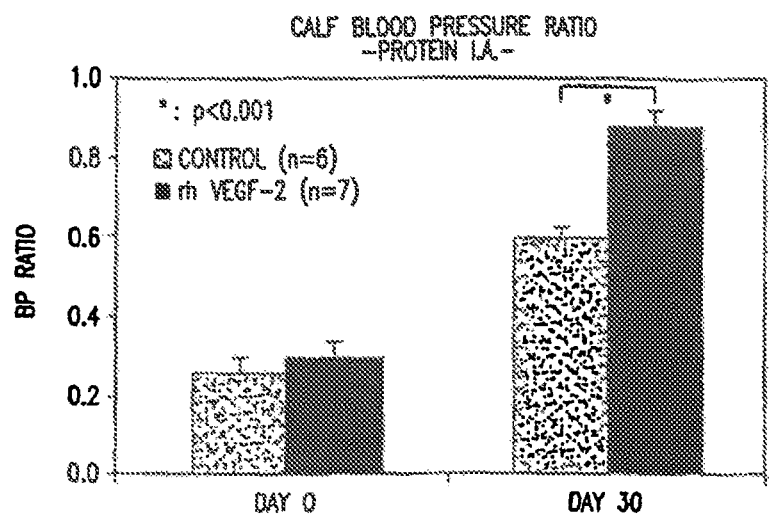
FIGS. 25A-25O depict restoration of certain parameters in the ischemic limb by VEGF-2 protein (FIGS. 25A, 25D, 25E, 25J, and 25M) and naked expression plasmid (FIGS. 25B, 25F, 25G, 25K, and 25N): BP ratio (FIGS. 25A-25C); Blood Flow and Flow Reserve (FIGS. 25D-25I); Angiographic Score (FIGS. 25J-25L); Capillary density (FIGS. 25M-25O).
Figure 25B:
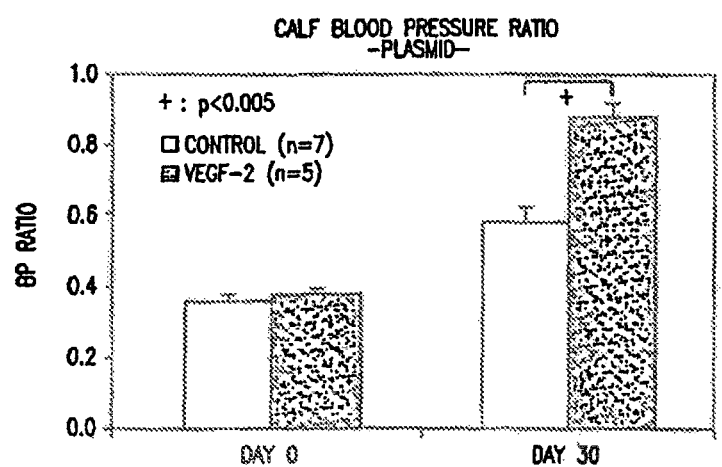
Figure 25C:
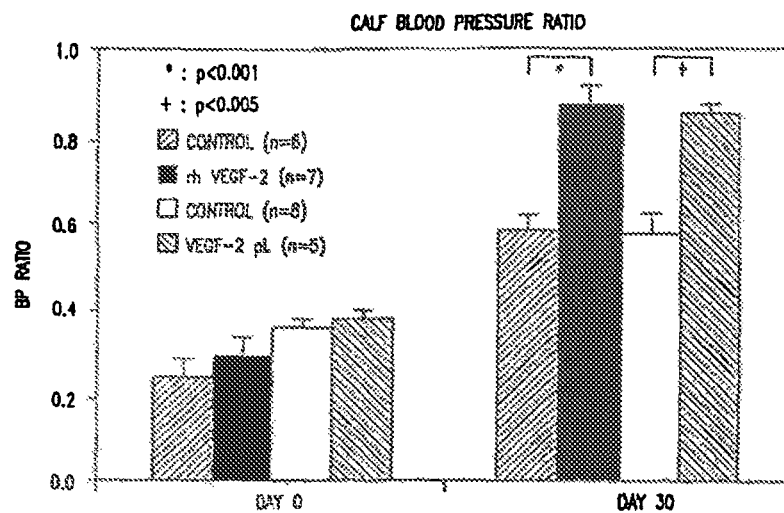
Figure 25D:
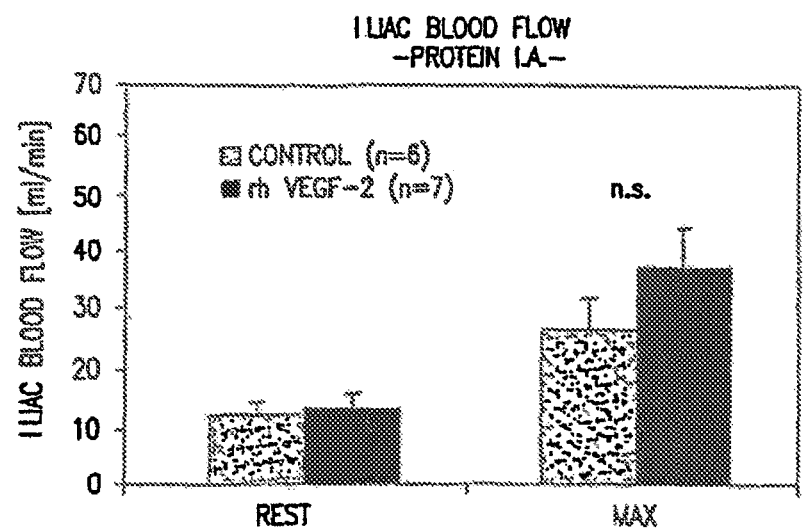
Figure 25E:
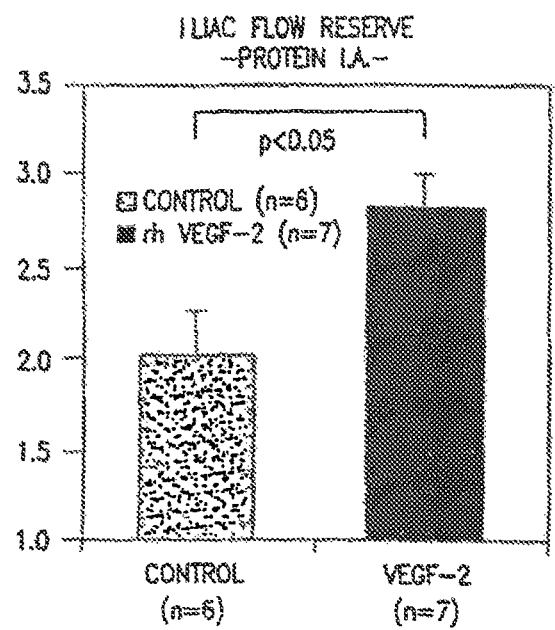
Figure 25F:
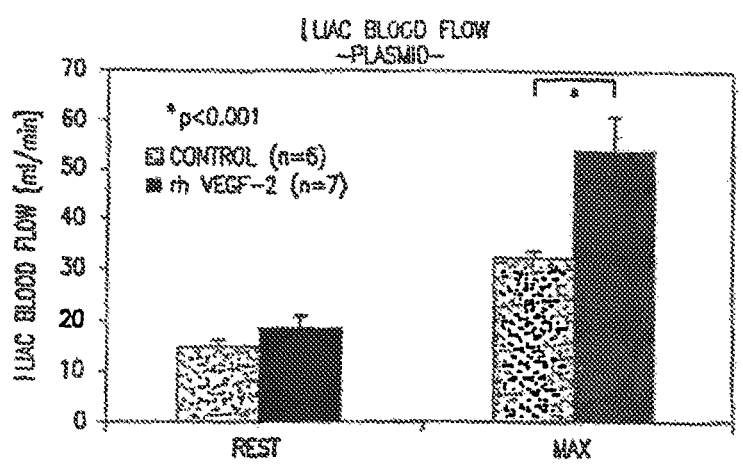
Figure 25G:
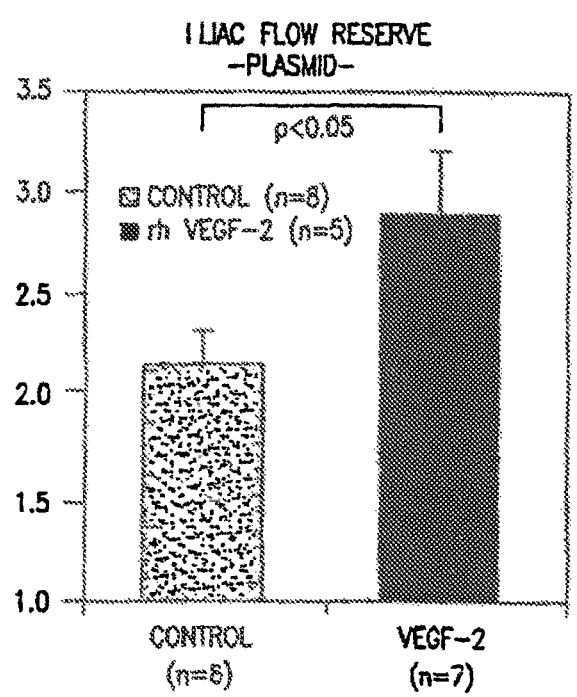
Figure 25H:
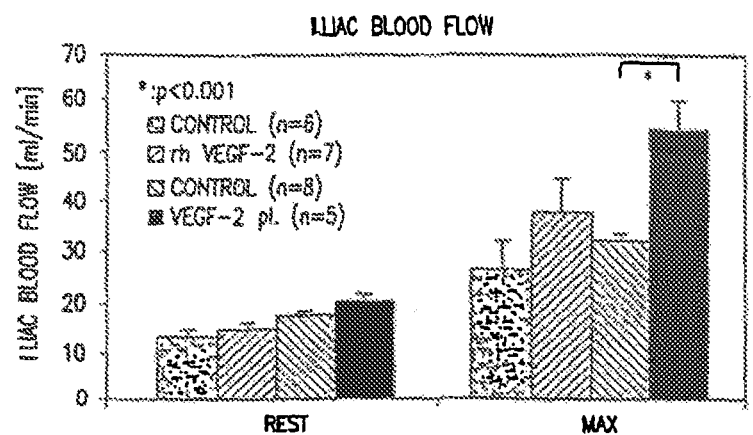
Figure 25I:
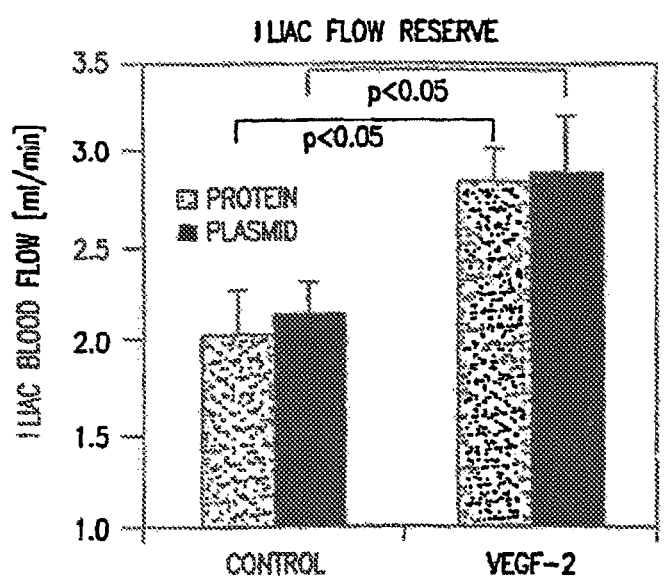

1. BP Ratio (FIGS. 25A-C)

The blood pressure ratio of systolic pressure of the ischemic limb to that of normal limb.

2. Blood Flow and Flow Reserve (FIGS. 25D-I)

Resting FL: the blood flow during un-dilated condition

Max FL: the blood flow during fully dilated condition (also an indirect measure of the blood vessel amount)

Flow Reserve is reflected by the ratio of max FL:resting FL.

Figure 25J:
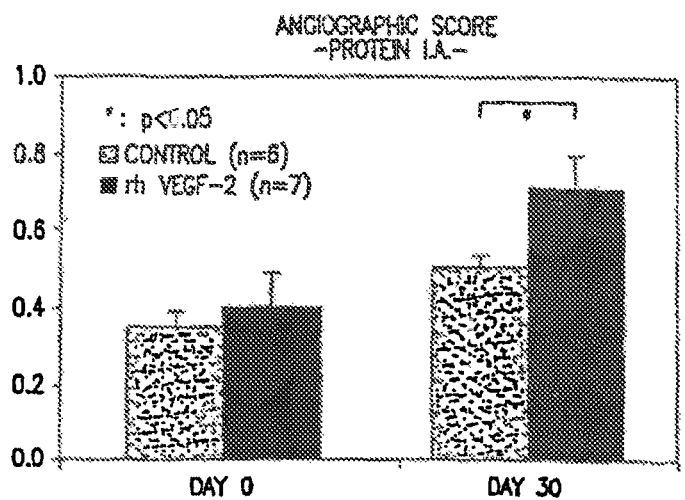
Figure 25K:
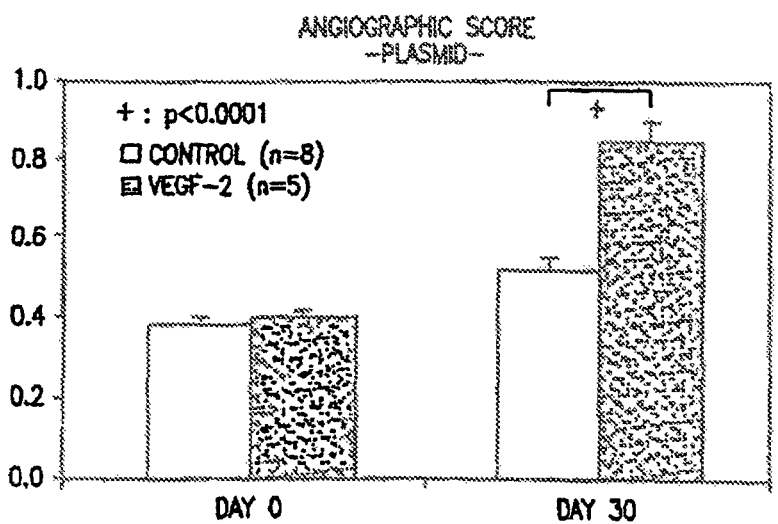
Figure 25L:
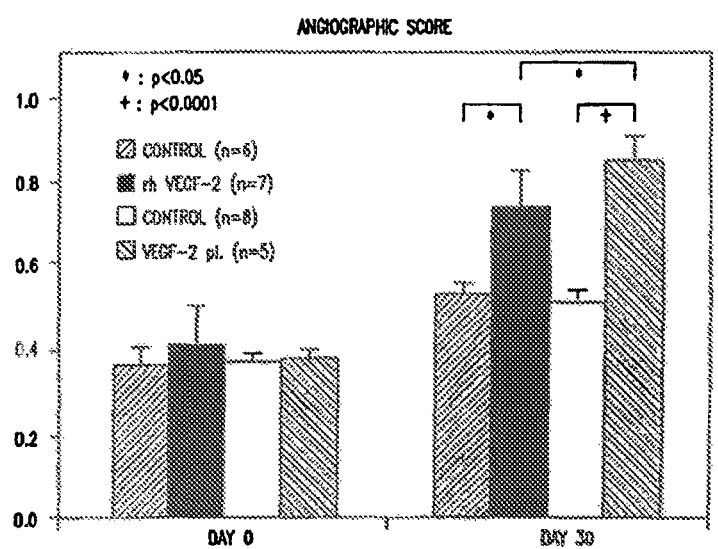

3. Angiographic Score (FIGS. 25J-L)

This is measured by the angiogram of collateral vessels. A score was determined by the percentage of circles in an overlaying grid that with crossing opacified arteries divided by the total number m the rabbit thigh.

Figure 25M:
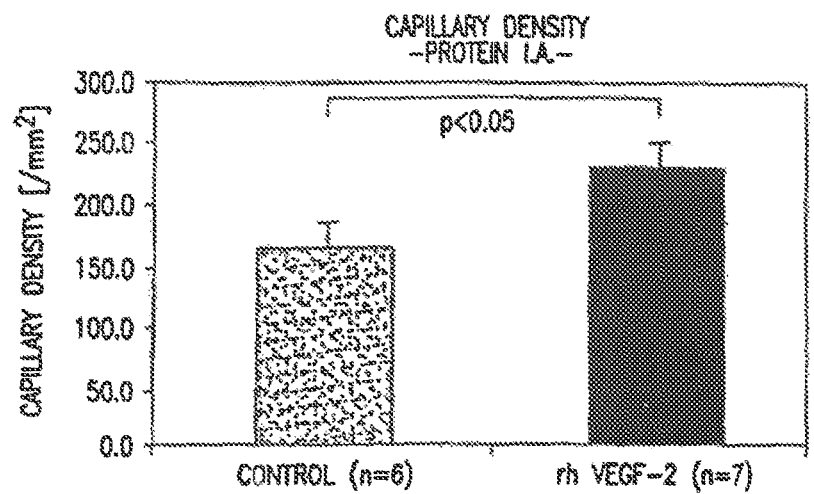
Figure 25N:
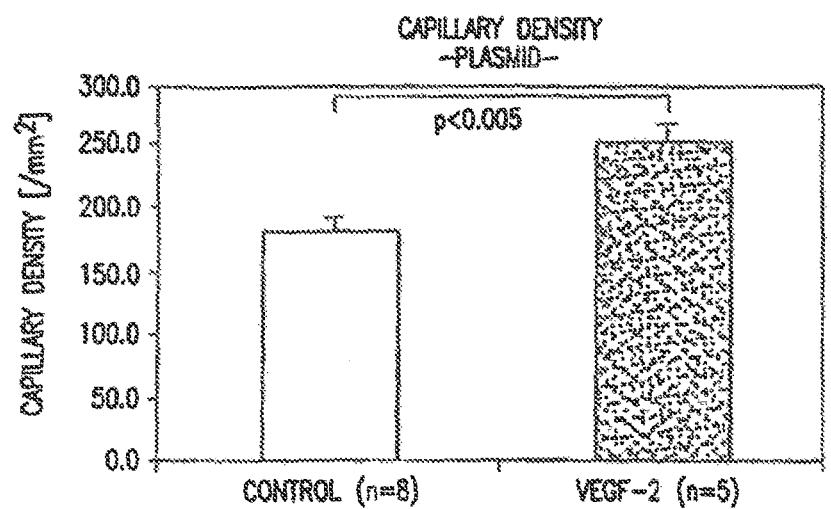
Figure 25O:
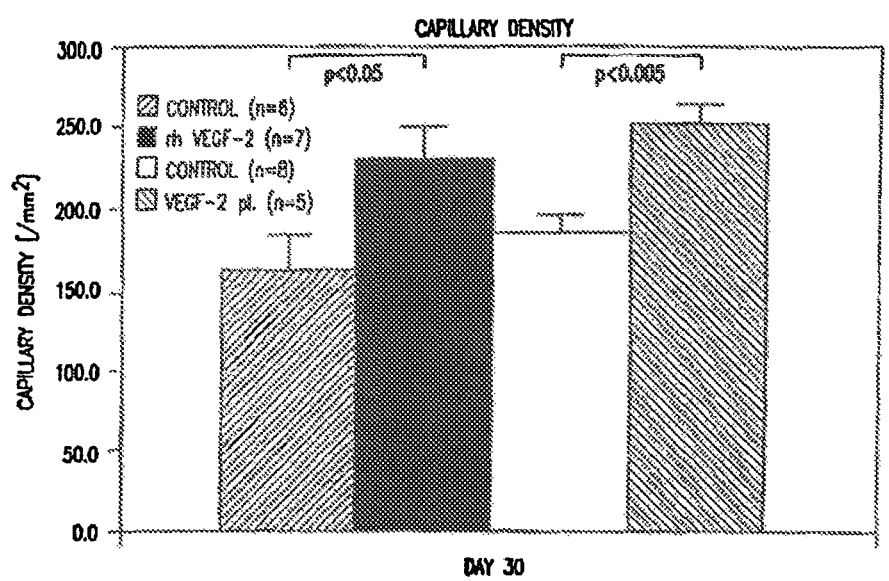

4. Capillary Density (FIGS. 25M-O)

The number of collateral capillaries determined in light microscopic sections taken from hindlimbs.

As discussed, VEGF-2 is processed to an N-terminal and a C-terminal fragment which are co-purified. The N-terminal fragment contains the intact putative functional domain and may be responsible for the biologic activity.

Example 19

Effect of VEGF-2 on Vasodilation

Figure 26A:
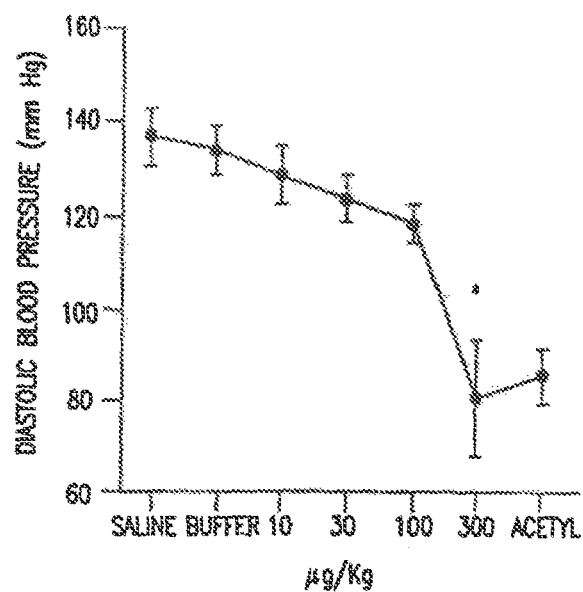
Figure 26B:
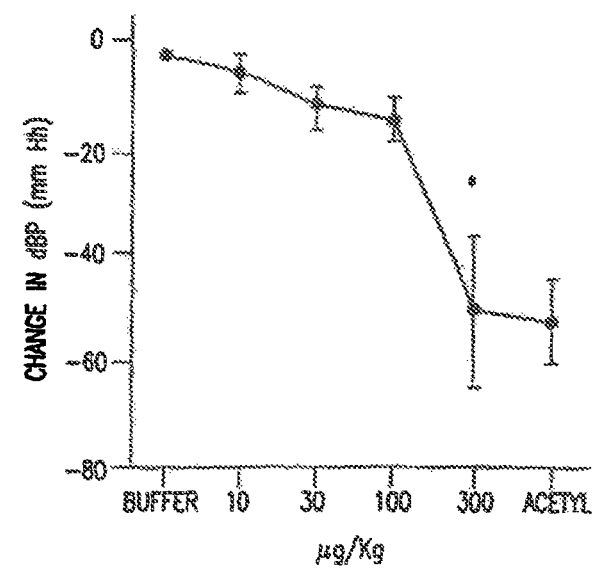
Figure 26C:
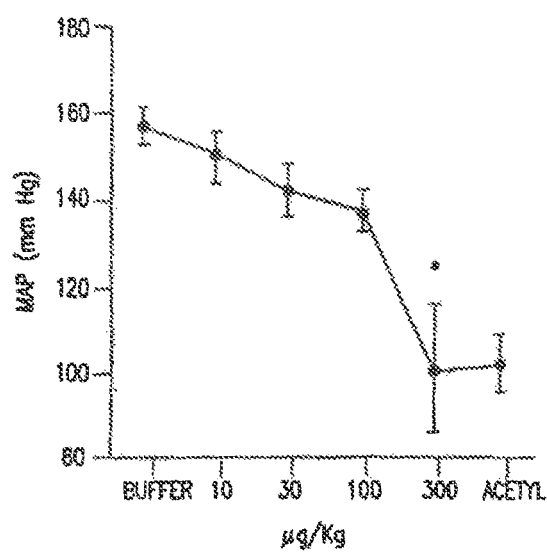
Figure 26D:
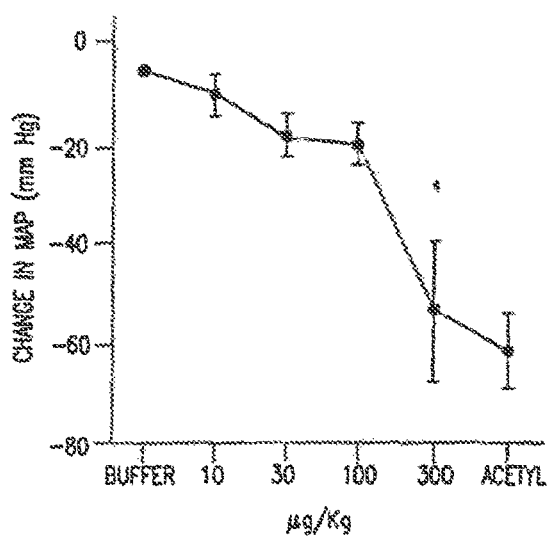
Figures 26E, 26F:
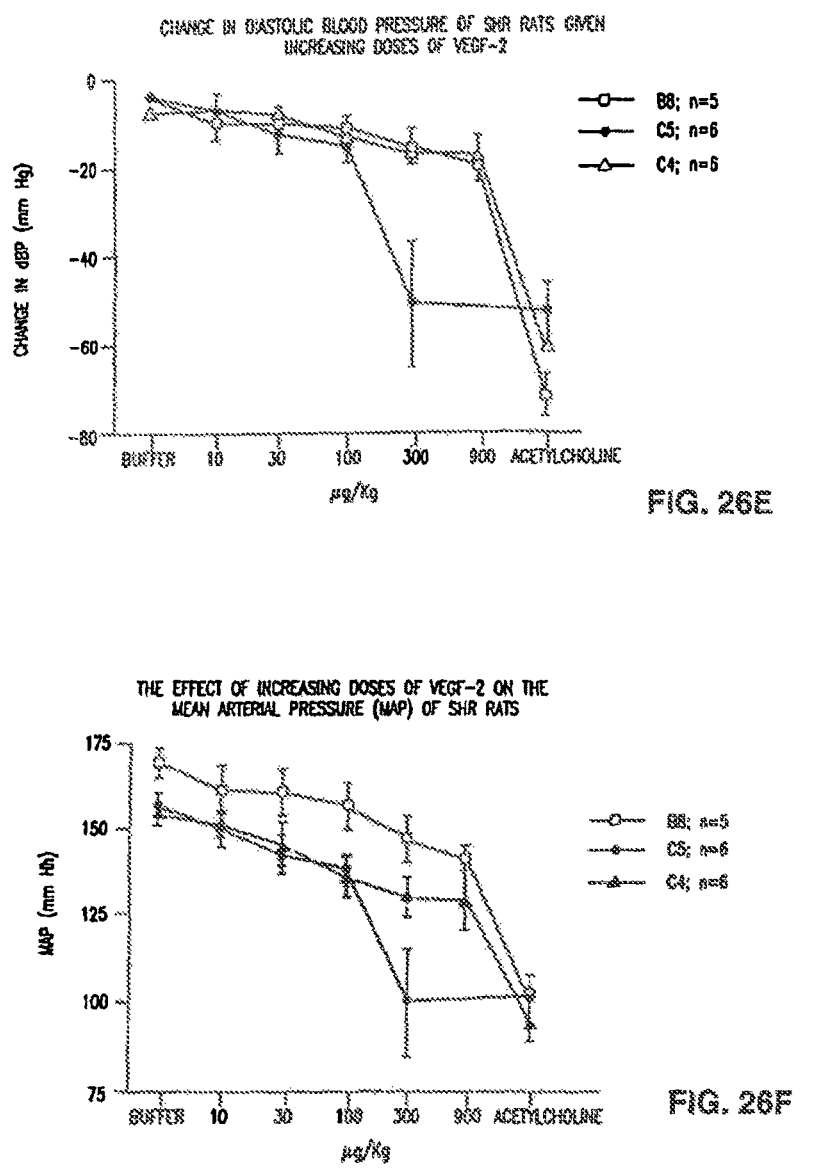
Figure 26G:
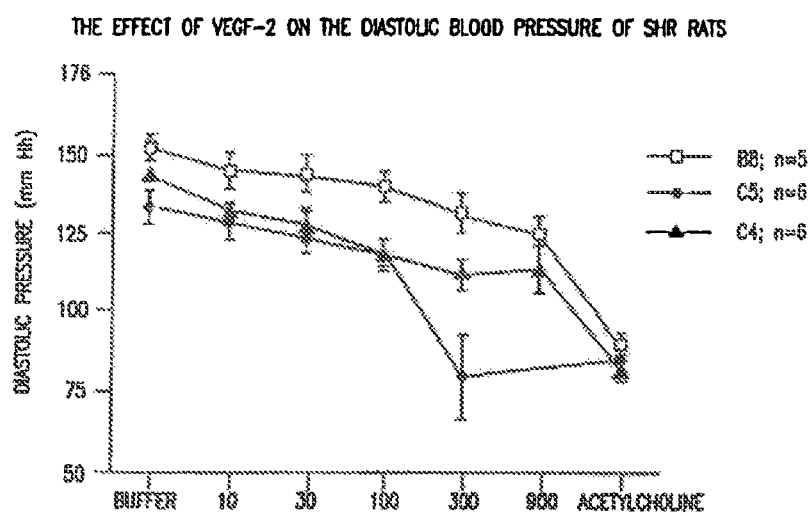
Figure 27:
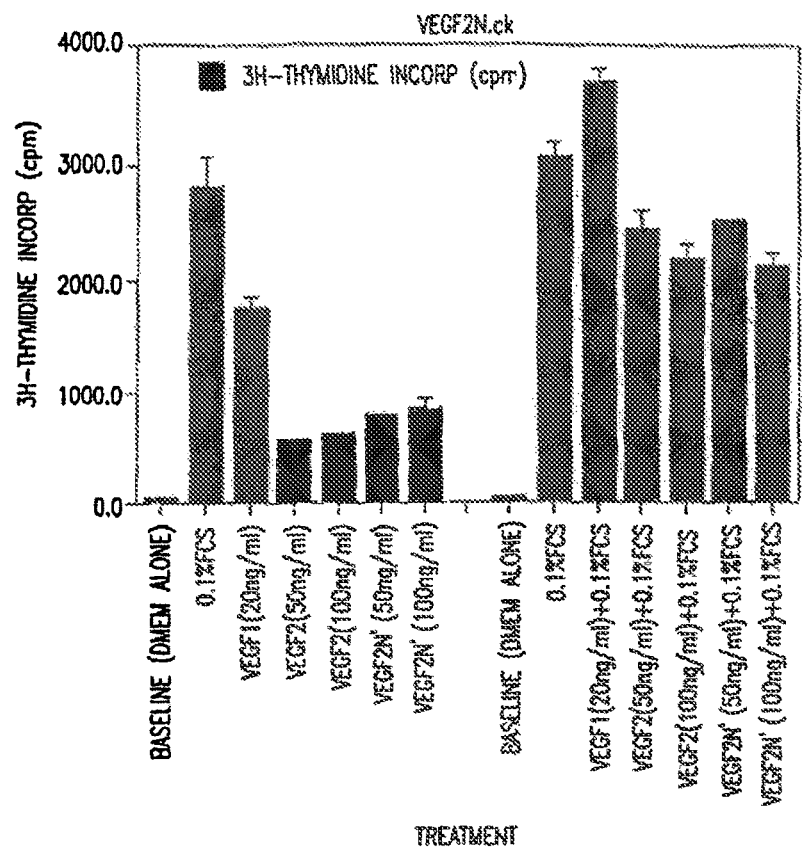
FIG. 27 depicts inhibition of VEGF-2N= and VEGF-2-induced proliferation.

As described above, VEGF-2 can stimulate NO release, a mediator of vascular endothelium dilation. Since dilation of vascular endothelium is important in reducing blood pressure, the ability of VEGF-2 to affect the blood pressure in spontaneously hypertensive rats (SHR) was examined. VEGF-2 caused a dose-dependent decrease in diastolic blood pressure (FIGS. 26a and b). There was a steady decline in diastolic blood pressure with increasing doses of VEGF-2 which attained statistical significance when a dose of 300 mg/kg was administered. The changes observed at this dose were not different than those seen with acetylcholine (0.5 mg/kg). Decreased mean arterial pressure (MAP) was observed as well (FIGS. 26c and d). VEGF-2 (300 mg/kg) and acetylcholine reduced the MAP of these SHR animals to normal levels.

Additionally, increasing doses (0, 10, 30, 100, 300, and 900 mg/kg) of the B8, C5, and C4 preps of VEGF-2 were administered to 13-14 week old spontaneously hypertensive rats (SHR). Data are expressed as the mean+/−SEM. Statistical analysis was performed with a paired t-test and statistical significance was defined as $p<0.05$. vs. the response to buffer alone.

Studies with VEGF-2 (C5 prep) revealed that although it significantly decreased the blood pressure, the magnitude of the response was not as great as that seen with VEGF-2 (B8 prep) even when used at a dose of 900 mg/kg.

Studies with VEGF-2 (C4 preparation) revealed that this CHO expressed protein preparation yielded similar results to that seen with C5 (i.e. statistically significant but of far less magnitude than seen with the B8 preparation) (see FIGS. 26A-D).

As a control and since the C4 and C5 batches of VEGF-2 yielded minor, but statistically significant, changes in blood pressure experiments were performed experiments with another CHO-expressed protein, M-CIF. Administration of M-CIF at doses ranging from 10-900 mg/kg produced no significant changes in diastolic blood pressure. A minor statistically significant reduction in mean arterial blood pressure was observed at doses of 100 and 900 mg/kg but no dose response was noted. These results suggest that the reductions in blood pressure observed with the C4 and C5 batches of VEGF-2 were specific, i.e. VEGF-2 related.

Example 20

Rat Ischemic Skin Flap Model

Experimental Design

The evaluation parameters include skin blood flow, skin temperature, and factor VIII immunohistochemistry or endothelial alkaline phosphatase reaction. VEGF-2 expression, during the skin ischemia, is studied using in situ hybridization.

The study in this model is divided into three parts as follows:
a) Ischemic skin
b) Ischemic skin wounds
c) Normal wounds The experimental protocol includes:
a) Raising a 3×4 cm, single pedicle full-thickness iandom skin flap (myocutaneous flap over the lower back of the animal).
b) An excisional wounding (4-6 mm in diameter) in the ischemic skin (skin-flap).
c) Topical treatment with VEGF-2 of the excisional wounds (day 0, 1, 2, 3, 4 post-wounding) at the following various dosage ranges: 1 mg to 100 mg.
d) Harvesting the wound tissues at day 3, 5, 7, 10, 14 and 21 post-wounding for histological, immunohistochemical, and in situ studies.

Example 21

Peripheral Artierial Disease Model

Angiogenic therapy using VEGF-2 has been developed as a novel therapeutic strategy to obtain restoration of blood flow around the ischemia in case of peripheral arterial diseases.
Experimental Design
The experimental protocol includes:
a) One side of the femoral artery is ligated to create ischemic muscle of the hindlimb, the other side of hindlimb serves as a control.
b) VEGF-2 protein, in a dosage range of 20 mg 500 mg, is delivered intravenously and/or intramuscularly 3 times (perhaps more) per week for 2-3 weeks.
c) The ischemic muscle tissue is collected after ligation of the femoral artery at 1, 2, and 3 weeks for the analysis of VEGF-2 expression and histology. Biopsy is also performed on the other side of normal muscle of the contralateral hindlimb.

Example 22

Ischemic Myocardial Disease Model

VEGF-2 is evaluated as a potent mitogen capable of stimulating the development of collateral vessels, and restructuring new vessels after coronary artery occlusion. Alteration of VEGF-2 expression is investigated in situ.
Experimental Design
The experimental protocol includes:
a) The heart is exposed through a left-side thoracotomy in the rat. Immediately, the left coronary artery is occluded with a thin suture (6-0) and the thorax is closed.
b) VEGF-2 protein, in a dosage range of 20 mg 500 mg, is delivered intravenously and/or intramuscularly 3 times (perhaps more) per week for 2-4 weeks.
c) Thirty days after the surgery, the heart is removed and cross-sectioned for morphometric and in situ analyzes.

Example 23

Rat Corneal Wound Healing Model

This animal model shows the effect of VEGF-2 on neovascularization.
Experimental Design
The experimental protocol includes:
a) Making a 1-1.5 mm long incision from the center of cornea into the stromal layer.
b) Inserting a spatula below the lip of the incision facing the outer corner of the eye.
c) Making a pocket (its base is 1-1.5 mm form the edge of the eye).
d) Positioning a pellet, containing 50 mg 500 mg VEGF-2, within the pocket.
e) VEGF-2 treatment can also be applied topically to the corneal wounds in a dosage range of 20 mg 500 mg (daily treatment for five days).
Alternative Protocol
In this protocol, the VEGF-2' polypeptide and/or VEGF-2 antibodies are delivered to the rat cornea using a filter disk which is inserted into the cornea as described below.
Filter Disk Preparation
Sterile cornea filter disks are stamped from 0.45 µm pore size Millipore HAWP01300 filters using a sterile 20 G needle with the standard bevel cut off and a machined bevel ground around the flattened tip under biosafety hood. Stamped disks are removed from the 20 G needle by means of a 24 G stylet. VEGF-2 polypeptides and or VEGF-2 antibody solution are prepared in sterile filtered 1×TBS (50 mM Tris-HCl pH 7.4/ 150 mM NaCl) as described below. The control groups will receive 1×TBS or flag peptide only.
Cornea Surgery and Insertion of Filter Disk Generally, 20 Sprague Dawley rats weighing 175-200 grams is used for these experiments. On the day of surgery, each animal is anesthetized with ketamine (50 mg/kg im; Phoenix #NDC 57319-291-02), xylazine (10 mg/kg im; Phoenix #NDC 57319-326-26), and acepromazine (1.0 mg/kg im; Fermenta #117-531). After the rat is anesthetized, the vibrissae is trimmed, and the rat is injected with 0.5 mg/kg atropine sulfate (RBI #A-105; Lot #69H0545). The rat is wrapped in sterile surgical drape. Sterile gloves is used for the surgical procedure. The surgical field (eye plus surrounding fur) is rinsed with saline, followed by 5% povidone-iodine (Perdue Frederick #H8151-K97; Lot #6H31). The eye is then be rinsed with sterile saline and 2 drops of 2% lidocaine HCl (Phoenix #NDC-57319-093-05; Lot #0080991) are dropped onto the eye. Eyes are irrigated with saline throughout the procedure to prevent desiccation. An incision is made with a sterile #15 scalpel blade 2 mm from the corneal limbus. The incision is made approximately half way through the thickness of the cornea. After the incision is made, sterile microsurgical scissors are used to create a pocket that extends from the point of the incision to approximately 0.75 mm from the limbus. The presoaked disk (soaked in a sterile petri dish on ice overnight in 20 µL of the respective test solution) is inserted into this pocket so that the leading edge of the disk is 1 mm from the limbus.

After the surgery is complete, the eyelid is closed, and gently held together with a microaneurysm clamp. The rat is then be turned over, and the procedure starting at step #6 is repeated. After both eyes are finished, the rat is placed in an isolation cage to wake up. As soon as the rat begins to regain consciousness, the microaneurysm clamps are removed.
Imaging:

Five days following the surgery, the rat is dosed with 0.5 mg/kg atropine. Upon observation of mydriasis, the animal is euthanized. Each rat eye is digitally imaged using ImagePro Plus at 4.0×. The surface area (pixels) and density (percent of area of interest) is quantitated in the area directly beneath and on either side of the filter disk. Nine surface area measurements are obtained per eye. A mean angiogenic surface area is obtained for each eye.

One of skill in the art could readily modify the above protocol to test the effect of agonists and/or antagonists of VEGF-2 (e.g., VEGF-2 antibodies) on VEGF-2 modulated neovascularization. In one modification, the filter disks might be soaked with an equimolar amount of VEGF-2 and VEGF-2 antibody. Alternatively, one could treat the corneas directly only with VEGF-2 polypeptides and administer VEGF-2 antibody systemically, via intraperitoneal, intravenous, or subcutaneous injection. When systemic injection is used, afor exmaple, the rat may be given one or more doses of between 0.1 to 10 mg/kg.

Example 24

Diabetic Mouse and Glucocorticoid-Impaired Wound Healing Models

Experimental Design

The experimental protocol includes:

1. Diabetic db+/db+ mouse model.

To demonstrate that VEGF-2 accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Nail. Acad. Sci. USA* 77:283-293 (1982)). Animals show polyphagia, polydipsia and polyuria. Mutani diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1-7 (1983); Leiter et al., *Am. J. of Pathol.* 114:46-55 (1985)). Peripheral neuropathy, myocardial complications, and microvascular lesions, basement membrane thickening and glomerular filtration abnormalities have been described in these animals (Norido, F. et al., *Exp. Neurol.* 83(2):221-232 (1984); Robertson et al., *Diabetes* 29(1):60-67 (1980); Giacomelli et al., *Lab Invest.* 40(4):460-473 (1979); Coleman, D. L., *Diabetes* 31 (*Suppl*):1-6 (1982)). These homozygous diabetic mice develop hyperglycemia that is resistant to insulin analogous to human type II diabetes (Mandel et al., *J. Immunol.* 120:1375-1377 (1978)).

The characteristics observed in these animals suggests that healing in this model may be similar to the healing observed in human diabetes (Greenhalgh, et al., *Am. J. of Pathol.* 136:1235-1246 (1990)).

Animals

Genetically diabetic female C57BL/KsJ (db+/db+) mice and their non-diabetic (db+/+m) heterozygous littermates are used in this study (Jackson Laboratories). The animals are purchased at 6 weeks of age and were 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Surgical Wounding

Wounding protocol is performed according to previously reported methods (Tsuboi, R. and Rifkin, D. B., *J. Exp. Med.* 172:245-251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

VEGF-2 is administered using at a range different doses of VEGF-2, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Experimental Design

Three groups of 10 animals each (5 diabetic and 5 non-diabetic controls) are evaluated: 1) Vehicle placebo control, 2) VEGF-2.

Measurement of Wound Area and Closure

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 was 64 mm$^2$, the corresponding size of the dermal punch; Calculations are made using the following formula:

$$[\text{Open area on day 8}] - [\text{Open area on day 1}]/[\text{Open area on day 1}]$$

Histology

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with VEGF-2. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Immunohistochemistry

Re-epithelialization

Tissue sections are stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Cell Proliferation Marker

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0-8, the lower side of the scale reflecting slight proliferation to the higher side reflecting intense proliferation.

Statistical Analysis

Experimental data are analyzed using an unpaired t test. A p value of <0.05 is considered significant.

2. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280-302 (1989); Wahl, S. M. et al., *J. Immunol.* 115: 476-481 (1975); Werb, Z. et al., *J. Exp. Med.* 147:1684-1694 (1978)). Glucocorticoids retard wound healing by inhibiting angiogenesis, decreasing vascular permeability (Ebert, R. H., et al., *An. Intern. Med.* 37:701-705 (1952)), fibroblast proliferation, and collagen synthesis (Beck, L. S. et al., *Growth Factors.* 5: 295-304 (1991); Haynes, B. F. et al., *J. Clin. Invest.* 61: 703-797 (1978)) and producing a transient reduction of circulating monocytes (Haynes, B. F., et al., *J. Clin. Invest.* 61: 703-797 (1978); Wahl, S. M., "Glucocorticoids and wound healing", In: Antiinflammatory Steroid Action: Basic and Clinical Aspects, Academic Press, New York, pp. 280-302 (1989)). The systemic administration of steroids to impaired wound healing is a well establish phenomenon in rats (Beck, L. S. et al., *Growth Factors.* 5: 295-304 (1991); Haynes, B. F., et al., *J. Clin. Invest.* 61: 703-797 (1978); Wahl, S. M., "Glucocorticoids and wound healing", In: Antiinflammatory Steroid Action Basic and Clinical Aspects, Academic Press, New York, pp. 280-302 (1989); Pierce, G. F. et al., *Proc. Natl. Acad. Sci. USA* 86: 2229-2233 (1989)).

To demonstrate that VEGF-2 can accelerate the healing process, the effects of multiple topical applications of VEGF-2 on full thickness excisional skin wounds in rats in which healing has been impaired by the systemic administration of methylprednisolone is assessed.

Animals

Young adult male Sprague Dawley rats weighing 250-300 g (Charles River Laboratories) are used -continued 3. "SP-42": MSKLDVYRQVHSIIRR
    (amino acids 212-227 in SEQ ID NO: 18)

4. "SP-43": MFSSDAGDDSTDGFHDI
    (amino acids 263-279 in SEQ ID NO: 18)

Example 26

Lymphadema Animal Model

The purpose of this experimental approach is to create an appropriate and consistent lymphedema model for testing the therapeutic effects of VEGF-2 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7-10 days. Perhaps more importantly, the chronic progress of the edema is followed for up to 3-4 weeks.

Experimental Procedure

Prior to beginning surgery, blood sample was drawn for protein concentration analysis. Male rats weighing approximately ~350 g are dosed with Pentobarbital. Subsequently, the right legs were shaved from knee to hip. The shaved area is swabbed with gauze soaked in 70% EtOH. Blood is drawn for serum total protein testing. Circumference and volumetric measurements were made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located.

The 2 proximal and 2 distal lymphatic vessels and distal blood supply of the popliteal node are then and ligated by suturing. The popliteal lymph node, and any accompanying adipose tissue, is then removed by cutting connective tissues.

Care was taken to control any mild bleeding resulting from this' procedure. After lymphatics were occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals were checked daily through the optimal edematous peak, which typically occurred by day 5-7. The plateau edematous peak was then observed. To evaluate the intensity of the lymphedema, we measured the circumference and volumes of 2 designated places on each paw before operation and daily for 7 days. The effect plasma proteins have on lymphedema and determined if protein analysis is a useful testing perimeter is also investigated. The weights of both control and edematous limbs are evaluated at 2 places. Analysis is performed in a blind manner.

Circumference Measurements:

Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements:

On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma Protein Measurements:

Blood is drawn, spun, and serum separated prior to surgery and then at conclusion for total protein and Ca2+ comparison.

Limb Weight Comparison:

After drawing blood, the animal is prepared for tissue collection. The limbs were amputated using a quillitine, then both experimental and control legs were cut at the ligature and weighed. A second weighing is done as the tibio-cacaneal joint was disarticulated and the foot was weighed.

Histological Preparations:

The transverse muscle located behind the knee (popliteal) area is dissected and arranged in a metal mold, filled with freezeGel, dipped into cold methylbutane, placed into labeled sample bags at −80EC until sectioning. Upon sectioning, the muscle was observed under fluorescent microscopy for lymphatics. Other immuno/histological methods are currently being evaluated.

Example 27

Method of Treatment Using Gene Therapy for Production of VEGF-2 Polypeptide—In Vivo Another aspect of the present invention is using in vivo gene therapy methods to treat disorders, diseases and conditions. The gene therapy method relates to the introduction of naked nucleic acid (DNA, RNA, and antisense DNA or RNA) comprising VEGF-2 operably linked to a promoter into an animal to increase the expression of VEGF-2. Such gene therapy and delivery techniques and methods are known in the art, see, for example, WO 90/11092, WO 98/11779; U.S. Pat. Nos. 5,693,622, 5,705,151, 5,580,859; Tabata H. et al. (1997) *Cardiovasc. Res.* 35(3):470-479, Chao, J et al. (1997) *Pharmacol. Res.* 35(6):517-522, Wolff, J. A. (1997) *Neuromuscul. Disord.* 7(5):314-318, Schwartz, B. et al. (1996) *Gene Ther.* 3(5):405-411, Tsurumi, Y. et al. (1996) *Circulation* 94(12):3281-3290 (incorporated herein by reference).

The VEGF-2 polynucleotide constructs may be delivered by any method that delivers injectable materials to the cells of an animal, such as, injection into the interstitial space of tissues (heart, muscle, skin, lung, liver, intestine and the like). The VEGF-2 polynucleotide constructs may also be delivered directly into arteries. The VEGF-2 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the VEGF-2 polynucleotide may also be delivered in liposome formulations (such as those taught in Felgner P. L. et al. (1995) *Ann. NY Acad. Sci.* 772:126-139 and Abdallah B. et al. (1995) *Biol. Cell* 85(1):1-7) which can be prepared by methods well known to those skilled in the art.

The VEGF-2 vector constructs used in the gene therapy method are preferably constructs that will not integrate into the host genome nor will they contain sequences that allow for replication. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods, of up to six months.

The VEGF-2 construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen, fibers of fibrous tissues, or that same matrix within connective tissue ensheathing muscle cells or in the lacunae of bone. It is similarly the space occupied by the plasma of the circulation and the lymph fluid of the lymphatic channels. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. Preferably, they are delivered by direct injection into the artery.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues, or directly into arteries. However, other parenteral routes may also be used, such as, inhalation of an aerosol formulation particularly for delivery to lungs or bronchial tissues, throat or mucous membranes of the nose. In addition, naked VEGF-2 constructs can be delivered to arteries during angioplasty by the catheter used in the procedure.

The dose response effects of injected VEGF-2 polynucleotide construct in arteries in vivo is determined as follows. Suitable template DNA for production of mRNA coding for VEGF-2 is prepared in accordance with a standard recombinant DNA methodology. The template DNA, which may be either circular or linear, is either used as naked DNA or complexed with liposomes. The arteries of rabbits are then injected with various amounts of the template DNA.

Hindlimb ischemia in rabbits is surgically induced, as described in Example 18. Immediately following this, five different sites in the adductor (2 sites), medial large (2 sites), and semimembranous muscles (1 site) are injected directly with plasmid DNA encoding VEGF-2 using a 3 ml syringe and 2-gauge needle advanced through a small skin incision. The skin is then closed using 4.0 nylon.

The ability to rescue hindlimb ischemia is determined by measuring the number of capillaries in light microsopic sections taken from the treated hindlimbs, compared to ischemic hindlimbs from untreated rabbits, measurement of calf blood pressure, and intra-arterial Doppler guidewire measurement of flow velocity (Takeshita et al., *J. Clin. Invest.* 93:662-670 (1994)). The results of the above experimentation in rabbits can be use to extrapolate proper dosages and other treatment parameters in humans and other animals using VEGF-2 polynucleotide naked DNA.

Example 28

Method of Treatment Using Gene Therapy—Ex Vivo

One method of gene therapy transplants fibroblasts, which are capable of expressing VEGF-2 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMfV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding VEGF-2 can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted VEGF-2.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the VEGF-2 gene is then added to the media and the packaging cells transduced with the vector. The packaging cells now produce infectious viral particles containing the VEGF-2 gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether VEGF-2 protein is produced.

The engineered fibroblasts are then transplanted onto the host, either alone or after having been grown to confluence on cytodex 3 microcarrier beads Example 29

Method of Treatment Using Gene Therapy Homologous Recombination

Another method of gene therapy according to the present invention involves operably associating the endogenous VEGF-2 sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932-8935 (1989); and Zijlstra et al., *Nature* 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous VEGF-2, flanking the promoter. The targeting sequence will be sufficiently near the 5' end of VEGF-2 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous VEGF-2 sequence. This results in the expression of VEGF-2 in the cell. Expression may be detected by immunological staining, or any other method known in the art. Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2$ $HPQ_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. To construct a plasmid for targeting to the VEGF-2 locus, plasmid pUC18 (MBI Fermentas, Amherst, N.Y.) is digested with HindIII. The CMV promoter is amplified by PCR with an XbaI site on the 5' end and a BamHI site on the 3' end. Two VEGF-2 non-coding sequences are amplified via PCR: one VEGF-2 non-coding sequence (VEGF-2 fragment 1) is amplified with a HindIII site at the 5' end and an Xba site at the 0.3' end; the other VEGF-2 non-coding sequence (VEGF-2 fragment 2) is amplified with a BamHI site at the 5' end and a HindIII site at the 3' end. The CMV promoter and VEGF-2 fragments are digested with the appropriate enzymes (CMV promoter—XbaI and BamHI; VEGF-2 fragment 1XbaI; VEGF-2 fragment 2-BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5\times10^6$ cells) is then added to the cuvette, and the cell suspension and DNA solutions are gently mixed. Electroporation is performed with a Gene-Pulser apparatus (Bio-Rad). Capacitance and voltage are set at 960 gF and 250-300 V, respectively. As voltage increases, cell survival decreases, but the percentage of surviving cells that stably incorporate the introduced DNA into their genome increases dramatically. Given these parameters, a pulse time of approximately 0.14-20 mSec should be observed.

Electroporated cells are maintained at room temperature for approximately 5 min, and the contents of the cuvette are then gently: removed with a sterile transfer pipette. The cells are added directly to 10 ml of prewarmed nutrient media (DMEM with 15% calf serum) in a 10 cm dish and incubated at 37EC. The following day, the media is aspirated and replaced with 10 ml of fresh media and incubated for a further 16-24 hours.

The engineered fibroblasts are then injected into the host, either aloie or after having been grown to confluence on cytodex 0.3 microcarrier beads. The fibroblasts now produce the protein product.

Example 30

VEGF-2 Transgenic Animals

The VEGF-2 polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997))., The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order: to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of VEGF-2 polypeptides, studying conditions and/or disorders associated with aberrant VEGF-2 expression, and in screening for compounds effective in ameliorating such conditions and/or disorders.

Example 31

VEGF-2 Knock-Out Animals

Endogenous VEGF-2 gene expression can also be reduced by inactivating or "knocking out" the VEGF-2 gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene. (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g, lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the VEGF-2 polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g, genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of VEGF-2 polypeptides, studying conditions and/or disorders associated with aberrant VEGF-2 expression, and in screening for compounds effective in ameliorating such conditions and/or disorders.

Example 32

Identification and Cloning of VH and VL Domains

One method to identify and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may be lysed in the TRIzol® reagent (Life Technologies, Rockville. MD) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Following washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can determined using optical density measurements.

cDNA may be synthesized, according to methods well-known in the art, from 1.5-2.5 micrograms of RNA using reverse transcriptase and random hexamer primers cDNA is then used as a template for PCR amplification of VH and VL domains. Primers used to amplify VH and VL genes are shown in Table 5. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1×PCR buffer, 2 mM of each dNTP, 0.7 units of High Fidelity Taq polymerse, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes are stored 4° C.

TABLE 3

Primer Sequences Used to Amplify VH and VL domains.

| Primer name | SEQ ID NO | Primer Sequence (5'-3') |
| --- | --- | --- |
| VH Primers | | |
| Hu VH1-5' | 36 | CAGGTGCAGCTGGTGCAGTCTGG |
| Hu VH2-5' | 37 | CAGGTCAACTTAAGGGAGTCTGG |
| Hu VH3-5' | 38 | GAGGTGCAGCTGGTGGAGTCTGG |
| Hu VH4-5' | 39 | CAGGTGCAGCTGCAGGAGTCGGG |
| Hu VH5-5' | 40 | GAGGTGCAGCTGTTGCAGTCTGC |
| Hu VH6-5' | 41 | CAGGTACAGCTGCAGCAGTCAGG |
| Hu JH1,2-5' | 42 | TGAGGAGACGGTGACCAGGGTGCC |
| Hu JH3-5' | 43 | TGAAGAGACGGTGACCATTGTCCC |
| Hu JH4,5-5' | 44 | TGAGGAGACGGTGACCAGGGTTCC |
| Hu JH6-5' | 45 | TGAGGAGACGGTGACCGTGGTCCC |
| VL Primers | | |
| Hu Vkappa1-5 | 46 | GACATCCAGATGACCCAGTCTCC |
| Hu Vkappa2a-5' | 47 | GATGTTGTGATGACTCAGTCTCC |
| Hu Vkappa2b-5' | 48 | GATATTGTGATGACTCAGTCTCC |
| Hu Vkappa3-5' | 49 | GAAATTGTGTTGACGCAGTCTCC |
| Hu Vkappa4-5' | 50 | GACATCGTGATGACCCAGTCTCC |
| Hu Vkappa5-5' | 51 | GAAACGACACTCACGCAGTCTCC |
| Hu Vkappa6-5' | 52 | GAAATTGTGCTGACTCAGTCTCC |
| Hu Vlambda1-5' | 53 | CAGTCTGTGTTGACGCAGCCGCC |
| Hu Vlambda2-5' | 54 | CAGTCTGCCCTGACTCAGCCTGC |
| Hu Vlambda3-5' | 55 | TCCTATGTGCTGACTCAGCCACC |
| Hu Vlambda3b-5' | 56 | TCTTCTGAGCTGACTCAGGACCC |
| Hu Vlambda4-5' | 57 | CACGTTATACTGACTCAACCGCC |
| Hu Vlambda5-5' | 58 | CAGGCTGTGCTCACTCAGCCGTC |
| Hu Vlambda6-5' | 59 | AATTTTATGCTGACTCAGCCCCA |

TABLE 3-continued

Primer Sequences Used to Amplify VH and VL domains.

| Primer name | SEQ ID NO | Primer Sequence (5'-3') |
|---|---|---|
| Hu Jkappa1-3' | 60 | ACGTTTGATTTCCACCTTGGTCCC |
| Hu Jkappa2-3' | 61 | ACGTTTGATCTCCAGCTTGGTCCC |
| Hu Jkappa3-3' | 62 | ACGTTTGATATCCACTTTGGTCCC |
| Hu Jkappa4-3' | 63 | ACGTTTGATCTCCACCTTGGTCCC |
| Hu Jkappa5-3' | 64 | ACGTTTAATCTCCAGTCGTGTCCC |
| Hu Jlambda1-3' | 65 | CAGTCTGTGTTGACGCAGCCGCC |
| Hu Jlambda2-3' | 66 | CAGTCTGCCCTGACTCAGCCTGC |
| Hu Jlambdia3-3' | 67 | TCCTATGTGCTGACTCAGCCACC |
| Hu Jlambda3b-3' | 68 | TCTTCTGAGCTGACTCAGGACCC |
| Hu Jlambda4-3' | 69 | CACGTTATACTGACTCAACCGCC |
| Hu Jlambda5-3' | 70 | CAGGCTGTGCTCACTCAGCCGTC |
| Hu Jlambda6-3' | 71 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commohly known in the art.

The PCR bands containing the VH domain and the VL domains can also be used to create full-length Ig expression vectors. VH and VL domains can be cloned into vectors containing the nucleotide sequences of a heavy (e.g., human IgG1 or human IgG4) or light chain (human kappa or human lambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods using polynucleotides encoding VH and VL antibody domains to generate expression vectors that encode complete antibody molecules are well known within the art.

Example 33

BIAcore Analysis of the Affinity of VEGF-2 Binding Polypeptides

Binding of VEGF-2 antibodies to VEGF-2, for example, can be analyzed by BIAcore analysis. Either VEGF-2 (or other antigen to which one wants to know the affinity of a VEGF-2 antibody) or VEGF-2 antibody can be covalently immobilized to a BIAcore sensor chip (CM5 chip) via amine groups using N-ethyl-N'-(dimethylaminopropyl)carboiimide/N-hydroxysuccinimide chemistry. Various dilutions of VEGF-2 antibodiess or VEGF-2 (or other antigen to which one wants to know the affinity of a VEGF-2 antibody), respectively, are flowed over the derivatized CM5 chip in flow cells at 25 microlters/min for a total volume of 50 microliters. The amount of bound protein is determined during washing of the flow cell with HBS buffer (10 mM HEPES, pH7.4, 150 mM NaCl, 3,4 mM EDTA, 0.005% surfactant p20). Binding specificity for the protein of interest is determined by competition with soluble competitor in the presence the protein of interest.

The flow cell surface can be regenerated by displacing bound protein by washing with 20 microliters of 10 mM glycins-HCl, pH2.3. For kinetic analysis, the flow cells are tested at different flow rates and different polypeptide densities on the CM5 chip. The on-rates and off-rates can be determined using the kinetic evaluation program in a BIAevaluation 3 software.

BIAcore technology may also be utilized, for example, to quantitatively determine the ability of an anti-VEGF-2 antibody to inhibit the ability of VEGF-2 to bind to its receptor.

Example 34

Endothelial Cell Proliferation Assay

VEGF-2 treatment induces vascular endothelial cells as well as lymphatic endothelial cells to undergo proliferation. One may use the following assay to follow this activity in VEGF-2 treated cells. Additionally, one may also use this assay to determine if VEGF-2 antibodies are able to inhibit the ability of VEGF-2 proteins to induce proliferation of endothelial cells. The following protocol demonstrates the assay to test the inhibitory activity of VEGF-2 antibodies, however, one of skill in the art could readily modify this assay to omit the VEGF-2 antibodies in order to test VEGF-2 proteins' ability to induce endothelial cell proliferation.

Continuous Subculture of Bovine Lymphatic Endothelial Cells (bLEC)

Bovine lymphatic endothelial cells (bLEC) cells (ATCC No. PTA-1149) are grown in complete medium (DMEM, 10% of heat-inactivatedFBS (Biowhittaker, Cat.#14-502F), 100 U/ml penicillin, 100 ug/ml streptomycin, 2 mM glutamine, 5 ml/500 ml media of Non-Essential Amino Acids Solution (NEAA), 150 ug/ml bovine brain extract (bovine brain extract is prepared as described in Maciag et al., Proc. Natl. Acad. Sci. USA 76, 5674-5678 (1979)), 100 ug/ml heparin) in a 75 cm2 flask. When confluence is reached, the culture medium is removed from the 75 cm2 flask, and cells are rinsed once with 20 ml of PBS without calcium and without magnesium, and then covered with 4 ml of trypsin-EDTA and returned to the incubator for 3-5 minutes. The cells are then detached from the plastic surface by gentle agitation, adding 4 ml of complete medium to inactivate the trypsin. The cell suspension is next transferred to the 15 ml centrifuge tube and centrifuged at 1000 rpm for 5 minutes to pellet cells. The supernatant is removed and the cell pellet resuspended in complete medium. The cells are split 1:3 and maintained in CO2 incubator at 37 degrees C. The medium is changed twice weekly regardless of the need to split the cells.

VEGF-2 Proliferation Assay Protocol

Day 1: Plate bLECs at 3500 cells per well in a 96 well plate excluding outer rows and culture overnight in complete medium. The following day, Day 2: Remove complete medium and add 100 microliters of starvation medium: EBM (Clonetics Cat. #CC-3121), 0.5% FBS.

Day 3: Dilute VEGF-2 protein in starvation medium yielding a 3× concentration. In 12 well plates, make serial dilutions of each antibody (using the 3× concentration of VEGF-2 in starvation medium as the diluent) for a total of 14 dilutions.

The final concentrations after adding the antibody to the experimental plates should range from 4000 ng/ml to 0.0006 ng/ml (3-fold dilutions) in triplicates. Transfer 50 microliters of each dilution starting from the least amount of antibody to the 96 well plate. Incubate the plates for 3 days at 37 degrees Celsius, 5% $CO_2$.

Day 6: Supplement each well with 50 microliters of starvation medium containing 3H-thymidine 0.5mCi per well (6.7 Ci/mM) and incubate cells for an additional 18-20 hours.

Day 7: Freeze plates at −80 degrees C. After 2-3 h, thaw the plates. Harvest cells and measure 3H-thymidine incorporation.

Example 35

Elk-1 Phosphorylation Assay

VEGF-2 induces a signalling cascade in VEGF-2 responsive cells that activates a kinase which phosphorylates Elk-1 protein. One may use the following assay to follow this activity in VEGF-2 treated cells. Additionally, one may also use this assay to determine if VEGF-2 antibodies are able to inhibit the ability of VEGF-2 proteins to induce Elk-1 phosphorylation. The following protocol demonstrates the assay to test the inhibitory activity of VEGF-2 antibodies, however, one of skill in the art could readily modify this assay to omit the VEGF-2 antibodies in order to test VEGF-2 proteins' ability to induce Elk-1 phosphorylation.

Briefly, 96-well flat bottom tissue culture plates are seeded with bovine lymphatic endothelial cells (bLEC) at 25,000 cells per well in a 100 microliter volume of complete growth medium (EGM-MV from Clonetics Corporation, Cat. No. CC-4143) and incubated overnight at 37 C in 5% $CO_2$. Working stock solutions of VEGF-2 (e.g., full length protein or the secreted form of VEGF-2) at 0.2 microgram/milliliter in PBS+0.05% BSA (low endotoxin) are prepared.

In a separate assay plate, mix either 6 ng of full length or 2 ng of the secreted form of VEGF-2 protein with 1,500 ng (which represents 100× molar excess of antibody) of VEGF-2 antibody, and adjust the total volume to 0.100 microliters with Human Endothelial-Serum-Free Medium (Life Technologies, Cat. No. 11111-044) (SFM). The final concentration full length VEGF-2, secreted VEGF-2 and antibody are 60 ng/mL, 20 ng/mL and 15 ug/mL, respectively). If the antibody samples are conditioned media, use the total IgG concentrations to calculate the amount of antibody needed in the assay. VEGF-2-antibody complexes are allowed to form for 1 hour at room temperature.

While the antibody-antigen complexes are forming, remove the complete growth medium from the cells and replace it with SFM starvation medium, and incubate the cells for 5 Incubate for one hour at 37 C in 5% $CO_2$. After the one hour incubation of the cells is over, decant the starvation media from the cells and transfer 50 microliters of each VEGF-2/VEGF-2 antibody sample from the assay plate to the cell plate. Then, incubate the cell plate for 15 minutes at 37 C. Following incubation, decant the liquid containing VEGF, 2-antiVEGF-2 complexes from the cells and 50 microliters per well of ice-cold lysis buffer (20 mM Tris-Cl (pH 7.5), 250 mM NaCl, 0.5% NP-40, 10% glycerol, 3 mM EDTA, 3 mM EGTA, 0.1 mM sodium orthovanadate, 1 mM NaF, 0.5 mM DTT [add fresh], 1X Roche Complete protease inhibitor [add fresh]) and let stand 1-3 minutes. The lysate should be used immediately in kinase assay or stored at −70 C.

Kinase Assay:

Dilute GST-Elk1 fusion protein (Cell Signaling Technologies #9184, or Boston Biologicals #1010) in PBS to 10 ug/mL, and add to a 0.96-well Dynex Microlite 2 plate (Catalogue #7417) at 50 microliters per well. Tap the plate gently to get liquid to cover the bottom completely. Incubate overnight at room temperature or for 1 hour at 37 C. Wash the plate once with 250 microliters per well of wash buffer (0.05% Tween 20, PBS+PBST). Next, block unoccupied binding sites in the wells with blocking buffer (1.0% Nonfat Dry Milk, PBST) at 150 microliters per well and incubate for 1 hour at room temperature. The plate are then washed three times with 250 microliters per well of wash buffer. To each well in the assay plate, and 15 microliters of samples (in duplicates) and 10 microliters of water. Initiate kinase reaction by adding 25 mictoliters per well of 2× kinase buffer (2× Kinase Reaction Buffer (100 mM Hepes (pH 7.5), 20 mM $MgCl_2$, 5 mM NaF, 0.2 mM sodium orthovanadate, 1 mM DTT [add fresh], 1 mM ATP [add fresh]) to each well. Include purified, activated and unactivated ERK1/2 kinase (Stratagene, #206110 and #206120, respectively).as controls. Incubate at room temperature for 1 hour (the reaction is linear between 1 to 3 hours).

Following incubation of the lysate or kinase controls with GST-Elk-1 fusion protein, wash the plate three times with 250 microliters per well of wash buffer. Then, dilute anti-phospho-Elk1 antibody 1:1000 (Cell Signaling Technologies, #9181) with antibody diluent (0.1% BSA, PBST), and add 50 microliters to each well. Incubate at room temperature for 1 hour.

Then, wash the plate three times with 250 microliters per well of wash buffer. Dilute Zymax goat anti-rabbit IgG-alkaline phosphatase (Zymed Laboratories Inc.,#81-6122) 1:4000 with antibody diluent. Transfer 50 microliters per well of diluted antibody to each well, and incubate for 1 hour at RT. Wash three times with 250 microliters per well of wash buffer. Then add 50 microliters per well BM chemiluminescent ELISA AP substrate (Roche Molecular Biochemicals, #1759779) prepared according to the "ELISA directions" in the package. Incubate at room temperature for 12 minutes before reading in a luminometer.

Example 36

Dorsal Chamber Model to Study Effect of VEGF-2 Antibodies of Tumor Vascularization Characterization of the multiple aspects of microvascular physiology in transparent window systems in mice have provided valuable data on angiogenesis, inflammation, microvascular transport, tissue rejection, and tumor physiology (Melder, R. J et al., *Biophys. J.* 69: 2131-2138, (1995); Fukumura, D. et al *Cancer Res.* 55: 4824-4829, (1995); Yamada, S. et al., *Blood,* 86: 3487-3492, (1995); Yamada, S., et al., *Blood,* 86: 4707-4708, (1995); Melder, R. J., et al., *Microvas.Res.* 50, 35-44, (1995); Melder, R. J. et al., *Nature Medicine* 2:992-997, (1996); Dellian, M., et al., *Am. J. Path.* 149: 59-71, (1996); and Leunig M., et al., Cancer Res 52: 6553-60 (1992)). This assay may be used to test the hypothesis that VEGF-2 polypeptides administered directly to the interstitial compartment of the skin or pial surface will induce a change in the structure and function of the microvasculature. These studies will specifically characterize activities on existing vasculature within the observation window and neogenic vasculature developing in response to these proteins in implanted gels. The following observations will be made:

a) length, diameter and density of the existing vascular network in the skin or pial surface in response to treatment with VEGF-2 polypeptides;
b) blood flow velocity and leukocyte flux in the treated vascular bed;
c) the frequency of rolling and adherent leukocytes in the treated vascular bed;
d) the permeability of existing vascular network in the skin or pial surface in response to treatment with VEGF-2 polypeptides;
e) the angiogenic response to VEGF-2 polypeptides in implanted collagen disks within the window preparations;
f) blood flow velocity leukocyte flux and frequency of rolling and adherent leukocytes in the implanted collagen disks within the window preparations;
g) The permeability of angiogenic vascular networks in response to VEGF-2 polypeptides in implanted collagen disks within the skin or cranial window preparations.

For this assay, Swiss nu/nu mice are used. The advantages of using Swiss nu/nu mice are several-fold, including a) reducing the possibility of immune response over the period of study, b) improving the optics of the system due to lack of pigmentation and hair in the skin, c) maintaining historical consistency with similar previous studies.

Each experimental and control group will have seven mice. Male mice are preferred since they are larger and will have more skin for surgical window implants. Samples for testing will include VEGF-2 polypeptides and recombinant protein controls. Each study examining protein activities on existing vascular beds will consist of five experimental groups:
Group 1: Test sample (dose 1) in buffer
Group 2: Test sample (dose 2) in buffer
Group 3: Test sample (dose 3) in buffer
Group 4: Buffer and BSA control
Group 5: Positive Control (b,GF, 10 ng).

Sterile protein solutions will be administered as a 10 µl volume directly into the window preparation of mice with dorsal skin windows. Alternatively, sterile collagen/sucralfate disks containing protein concentrations as listed above will be placed into the window preparations for evaluation of the angiogenic potential. Sterile antibody solutions will be administered intravenously.

These experiments are designed to test the hypothesis that +VEGF-2 polypeptides administered to the extravascular compartment of the skin will induce a change in the structure and function of the existing capillaries and postcapillary venules. Administration of polypeptides in collagen disks will examine their potential for modulating angiogenesis.

Methods

Animal Preparation.

The surgical procedures are performed ii Swiss nude mice. For the surgical procedures, animals (20-30 g) are anesthetized with a sub-cutaneous injection of a cocktail of 90 mg Ketamine and 9 mg Xylazine per kg body weight. All surgical procedures are performed under aseptic conditions in a horizontal laminar flow hood, with all equipment being steam, gas, or chemically sterilized. Sterility of the bench are maintained by U.V. lights when not in use. During surgery, the body temperature of the animals is kept constant by means of a heated work surface. All mice are housed individually in microisolator cages and all manipulations are done in laminar flow hoods. Following surgery, animals are observed for any discomfort/distress. The criteria for discomfort include, but are not limited to: loss of body weight. (20%), inability to ambulate, evidence of self-mutilation, or inability to eat or drink. Buprenorphine (0.1 mg/kg q 12 h) is used as an analgesic for 3 days post implantation. Any animal exhibiting the signs of discomfort for 3 days post surgery, are euthanized with $CO_2$ inhalation.

Dorsal Skin Chamber Implantation:

Chambers are implanted as described in Leunig et al., Cancer Res 0.52:6553-0.6560 (1992). Briefly, the chamber is positioned such that the chamber is positioned over a double layer of skin (i.e., a "pinch of skin") that extends above the dorsal surface. The full thickness of one side of the dorsal skin flap is removed in a circular area 15 mm in diameter. The second side of the flap (consisting of epidermis, fascia, and striated muscle) is positioned on the frame of the chamber and the opening ("window") is covered with a sterile, glass coverslip. The chamber is held in place with suture (silk, 4-0) which is threaded through the extended skin and holes along the top of the chamber. Mice are allowed to recover 72 hours.

Following this recovery, each mouse is positioned in a transparent, polycarbonate tube (25 mm diameter) for treatment. The coverslips are carefully removed, followed by addition of treatment factor(s). After addition of treatment factors, a new, sterile coverslip will then placed on the viewing surface. Measurements are made by morphometric analysis using a CCD and SIT camera, S-VHS videocassette recorder and direct digital image acquisition. Mice with implanted chambers are observed for 28 days, as indicated in the flow charts.

Measurements.

Mice are anesthetized with s.c. injection of a cocktail of 90 mg Ketamine and 9 mg Xylazine per kg body weight, then positioned on a sterile plastic stage assembly. Vascular maps of the window will then be made using transillumination (dorsal skin window) or following an injection of 100 µl of BSA-FITC (1 mg/ml, i.v.) and epi-illumination (cranial window). Video recordings of vascular beds are made at a range of magnifications (from 1× to 40×) as well as digital frames for off-line analysis. Images are quantified for vascular density, blood flow velocity and vascular dimensions (for shear rate analysis). In addition, circulating leukocyte interactions are evaluated by injection with 101 of Rhodamine 6-G followed by video microscopy of the capillaries and postcapillary venules. Permeability measurements are made from off-line analysis of images of BSA transport at 5, 10, 15 and 20 min. following BSA-FITC injection. Capillary density determinations of normal and angiogenic vascular beds are made from offline analysis of video tapes. Five sets of observations of experimental and control mice are at seven day intervals (total of 28 days).

Example 37

Colon Carcinoma LS174 T Dorsal Chamber Model

The colon carcinoma, LS174T, produces/secretes VEGF-2 polypeptide. It is therefore particularly interesting to test whether treatment with VEGF-2 antibodies slows or arrests LS174T tumor growth, or even effects LS174T tumor regression. To test this' hypothesis the dorsal chamber model described above, may be adapted to study tumor growth and vascularization within the dorsal chamber.

Three days after a dorsal chamber is implanted, 2 microliters of pelleted LS174T tumor cell suspension (containing approximately $2 \times 10^5$ cells) is innoculated onto the striated muscle layer of the subcutaneous tissue in the chamber. The innoculated tumor is then left for a period of time to allow it to "take" and grow to a specified size (e.g., 4-6 mm in diameter) prior to beginning VEGF-2 treatment.

Mice are initially injected with 0.4 milligrams of VEGF-2 antibody, followed by injections of 0.2 milligrams of VEGF-2 antibody given at five day intervals for 30 days. Injections may be given intraperitoneally (i.p.) or intravenously (i.v.).

Parameters that may be measured to assess the effect of VEGF-2 treatment on tumor growth include tumor size and (endothelial and lymphatic vascular density.

Additionally, this assay may easily be modified to test the effect of VEGF-2 treatment on other tumors, regardless of their production of endogenous VEGF-2 polypeptide.

Example 38

Effect of VEGF-2 Antibody Treatment on MDA-MB-231 Tumor

The MDA-MB-231 cell line (ATCC #HTB-26) is a breast cancer cell line.

The following assay may be used to test whether treatment with VEGF-2 antibodies slows or arrests MDA-MB-231 tumor growth, or effects MDA-MB-231 tumor regression. While the following example outlines an experimental protocol involving MDA-MB-231 cells, one of skill in the art could easily modify this protocol to test the effect of treatment with VEGF-2 antibodies on other tumor types.

On day zero, mice are injected in the mammary pads with one million MDA-MB-231 cells. The implanted tumor is allowed to grow to a 2 mm×2 mm which usually takes about 5 days. After the tumor has reached the 2×2 mm2 size, an animal is given an initial dose Of 04. Milligrams of VEGF-2 antibody. Thereafter, 0.2 milligrams of VEGF-2 antibody is administered on the fifth and 10th days after the initial injection. Additionally, animals in certain experimental groups ma, also be treated with 5 mg/kg of Taxol (or other suitable dose of another chemotherapeutic agent) daily.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

What is claimed is:

1. An isolated polynucleotide comprising a nucleotide sequence encoding an antibody or antigen binding fragment thereof that specifically binds a human VEGF-2 polypeptide, said antibody comprising:

(i) a first amino acid sequence that is at least 99% identical to the amino acid sequence of the VH domain of the antibody expressed by the hybridoma cell line deposited under ATCC Deposit No. PTA-4095, wherein the first amino acid sequence comprises the amino acid sequences of the VHCDR1, VHCDR2, and VHCDR3 regions of the antibody expressed by the hybridoma deposited under ATCC Deposit No. PTA-4095; and a second amino acid sequence comprising the amino acid sequence of the VL domain of the antibody expressed by the hybridoma cell line deposited under ATCC Deposit No. PTA-4095.

2. The isolated polynucleotide according to claim 1, wherein said polynucleotide is fused to a heterologous polynucleotide.

3. A vector comprising the isolated polynucleotide according to claim 1.

4. A host cell comprising the vector of claim 3.

5. A host cell comprising the isolated polynucleotide claim 1.

6. A method of making an antibody comprising:
   (a) expressing the antibody encoded by the isolated polynucleotide of claim 1; and
   (b) recovering said antibody.

7. An isolated polynucleotide comprising a nucleotide sequence encoding an antibody or antigen binding fragment thereof that specifically binds a human VEGF-2 polypeptide, said antibody comprising:
   (ii) a first amino acid sequence that is at least 99% identical to the amino acid sequence of the VH domain of the 69D09 ScFv shown in SEQ ID NO: 79, wherein the first amino acid sequence comprises: a VHCDR1 consisting of the amino acid sequence of amino acid residues 26-35 of SEQ ID NO: 79; a VHCDR2 consisting of the amino acid sequence of amino acid residues 50-66 of SEQ ID NO: 79; and a VHCDR3 consisting of the amino acid sequence of amino acid residues 99-107 of SEQ ID NO: 79; and a second amino acid sequence comprising the amino acid sequence of the VL domain of the 69D09 ScFv shown in SEQ ID NO: 79.

8. The isolated polynucleotide according to claim 7, wherein said polynucleotide is fused to a heterologous polynucleotide.

9. A vector comprising the isolated polynucleotide according to claim 7.

10. A host cell comprising the vector of claim 9.

11. A host cell comprising the isolated polynucleotide claim 7.

12. A method of making an antibody comprising:
    (a) expressing the antibody encoded by the isolated polynucleotide of claim 7; and
    (b) recovering said antibody.

* * * * *

SEQUENCE LISTING

```
<160> NUMBER OF SEQ ID NOS: 85

<210> SEQ ID NO 1
<211> LENGTH: 1674
<212> TYPE: DNA
<213> ORGANISM: Homo sapiens
<220> FEATURE:
<221> NAME/KEY: sig_peptide
<222> LOCATION: (12)..(80)
<220> FEATURE:
<221> NAME/KEY: CDS
<222> LOCATION: (12)..(1268)
<220> FEATURE:
<221> NAME/KEY: mat_peptide
<222> LOCATION: (81)..(1268)

<400> SEQUENCE: 1
gtccttccac c atg cac tcg ctg ggc ttc ttc tct gtg gcg tgt tct ctg        50
            Met His Ser Leu Gly Phe Phe Ser Val Ala Cys Ser Leu
                -20                         -15 ctc gcc gct gcg ctg ctc ccg ggt cct cgc gag gcg ccc gcc gcc gcc        98
Leu Ala Ala Ala Leu Leu Pro Gly Pro Arg Glu Ala Pro Ala Ala Ala
-10              -5              -1  1               5 gcc gcc ttc gag tcc gga ctc gac ctc tcg gac gcg gag ccc gac gcg       146
Ala Ala Phe Glu Ser Gly Leu Asp Leu Ser Asp Ala Glu Pro Asp Ala
                10                      15                      20 ggc gag gcc acg gct tat gca agc aaa gat ctg gag gag cag tta cgg       194
Gly Glu Ala Thr Ala Tyr Ala Ser Lys Asp Leu Glu Glu Gln Leu Arg
            25                      30                      35 tct gtg tcc agt gta gat gaa ctc atg act gta ctc tac cca gaa tat       242
Ser Val Ser Ser Val Asp Glu Leu Met Thr Val Leu Tyr Pro Glu Tyr
        40                      45                      50 tgg aaa atg tac aag tgt cag cta agg aaa gga ggc tgg caa cat aac       290
Trp Lys Met Tyr Lys Cys Gln Leu Arg Lys Gly Gly Trp Gln His Asn
55                      60                      65                  70 aga gaa cag gcc aac ctc aac tca agg aca gaa gag act ata aaa ttt       338
Arg Glu Gln Ala Asn Leu Asn Ser Arg Thr Glu Glu Thr Ile Lys Phe
                    75                      80                      85 gct gca gca cat tat aat aca gag atc ttg aaa agt att gat aat gag       386
Ala Ala Ala His Tyr Asn Thr Glu Ile Leu Lys Ser Ile Asp Asn Glu
                90                      95                      100
```

```
tgg aga aag act caa tgc atg cca cgg gag gtg tgt ata gat gtg ggg    434
Trp Arg Lys Thr Gln Cys Met Pro Arg Glu Val Cys Ile Asp Val Gly
        105                 110                 115 aag gag ttt gga gtc gcg aca aac acc ttc ttt aaa cct cca tgt gtg    482
Lys Glu Phe Gly Val Ala Thr Asn Thr Phe Phe Lys Pro Pro Cys Val
    120                 125                 130 tcc gtc tac aga tgt ggg ggt tgc tgc aat agt gag ggg ctg cag tgc    530
Ser Val Tyr Arg Cys Gly Gly Cys Cys Asn Ser Glu Gly Leu Gln Cys
135                 140                 145                 150 atg aac acc agc acg agc tac ctc agc aag acg tta ttt gaa att aca    578
Met Asn Thr Ser Thr Ser Tyr Leu Ser Lys Thr Leu Phe Glu Ile Thr
                155                 160                 165 gtg cct ctc tct caa ggc ccc aaa cca gta aca atc agt ttt gcc aat    626
Val Pro Leu Ser Gln Gly Pro Lys Pro Val Thr Ile Ser Phe Ala Asn
        170                 175                 180 cac act tcc tgc cga tgc atg tct aaa ctg gat gtt tac aga caa gtt    674
His Thr Ser Cys Arg Cys Met Ser Lys Leu Asp Val Tyr Arg Gln Val
    185                 190                 195 cat tcc att att aga cgt tcc ctg cca gca aca cta cca cag tgt cag    722
His Ser Ile Ile Arg Arg Ser Leu Pro Ala Thr Leu Pro Gln Cys Gln
200                 205                 210 gca gcg aac aag acc tgc ccc acc aat tac atg tgg aat aat cac atc    770
Ala Ala Asn Lys Thr Cys Pro Thr Asn Tyr Met Trp Asn Asn His Ile
215                 220                 225                 230 tgc aga tgc ctg gct cag gaa gat ttt atg ttt tcc tcg gat gct gga    818
Cys Arg Cys Leu Ala Gln Glu Asp Phe Met Phe Ser Ser Asp Ala Gly
            235                 240                 245 gat gac tca aca gat gga ttc cat gac atc tgt gga cca aac aag gag    866
Asp Asp Ser Thr Asp Gly Phe His Asp Ile Cys Gly Pro Asn Lys Glu
        250                 255                 260 ctg gat gaa gag acc tgt cag tgt gtc tgc aga gcg ggg ctt cgg cct    914
Leu Asp Glu Glu Thr Cys Gln Cys Val Cys Arg Ala Gly Leu Arg Pro
    265                 270                 275 gcc agc tgt gga ccc cac aaa gaa cta gac aga aac tca tgc cag tgt    962
Ala Ser Cys Gly Pro His Lys Glu Leu Asp Arg Asn Ser Cys Gln Cys
280                 285                 290 gtc tgt aaa aac aaa ctc ttc ccc agc caa tgt ggg gcc aac cga gaa    1010
Val Cys Lys Asn Lys Leu Phe Pro Ser Gln Cys Gly Ala Asn Arg Glu
295                 300                 305                 310 ttt gat gaa aac aca tgc cag tgt gta tgt aaa aga acc tgc ccc aga    1058
Phe Asp Glu Asn Thr Cys Gln Cys Val Cys Lys Arg Thr Cys Pro Arg
            315                 320                 325 aat caa ccc cta aat cct gga aaa tgt gcc tgt gaa tgt aca gaa agt    1106
Asn Gln Pro Leu Asn Pro Gly Lys Cys Ala Cys Glu Cys Thr Glu Ser
        330                 335                 340 cca cag aaa tgc ttg tta aaa gga aag aag ttc cac cac caa aca tgc    1154
Pro Gln Lys Cys Leu Leu Lys Gly Lys Lys Phe His His Gln Thr Cys
    345                 350                 355 agc tgt tac aga cgg cca tgt acg aac cgc cag aag gct tgt gag cca    1202
Ser Cys Tyr Arg Arg Pro Cys Thr Asn Arg Gln Lys Ala Cys Glu Pro
360                 365                 370 gga ttt tca tat agt gaa gaa gtg tgt cgt tgt gtc cct tca tat tgg    1250
Gly Phe Ser Tyr Ser Glu Glu Val Cys Arg Cys Val Pro Ser Tyr Trp
375                 380                 385                 390 caa aga cca caa atg agc taagattgta ctgttttcca gttcatcgat            1298
Gln Arg Pro Gln Met Ser
            395 tttctattat ggaaaactgt gttgccacag tagaactgtc tgtgaacaga gagacccttg    1358 tgggtccatg ctaacaaaga caaaagtctg tctttcctga accatgtgga taactttaca    1418
```

```
gaaatggact ggagctcatc tgcaaaaggc ctcttgtaaa gactggtttt ctgccaatga    1478
ccaaacagcc aagattttcc tcttgtgatt tctttaaaag aatgactata taatttattt    1538
ccactaaaaa tattgtttct gcattcattt ttatagcaac aacaattggt aaaactcact    1598
gtgatcaata ttttatatc atgcaaaata tgtttaaaat aaaatgaaaa ttgtatttat     1658
aaaaaaaaaa aaaaaa                                                     1674
```

<210> SEQ ID NO 2
<211> LENGTH: 419
<212> TYPE: PRT
<213> ORGANISM: Homo sapiens

<400> SEQUENCE: 2

```
Met His Ser Leu Gly Phe Phe Ser Val Ala Cys Ser Leu Leu Ala Ala
        -20              -15              -10

Ala Leu Leu Pro Gly Pro Arg Glu Ala Pro Ala Ala Ala Ala Ala Phe
         -5           -1   1               5

Glu Ser Gly Leu Asp Leu Ser Asp Ala Glu Pro Asp Ala Gly Glu Ala
 10              15              20              25

Thr Ala Tyr Ala Ser Lys Asp Leu Glu Glu Gln Leu Arg Ser Val Ser
                 30              35              40

Ser Val Asp Glu Leu Met Thr Val Leu Tyr Pro Glu Tyr Trp Lys Met
             45              50              55

Tyr Lys Cys Gln Leu Arg Lys Gly Gly Trp Gln His Asn Arg Glu Gln
         60              65              70

Ala Asn Leu Asn Ser Arg Thr Glu Glu Thr Ile Lys Phe Ala Ala Ala
     75              80              85

His Tyr Asn Thr Glu Ile Leu Lys Ser Ile Asp Asn Glu Trp Arg Lys
 90              95             100             105

Thr Gln Cys Met Pro Arg Glu Val Cys Ile Asp Val Gly Lys Glu Phe
                110             115             120

Gly Val Ala Thr Asn Thr Phe Phe Lys Pro Pro Cys Val Ser Val Tyr
            125             130             135

Arg Cys Gly Gly Cys Cys Asn Ser Glu Gly Leu Gln Cys Met Asn Thr
        140             145             150

Ser Thr Ser Tyr Leu Ser Lys Thr Leu Phe Glu Ile Thr Val Pro Leu
    155             160             165

Ser Gln Gly Pro Lys Pro Val Thr Ile Ser Phe Ala Asn His Thr Ser
170             175             180             185

Cys Arg Cys Met Ser Lys Leu Asp Val Tyr Arg Gln Val His Ser Ile
            190             195             200

Ile Arg Arg Ser Leu Pro Ala Thr Leu Pro Gln Cys Gln Ala Ala Asn
        205             210             215

Lys Thr Cys Pro Thr Asn Tyr Met Trp Asn Asn His Ile Cys Arg Cys
    220             225             230

Leu Ala Gln Glu Asp Phe Met Phe Ser Ser Asp Ala Gly Asp Asp Ser
235             240             245

Thr Asp Gly Phe His Asp Ile Cys Gly Pro Asn Lys Glu Leu Asp Glu
250             255             260             265

Glu Thr Cys Gln Cys Val Cys Arg Ala Gly Leu Arg Pro Ala Ser Cys
            270             275             280

Gly Pro His Lys Glu Leu Asp Arg Asn Ser Cys Gln Cys Val Cys Lys
        285             290             295
```

-continued

```
Asn Lys Leu Phe Pro Ser Gln Cys Gly Ala Asn Arg Glu Phe Asp Glu
            300                 305                 310

Asn Thr Cys Gln Cys Val Cys Lys Arg Thr Cys Pro Arg Asn Gln Pro
    315                 320                 325

Leu Asn Pro Gly Lys Cys Ala Cys Glu Cys Thr Glu Ser Pro Gln Lys
330                 335                 340                 345

Cys Leu Leu Lys Gly Lys Lys Phe His His Gln Thr Cys Ser Cys Tyr
                350                 355                 360

Arg Arg Pro Cys Thr Asn Arg Gln Lys Ala Cys Glu Pro Gly Phe Ser
            365                 370                 375

Tyr Ser Glu Glu Val Cys Arg Cys Val Pro Ser Tyr Trp Gln Arg Pro
        380                 385                 390

Gln Met Ser
    395

<210> SEQ ID NO 3
<211> LENGTH: 1525
<212> TYPE: DNA
<213> ORGANISM: Homo sapiens
<220> FEATURE:
<221> NAME/KEY: sig_peptide
<222> LOCATION: (71)..(142)
<220> FEATURE:
<221> NAME/KEY: CDS
<222> LOCATION: (71)..(1120)
<220> FEATURE:
<221> NAME/KEY: mat_peptide
<222> LOCATION: (143)..(1120)

<400> SEQUENCE: 3
cgaggccacg gcttatgcaa gcaaagatct ggaggagcag ttacggtctg tgtccagtgt        60
agatgaactc atg act gta ctc tac cca gaa tat tgg aaa atg tac aag       109
             Met Thr Val Leu Tyr Pro Glu Tyr Trp Lys Met Tyr Lys
                 -20                 -15 tgt cag cta agg aaa gga ggc tgg caa cat aac aga gaa cag gcc aac       157
Cys Gln Leu Arg Lys Gly Gly Trp Gln His Asn Arg Glu Gln Ala Asn
    -10                 -5                  -1  1                   5 ctc aac tca agg aca gaa gag act ata aaa ttt gct gca gca cat tat       205
Leu Asn Ser Arg Thr Glu Glu Thr Ile Lys Phe Ala Ala Ala His Tyr
                10                  15                  20 aat aca gag atc ttg aaa agt att gat aat gag tgg aga aag act caa       253
Asn Thr Glu Ile Leu Lys Ser Ile Asp Asn Glu Trp Arg Lys Thr Gln
            25                  30                  35 tgc atg cca cgg gag gtg tgt ata gat gtg ggg aag gag ttt gga gtc       301
Cys Met Pro Arg Glu Val Cys Ile Asp Val Gly Lys Glu Phe Gly Val
        40                  45                  50 gcg aca aac acc ttc ttt aaa cct cca tgt gtg tcc gtc tac aga tgt       349
Ala Thr Asn Thr Phe Phe Lys Pro Pro Cys Val Ser Val Tyr Arg Cys
55                  60                  65 ggg ggt tgc tgc aat agt gag ggg ctg cag tgc atg aac acc agc acg       397
Gly Gly Cys Cys Asn Ser Glu Gly Leu Gln Cys Met Asn Thr Ser Thr
70                  75                  80                  85 agc tac ctc agc aag acg tta ttt gaa att aca gtg cct ctc tct caa       445
Ser Tyr Leu Ser Lys Thr Leu Phe Glu Ile Thr Val Pro Leu Ser Gln
                90                  95                  100 ggc ccc aaa cca gta aca atc agt ttt gcc aat cac act tcc tgc cga       493
Gly Pro Lys Pro Val Thr Ile Ser Phe Ala Asn His Thr Ser Cys Arg
            105                 110                 115 tgc atg tct aaa ctg gat gtt tac aga caa gtt cat tcc att att aga       541
Cys Met Ser Lys Leu Asp Val Tyr Arg Gln Val His Ser Ile Ile Arg
        120                 125                 130
```

```
cgt tcc ctg cca gca aca cta cca cag tgt cag gca gcg aac aag acc     589
Arg Ser Leu Pro Ala Thr Leu Pro Gln Cys Gln Ala Ala Asn Lys Thr
    135                 140                 145 tgc ccc acc aat tac atg tgg aat aat cac atc tgc aga tgc ctg gct     637
Cys Pro Thr Asn Tyr Met Trp Asn Asn His Ile Cys Arg Cys Leu Ala
150                 155                 160                 165 cag gaa gat ttt atg ttt tcc tcg gat gct gga gat gac tca aca gat     685
Gln Glu Asp Phe Met Phe Ser Ser Asp Ala Gly Asp Asp Ser Thr Asp
                170                 175                 180 gga ttc cat gac atc tgt gga cca aac aag gag ctg gat gaa gag acc     733
Gly Phe His Asp Ile Cys Gly Pro Asn Lys Glu Leu Asp Glu Glu Thr
            185                 190                 195 tgt cag tgt gtc tgc aga gcg ggg ctt cgg cct gcc agc tgt gga ccc     781
Cys Gln Cys Val Cys Arg Ala Gly Leu Arg Pro Ala Ser Cys Gly Pro
        200                 205                 210 cac aaa gaa cta gac aga aac tca tgc cag tgt gtc tgt aaa aac aaa     829
His Lys Glu Leu Asp Arg Asn Ser Cys Gln Cys Val Cys Lys Asn Lys
    215                 220                 225 ctc ttc ccc agc caa tgt ggg gcc aac cga gaa ttt gat gaa aac aca     877
Leu Phe Pro Ser Gln Cys Gly Ala Asn Arg Glu Phe Asp Glu Asn Thr
230                 235                 240                 245 tgc cag tgt gta tgt aaa aga acc tgc ccc aga aat caa ccc cta aat     925
Cys Gln Cys Val Cys Lys Arg Thr Cys Pro Arg Asn Gln Pro Leu Asn
                250                 255                 260 cct gga aaa tgt gcc tgt gaa tgt aca gaa agt cca cag aaa tgc ttg     973
Pro Gly Lys Cys Ala Cys Glu Cys Thr Glu Ser Pro Gln Lys Cys Leu
            265                 270                 275 tta aaa gga aag aag ttc cac cac caa aca tgc agc tgt tac aga cgg    1021
Leu Lys Gly Lys Lys Phe His His Gln Thr Cys Ser Cys Tyr Arg Arg
        280                 285                 290 cca tgt acg aac cgc cag aag gct tgt gag cca gga ttt tca tat agt    1069
Pro Cys Thr Asn Arg Gln Lys Ala Cys Glu Pro Gly Phe Ser Tyr Ser
    295                 300                 305 gaa gaa gtg tgt cgt tgt gtc cct tca tat tgg caa aga cca caa atg    1117
Glu Glu Val Cys Arg Cys Val Pro Ser Tyr Trp Gln Arg Pro Gln Met
310                 315                 320                 325 agc taagattgta ctgttttcca gttcatcgat tttctattat ggaaaactgt         1170
Ser gttgccacag tagaactgtc tgtgaacaga gagacccttg tgggtccatg ctaacaaga   1230 caaaagtctg tctttcctga accatgtgga taactttaca gaaatggact ggagctcatc  1290 tgcaaaggc ctcttgtaaa gactggtttt ctgccaatga ccaaacagcc aagattttcc   1350
tcttgtgatt tctttaaaag aatgactata taatttattt ccactaaaaa tattgttcct  1410
gcattcattt ttatagcaac aacaattggt aaaaactcact gtgatcaata ttttatatc   1470 atgcaaaata tgtttaaaat aaaatgaaaa ttgtattata aaaaaaaaaa aaaaa        1525

<210> SEQ ID NO 4
<211> LENGTH: 350
<212> TYPE: PRT
<213> ORGANISM: Homo sapiens

<400> SEQUENCE: 4

Met Thr Val Leu Tyr Pro Glu Tyr Trp Lys Met Tyr Lys Cys Gln Leu
                -20                 -15                 -10

Arg Lys Gly Gly Trp Gln His Asn Arg Glu Gln Ala Asn Leu Asn Ser
         -5                  -1  1                   5

Arg Thr Glu Glu Thr Ile Lys Phe Ala Ala Ala His Tyr Asn Thr Glu
```

```
            10              15                  20
Ile Leu Lys Ser Ile Asp Asn Glu Trp Arg Lys Thr Gln Cys Met Pro
 25              30                  35                  40

Arg Glu Val Cys Ile Asp Val Gly Lys Glu Phe Gly Val Ala Thr Asn
                 45                  50                  55

Thr Phe Phe Lys Pro Pro Cys Val Ser Val Tyr Arg Cys Gly Gly Cys
                 60                  65                  70

Cys Asn Ser Glu Gly Leu Gln Cys Met Asn Thr Ser Thr Ser Tyr Leu
             75                  80                  85

Ser Lys Thr Leu Phe Glu Ile Thr Val Pro Leu Ser Gln Gly Pro Lys
             90                  95                 100

Pro Val Thr Ile Ser Phe Ala Asn His Thr Ser Cys Arg Cys Met Ser
105                 110                 115                 120

Lys Leu Asp Val Tyr Arg Gln Val His Ser Ile Ile Arg Arg Ser Leu
                    125                 130                 135

Pro Ala Thr Leu Pro Gln Cys Gln Ala Ala Asn Lys Thr Cys Pro Thr
                140                 145                 150

Asn Tyr Met Trp Asn Asn His Ile Cys Arg Cys Leu Ala Gln Glu Asp
                155                 160                 165

Phe Met Phe Ser Ser Asp Ala Gly Asp Asp Ser Thr Asp Gly Phe His
                170                 175                 180

Asp Ile Cys Gly Pro Asn Lys Glu Leu Asp Glu Glu Thr Cys Gln Cys
185                 190                 195                 200

Val Cys Arg Ala Gly Leu Arg Pro Ala Ser Cys Gly Pro His Lys Glu
                    205                 210                 215

Leu Asp Arg Asn Ser Cys Gln Cys Val Cys Lys Asn Lys Leu Phe Pro
                220                 225                 230

Ser Gln Cys Gly Ala Asn Arg Glu Phe Asp Glu Asn Thr Cys Gln Cys
                235                 240                 245

Val Cys Lys Arg Thr Cys Pro Arg Asn Gln Pro Leu Asn Pro Gly Lys
                250                 255                 260

Cys Ala Cys Glu Cys Thr Glu Ser Pro Gln Lys Cys Leu Leu Lys Gly
265                 270                 275                 280

Lys Lys Phe His His Gln Thr Cys Ser Cys Tyr Arg Arg Pro Cys Thr
                285                 290                 295

Asn Arg Gln Lys Ala Cys Glu Pro Gly Phe Ser Tyr Ser Glu Glu Val
                300                 305                 310

Cys Arg Cys Val Pro Ser Tyr Trp Gln Arg Pro Gln Met Ser
                315                 320                 325

<210> SEQ ID NO 5
<211> LENGTH: 196
<212> TYPE: PRT
<213> ORGANISM: Homo sapiens

<400> SEQUENCE: 5

Met Arg Thr Leu Ala Cys Leu Leu Leu Gly Cys Gly Tyr Leu Ala
 1               5                  10                  15

His Val Leu Ala Glu Glu Ala Glu Ile Pro Arg Glu Val Ile Glu Arg
                 20                  25                  30

Leu Ala Arg Ser Gln Ile His Ser Ile Arg Asp Leu Gln Arg Leu Leu
                 35                  40                  45

Glu Ile Asp Ser Val Gly Ser Glu Asp Ser Leu Asp Thr Ser Leu Arg
             50                  55                  60
```

```
Ala His Gly Val His Ala Thr Lys His Val Pro Glu Lys Arg Pro Leu
 65                  70                  75                  80

Pro Ile Arg Arg Lys Arg Ser Ile Glu Glu Ala Val Pro Ala Val Cys
                 85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

<210> SEQ ID NO 6
<211> LENGTH: 241
<212> TYPE: PRT
<213> ORGANISM: Homo sapiens

<400> SEQUENCE: 6

Met Asn Arg Cys Trp Ala Leu Phe Leu Ser Leu Cys Cys Tyr Leu Arg
 1               5                  10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
        50                  55                  60

Thr Arg Ser His Ser Gly Gly Glu Leu Glu Ser Leu Ala Arg Gly Arg
 65                  70                  75                  80

Arg Ser Leu Gly Ser Leu Thr Ile Ala Glu Pro Ala Met Ile Ala Glu
                 85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240
```

Ala

<210> SEQ ID NO 7
<211> LENGTH: 232
<212> TYPE: PRT
<213> ORGANISM: Homo sapiens

<400> SEQUENCE: 7

```
Met Asn Phe Leu Leu Ser Trp Val His Trp Ser Leu Ala Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
50                      55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
                180                 185                 190

His Leu Phe Val Gln Asp Pro Gln Thr Cys Lys Cys Ser Cys Lys Asn
                195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

<210> SEQ ID NO 8
<211> LENGTH: 14
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is equal to any of the naturally occurring
      amino acids
<220> FEATURE:
<221> NAME/KEY: MISC_FEATURE
<222> LOCATION: (5)..(5)
<223> OTHER INFORMATION: X is equal to any of the naturally occurring
      amino acids
<220> FEATURE:
<221> NAME/KEY: MISC_FEATURE
<222> LOCATION: (6)..(6)
<223> OTHER INFORMATION: X is equal to any of the naturally occurring
      amino acids
<220> FEATURE:
<221> NAME/KEY: MISC_FEATURE
<222> LOCATION: (7)..(7)

```
<223> OTHER INFORMATION: X is equal to any of the naturally occurring
      amino acids
<220> FEATURE:
<221> NAME/KEY: MISC_FEATURE
<222> LOCATION: (10)..(10)
<223> OTHER INFORMATION: X is equal to any of the naturally occurring
      amino acids

<400> SEQUENCE: 8

Pro Xaa Cys Val Xaa Xaa Xaa Arg Cys Xaa Gly Cys Cys Asn
1               5                   10

<210> SEQ ID NO 9
<211> LENGTH: 18
<212> TYPE: DNA
<213> ORGANISM: Artificial sequence
<220> FEATURE:
<223> OTHER INFORMATION: M13-2 Reverse Primer
<400> SEQUENCE: 9
atgcttccgg ctcgtatg 18

<210> SEQ ID NO 10
<211> LENGTH: 19
<212> TYPE: DNA
<213> ORGANISM: Artificial sequence
<220> FEATURE:
<223> OTHER INFORMATION: M13-2 forward primer
<400> SEQUENCE: 10
gggttttccc agtcacgac 19

<210> SEQ ID NO 11
<211> LENGTH: 21
<212> TYPE: DNA
<213> ORGANISM: Artificial sequence
<220> FEATURE:
<223> OTHER INFORMATION: VEGF primer F4

<400> SEQUENCE: 11
ccacatggtt caggaaagac a 21

<210> SEQ ID NO 12
<211> LENGTH: 50
<212> TYPE: DNA
<213> ORGANISM: Artificial sequence
<220> FEATURE:
<223> OTHER INFORMATION: Forward primer used to amplify DNA encoding
      truncated VEGF-2 protein
<400> SEQUENCE: 12
tgtaatacga ctcactatag ggatcccgcc atggaggcca cggcttatgc 50

<210> SEQ ID NO 13
<211> LENGTH: 28
<212> TYPE: DNA
<213> ORGANISM: Artificial sequence
<220> FEATURE:
<223> OTHER INFORMATION: Reverse primer used to amplify DNA encoding
      truncated VEGF-2 protein
<400> SEQUENCE: 13
gatctctaga ttagctcatt tgtggtct 28

<210> SEQ ID NO 14
<211> LENGTH: 27
<212> TYPE: DNA

```
<213> ORGANISM: Artificial sequence
<220> FEATURE:
<223> OTHER INFORMATION: Forward primer used to amplify DNA encoding
      truncated VEGF-2 protein

<400

```
gcgattaaat ctcgcgccga tcaactgggt gccagcgtgg tggtgtcgat ggtagaacga   1560
agcggcgtcg aagcctgtaa agcggcggtg cacaatcttc tcgcgcaacg cgtcagtggg   1620
ctgatcatta actatccgct ggatgaccag gatgccattg ctgtggaagc tgcctgcact   1680
aatgttccgg cgttatttct tgatgtctct gaccagacac ccatcaacag tattattttc   1740
tcccatgaag acggtacgcg actgggcgtg gagcatctgg tcgcattggg tcaccagcaa   1800
atcgcgctgt tagcgggccc attaagttct gtctcggcgc gtctgcgtct ggctggctgg   1860
cataaatatc tcactcgcaa tcaaattcag ccgatagcgg aacgggaagg cgactggagt   1920
gccatgtccg gttttcaaca aaccatgcaa atgctgaatg agggcatcgt tcccactgcg   1980
atgctggttg ccaacgatca gatggcgctg ggcgcaatgc gcgccattac cgagtccggg   2040
ctgcgcgttg gtgcggatat ctcggtagtg ggatacgacg ataccgaaga cagctcatgt   2100
tatatcccgc cgttaaccac catcaaacag gattttcgcc tgctgggcaa aaccagcgtg   2160
gaccgcttgc tgcaactctc tcagggccag gcggtgaagg gcaatcagct gttgcccgtc   2220
tcactggtga aagaaaaac caccctggcg cccaatacgc aaaccgcctc tccccgcgcg   2280
ttggccgatt cattaatgca gctggcacga caggtttccc gactggaaag cgggcagtga   2340
gcgcaacgca attaatgtaa gttagcgcga attgtcgacc aaagcggcca tcgtgcctcc   2400
ccactcctgc agttcggggg catggatgcg cggatagccg ctgctggttt cctggatgcc   2460
gacggatttg cactgccggt agaactccgc gaggtcgtcc agcctcaggc agcagctgaa   2520
ccaactcgcg aggggatcga gcccggggtg ggcgaagaac tccagcatga gatccccgcg   2580
ctggaggatc atccagccgg cgtcccggaa aacgattccg aagcccaacc tttcatagaa   2640
ggcggcggtg aatcgaaat ctcgtgatgg caggttgggc gtcgcttggt cggtcatttc   2700
gaaccccaga gtcccgctca aagaactcg tcaagaaggc gatagaaggc gatgcgctgc   2760
gaatcgggag cggcgatacc gtaaagcacg aggaagcggt cagcccattc gccgccaagc   2820
tcttcagcaa tatcacgggt agccaacgct atgtcctgat agcggtccgc cacacccagc   2880
cggccacagt cgatgaatcc agaaaagcgg ccatttttcca ccatgatatt cggcaagcag   2940
gcatcgccat gggtcacgac gagatcctcg ccgtcgggca tgcgcgcctt gagcctggcg   3000
aacagttcgg ctggcgcgag cccctgatgc tcttcgtcca gatcatcctg atcgacaaga   3060
ccggcttcca tccgagtacg tgctcgctcg atgcgatgtt tcgcttggtg gtcgaatggg   3120
caggtagccg gatcaagcgt atgcagccgc cgcattgcat cagccatgat ggatactttc   3180
tcggcaggag caaggtgaga tgacaggaga tcctgccccg gcacttcgcc caatagcagc   3240
cagtcccttc ccgcttcagt gacaacgtcg agcacagctg cgcaaggaac gcccgtcgtg   3300
gccagccacg atagccgcgc tgcctcgtcc tgcagttcat tcagggcacc ggacaggtcg   3360
gtcttgacaa aagaaccgg gcgcccctgc gctgacagcc ggaacacggc ggcatcagag   3420
cagccgattg tctgttgtgc ccagtcatag ccgaatagcc tctccaccca gcggccgga   3480 gaacctgcgt gcaatccatc ttgttcaatc atgcgaaacg atcctcatcc tgtctcttga   3540
tcagatcttg atcccctgcg ccatcagatc cttggcggca agaaagccat ccagtttact   3600
ttgcagggct tcccaacctt accagagggc gccccagctg gcaattccgg ttcgcttgct   3660
gtccataaaa ccgcccagtc tagctatcgc catgtaagcc cactgcaagc tacctgcttt   3720
ctctttgcgc ttgcgttttc ccttgtccag atagcccagt agctgacatt catccggggt   3780
cagcaccgtt tctgcggact ggctttctac gtgttccgct tcctttagca gcccttgcgc   3840
```

```
cctgagtgct tgcggcagcg tgaagcttaa aaaactgcaa aaaatagttt gacttgtgag    3900
cggataacaa ttaagatgta cccaattgtg agcggataac aatttcacac attaaagagg    3960
agaaattaca tatg                                                      3974
```

<210> SEQ ID NO 17
<211> LENGTH: 112
<212> TYPE: DNA
<213> ORGANISM: Escherichia coli
<220> FEATURE:
<221> NAME/KEY: promoter
<222> LOCATION: (1)..(112)
<223> OTHER INFORMATION: regulatory elements of the pHE4a promoter

<400> SEQUENCE: 17

```
aagcttaaaa aactgcaaaa aatagtttga cttgtgagcg gataacaatt aagatgtacc     60
caattgtgag cggataacaa tttcacacat taaagaggag aaattacata tg           112
```

<210> SEQ ID NO 18
<211> LENGTH: 419
<212> TYPE: PRT
<213> ORGANISM: Homo sapiens

<400> SEQUENCE: 18

```
Met His Ser Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
```

```
                    260                 265                 270
Thr Asp Gly Phe His Asp Ile Cys Gly Pro Asn Lys Glu Leu Asp Glu
                275                 280                 285
Glu Thr Cys Gln Cys Val Cys Arg Ala Gly Leu Arg Pro Ala Ser Cys
            290                 295                 300
Gly Pro His Lys Glu Leu Asp Arg Asn Ser Cys Gln Cys Val Cys Lys
305                 310                 315                 320
Asn Lys Leu Phe Pro Ser Gln Cys Gly Ala Asn Arg Glu Phe Asp Glu
                325                 330                 335
Asn Thr Cys Gln Cys Val Cys Lys Arg Thr Cys Pro Arg Asn Gln Pro
            340                 345                 350
Leu Asn Pro Gly Lys Cys Ala Cys Glu Cys Thr Glu Ser Pro Gln Lys
        355                 360                 365
Cys Leu Leu Lys Gly Lys Lys Phe His His Gln Thr Cys Ser Cys Tyr
    370                 375                 380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Gln Arg Pro
                405                 410                 415
Gln Met Ser

<210> SEQ ID NO 19
<211> LENGTH: 30
<212> TYPE: DNA
<213> ORGANISM: Artificial sequence
<220> FEATURE:
<223> OTHER INFORMATION: Forward primer used in cloning DNA encoding
      VEGF-2 T103-L215 and VEGF-2 T103-R227

<400> SEQUENCE: 19
gcagcacata tgacagaaga gactataaaa                                    30

<210> SEQ ID NO 20
<211> LENGTH: 30
<212> TYPE: DNA
<213> ORGANISM: Artificial sequence
<220> FEATURE:
<223> OTHER INFORMATION: Reverse primer used in cloning DNA encoding
      VEGF-2 T103-L215

<400> SEQUENCE: 20
gcagcaggta cctcacagtt tagacatgca                                    30

<210> SEQ ID NO 21
<211> LENGTH: 30
<212> TYPE: DNA
<213> ORGANISM: Artificial sequence
<220> FEATURE:
<223> OTHER INFORMATION: Reverse primer used in cloning DNA encoding
      VEGF-2 T103-R227

<400> SEQUENCE: 21
gcagcaggta cctcaacgtc taataatgga                                    30

<210> SEQ ID NO 22
<211> LENGTH: 30
<212> TYPE: DNA
<213> ORGANISM: Artificial sequence
<220> FEATURE:
<223> OTHER INFORMATION: Forward primer used in cloning DNA encoding
      VEGF-2.T103-L215
```

<400> SEQUENCE: 22
gcagcaggat cccacagaag agactataaa                                    30

<210> SEQ ID NO 23
<211> LENGTH: 30
<212> TYPE: DNA
<213> ORGANISM: Artificial sequence
<220> FEATURE:
<223> OTHER INFORMATION: Reverse primer used in cloning DNA encoding
      VEGF-2.T103-L215

<400> SEQUENCE: 23
gcagcatcta gatcacagtt tagacatgca                                    30

<210> SEQ ID NO 24
<211> LENGTH: 39
<212> TYPE: DNA
<213> ORGANISM: Artificial sequence
<220> FEATURE:
<223> OTHER INFORMATION: Forward primer used in cloning DNA encoding
      VEGF-2.T103-R227

<400> SEQUENCE: 24
gcagcaggat cccacagaag agactataaa atttgctgc                          39

<210> SEQ ID NO 25
<211> LENGTH: 36
<212> TYPE: DNA
<213> ORGANISM: Artificial sequence
<220> FEATURE:
<223> OTHER INFORMATION: Reverse primer used in cloning DNA encoding
      VEGF-2.T103-R227

<400> SEQUENCE: 25
gcagcatcta gatcaacgtc taataatgga atgaac                             36

<210> SEQ ID NO 26
<211> LENGTH: 55
<212> TYPE: DNA
<213> ORGANISM: Artificial sequence
<220> FEATURE:
<223> OTHER INFORMATION: Forward primer used to amplify truncated VEGF-2

<400> SEQUENCE: 26
gatcgatcca tcatgcactc gctgggcttc ttctctgtgg cgtgttctct gctcg        55

<210> SEQ ID NO 27
<211> LENGTH: 39
<212> TYPE: DNA
<213> ORGANISM: Artificial sequence
<220> FEATURE:
<223> OTHER INFORMATION: Reverse primer used to amplify truncated VEGF-2

<400> SEQUENCE: 27
gcagggtacg gatcctagat tagctcattt gtggtctttt                         39

<210> SEQ ID NO 28
<211> LENGTH: 39
<212> TYPE: DNA
<213> ORGANISM: Artificial sequence
<220> FEATURE:
<223> OTHER INFORMATION: Forward primer used in cloning VEGF-2 M1-M263

<400> SEQUENCE: 28
gactggatcc gccaccatgc actcgctggg cttcttctc                          39

```
<210> SEQ ID NO 29
<211> LENGTH: 35
<212> TYPE: DNA
<213> ORGANISM: Artificial sequence
<220> FEATURE:
<223> OTHER INFORMATION: Reverse primer used in cloning VEGF-2 M1-M263

<400> SEQUENCE: 29
gactggtacc ttatcacata aaatcttcct gagcc                                35

<210> SEQ ID NO 30
<211> LENGTH: 39
<212> TYPE: DNA
<213> ORGANISM: Artificial sequence
<220> FEATURE:
<223> OTHER INFORMATION: Forward primer used in cloning VEGF-2 M1-D311

<400> SEQUENCE: 30
gactggatcc gccaccatgc actcgctggg cttcttctc                            39

<210> SEQ ID NO 31
<211> LENGTH: 34
<212> TYPE: DNA
<213> ORGANISM: Artificial sequence
<220> FEATURE:
<223> OTHER INFORMATION: Reverse primer used in cloning VEGF-2 M1-D311

<400> SEQUENCE: 31
gactggtacc ttatcagtct agttctttgt gggg                                 34

<210> SEQ ID NO 32
<211> LENGTH: 39
<212> TYPE: DNA
<213> ORGANISM: Artificial sequence
<220> FEATURE:
<223> OTHER INFORMATION: Forward primer used in cloning VEGF-2 M1-Q367

<400> SEQUENCE: 32
gactggatcc gccaccatgc actcgctggg cttcttctc                            39

<210> SEQ ID NO 33
<211> LENGTH: 37
<212> TYPE: DNA
<213> ORGANISM: Artificial sequence
<220> FEATURE:
<223> OTHER INFORMATION: Reverse primer used in cloning VEGF-2 M1-Q367

<400> SEQUENCE: 33
gactggtacc tcattactgt ggactttctg tacattc                              37

<210> SEQ ID NO 34
<211> LENGTH: 38
<212> TYPE: DNA
<213> ORGANISM: Artificial sequence
<220> FEATURE:
<223> OTHER INFORMATION: Forward primer used for cloning DNA encoding
      VEGF-2 T103-L215

<400> SEQUENCE: 34
gcagcaggat ccacagaaga gactataaaa tttgctgc                             38

<210> SEQ ID NO 35
<211> LENGTH: 37
<212> TYPE: DNA
<213> ORGANISM: Artificial sequence
<220> FEATURE:
```

```
<223> OTHER INFORMATION: Reverse primer used for cloning DNA encoding
      VEGF-2 T103-L215

<400> SEQUENCE: 35
cgtcgttcta gatcacagtt tagacatgca tcggcag                             37

<210> SEQ ID NO 36
<211> LENGTH: 23
<212> TYPE: DNA
<213> ORGANISM: Artificial sequence
<220> FEATURE:
<223> OTHER INFORMATION: VH Primer Hu VH1-5'

<400> SEQUENCE: 36
caggtgcagc tggtgcagtc tgg                                            23

<210> SEQ ID NO 37
<211> LENGTH: 23
<212> TYPE: DNA
<213> ORGANISM: Artificial sequence
<220> FEATURE:
<223> OTHER INFORMATION: VH Primer Hu VH2-5'

<400> SEQUENCE: 37
caggtcaact taagggagtc tgg                                            23

<210> SEQ ID NO 38
<211> LENGTH: 23
<212> TYPE: DNA
<213> ORGANISM: Artificial sequence
<220> FEATURE:
<223> OTHER INFORMATION: VH Primer Hu VH3-5'

<400> SEQUENCE: 38
gaggtgcagc tggtggagtc tgg                                            23

<210> SEQ ID NO 39
<211> LENGTH: 23
<212> TYPE: DNA
<213> ORGANISM: Artificial sequence
<220> FEATURE:
<223> OTHER INFORMATION: VH Primer Hu VH4-5'

<400> SEQUENCE: 39
caggtgcagc tgcaggagtc ggg                                            23

<210> SEQ ID NO 40
<211> LENGTH: 23
<212> TYPE: DNA
<213> ORGANISM: Artificial sequence
<220> FEATURE:
<223> OTHER INFORMATION: VH Primer Hu VH5-5'

<400> SEQUENCE: 40
gaggtgcagc tgttgcagtc tgc                                            23

<210> SEQ ID NO 41
<211> LENGTH: 23
<212> TYPE: DNA
<213> ORGANISM: Artificial sequence
<220> FEATURE:
<223> OTHER INFORMATION: VH Primer Hu VH6-5'

<400> SEQUENCE: 41
caggtacagc tgcagcagtc agg                                            23
```

<210> SEQ ID NO 42
<211> LENGTH: 24
<212> TYPE: DNA
<213> ORGANISM: Artificial sequence
<220> FEATURE:
<223> OTHER INFORMATION: VH Primer Hu JH1,2-5'

<400> SEQUENCE: 42
tgaggagacg gtgaccaggg tgcc                                          24

<210> SEQ ID NO 43
<211> LENGTH: 24
<212> TYPE: DNA
<213> ORGANISM: Artificial sequence
<220> FEATURE:
<223> OTHER INFORMATION: VH Primer Hu JH3-5'

<400> SEQUENCE: 43
tgaagagacg gtgaccattg tccc                                          24

<210> SEQ ID NO 44
<211> LENGTH: 24
<212> TYPE: DNA
<213> ORGANISM: Artificial sequence
<220> FEATURE:
<223> OTHER INFORMATION: VH Primer Hu JH4,5-5'

<400> SEQUENCE: 44
tgaggagacg gtgaccaggg ttcc                                          24

<210> SEQ ID NO 45
<211> LENGTH: 24
<212> TYPE: DNA
<213> ORGANISM: Artificial sequence
<220> FEATURE:
<223> OTHER INFORMATION: VH Primer Hu JH6-5'

<400> SEQUENCE: 45
tgaggagacg gtgaccgtgg tccc                                          24

<210> SEQ ID NO 46
<211> LENGTH: 23
<212> TYPE: DNA
<213> ORGANISM: Artificial sequence
<220> FEATURE:
<223> OTHER INFORMATION: VL Primer Hu Vkappa1-5'

<400> SEQUENCE: 46
gacatccaga tgacccagtc tcc                                           23

<210> SEQ ID NO 47
<211> LENGTH: 23
<212> TYPE: DNA
<213> ORGANISM: Artificial sequence
<220> FEATURE:
<223> OTHER INFORMATION: VL Primer Hu Vkappa2a-5'

<400> SEQUENCE: 47
gatgttgtga tgactcagtc tcc                                           23

<210> SEQ ID NO 48
<211> LENGTH: 23
<212> TYPE: DNA
<213> ORGANISM: Artificial sequence
<220> FEATURE:
<223> OTHER INFORMATION: VL Primer Hu Vkappa2b-5'

-continued

```
<400> SEQUENCE: 48
gatattgtga tgactcagtc tcc                                              23

<210> SEQ ID NO 49
<211> LENGTH: 23
<212> TYPE: DNA
<213> ORGANISM: Artificial sequence
<220> FEATURE:
<223> OTHER INFORMATION: VL Primer Hu Vkappa3-5'

<400> SEQUENCE: 49
gaaattgtgt tgacgcagtc tcc                                              23

<210> SEQ ID NO 50
<211> LENGTH: 23
<212> TYPE: DNA
<213> ORGANISM: Artificial sequence
<220> FEATURE:
<223> OTHER INFORMATION: VL Primer Hu Vkappa4-5'

<400> SEQUENCE: 50
gacatcgtga tgacccagtc tcc                                              23

<210> SEQ ID NO 51
<211> LENGTH: 23
<212> TYPE: DNA
<213> ORGANISM: Artificial sequence
<220> FEATURE:
<223> OTHER INFORMATION: VL Primer Hu Vkappa5-5'

<400> SEQUENCE: 51
gaaacgacac tcacgcagtc tcc                                              23

<210> SEQ ID NO 52
<211> LENGTH: 23
<212> TYPE: DNA
<213> ORGANISM: Artificial sequence
<220> FEATURE:
<223> OTHER INFORMATION: VL Primer Hu Vkappa6-5'

<400> SEQUENCE: 52
gaaattgtgc tgactcagtc tcc                                              23

<210> SEQ ID NO 53
<211> LENGTH: 23
<212> TYPE: DNA
<213> ORGANISM: Artificial sequence
<220> FEATURE:
<223> OTHER INFORMATION: VL Primer Hu Vlambda1-5'

<400> SEQUENCE: 53
cagtctgtgt tgacgcagcc gcc                                              23

<210> SEQ ID NO 54
<211> LENGTH: 23
<212> TYPE: DNA
<213> ORGANISM: Artificial sequence
<220> FEATURE:
<223> OTHER INFORMATION: VL Primer Hu Vlambda2-5'

<400> SEQUENCE: 54
cagtctgccc tgactcagcc tgc                                              23

<210> SEQ ID NO 55
```

```
<211> LENGTH: 23
<212> TYPE: DNA
<213> ORGANISM: Artificial sequence
<220> FEATURE:
<223> OTHER INFORMATION: VL Primer Hu Vlambda3-5'

<400> SEQUENCE: 55
tcctatgtgc tgactcagcc acc                                          23

<210> SEQ ID NO 56
<211> LENGTH: 23
<212> TYPE: DNA
<213> ORGANISM: Artificial sequence
<220> FEATURE:
<223> OTHER INFORMATION: VL Primer Hu Vlambda3b-5'

<400> SEQUENCE: 56
tcttctgagc tgactcagga ccc                                          23

<210> SEQ ID NO 57
<211> LENGTH: 23
<212> TYPE: DNA
<213> ORGANISM: Artificial sequence
<220> FEATURE:
<223> OTHER INFORMATION: VL Primer Hu Vlambda4-5'

<400> SEQUENCE: 57
cacgttatac tgactcaacc gcc                                          23

<210> SEQ ID NO 58
<211> LENGTH: 23
<212> TYPE: DNA
<213> ORGANISM: Artificial sequence
<220> FEATURE:
<223> OTHER INFORMATION: VL Primer Hu Vlambda5-5'

<400> SEQUENCE: 58
caggctgtgc tcactcagcc gtc                                          23

<210> SEQ ID NO 59
<211> LENGTH: 23
<212> TYPE: DNA
<213> ORGANISM: Artificial sequence
<220> FEATURE:
<223> OTHER INFORMATION: VL Primer Hu Vlambda6-5'

<400> SEQUENCE: 59
aattttatgc tgactcagcc cca                                          23

<210> SEQ ID NO 60
<211> LENGTH: 24
<212> TYPE: DNA
<213> ORGANISM: Artificial sequence
<220> FEATURE:
<223> OTHER INFORMATION: VL Primer Hu Jkappa1-3'

<400> SEQUENCE: 60
acgtttgatt tccaccttgg tccc                                         24

<210> SEQ ID NO 61
<211> LENGTH: 24
<212> TYPE: DNA
<213> ORGANISM: Artificial sequence
<220> FEATURE:
<223> OTHER INFORMATION: VL Primer Hu Jkappa2-3'

<400> SEQUENCE: 61
```

```
acgtttgatc tccagcttgg tccc                                          24
```

<210> SEQ ID NO 62
<211> LENGTH: 24
<212> TYPE: DNA
<213> ORGANISM: Artificial sequence
<220> FEATURE:
<223> OTHER INFORMATION: VL Primer Hu Jkappa3-3'

<400> SEQUENCE: 62

```
acgtttgata tccactttgg tccc                                          24
```

<210> SEQ ID NO 63
<211> LENGTH: 24
<212> TYPE: DNA
<213> ORGANISM: Artificial sequence
<220> FEATURE:
<223> OTHER INFORMATION: VL Primer Hu Jkappa4-3'

<400> SEQUENCE: 63

```
acgtttgatc tccaccttgg tccc                                          24
```

<210> SEQ ID NO 64
<211> LENGTH: 24
<212> TYPE: DNA
<213> ORGANISM: Artificial sequence
<220> FEATURE:
<223> OTHER INFORMATION: VL Primer Hu Jkappa5-3'

<400> SEQUENCE: 64

```
acgtttaatc tccagtcgtg tccc                                          24
```

<210> SEQ ID NO 65
<211> LENGTH: 23
<212> TYPE: DNA
<213> ORGANISM: Artificial sequence
<220> FEATURE:
<223> OTHER INFORMATION: VL Primer Hu Jlambda1-3'

<400> SEQUENCE: 65

```
cagtctgtgt tgacgcagcc gcc                                           23
```

<210> SEQ ID NO 66
<211> LENGTH: 23
<212> TYPE: DNA
<213> ORGANISM: Artificial sequence
<220> FEATURE:
<223> OTHER INFORMATION: VL Primer Hu Jlambda2-3'

<400> SEQUENCE: 66

```
cagtctgccc tgactcagcc tgc                                           23
```

<210> SEQ ID NO 67
<211> LENGTH: 23
<212> TYPE: DNA
<213> ORGANISM: Artificial sequence
<220> FEATURE:
<223> OTHER INFORMATION: VL Primer Hu Jlambda3-3'

<400> SEQUENCE: 67

```
tcctatgtgc tgactcagcc acc                                           23
```

<210> SEQ ID NO 68
<211> LENGTH: 23
<212> TYPE: DNA

```
<213> ORGANISM: Artificial sequence
<220> FEATURE:
<223> OTHER INFORMATION: VL Primer Hu Jlambda3b-3'

<400> SEQUENCE: 68
tcttctgagc tgactcagga ccc                                              23

<210> SEQ ID NO 69
<211> LENGTH: 23
<212> TYPE: DNA
<213> ORGANISM: Artificial sequence
<220> FEATURE:
<223> OTHER INFORMATION: VL Primer Hu Jlambda4-3'

<400> SEQUENCE: 69
cacgttatac tgactcaacc gcc                                              23

<210> SEQ ID NO 70
<211> LENGTH: 23
<212> TYPE: DNA
<213> ORGANISM: Artificial sequence
<220> FEATURE:
<223> OTHER INFORMATION: VL Primer Hu Jlambda5-3'

<400> SEQUENCE: 70
caggctgtgc tcactcagcc gtc                                              23

<210> SEQ ID NO 71
<211> LENGTH: 23
<212> TYPE: DNA
<213> ORGANISM: Artificial sequence
<220> FEATURE:
<223> OTHER INFORMATION: VL Primer Hu Jlambda6-3'

<400> SEQUENCE: 71
aattttatgc tgactcagcc cca                                              23

<210> SEQ ID NO 72
<211> LENGTH: 250
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Val Ser Gly Val Gly Trp Phe Asp Pro Trp Gly
            100                 105                 110

Arg Gly Thr Met Val Thr Val Ser Ser Gly Gly Gly Gly Ser Gly Gly
        115                 120                 125

Gly Gly Ser Gly Gly Gly Gly Ser Ala Leu Ser Tyr Glu Leu Thr Gln
    130                 135                 140
```

Pro Pro Ser Ser Ser Gly Thr Pro Gly Gln Arg Val Thr Ile Ser Cys
145                 150                 155                 160

Ser Gly Ser Ser Ser Asn Ile Gly Arg His Thr Val Ser Trp Tyr Gln
            165                 170                 175

Gln Val Pro Gly Thr Ala Pro Lys Leu Leu Ile Tyr Ser Asp Asp His
            180                 185                 190

Arg Pro Ser Gly Val Pro Asp Arg Phe Ser Ala Ser Lys Ser Gly Thr
        195                 200                 205

Ser Ala Ser Leu Thr Ile Thr Gly Leu Gln Ser Glu Asp Glu Ala Asp
    210                 215                 220

Tyr Tyr Cys Ala Ala Trp Asp Asp Ser Leu Asn Gly Pro Trp Val Phe
225                 230                 235                 240

Gly Gly Gly Thr Lys Leu Thr Val Leu Gly
            245                 250

<210> SEQ ID NO 73
<211> LENGTH: 252
<212> TYPE: PRT
<213> ORGANISM: Homo sapiens

<400> SEQUENCE: 73

Gln Met Gln Leu Val Gln Ser Gly Ala Glu Val Lys Lys Pro Gly Ser
1               5                   10                  15

Ser Val Lys Val Ser Cys Lys Ala Ser Gly Ile Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Arg Phe Gly Thr Ala Asn Tyr Ala Gln Lys Phe
50                  55                  60

Glu Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Gln Val Arg Ala Ser Gly Ser Tyr Pro Tyr Tyr Tyr Tyr
            100                 105                 110

Tyr Tyr Met Asp Val Trp Gly Gln Gly Thr Leu Val Thr Val Ser Ser
            115                 120                 125

Gly Gly Gly Gly Ser Gly Gly Gly Ser Gly Gly Gly Gly Ser Ala
            130                 135                 140

Leu Ser Tyr Val Leu Thr Gln Pro Pro Ser Met Ser Val Ser Pro Gly
145                 150                 155                 160

Gln Thr Ala Arg Ile Thr Cys Ser Gly Asp Lys Leu Gly Asp Lys Tyr
            165                 170                 175

Ala Ser Trp Tyr Gln Gln Lys Pro Gly Gln Ser Pro Val Leu Val Ile
            180                 185                 190

Tyr Gln Asp Ser Glu Arg Pro Ser Gly Ile Pro Glu Arg Phe Ser Gly
            195                 200                 205

Ser Asn Ser Gly Asn Thr Ala Thr Leu Thr Ile Arg Gly Thr Gln Pro
    210                 215                 220

Leu Asp Glu Ala Asp Tyr Tyr Cys Gln Thr Trp Asp Ser Thr Gly
225                 230                 235                 240

Val Phe Gly Gly Gly Thr Gln Leu Thr Val Leu Ser
            245                 250

<210> SEQ ID NO 74

```
<211> LENGTH: 247
<212> TYPE: PRT
<213> ORGANISM: Homo sapiens

<400> SEQUENCE: 74

Glu Val Gln Leu Val Glu Thr Gly Gly Gly Phe Val Arg Pro Gly Gly
1               5                   10                  15

Ser Leu Arg Leu Ser Cys Ala Ala Ser Gly Phe Thr Phe Ser Asn Tyr
                20                  25                  30

Ala Met Thr Trp Phe Arg Gln Ala Pro Gly Lys Gly Leu Glu Trp Val
            35                  40                  45

Ser Asp Ile Ser Gly Asp Gly Ile Gly Thr Tyr Asn Ala Asp Ser Val
    50                  55                  60

Lys Gly Arg Phe Thr Ile Ser Arg Asp Asn Ser Asn Ser Ile Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Trp Tyr Thr Ser Gly Trp Ile Phe Asp Tyr Trp Gly
            100                 105                 110

Lys Gly Thr Leu Val Thr Val Ser Ser Gly Gly Gly Ser Gly Gly
            115                 120                 125

Gly Gly Ser Gly Gly Gly Ser Ala Gln Ala Val Leu Thr Gln Pro
        130                 135                 140

Ser Ser Met Ser Gly Ala Pro Gly Gln Arg Val Thr Ile Ser Cys Thr
145                 150                 155                 160

Gly Ser Ser Asn Ile Gly Ala Gly Tyr Asp Val His Trp Tyr Gln
            165                 170                 175

Gln Leu Pro Gly Thr Ala Pro Lys Leu Leu Ile Tyr Ala Asn Asn Asn
            180                 185                 190

Arg Pro Ser Gly Val Pro Ala Arg Phe Ser Gly Ser Lys Ser Gly Thr
            195                 200                 205

Ser Ala Tyr Leu Ala Ile Ala Gly Leu Gln Ala Ala Asp Glu Ser Asp
    210                 215                 220

Tyr Tyr Cys Gln Ser Tyr Asp Ser Tyr Leu Gly Asp Ser Val Phe Gly
225                 230                 235                 240

Gly Gly Thr Lys Leu Thr Val
            245

<210> SEQ ID NO 75
<211> LENGTH: 251
<212> TYPE: PRT
<213> ORGANISM: Homo sapiens

<400> SEQUENCE: 75

Gln Val Gln Leu Gln Glu Ser Gly Pro Gly Leu Val Lys Pro Ser Gln
1               5                   10                  15

Thr Leu Ser Leu Thr Cys Ser Val Ser Gly Gly Ser Ile Ser Ser Arg
                20                  25                  30

Gly Tyr Tyr Trp Ser Trp Ile Arg Gln His Pro Gly Lys Gly Leu Glu
            35                  40                  45

Trp Ile Gly Tyr Ile Tyr His Asn Gly Asn Thr Tyr Tyr Asn Pro Ser
    50                  55                  60

Leu Lys Ser Arg Ile Thr Met Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95
```

```
Cys Ala Arg Asp Lys Val Val Thr Gly Ile Ser Gly Gly Phe Asp Leu
                100                 105                 110
Trp Gly Arg Gly Thr Leu Val Thr Val Ser Ser Gly Gly Gly Gly Ser
            115                 120                 125
Gly Gly Gly Gly Ser Gly Gly Gly Ser Ala Gln Ala Val Leu Thr
        130                 135                 140
Gln Pro Ser Ser Leu Ser Gly Ala Pro Gly Gln Arg Val Thr Ile Ser
145                 150                 155                 160
Cys Thr Gly Ser Ser Ser Asn Ile Gly Ala Gly Tyr Asp Val His Trp
                165                 170                 175
Tyr Gln His Leu Pro Gly Thr Ala Pro Lys Leu Leu Ile Tyr Gly Asn
            180                 185                 190
Asn Asn Arg Pro Ser Gly Val Pro Asp Arg Phe Ser Gly Ser Lys Ser
        195                 200                 205
Gly Thr Ser Ala Ser Leu Thr Ile Thr Gly Leu Gln Ala Glu Asp Glu
    210                 215                 220
Ala Asp Tyr Tyr Cys Gln Ser Asp Asp Ser Leu Ser Asp Ser Val Val
225                 230                 235                 240
Phe Gly Gly Gly Thr Gln Leu Thr Val Leu Ser
                245                 250

<210> SEQ ID NO 76
<211> LENGTH: 253
<212> TYPE: PRT
<213> ORGANISM: Homo sapiens

<400> SEQUENCE: 76

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Ser Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Asn Arg Val Cys Ser Gly Thr Gly Cys Tyr Ser Asp Gly
            100                 105                 110
Met Asp Val Trp Gly Gln Gly Thr Leu Val Thr Val Ser Ser Gly Gly
        115                 120                 125
Gly Gly Ser Gly Gly Gly Gly Ser Gly Gly Gly Ser Ala Gln Ser
    130                 135                 140
Val Leu Thr Gln Pro Pro Ser Ala Ser Gly Thr Pro Gly Gln Arg Val
145                 150                 155                 160
Thr Ile Ser Cys Ser Gly Ser Ser Ser Asn Ile Gly Ser Asn Tyr Val
                165                 170                 175
Tyr Trp Tyr Gln Gln Leu Pro Gly Thr Ala Pro Lys Leu Leu Ile Tyr
            180                 185                 190
Arg Asn Asn Gln Arg Pro Ser Gly Val Pro Asp Arg Phe Ser Gly Ser
        195                 200                 205
Lys Ser Gly Thr Ser Ala Ser Leu Ala Ile Ser Gly Leu Arg Ser Glu
```

```
                210                 215                 220
Asp Glu Ala Asp Tyr Tyr Cys Ala Thr Trp Asp Asp Asn Leu Ser Gly
225                 230                 235                 240

Val Val Phe Gly Gly Gly Thr Lys Val Thr Val Leu Gly
                245                 250

<210> SEQ ID NO 77
<211> LENGTH: 244
<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Ala Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Ser Arg Asn Ser Trp Glu Asn Trp Gly Arg Gly Thr Leu
            100                 105                 110

Val Thr Val Ser Ser Gly Gly Gly Ser Gly Gly Gly Gly Ser Gly
        115                 120                 125

Gly Gly Gly Ser Ala Gln Ala Val Val Ile Gln Glu Pro Ser Phe Ser
130                 135                 140

Val Ser Pro Gly Gly Thr Val Thr Leu Thr Cys Gly Leu Ser Ser Gly
145                 150                 155                 160

Ser Val Ser Thr Ser Asn Tyr Pro Ser Trp His Arg Gln Thr Pro Gly
                165                 170                 175

Gln Ala Pro Arg Thr Leu Ile Tyr Asn Thr Asn Thr Arg Ser Ser Gly
            180                 185                 190

Val Pro Asp Arg Phe Ser Gly Ser Ile Leu Gly Asn Lys Ala Ala Leu
        195                 200                 205

Thr Ile Thr Gly Ala Gln Ala Asp Asp Glu Ser Asp Tyr Tyr Cys Ala
    210                 215                 220

Leu His Met Arg Ser Gly Leu Ser Val Phe Gly Gly Gly Thr Lys Val
225                 230                 235                 240

Thr Val Leu Gly

<210> SEQ ID NO 78
<211> LENGTH: 248
<212> TYPE: PRT
<213> ORGANISM: Homo sapiens

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Ala Arg Gln Ala Pro Gly Lys Gly Leu Glu Trp Val
            35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Val Gly Asn Glu Gly Ser Trp Ser Asp Trp Gly Gln
            100                 105                 110

Gly Thr Leu Val Thr Val Ser Ser Gly Gly Gly Ser Gly Gly
            115                 120                 125

Gly Ser Gly Gly Gly Ser Ala Leu Asn Phe Met Leu Thr Gln Pro
    130                 135                 140

His Ser Val Ser Glu Ser Pro Gly Lys Thr Val Thr Ile Ser Cys Thr
145                 150                 155                 160

Arg Ser Gly Gly Ser Ile Ala Ser Asn Tyr Val Gln Trp Tyr Gln Gln
                165                 170                 175

Arg Pro Gly Ser Val Pro Thr Thr Leu Ile Tyr Glu Asp His Lys Arg
            180                 185                 190

Pro Ser Gly Val Pro Asp Arg Phe Ser Gly Ser Ile Asp Ser Ser Ser
    195                 200                 205

Asn Ser Ala Ser Leu Thr Ile Ser Gly Leu Lys Thr Glu Asp Glu Ala
210                 215                 220

Asp Tyr Tyr Cys Gln Ser Tyr Asp Thr Ser Ala Trp Val Phe Gly Gly
225                 230                 235                 240

Gly Thr Lys Leu Thr Val Leu Gly
                245

<210> SEQ ID NO 79
<211> LENGTH: 247
<212> TYPE: PRT
<213> ORGANISM: Homo sapiens

<400> SEQUENCE: 79

Glu Val Arg Leu Leu Glu Ser Gly Gly Leu Val Gln Pro Gly Gly
  1               5                  10                  15

Ser Leu Arg Leu Ser Cys Ala Ala Ser Gly Phe Thr Phe Arg Pro Arg
                20                  25                  30

Ala Met Ala Trp Val Arg Gln Ala Pro Gly Lys Gly Leu Glu Trp Val
            35                  40                  45

Ser Ser Ile Ser Ala Gln Gly Ala Ser Ala Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Ser Val Ser Gly Phe Gly Pro Trp Gly Arg Gly Thr
            100                 105                 110

Met Val Ala Val Ser Ser Gly Gly Gly Pro Gly Gly Gly Gly Ser
            115                 120                 125

Gly Gly Gly Arg Ser Ala Leu Ser Tyr Glu Leu Thr Gln Pro Pro Ser
    130                 135                 140

Ser Ser Gly Thr Pro Gly Gln Arg Val Thr Ile Ser Cys Ser Gly Ser
145                 150                 155                 160

Ser Ser Asn Ile Gly Arg His Thr Val Ser Trp Tyr Gln Gln Val Pro
```

165                 170                 175

Gly Thr Ala Pro Lys Leu Leu Ile Tyr Ser Asp Asp His Arg Pro Ser
            180                 185                 190

Gly Val Pro Asp Arg Phe Ser Ala Ser Lys Ser Gly Thr Ser Ala Ser
            195                 200                 205

Leu Thr Ile Thr Gly Leu Gln Ser Glu Asp Glu Ala Asp Tyr Tyr Cys
210                 215                 220

Ala Ala Trp Asp Ser Leu Asn Gly Pro Trp Val Phe Gly Gly Gly
225                 230                 235                 240

Thr Lys Leu Thr Val Leu Gly
                245

<210> SEQ ID NO 80
<211> LENGTH: 246
<212> TYPE: PRT
<213> ORGANISM: Homo sapiens

<400> SEQUENCE: 80

Glu Val Gln Leu Leu Lys Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Ala Gly Phe Phe Asp Pro Trp Gly Arg Gly Thr
            100                 105                 110

Met Val Thr Val Ser Ser Gly Gly Gly Gly Ser Gly Gly Gly Gly Ser
        115                 120                 125

Gly Gly Gly Gly Ser Ala Gln Ser Val Leu Thr Gln Pro Pro Ser Ser
    130                 135                 140

Ser Gly Thr Pro Gly Gln Arg Val Thr Ile Ser Cys Ser Gly Ser Ser
145                 150                 155                 160

Ser Asn Ile Gly Arg His Thr Val Ser Trp Tyr Gln Gln Val Pro Gly
                165                 170                 175

Thr Ala Pro Lys Leu Leu Ile Tyr Ser Asp Asp His Arg Pro Ser Gly
            180                 185                 190

Val Pro Asp Arg Phe Ser Ala Ser Lys Ser Gly Thr Ser Ala Ser Leu
        195                 200                 205

Thr Ile Thr Gly Leu Gln Ser Glu Asp Glu Ala Asp Tyr Tyr Cys Ala
    210                 215                 220

Ala Trp Asp Ser Leu Asn Gly Pro Trp Val Phe Gly Gly Gly Thr
225                 230                 235                 240

Lys Leu Thr Val Leu Gly
                245

<210> SEQ ID NO 81
<211> LENGTH: 247
<212> TYPE: PRT
<213> ORGANISM: Homo sapiens

<400> SEQUENCE: 81

```
Glu Val Gln Leu Leu Glu Ser Gly Gly Gly Leu Val Gln Pro Glu Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Asp Ser Lys Phe Asp Pro Trp Gly Arg Gly Ser
            100                 105                 110

Met Val Thr Val Ser Ser Gly Gly Gly Ser Gly Gly Gly Gly Gly Ser
        115                 120                 125

Gly Gly Gly Gly Ser Ala Leu Ser Tyr Glu Leu Thr Gln Pro Pro Ser
    130                 135                 140

Ser Ser Gly Thr Pro Gly Gln Arg Val Thr Ile Ser Cys Ser Gly Ser
145                 150                 155                 160

Ser Ser Asn Ile Gly Arg His Thr Val Ser Trp Tyr Gln Gln Val Pro
                165                 170                 175

Gly Thr Ala Pro Lys Leu Leu Ile Tyr Ser Asp Asp His Arg Pro Ser
            180                 185                 190

Gly Val Pro Asp Arg Phe Ser Ala Ser Lys Ser Gly Thr Ser Ala Ser
        195                 200                 205

Leu Thr Ile Thr Gly Leu Gln Ser Glu Asp Glu Ala Asp Tyr Tyr Cys
    210                 215                 220

Ala Ala Trp Asp Asp Ser Leu Asn Gly Pro Trp Val Phe Gly Gly Gly
225                 230                 235                 240

Thr Lys Leu Thr Val Leu Gly
                245

<210> SEQ ID NO 82
<211> LENGTH: 235
<212> TYPE: PRT
<213> ORGANISM: Homo sapiens

<400> SEQUENCE: 82

Gln Met Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Arg Phe Gly Thr Ala Asn Tyr Ala Gln Lys Phe
    50                  55                  60

Glu Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Val Lys Ser Ser Gly Ser Tyr Pro Tyr Tyr Asn Tyr
            100                 105                 110
```

```
Tyr Tyr Met Asp Val Trp Gly Gln Gly Thr Leu Val Thr Val Ser Ser
            115                 120                 125

Ser Tyr Val Leu Thr Gln Pro Pro Ser Val Ser Val Ser Pro Gly Gln
    130                 135                 140

Thr Ala Ser Ile Thr Cys Ser Gly Asp Lys Leu Gly Asp Lys Tyr Ala
145                 150                 155                 160

Ser Trp Tyr Gln Gln Lys Pro Gly Gln Ser Pro Val Leu Val Ile His
                165                 170                 175

Gln Asp Asn Lys Arg Pro Ser Gly Ile Pro Glu Arg Phe Ser Gly Ser
            180                 185                 190

Asn Ser Gly Asn Thr Ala Thr Leu Thr Ile Ser Gly Thr Gln Ala Met
            195                 200                 205

Asp Glu Ala Asp Tyr Tyr Cys Gln Ala Trp Asp Ser Ser Leu Gly Val
210                 215                 220

Phe Gly Thr Gly Thr Lys Val Thr Val Leu Gly
225                 230                 235

<210> SEQ ID NO 83
<211> LENGTH: 235
<212> TYPE: PRT
<213> ORGANISM: Homo sapiens

<400> SEQUENCE: 83

Gln Met Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Arg Phe Gly Thr Ala Asn Tyr Ala Gln Lys Phe
    50                  55                  60

Glu Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Val Arg Ala Ser Gly Asn Tyr Pro Tyr Tyr Tyr Tyr
            100                 105                 110

Tyr Tyr Met Asp Val Trp Gly Gln Gly Thr Leu Val Thr Val Ser Ser
            115                 120                 125

Ser Tyr Val Leu Thr Gln Pro Pro Ser Val Ser Val Ser Pro Gly Gln
    130                 135                 140

Thr Ala Ser Ile Thr Cys Ser Gly Asp Lys Leu Gly Asp Lys Tyr Ala
145                 150                 155                 160

Ser Trp Tyr Gln Gln Lys Pro Gly Gln Ser Pro Val Leu Val Ile His
                165                 170                 175

Gln Asp Asn Lys Arg Pro Ser Gly Ile Pro Glu Arg Phe Ser Gly Ser
            180                 185                 190

Asn Ser Gly Asn Thr Ala Thr Leu Thr Ile Ser Gly Thr Gln Ala Met
            195                 200                 205

Asp Glu Ala Asp Tyr Tyr Cys Gln Ala Trp Asp Ser Ser Leu Gly Val
210                 215                 220

Phe Gly Thr Gly Thr Lys Val Thr Val Leu Gly
225                 230                 235

<210> SEQ ID NO 84
```

```
<211> LENGTH: 741
<212> TYPE: DNA
<213> ORGANISM: Homo sapiens

<400> SEQUENCE: 84
gaggtgcggc tgttggagtc tggggggaggc ttggtacagc ctggggggtc cctgagactc      60
tcctgtgcag cctctggatt cacctttcgc ccccgcgcga tggcgtgggt ccgccaggct     120
ccagggaagg ggctggagtg ggtctcatcc atttcggccc agggtgccag cgcctactac     180
gcagactccg tgaagggccg gttcaccatc tccagagaca attccaagaa cacgctgtat     240
ctgcaaatga acagcctgag agccgaggac acggccgtgt attactgtgc gagagatttg     300
agtgtcagcg gcttcggccc ctggggccga gggacaatgg tcgccgtctc gagtggaggc     360
ggcggtccag gcggaggtgg ctctggcggt ggcagaagtg cactttccta tgagctgact     420
cagccaccct catcatccgg gacccccggg cagagagtca ccatctcttg ttccggaagc     480
agctccaaca tcggacgtca tactgtaagt tggtaccagc aggtcccagg aacggcccc      540 aaactcctca tctatagtga tgatcatcgg ccctcaggag tccctgaccg gttttctgcc     600
tccaagtctg gcacctcagc ctccctgacc atcactgggc tccagtctga ggatgaggcc     660
gattattact gtgcagcatg ggatgacagt ctgaatggtc cttgggtgtt cggcggaggg     720
accaagctga ccgtcctagg t                                               741

<210> SEQ ID NO 85
<211> LENGTH: 738
<212> TYPE: DNA
<213> ORGANISM: Homo sapiens

<400> SEQUENCE: 85
gaggtgcagc tgttgaagtc tggggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatttg     300
agtgcggggt tcttcgaccc ctggggccga gggacaatgg tcaccgtctc gagtggaggc     360
ggcggttcag gcggaggtgg ctctggcggt ggcggaagtg cacagtctgt gctgactcag     420
ccaccctcat catccgggac ccccgggcag agagtcacca tctcttgttc cggaagcagc     480
tccaacatcg gacgtcatac tgtaagttgg taccagcagg tcccaggaac ggcccccaaa     540
cttctcatct atagtgatga tcatcggccc tcaggagtcc ctgaccggtt ttctgcctcc     600
aagtctggca cctcagcctc cctgaccatc actgggctcc agtctgagga tgaggccgat     660
tattactgtg cagcatggga tgacagtctg aatggtcctt gggtgttcgg cggagggacc     720
aagctgaccg tcctaggt                                                   738
```